(12) United States Patent
Jones et al.

(10) Patent No.: US 7,273,701 B2
(45) Date of Patent: Sep. 25, 2007

(54) COMPOSITIONS AND METHODS FOR GENETIC ANALYSIS OF POLYCYSTIC KIDNEY DISEASE

(75) Inventors: Jeffrey G. Jones, Wilbraham, MA (US); Aidan N. Hennigan, Millbury, MA (US); John A. Curran, Worcester, MA (US); Susan K. Allen, Worcester, MA (US); Normand J. Robichaud, Leominster, MA (US); Jing Wang, Worcester, MA (US); Kerry E. Flynn, Grafton, MA (US); Jorge A. Garcés, Dudley, MA (US); Christopher M. Palatucci, Shrewsbury, MA (US); William K. Seltzer, Holden, MA (US)

(73) Assignee: Athena Diagnostics, Inc., Worcester, MA (US)

( * ) Notice: Subject to any disclaimer, the term of this patent is extended or adjusted under 35 U.S.C. 154(b) by 620 days.

(21) Appl. No.: 10/411,915

(22) Filed: Apr. 11, 2003

(65) Prior Publication Data

US 2005/0100898 A1    May 12, 2005

Related U.S. Application Data

(63) Continuation-in-part of application No. 10/083,246, filed on Feb. 26, 2002, now Pat. No. 6,916,619.

(60) Provisional application No. 60/328,739, filed on Oct. 12, 2001.

(51) Int. Cl.
    *C12Q 1/68* (2006.01)
    *C12P 19/34* (2006.01)
(52) U.S. Cl. .......................... 435/6; 435/91.1; 435/91.2
(58) Field of Classification Search .................... 435/6, 435/91.1, 91.2
    See application file for complete search history.

(56) References Cited

U.S. PATENT DOCUMENTS

| | | | | |
|---|---|---|---|---|
| 5,891,628 | A * | 4/1999 | Reeders et al. | 435/6 |
| 6,031,088 | A | 2/2000 | Somlo et al. | 536/23.5 |
| 6,071,717 | A | 6/2000 | Klinger et al. | 435/69.1 |
| 6,228,591 | B1 | 5/2001 | Somlo et al. | 435/6 |
| 6,656,681 | B1 * | 12/2003 | Harris et al. | 435/6 |
| 2003/0008288 | A1 | 1/2003 | Germino et al. | 435/6 |

FOREIGN PATENT DOCUMENTS

WO    WO 02/06529 A2    1/2002

OTHER PUBLICATIONS

Inoue et al., Human Mutation 19, 622-628 (May 3, 2002).*
Aguiari et al., American Journal of Kidney Diseases 33(5), 880-885 (1999).*
Phakdeekitcharoen, B. et al., (2001), "Mutation Analysis of the Entire Replicated Portion of *PKD1* Using Genomic DNA Samples", *J. Am. Soc. Nephrol*, 12:955-963.
Perrichot, R.A. et al., (1999), "DGGE screening of *PKD1* gene reveals novel mutations in a large cohort of 146 unrelated patients", *Hum. Genet.*, 105:231-239.
Thomas, R. et al., (1999), "Identification of Mutations in the Repeated Part of the Autosomal Dominant Polycystic Kidney Disease Type 1 Gene, PKD1, by Long-Range PCR", *Am. J. Hum. Genet.*, 65:39-49.
Watnick, T. et al., (1999), "Mutation Detection of *PKD1* Identifies a Novel Mutation Common to Three Families with Aneurysms and/or Very-Early-Onset Disease", *Am. J. Hum. Genet.*, 65:1561-1571.
Watnick, T.J. et al., (1998), "Somatic Mutation in Individual Liver Cysts Supports a Two-Hit Model of Cystogenesis in Autosomal Dominant Polycystic Kidney Disease", *Molecular Cell*, 2:247-251.
Roelfsema, J.H. et al., (1997), "Mutation Detection in the Repeated Part of the PKD1 Gene", *Am. J. Hum. Genet.*, 61:1044-1052.
Watnick, T.J. et al., (1997), "An unusual pattern of mutation in the duplicated portion of *PKD1* is revealed by use of a novel strategy for mutation detection", *Human Molecular Genetics*, 6(9):1473-1481.
Neophytou, P. et al., (1996), "Detection of a novel nonsense mutation and an intragenic polymorphism in he PKD1 gene of a Cypriot family with autosomal dominant polycystic kidney disease", *Hum. Genet.*, 98:437-442.
Peral, B. et al., (1996), "Screening the 3' Region of the Polycystic Kidney Disease 1 (*PKD1*) Gene Reveals Six Novel Mutations", *Am. J. Hum. Genet.*, 58:86-96.
Turco, A.E. et al., (1995), "A novel nonsense mutation in the PKD1 gene (C3817T) is associated with autosomal dominant polycystic kidney disease (ADPKD) in a large three-generation Italian family", *Human Molecular Genetics*, 4(8):1331-1335.
Ward, C.J. et al., (1995), "*Homo sapiens* polycystic kidney disease-associated protein (PKD1) gene, complete cds", Database *EMBL* Online, Database Accession No. L39891:1-20.
International Search Report of International Application No. PCT/US01/22035.
Rossetti, s. et al., "Mutation Analysis of the Entire PKD1 Gene: Genetic and Diagnostic Implications", 2001, *Am. J. Hum. Genet.*, 68:46-63.
Underhill, P.A. et al., "Detection of Numerous Y Chromosome Biallelic Polymorphisms by Denaturing High-Performance Liquid Chromatography", 1997, *Genome Research*, 7:996-1005.
Liu, W. et al., "Denaturing high performance liquid chromatography (DHPLC) used in the detection of germline and somatic mutations", 1998, *Nucleic Acids Research*, 26(6):1396-1400.

* cited by examiner

*Primary Examiner*—Kenneth R. Horlick
(74) *Attorney, Agent, or Firm*—Hamilton, Brook, Smith & Reynolds, P.C.

(57) ABSTRACT

The subject invention relates to nucleic acid sequences for detection of mutations in a PKD-1 or PKD-2 gene, as well as biomarkers for ADPKD. The invention further relates to methods for diagnosing ADPKD in an individual, and kits for performing the methods of the invention. The invention also provides a method for determining in an individual the presence or absence of a mutant PKD gene.

18 Claims, 108 Drawing Sheets

Figure 1

| Codon Number | | |
|---|---|---|
| 1 | 212 | Exon 1 atgccacccgccgcgcccgcccgcctggcgctcgccctggccctg M P P A A P A R L A L A L G L |
| 16 | 257 | ggcctgtggctcagggcgctggcaggggccccgggcgcggctgc G L W L G A L A G G P G R G C |
| 31 | 302 | gggccctgcgagccccctgcctctgcgcccagcgcccggcgcc G P C E P P C L C G P A P G A |
| 46 | 347 | gctgccgcgtcaactgctcgggccgcggctgcggacgctcggt A C R V N C S G R G L R T L C |
| 61 | 392 | cccgcactgcgcatcccgcgacgccacagcgct Exon 2 P A L R I P A D A T A L |
| 76 | 437 | |
| 91 | 482 | Exon 3 D I S N N K I S T |
| 106 | 527 | ttagaagaaggaatatttgctaatttatttaatttaagtgaaat Exon 4 L E E G I F A N L F N L S E |
| 121 | 572 | |
| 136 | 617 | |
| 151 | 662 | |
| 166 | 707 | Exon 5-A gtgaggagtat G E E Y |
| 181 | 752 | gtcgcctgcctccctgacaacagctcaggcaccgtggcagcagtg V A C L P D N S S G T V A A V |

FIG. 1A

Figure 1 con.

```
 797 tcctttcagctgcccacgaagccctgcttcagccagagcctgc
 196  S  F  S  A  A  H  E  G  L  L  Q  P  E  A  C 842 agcgccttctccttctccaccggccaggccctcacagccctctcc
 211  S  A  F  C  F  S  T  G  Q  G  L  A  A  L  S
                              → 5-B
 887 gagcacggctggtgcctgtgtggagcggccagccctccagtgcc
 226  E  Q  G  W  C  L  C  G  A  A  Q  P  S  S  A
                ←     5-A
 932 tcctttgcctgcctgtccctctgctccggccccccgccacctcct
 241  S  F  A  C  L  S  L  C  S  G  P  P  P  P 977 gcccccacctgtaggggcccacctcctccagcacatcttccct
 256  A  P  T  C  R  G  P  T  L  L  Q  H  V  F 1022 ggctcccagggggccacctggtggagcccacggacctctggcc
 271  A  S  P  G  A  T  L  V  G  P  H  G  P  L  A 1067 tctggccagctagcagccttccacatcgctgcccgctccctgtc
 286  S  G  Q  L  A  A  F  H  I  A  A  P  L  P  V
                                       → 5-C
1112 actgccacacgctgggacttcggagacagctccgccgagtggat
 301  T  A  T  R  W  D  F  G  D  G  S  A  E  V  D
                                ←       5-B
1157 gccgctggaccgactgcctcgcatcgctatgtgctgcctgggcg
 316  A  A  G  P  A  A  S  H  R  Y  V  L  P  G  R 1202 tatcacgtgacgaccgtgctggccctgggagccggctcagccctg
 331  Y  H  V  T  A  V  L  A  L  G  A  G  S  A  L 1247 ctggggacagacgtgcaggtggaagcggcacctgccgccctgcac
 346  L  G  T  D  V  Q  V  E  A  A  P  A  A  L  E 1292 ctcctgtgcccgtcctcggtgcagagtgacgagaccttgacctc
 361  L  V  C  P  S  S  V  Q  S  D  E  S  L  D  L 1337 agcatccagaaccgcggtggttcagccctggagaccgcctacagc
 376  S  I  Q  N  R  G  G  S  G  L  E  A  A  Y  S
                                    Exon6
1382 atcgtcgccctgggcgaggagccggccgac
 391  I  V  A  L  G  E  E  P  A  R
```

FIG. 1B

Figure 1 con.

```
1427 ...
406  ...

1472 ...
421  ...

1517 ...
436  ...
                                         Exon 7
1562 ................................gagctagac
451  ..........................       S  L  E 1607 atgtggatcggcttctcgactgtcagggggtggaggtgggccca
466   V  W  I  G  F  S  T  V  Q  G  V  E  V  G  P 1652 gcgcccaggacgaggccttcagcctggagagctgccagaactgc
481   A  P  Q  G  E  A  F  S  L  E  S  C  Q  N  C 1697 ctgcccggggagccacacccagccacagccgagcactgcgtccgc
496   L  P  G  E  P  H  P  A  T  A  E  H  C  V  R 1742 ctcggcccacgggtggtgtaacaccgacctgtgctcagcgccc
511   L  G  P  T  G  W  C  N  T  D  L  C  S  A  P
                                       Exon 8
1787 cacagctacgtctgcgagctgcagcccggag............
526   H  S  Y  V  C  E  L  Q  P  G ............

1832 ...
541  ...

1877 ...
556  ...
      Exon 9
1922 .........gtcatggtattcccgagcctgcgtctgagccgt
571   ......   V  M  V  F  P  G  L  R  L  S  R 1967 gaagccttcctcaccacgaccgaatttggacccaggagctccgc
586   E  A  F  L  T  T  A  E  F  G  T  Q  E  L  R 2012 cggcccgcccagctgcggctgcaggtgtaccgctcctcagcaca
601   R  P  A  Q  L  R  L  Q  V  Y  R  L  L  S  T
          Exon 10
2057 gcag........................................
616   A  .......................................
```

FIG. 1C

Figure 1 con.

```
       2102 gcgcgcgtgctgggccgtgccgccgccgcg
631         ...             ...      M E L G
       2147 ...
646         ...             ...
       2192 ...
661         ...             ...
       2237 ...
676         ...             ...      Ex.. 11-A
       2282 ...                      gtcaccctccacggccac
691         ...                      V T L H G
       2327 gatgtcctcatgctccctggtgacctcgttggcttgcagcacgac
706         D V L M P G D L V G L Q H
       2372 gctagccctggcgccctcctgcactgctcaccagctcccgaccac
721         A G P G A L L H C S P A P G
       2417 cctggtccccaggccccgtacctctccgccaacgcctcgtcatgg
736         P G P Q A P Y L S A N A S S
                                           → 11-B
       2462 ctgccccacttgccagcccagctcgagggcacttgggcctgccct
751         L P H L P A Q L E G T W A C
       2507 gcctgtgccctgcggctgcttgcagccacggaacagctcaccgtg
766         A C A L R L L A A T E Q L T V
            ←    11-A
       2552 ctgctgggcttgagcccaaccctggactgcgatgcctggcgc
781         L L G L R P N P G L R M P G
       2597 tatgaggtccgggcagaggtgggcaatggcgtgtccaggcacaac
796         Y E V R A E V G N G V S R H
       2642 ctctcctgcagctttgacgtggtctcccagtggctgggctgcgg
811         L S C S F D V V S P V A G L
       2687 gtcatctaccctgccccccgcgacggccgcctctacgtgcccacc
826         V I Y P A P R D G R L Y V P T
       2732 aacggctcagccttggtgctccaggtggactctggtgccaacgcc
841         N G S A L V L Q V D S G A N
```

FIG. 1D

Figure 1 con.

```
     2777 acggccacggctcgctgccctggggcagtgtcagcgcccgcttt
856       T  A  T  A  R  W  P  G  G  S  V  S  A  R  E
                                                    11-C →

2822 gagaatgtctgccctgcctggtgaccaccttcatgcccggctgc
871       E  N  V  C  P  A  L  V  A  T  F  V  P  G  C 2867 ccctgggagaccaacgatacctgttctcagtggtagcactgccg
886       P  W  E  T  N  D  T  L  F  S  V  V  A  L  P
                                          ← 11-B 2912 tggctcagtgagcaggagcacgtggtggacgtggtggtggaaaac
901       W  L  S  E  G  E  H  V  V  D  V  V  V  E  N 2957 agcgccagccgggccaacctcagcctgcgggtgacgacggaggag
916       S  A  S  R  A  N  L  S  L  R  V  T  A  E  E 3002 cccatctgtggcctccacgccacgcccagccccgaggcccgtgta
931       P  I  C  G  L  R  A  T  P  S  P  E  A  R  V
                                    Exon 12

3047 ctgcaggagtcctagtg...
946       L  Q  G  V  L  V 3092 
961

3137 
976                                   Exon 13

3182 ...ctgacggcctccaaccacgtgagcaacgtc
991                    L  T  A  S  N  H  V  S  N  V 3227 accgtgaactacaacgtaaccgtggagcggatgaacaggatgcag
1006      T  V  N  Y  N  V  T  V  E  R  M  N  R  M  Q 3272 ggtctgcaggtctccacagtgccggccgtgctgtccccaatgcc
1021      G  L  Q  V  S  T  V  P  A  V  L  S  P  N  A 3317 acgctagcactgacggcgggcgtgctggtggactcggccctggag
1036      T  L  A  L  T  A  G  V  L  V  D  S  A  V  E
                                    Exon 14

3362 gtggccttcct...
1051      V  A  F  L 3407 
1066      
```

FIG. 1E

Figure 1 con.

```
3452 ................................................
1081 ................................................
                    Exoi. 15-A
3497 ............gtgagtacctcctgaccgtgctggcatctaatgcc
1096    ......G  E  Y  L  L  T  V  L  A  S  N  A 3542 ttcgagaacctgacgcagcaggtacctgtgagcgtgcgcgcctcc
1111    F  E  N  L  T  Q  Q  V  P  V  S  V  R  A  S 3587 ctgccctccgtggctgtgggtgtgagtgacggcgtcctggtgccc
1126    L  P  S  V  A  V  G  V  S  D  G  V  L  V  A
                                           →15-B 3632 ggccggcccgtcaccttctacccgcacccgctgccctcgcctggg
1141    G  R  P  V  T  F  Y  P  H  P  L  P  S  P  G 3677 ggtgttctttacacgtggacttcggggacggctcccctatcctg
1156    G  V  L  Y  T  W  D  F  G  D  G  S  P  V  L
     ←      15-A 3722 acccagagccagccggctgccaaccacacctatgcctcgaggggc
1171    T  Q  S  Q  P  A  A  N  H  T  Y  A  S  R  G 3767 acctaccacgtacgcctggaggtcaacaacacggtgagcggtgcc
1186    T  Y  H  V  R  L  E  V  N  N  T  V  S  G  A 3812 gcggcccaggcggatgtgcgcgtcttcgaggagctccgcggactc
1201    A  A  Q  A  D  V  R  V  F  E  E  L  R  G  L
                                           →15-C 3857 agcgtggacatgagcctggccgtggagcaggcgcccccgtggtg
1216    S  V  D  M  S  L  A  V  E  Q  G  A  P  V  V
                                   ←    15-B 3902 gtcagcgccgcggtgcagacgggcgacaacatcacgtggaccttc
1231    V  S  A  A  V  Q  T  G  D  N  I  T  W  T  F 3947 gacatgggggacggcaccgtgctgtcgggcccagaggcaacagtc
1246    D  M  G  D  G  T  V  L  S  G  P  E  A  T  V 3992 gagcatgtgtacctgcgggcacagaactgcacagtgaccgtgggt
1261    E  H  V  Y  L  R  A  Q  N  C  T  V  T  V  G 4037 gcggccagccccgccggccacctggcccgaagcctgcacgtgctg
1276    A  A  S  P  A  G  H  L  A  R  S  L  H  V  L
              →15-D 4082 gtcttcgtcctggacgtgctgcgcgttgaaccggccgcctgcatc
1291    V  F  V  L  E  V  L  R  V  E  P  A  A  C  I
         ←    15-C
```

FIG. 1F

Figure 1 con.

```
       4127 ccacgcagcctgacgcgcggctcacggcctacgtcaccgggaac
1306        P  T  Q  P  D  A  R  L  T  A  Y  V  T  G  N 4172 ccggcccactacctcttcgactggaccttcggggatggctcctcc
1321        P  A  H  Y  L  F  D  W  T  F  G  D  G  S  S 4217 aacacgaccgtgcgagggtgcccgacggtgacacacaacttcacg
1336        N  T  T  V  R  G  C  P  T  V  T  H  N  F  T
                                                 →15-E 4262 cggagcggcacgttccccctggcgctggtgctgtccagccgcgtg
1351        R  S  C  T  F  P  L  A  V  L  S  S  R  V
                                        ←       15-D 4307 aacagggcgcattacttcaccagcatctgcgtggagccagaggtg
1366        N  R  A  H  Y  F  T  S  I  C  V  E  P  E  V 4352 ggcaacgtcaccctgcagccagagaggcagtttgtgcagctcgg
1381        G  N  V  T  L  Q  P  E  R  Q  F  V  Q  L  G 4397 gacgagccctggctgntgacatgtgcctggcccccattccctac
1396        D  E  A  W  L  V  A  C  A  W  P  P  F  P  Y 4442 cgctacacctgggactttggcaccgaggaagccgcccccacccgt
1411        R  Y  T  W  D  F  G  T  E  E  A  A  P  T  R
                                                 →15-F 4487 gccagggccctgaggtgacgttcatctaccgagacccaggctcc
1426        A  R  G  P  E  V  T  F  I  Y  R  D  P  G  S
                                        ←       15-E 4532 tatcttgtgacagtcaccgcgtccaacaacatctctgctgccaat
1441        Y  L  V  T  V  T  A  S  N  N  I  S  A  A  N 4577 gactcagccctggtgaagtgcagcagcccgtgctggtcaccagc
1456        D  S  A  L  V  E  V  Q  E  P  V  L  V  T  S 4622 atcaaggtcaatggctcccttgggctggagctgcagcagccgtac
1471        I  K  V  N  G  S  L  G  L  E  L  Q  Q  P  Y
                                                 →15-G 4667 ctgttctctgctgtgcgccgtgggcgccccgccagctacctgtgg
1486        L  F  S  A  V  G  R  G  R  P  A  S  Y  L  W 4712 gatctggggacggtgggtgactccaaggtccagaggtcacccac
1501        D  L  G  D  G  W  L  E  G  P  E  V  T  H
                              ←       15-F 4757 gcttacaacagcacaggtgacttcaccgttagggtagccggctgg
1516        A  Y  N  S  T  G  D  F  T  V  R  V  A  G  W
```

FIG. 1G

Figure 1 con.

```
      4802 aatgaggtgagccgcagcgaggcctggctcaatgtgacggtgaag
1531       N  E  V  S  R  S  E  A  W  L  N  V  T  V  K
                     → 15-H
      4847 cggcgcgtgcgggggctcgtcgtcaatgcaagccgcacggtggtc
1546       R  R  V  R  G  L  V  V  N  A  S  R  T  V  V
                             ←           15-G
      4892 ccctgaatggagcgtgagcttcagcacgtcgctggagccggc
1561       P  L  N  G  S  V  S  F  S  T  S  L  E  A  G
      4937 agtgatgtgcgctattcctgggtgctctgtgaccgctgcacgccc
1576       S  D  V  R  Y  S  W  V  L  C  D  R  C  T  P
      4982 atccctgggggtcctaccatctcttacaccttccgctccgtgggc
1591       I  P  G  G  P  T  I  S  Y  T  F  R  S  V  G
                                              → 15-I
      5027 accttcaatatcatcgtcacggctgagaacgaggtgggctccgcc
1606       T  F  N  I  I  V  T  A  E  N  E  V  G  S  A
      5072 caggacagcatcttcgtctatgtcctgcagctcatagagggctg
1621       Q  D  S  I  F  V  Y  V  L  Q  L  I  E  G  L
           ←    15-H
      5117 caggtggtggacggtggccgctacttccccaccaaccacacggta
1636       Q  V  V  G  G  R  Y  F  P  T  N  H  T  V
      5162 cagctgcaggccgtggttagagatggcaccaacgtctcctacagc
1651       Q  L  Q  A  V  V  R  D  G  T  N  V  S  Y  S
                                             → 15-J
      5207 tggactgcctggagggacagggacccggccctggccggcagcggc
1666       W  T  A  W  R  D  R  G  P  A  L  A  G  S  G
      5252 aaaggcttctcgctcaccgtgctcgaggccggcacctaccatgtc
1681       K  G  F  S  L  T  V  L  E  A  G  T  Y  H  V
                               ←       15-I
      5297 cagctgcgggccaccaacatgctgggcagcgcctgggccgactgc
1696       Q  L  R  A  T  N  M  L  G  S  A  W  A  D  C
      5342 accatggacttcgtggagcctgtgcggtgctgatggtgaccgcc
1711       T  M  D  F  V  E  P  V  G  W  L  M  V  T  A
      5387 tcccccgaacccagctgccgtcaacacaagcgtcaccctcagtgcc
1726       S  P  N  P  A  A  V  N  T  S  V  T  L  S  A
      5432 gagctggctggtggcagtggtgtcgtatacacttggtccttggag
1741       E  L  A  G  G  S  G  V  V  Y  T  W  S  L  E
```

FIG. 1H

Figure 1 con.

```
        →15-K
    5477 gaggggctgagctgggagacctccgagccatttaccacccatagc
1756      E  G  L  S  W  E  T  S  E  P  F  T  T  H  S 5522 ttccccacacccggcctgcacttggtcaccatgacggcagggaac
1771      F  P  T  P  G  L  H  V  T  M  T  A  G  N 5567 ccgctgggctcagccaacgccaccgtggaggtggatgtgcaggtg
1786      P  L  G  S  A  N  A  T  V  E  V  D  V  Q  V 5612 cctgtgagtggcctcagcatcagggccagcgagcccggaggcagc
1801      P  V  S  G  L  S  I  R  A  S  E  P  G  G  S 5657 ttcgtggcggccggtcctctgtgcccttttgggggcagctggcc
1816      F  V  A  A  G  S  S  V  P  F  W  G  Q  L  A
                             ←    15-J
    5702 acgggcaccaatgtgagctggtgctgggctgtgcccggcggcagc
1831      T  G  T  N  V  S  W  C  W  A  V  P  G  G  S 5747 agcaagcgtggccctcatgtcaccatggtcttcccggatgctggc
1846      S  K  R  G  P  H  V  T  M  V  F  P  D  A  G 5792 accttctccatccggctcaatgcctccaacgcagtcagctgggtc
1861      T  F  S  I  R  L  N  A  S  N  A  V  S  W  V 5837 tcagccacgtacaacctcacggcggaggagcccatcgtggggctg
1876      S  A  T  Y  N  L  T  A  E  E  P  I  V  G  L
              →15-L
    5882 gtgctgtgggccagcagcaaggtggtggcgcccggcagctggtc
1891      V  L  W  A  S  S  K  V  V  A  P  G  Q  L  V
                          ←    15-K
    5927 cattttcagatcctgctggctgccggctcagctgtcaccttccgc
1906      H  F  Q  I  L  L  A  A  G  S  A  V  T  F  R 5972 ctgcagatcggcggggccaaccccgaggtgctccccgggccccgt
1921      L  Q  V  G  G  A  N  P  E  V  L  P  G  P  R 6017 ttctcccacagcttccccgcgtcggagaccacgtggtgaacgtg
1936      F  S  H  S  F  P  R  V  G  D  H  V  V  S  V 6062 cggggcaaaaaccacgtgagctgggcccaagcgcaggtgcgcatc
1951      R  G  K  N  H  V  S  W  A  Q  A  Q  V  R  I 6107 gtggtgctggaggccgtgagtggctgcagatgcccaactgctgc
1966      V  V  L  E  A  V  S  G  L  Q  M  P  N  C  C
```

FIG. 1I

Figure 1 con.

| | | |
|---|---|---|
| 1981 | 6152 | gagcctggcatcgccacgggcactgagaggaacttcacagcccgc<br>E P G I A T G T E R N F T A R |
| 1996 | 6197 | gtgcagcgcggctctcgggtcgcctacgcctggtacttctcgctc<br>V Q R G S R V A Y A W Y F S L<br>→15-M |
| 2011 | 6242 | cagaaggtccaggcgactcgctggtcatcctgtcgggccgcgac<br>Q K V Q G D S L V I L S G R D |
| 2026 | 6287 | gtcacctacacgcccgtggccgcgggctgttggagatccaggtg<br>V T Y T P V A A G L L E I Q V<br>← 15-L |
| 2041 | 6332 | cgcgccttcaacgccctgggcagtgagaaccgcacgctggtgctg<br>R A F N A L G S E N R T L V L |
| 2056 | 6377 | gaggttcaggacgccgtccagtatgtggccctgcagagcggcccc<br>E V Q D A V Q Y V A L Q S G P |
| 2071 | 6422 | tgcttcaccaaccgctcggcgcagtttgaggccgccaccagcccg<br>C F T N R S A Q F E A A T S P |
| 2086 | 6467 | agccccggcgtgtggctaccactgggactttggggatggtcc<br>S P R V A Y H W D F G D G S |
| 2101 | 6512 | ccagggcaggacacagatgagcccagggccgaccactcctacctg<br>P G Q D T D E P R A E H S Y L |
| 2116 | 6557 | aggcctggggactaccgcgtgcaggtcaacgcctccaacctggtc<br>R P G D Y R V Q V N A S N L V |
| 2131 | 6602 | agcttcttcgtgccgcagaccacggtgaccgtccaggtgctgcc<br>S F F V A Q A T V T V Q V L A |
| 2146 | 6647 | tgccgggagccgcgagtggacgtggtcctgcccctgcaggtgctg<br>C R E P E V D V V L P L Q V L<br>→15-N |
| 2161 | 6692 | atgcggcgatcacagcgcaactacttggaggccacgttgacctg<br>M R R S Q R N Y L E A H V D L |
| 2176 | 6737 | cgcgactgcgtcacctaccagactgagtaccgctgggaggtgtat<br>R D C V T Y Q T E Y R W E V Y |
| 2191 | 6782 | cgcaccgccagctgccaccggccagggcgccagcgcgtgtcgcc<br>R T A S C Q R P G R P A R V A |

FIG. 1J

Figure 1 con.

```
        15-M
    6827 ctgcccggcgtggacgtgagccggcctcggctggtgctgccacgg
2206     L  P  G  V  D  V  S  R  P  R  L  V  L  P  R 6872 ctggcgctgcctgtggggcactactgctttgtgtttgtcgtgtca
2221     L  A  L  P  V  G  H  Y  C  F  V  F  V  V  S 6917 tttggggacacgccactgacacagagcatccaggccaatctgacc
2236     F  G  D  T  P  L  T  Q  S  I  Q  A  N  V  T 6962 gtggcccccgagcgcctggtgcccatcattgagggtggctcatac
2251     V  A  P  E  R  L  V  P  I  I  E  G  G  S  Y 7007 cgcgtgtggtcagacacacgggacctggtgctggatgggagcgac
2266     R  V  W  S  D  T  R  D  L  V  L  D  G  S  E 7052 tcctacgaccccaacctggaggacggcgaccagacgccgctcagt
2281     S  Y  D  P  N  L  E  D  G  D  Q  T  P  L  S
                                          Exon 16
    7097 ttccactgggcctgtgtggcttcgacacac...
2296     F  H  W  A  C  V  A  S  T  Q

7142 ...
2311

7187 ...
2326

7232 ...
2341
         Exon 17
    7277 gtgctgatccggagtgcccggtgcccattgtgtccttggagtgt
2356     V  L  I  R  S  G  R  V  P  I  V  S  L  E  C 7322 gtgtcctgcaaggcacaggccgtgtacgaagtgagccgcagctcc
2371     V  S  C  K  A  Q  A  V  Y  E  V  S  R  S  S 7367 tacgtgtacttggagggccgctgcctcaattgcagcagcggctcc
2386     Y  V  Y  L  E  G  R  C  L  N  C  S  S  G  S
              Exon 18
    7412 aagcgagg...
2401     K  R  G

Figure 1 con.

```
        7502  [sequence obscured]
2431          [protein obscured]

7547  [sequence obscured]
2446          [protein obscured]

7592  [sequence obscured]
2461          [protein obscured]

7637  [sequence obscured]
2476          [protein obscured]
                                        Exon 19
        7682  [obscured]gctggcatgacgcggaggatgctggc
2491          [obscured]  G  W  H  D  A  E  D  A  C 7727  ccccgctggtatacgccctgctgctgcggcgctgtcgccaggc
2506          A  P  L  V  Y  A  L  L  L  R  R  C  R  Q  G 7772  cactgcgaggagttctgtgtctacaagggcagcctctccagctac
2521          H  C  E  E  F  C  V  Y  K  G  S  L  S  S  Y 7817  ggagccgtactgcccccggatttcaggccacacttcgaggtggc
2536          G  A  V  L  P  P  G  F  R  P  H  F  E  V  G 7862  ctggccgtggtggtgcaagaccagctgggagccgctgtggtcgcc
2551          L  A  V  V  V  Q  D  Q  L  G  A  A  V  V  A
                                Exon 20
        7907  ctcaaca[obscured]
2566          L  N  R[obscured]

7952  [sequence obscured]
2581          [protein obscured]

7997  [sequence obscured]
2596          [protein obscured]
                                            Exon 21
        8042  [obscured]tacgagcggcc
2611          [obscured]  Y  E  R  A 8087  ctggacgtggcggcagagcccaagcacgagcggcagcaccgagcc
2626          L  D  V  A  A  E  P  K  H  E  R  Q  H  R  A 8132  cagatacgcaagaacatcacggagactctggtgtccctgagggtc
2641          Q  I  R  K  N  I  T  E  T  L  V  S  L  R  V
```

FIG. 1L

Figure 1 con.

```
      8177 cacactgtggatgacatccagcagatcgctgctgcgctggccag
2656       H  T  V  D  D  I  Q  Q  I  A  A  A  L  A  Q
                                   Exon 22
      8222 cgcatg...
2671       C  M  ...

8267 ...
2686       ...

8312 ...
2701                              Exon 23-A
      8357 ...........gagacctcatccacctggccagctcggac
2716                  G  D  L  I  H  L  A  S  S  D 8402 gtgcggcaccacagccctcagagctggagccgaatcaccatct
2731       V  R  A  P  Q  P  S  E  L  G  A  E  S  P  S 8447 cggatggtagcgtcccaggcctacaacctgacctctgccctcatg
2746       R  M  V  A  S  Q  A  Y  N  L  T  S  A  L  M 8492 cgcatcctcatgcgctcccgcgtgctcaacgaggagcccctgacg
2761       R  I  L  M  R  S  R  V  L  N  E  E  P  L  T
                                                  → 23-B
      8537 ctggcggcgaggagatcctggcccagggcaagcctcggaccg
2776       L  A  G  E  E  I  V  A  Q  G  K  R  S  D  E 8582 cggagcctgctgtgctatggcggcgccccagggcctggctgccac
2791       R  S  L  C  Y  G  G  A  P  G  P  G  C  H 8627 ttctccatcccgaggctttcagcggggccctggccaacctcagt
2806       F  S  I  P  E  A  F  S  G  A  L  A  N  L  S
                                            → 23-C
      8672 gacgtggtgcagctcatctttctggtggactccaatccctttcc
2821       D  V  V  Q  L  I  F  L  V  D  S  N  P  F  P
   ←       23-A              ←      23-B
      8717 tttggctatatcagcaactacaccgtctccaccaaggtggcctcc
2836       F  G  Y  I  S  N  Y  T  V  S  T  K  V  A  S 8762 atggcattccagacacaggccggcgcccagatccccatcgagcgc
2851       M  A  F  Q  T  Q  A  G  A  Q  I  P  I  E  R 8807 ctggcctcagagcgcgccatcaccgtgaaggtccccaacaactcg
2866       L  A  S  E  R  A  I  T  V  K  V  P  N  N  S
```

FIG. 1M

Figure 1 con.

| pos | sequence | aa pos | translation |
|---|---|---|---|
| 8852 | gactgggctgcccggggccaccgcagctccgccaactccgccaac | 2881 | D W A A R G H R S S A N S A N |
| 8897 | tccgttgtggtccagccccaggcctccgtcggtgctgtggtcacc | 2896 | S V V V Q P Q A S V G A V V T |
| 8942 | ctggacagcagcaaccctgcggccgggctgcatctgcagctcaac | 2911 | L D S S N P A A G L H L Q L N |
| 8987 | tatacgctgctggacg... | 2926 | Y T L D ... |
| 9032 | ... | 2941 | ... |
| 9077 | ... | 2956 | ... |
| 9122 | ...agcaga | 2971 | ... S R |
| 9167 | gacccagcgcggagttaccatctgaacctctccagccacttccgc | 2986 | D P A G S Y H L N L S S H F R |
| 9212 | tggtcggcgctgcaggtgtccgtgggcctatacacgtccctgtgc | 3001 | W S A L Q V S V G L Y T S L C |
| 9257 | cagtacttcagcgaggaggacatggtgtggcggacagagggactg | 3016 | Q Y F S E E D M V W R T E G L |
| 9302 | ctgcccctggaagagacctcgccccgccaggccgtctgcctcacc | 3031 | L P L E E T S P R Q A V C L T |
| 9347 | cgccacctcaccgccttcggcgccagcctcttcgtgccccaagc | 3046 | R H L T A F G A S L F V P P S |
| 9392 | catgtccgctttgtgtttcct... | 3061 | H V R F V P ... |
| 9437 | ... | 3076 | ... |
| 9482 | ... | 3091 | ... |

Exon 24 (near 2911)
Exon 25 (near 2971)
Exon 26 (near 3046)

FIG. 1N

Figure 1 con.

```
      9527 ...
3106  ...
                                              Exon 27
      9572 ...gtaccacg
3121  ...                            G   T   T
      9617 gcccacgtgggcatcatgctgtatgggtggacagccggagcggc
3136       A  H  V  G  I  M  L  Y  G  V  D  S  R  S  G
      9662 caccggcacctggacgcgacagagccttccaccgcaacagcctc
3151       H  R  H  L  D  G  D  R  A  F  H  R  N  S  L
      9707 gacatcttccggatcgccacccccacagcctgggtagcgtgtgg
3166       D  I  F  R  I  A  T  P  H  S  L  G  S  V  W
                                              Exon 28
      9752 aagatccgagtgtggcacgacaacaaac...
3181       K  I  R  V  W  H  D  N  K  ...
      9797 ...
3196  ...
      9842 ...
3211  ...                                     Exon 29
      9887 ...gcgacgca
3226  ...                                     S  D  A
      9932 gcccttttgcgcttccggcgcctctggtggctgaagctgcagcgt
3241       A  L  L  R  F  R  R  L  L  V  A  E  L  Q  R
      9977 ggcttcttgacaagcacatctggctctccatatgggaccggccc
3256       G  F  F  D  K  H  I  W  L  S  I  W  D  R  P
     10022 cctcgtagccgtttcactcgcatccagagagccacctgctgcgtt
3271       P  R  S  R  F  T  R  I  Q  R  A  T  C  C  V
     10067 ctcctcatctgcctcttcctgggcgccaacgccgtgtggtacggg
3286       L  L  I  C  L  F  L  G  A  N  A  V  W  Y  G
                                              Exon 30
     10112 gctgttggccactctgcctacag...
3301       A  V  G  D  S  A  Y  S  ...
     10157 ...
3316  ...
```

FIG. 10

Figure 1 con.

```
       10202 ░░░░░░░░░░░░░░░░░░░░░░░░░░░░░░░░░░░░░░░░░░░░░
3331         ░░░░░░░░░░░░░░░░░░░░░░░░░░░░░░░░░░░░░░░░░░░░░
                                    Exon 31
       10247 ░░░░░░░░░░░░░gtggctggagcccgagcccacacctgcc
3346         ░░░░░░░░░░░░░ V  A  G  S  P  T  P  A 10292 gggcagcaggtgctggacatcgacagctgcctggactcgtccgtg
3361         G  Q  Q  V  L  D  I  D  S  C  L  D  S  S  V
                                                        Exon32
       10337 ctggacagctccttcctcacgttctcaggcctccacgctgag░░
3376         L  D  S  S  F  L  T  F  S  G  L  H  A  E ░

10382 ░░░░░░░░░░░░░░░░░░░░░░░░░░░░░░░░░░░░░░░░░░░░
3391         ░░░░░░░░░░░░░░░░░░░░░░░░░░░░░░░░░░░░░░░░░░░░
                       Exon 33
       10427 a░tctggtgtgctggccctccggcgagggaacgctcaattggccg
3406         S  L  V  C  W  P  S  G  E  G  T  L  S  W  P 10472 gacctgctcagtgacccgtccattgtgggtagcaatctgcggcag
3421         D  L  L  S  D  P  S  I  V  G  S  N  L  R  Q 10517 ctggcacgggggcaggcgaggccatgggctggggccagaggaggac
3436         L  A  R  G  Q  A  G  E  G  L  G  P  E  E  D 10562 ggcttctccctggccagcccctactcgcctgccaaatccttctcc
3451         G  F  S  L  A  S  P  Y  S  P  A  K  S  F  S
                                Exon34
       10607 gcatcag░░░░░░░░░░░░░░░░░░░░░░░░░░░░░░░░░░░░░
3466         A  S ░░░░░░░░░░░░░░░░░░░░░░░░░░░░░░░░░░░░░░░░

10652 ░░░░░░░░░░░░░░░░░░░░░░░░░░░░░░░░░░░░░░░░░░░░
3481         ░░░░░░░░░░░░░░░░░░░░░░░░░░░░░░░░░░░░░░░░░░░░
                       Exon 35
       10697 ░░░░░░░░gtccagcactcctggggagaagacagagacgctc
3496         ░░░░░░░░ S  S  T  P  G  E  K  T  E  T  L 10742 gcgctgcagaggctggggagctggggccacccagcccaggcctg
3511         A  L  Q  R  L  G  E  L  G  P  P  S  P  G  L
                                                        Exon36
       10787 aactgggaacagccccaggcagcgaggctgtccaggacag░░░░
3526         N  W  E  Q  P  Q  A  A  R  L  S  R  T ░░░░

Figure 1 con.

```
10877 ................................................
3556  ................................................

10922 ................................................
3571  ................................................

10967 ................................................
3586  ................................... Exon 37

11012 ............qtcttgctggaagccctgtacttctca
3601  ...........  V  L  L  A  L  Y  F  S 11057 ctggtggccaagcggctgcacccggatgaagatgacaccctggta
3616   L  V  A  K  R  L  H  P  D  E  D  D  T  L  V 11102 gagagcccggctgtgacgcctgtgagcgcacgtgtgccccgcgta
3631   E  S  P  A  V  T  P  V  S  A  R  V  P  R  V 11147 cggccagcccacggctttgcactcttcctggccaaggaagaagcc
3646   R  P  P  H  G  F  A  L  F  L  A  K  E  E  A
                                        Exon 38
11192 cgcaaggtcaagaggctacatggcatgctgcgg.............
3661   R  K  V  K  R  L  H  G  M  L  R .............

11237 ................................................
3676  ................................................

11282 ................................................
3691  ...................................... Exon 39

11327 ...........................................gtctgac
3706  ...........................................  S  E 11372 gagctctggccatggatggcccacgtgctgctgccctacgtccac
3721   E  L  W  P  W  M  A  H  V  L  L  P  Y  V  H 11417 gggaaccagtccagcccagagctggggcccccacggctgcggcag
3736   G  N  Q  S  S  P  E  L  G  P  P  R  L  R  Q
                        Exon 40
11462 gtgcggctgcaggaag................................
3751   V  R  L  Q  E  ................................

Figure 1 con.

```
     11552 ................................................
3781       D ......................................
                              Exon 41
     11597 ..........................gacatggtcctggcgctcctgt
3796       ..................  A  W  S  G  S  C 11642 gccgtgtatgacagcggggctacgtgcaggagctgggcctgagc
3811       A  V  Y  D  S  G  G  Y  V  Q  E  L  G  L  S 11687 ctggaggagagccgcgaccggctgcgcttcctgcagctgcacaac
3826       L  E  E  S  R  D  R  L  R  F  L  Q  L  H  N
                              Exon 42
     11732 tggctggacaacag..................................
3841       W  L  D  N  R.....................

11777 ................................................
3856       ................................

11822 ................................................
3871       ................................

11867 ................................................
3886       ................................
                              Exon 43
     11912 ............gtgtgcctgctgctgttcgccgtgcacttcgccgtc
3901       ........ V  C  L  L  L  F  A  V  H  F  A  V 11957 gccgagcccgtacttggcacaggaaacggcgctggcgcgtgctg
3916       A  E  A  R  T  W  H  R  E  G  R  W  R  V  L 12002 cggctcggagcctgggcgcggtggctgctggtgcgctgacagcc
3931       R  L  G  A  W  A  R  W  L  L  V  A  L  T  A 12047 gccacggcactggtacgcctcgcccagctgggtgccgctgaccgc
3946       A  T  A  L  V  R  L  A  Q  L  G  A  A  D  R 12092 cagtggacccgtttcgtgcgcggaccgccgcgccgcttcactagc
3961       Q  W  T  R  F  V  R  G  R  P  R  R  F  T  S 12137 ttcgaccaggtggcgcagctgagctccgcagcccgtggcctggcc
3976       F  D  Q  V  A  Q  L  S  S  A  A  R  G  L  A
                                          Exon 44
     12182 gcctcgctgctcttcctgcttttggtcaag..................
3991       A  S  L  L  F  L  L  L  V  K  ..............
```

FIG. 1R

Figure 1 con.

```
       12227
4006

12272
4021

Exon 45
       12317                              ctgtgtcttctgt
4036                                    E L V S S C 12362 gtggactccctctggagcgtgcccagccctgttggtgctgtgc
4051        V D S L W S V A Q A L L V L C 12407 cctgggactgggctctctaccctgtgtcctgccgagtcctggcac
4066        P G T G L S T L C P A E S W H 12452 ctgtcacccctgctgtgtgtggggctctgggcactgcggctgtgg
4081        L S P L L C V G L W A L R L W 12497 ggcgccctacggctgggcgctgttattctccgctggcgctaccac
4096        G A L R L G A V I L R W R Y H 12542 gccttgcgtggagagctgtaccggccggcctgggagccccaggac
4111        A L R G E L Y R P A W E P Q D 12587 tacgagatggtggagttgttcctgcgcaggctgcgcctctggatg
4126        Y E M V E L F L R R L R L W M
                                Exon 46
       12632 ggcctcagcaaggtcaagga
4141        G L S K V K E 12677
4156

Figure 1 con.

Exon 1—Homolog 1

```
Query:  3844  ccgcggacgccacagcgctgtgagtagcgggcccagcggcacccgggagaggccgcggga  3903
              ||||||||||||||||||||||||||||||||||||||||||||||||||||||||||||
Sbjct: 16586  ccgcggacgccacagcgctgtgagtagcgggcccagcggcacccgggagaggccgcggga 16645

Query:  3904  cggcgggcgtggggcgggttccctggcccgggacgggaagcaggacgcgggccaggacgc  3963
              |||||||||||||||| |||||||||||||||||||||||||||||||||||||||||||
Sbjct: 16646  cggcgggcgtgggcgcgttccctggcccgggacgggaagcaggacgcgggccaggacgc  16705

Query:  3964  tcccagggcgaggctccggcgcggcacggcgggccctgctaaataaggaacgcctggag  4023
              ||||||||  |||||||||||||||||  |||||  ||||||||||||||||||||||
Sbjct: 16706  tcccaggg-cgaggctccggcgcggcacagcgg-ccctgctaaataaggaacgcctggag 16763

Query:  4024  ccgcggttggcacggccccggggagccgaaaaacccgggtctggagacagacgtcccac  4083
              ||||||||||||||||||||||||||||||||||||||||||||||||||||||||||
Sbjct: 16764  ccgcggttggcacggccccggggagccgaaaaacccgggtctggagacagacgtcccac 16823

PstI
Query:  4084  ccggggctctgcagacgccagcggggcgggcgcggaggccgcgctcagctgggagga    4143
              |||||||||||| |||||||||||||||||||||||||||||| |||||||||||||
Sbjct: 16824  ccggggctctgcggacgccagcggggcgggcgcggaggccgcgctcagctgggagga   16883

Query:  4144  caaacagtcgctaattggagaggaattgggatgcggcctggggctgcggggtacccggag 4203
              |||||||||||||||||||||||||||||||| |||||||||||||||||||||||||
Sbjct: 16884  caaacagtcgctaattggagaggaattgggattcggcctggggctgcggggtacccggag 16943

Query:  4204  agctgggatggctgtaggggggcggcaggaagagttccaggaggtgtctggaaaaggat  4263
              |  ||| |||||||||||||||  ||||||||||||||||||||||||||||  ||||
Sbjct: 16944  agatgggatggctgtagggggctgcagggaagagttccaggaggtgtctggacaaggat 17003
```

Exon 1—Homolog 1

```
Query:  3844  ccgcggacgccacagcgctgtgagtagcgggcccagcggcacccgggagaggccgcggga  3903
              ||||||||||||||||||||||||||||||||||||||||||||||||||||||||||||
Sbjct: 16586  ccgcggacgccacagcgctgtgagtagcgggcccagcggcacccgggagaggccgcggga 16645

Query:  3904  cggcgggcgtgggcgggttccctggcccgggacgggaagcaggacgcgggccaggacgc  3963
              ||||||||||||||| ||||||||||||||||||||||||||||||||||||||||||
Sbjct: 16646  cggcgggcgtgggcgcgttccctggcccgggacgggaagcaggacgcgggccaggacgc 16705

Query:  3964  tcccagggcgaggctccggcgcggcacggcgggccctgctaaataaggaacgcctggag  4023
              ||||||||  |||||||||||||||||  |||||  ||||||||||||||||||||||
Sbjct: 16706  tcccaggg-cgaggctccggcgcggcacagcgg-ccctgctaaataaggaacgcctggag 16763
```

FIG. 2A

Figure 2 con.

Stretch of Exon 6-Homolog 1

```
Query: 21589  tcgttcccaccggtctccagcggtgcacccgctctgccoctcggacacggagatcttccc  21648
              ||||||||||||||||||||||||||||||||||||||||||||||||||||||||||
Sbjct: 23917  tcgttcccaccggtctccagcggtgcaccgctctgcccctcggacacggagatcttctc  23976

Query: 21649  tggcaacgggcactgctaccgcctggtggtggagaaggcggcctggctgcaggcgcagga  21708
              |||||| |||||||||||||||||||||||||||||||||||||||||||||||||||
Sbjct: 23977  tggcaatgggcactgctaccgcctggtggtggagaaggcggcctggctgcaggcgcagga  24036

StuI
Query: 21709  gcagtgtcaggcctgggccggggccgccctggcaatggtggacagtcccgccgtgcagcg  21768
              ||||||||  ||||||||||||||||||||||||||||||||||||||||||||||||
Sbjct: 24037  gcagtgtcgggcctgggccggggccaccctggcaatggtggacagtcccgccgtgcagcg  24096
```

Stretch of Exon 6-Homolog 2

```
Query: 21589  tcgttcccaccggtctccagcggtgcacccgctctgcccctcggacacggagatcttccc  21648
              |||||||||||||||||||||||||||||||||||||||||||||||||||||||| |
Sbjct: 63611  tcgttcccaccggtctccagcggtgcaccgctctgcccctcggacacggagatcttctc  63670

Query: 21649  tggcaacgggcactgctaccgcctggtggtggagaaggcggcctggctgcaggcgcagga  21708
              |||||||| ||||||||||||||||| ||||||||||||||||||||||||||||||
Sbjct: 63671  tggcaacgggcactgctaccgcctggtggtcgagaaggcggcctggctgcaggcgcagga  63730

Query: 21709  gcagtgtcaggcctgggccggggccgccctggcaatggtggacagtcccgccgtgcagcg  21768
              ||||||||  |||||||||||||||  |||||||||||||||||||||||||||||||
Sbjct: 63731  gcagtgtcgggcctgggccggggccaccctggcaatggtggacagtcccgccgtgcagcg  63790
```

FIG. 2B

Figure 2 con.

Stretch of Exon 10-Homolog 1

```
Query: 23622  aaatcagggccccaacaccctccctcctcacagggaccccggagaacggcagcgagcct  23681
              |||·||||||||||||||||||||||| ||||||||||||||||||||||||||||
Sbjct: 25938  gaatgagggccccaacaccctccctcctcgcagggacccggagaacggcagcgagcct  25997

Query: 23682  gagagcaggtccccggacaacaggaccagctggccccgcgtgcatgccaggggacgc   23741
              |||||||||||||||||||||||||||||||||||||||||||||||||||||||
Sbjct: 25998  gagagcaggtccccggacaacaggaccagctggccccgcgtgcatgccaggggacgc   26057

Query: 23742  tggtgccctggagccaacatctgcttgccgctggacgcctcctgccaccccaggcctgc  23801
              ||||||||||||||||||||||||||||||||||||| |||||||||||| ||||||||
Sbjct: 26058  tggtgccctggagccaacatctgcttgccgctggacacctcctgccacccc-aggcctgc 26116

XmaI
Query: 23802  gccaatggctgcacgtcaggg-ccaggggctacccggggccccctatgcgctatggagaga 23860
              |||||||||||||||||||||  |||||||||  ||||||||||||||||||||||||||
Sbjct: 26117  gccaatggctgcacgtcagggccagggctactcggggccccctatgcgctatggagaga  26176

Query: 23861  gttcctcttctccgttcccgcggggccccccgcgcagtactcggtgtgtggccctgacct 23920
              ||||||||||||||||||||||||||||||||||||||||||||||||||||||||||
Sbjct: 26177  gttcctcttctccgttcccgcggggccccccgcgcagtactcggtgtgtggccctgacct 26236

Query: 23921  gggtctgttccctgcatctcctcaggccaccttcctgtctgctgcccagggtctgggtct 23980
              |||||||||||||||||||||||||||||||||||||||||||||||||||||||||||
Sbjct: 26237  gggtctgttccctgcatctcctcaggccaccttcctgtctgctgcccagggtctgggtct 26296
```

Stretch of Exon 10-Homolog 2

```
Query: 23622  aaatcagggccccaacaccctccctcctcacagggaccccggagaacggcagcgagcct  23681
              |||·||||||||||||||||||||||| ||||||||||||||||||||||||||||
Sbjct: 65628  gaatgagggccccaacaccctccctcctcgcagggacccggagaacggcagcgagcct  65687

Query: 23682  gagagcaggtccccggacaacaggaccagctggccccgcgtgcatgccaggggacgc   23741
              |||||||||||||||||||||||||||||||||||||||||||||||||||||||
Sbjct: 65688  gagagcaggtccccggacaacaggaccagctggccccgcgtgcatgccaggggacgc   65747

Query: 23742  tggtgccctggagccaacatctgcttgccgctggacgcctcctgccaccccaggcctgc  23801
              ||||||||||||||||||||||||||||||||||||| |||||||||||| ||||||||
Sbjct: 65748  tggtgccctggagccaacatctgcttgccgctggacgcctcctgccacccc-aggcctgc 65806

Query: 23802  gccaatggctgcacgtcaggg-ccaggggctacccggggccccctatgcgctatggagaga 23860
              |||||||||||||||||||||  |||||||||  ||||||||||||||||||||||||||
Sbjct: 65807  gccaatggctgcacgtcagggccagggctactcggggccccctatgcgctatggagaga  65866

Query: 23861  gttcctcttctccgttcccgcggggccccccgcgcagtactcggtgtgtggccctgacct 23920
              ||||||||||||||||||||||||||||||||||||||||||||||||||||||||||
Sbjct: 65867  gttcctcttctccgttcccgcggggccccccgcgcagtactcggtgtgtggccctgacct 65926

Query: 23921  gggtctgttccctgcatctcctcaggccaccttcctgtctgctgcccagggtctgggtct 23980
              |||||||||||||||||||||||||||||||||||||||||||||||||||||||||||
Sbjct: 65927  gggtctgttccctgcatctcctcaggccaccttcctgtctgctgcccagggtctgggtct 65986
```

FIG. 2C

Figure 2 con. -

Exon 11-Homolog 1

```
Query: 24267 agccctgcgtgtccaccctcatccgtcgtgcggggtccacgggccatgaccgtgaggac 24326
              |||||||||||||||||||||||||||||| |||||||||||||||||||||||||||
Sbjct: 26604 agcccrgcgtgtccaccctcatccgtcgtgcaggggtccacgggccatgaccgtgaggac 26663

Query: 24327 gtgatgcagccctgcctccctctccacaggtcaccctccacggccaggatgtcctcatgc 24386
              |||||||||||||||||||||||||||||||||| ||||||||||||||||||||||||
Sbjct: 26664 gtgatgcagccctgcctccctctccacaggtcaccctccacagccaggatgtcctcatgc 26723

Query: 24387 tccctggtgacctcgttggcttgcagcacgacgctggccctggcgccctcctgcactgct 24446
              ||||||||||||||||||||||||||||||||||||||||||||||||||||||||||||
Sbjct: 26724 tccctggtgacctcgttggcttgcagcacgacgctggccctggcgccctcctgcactgct 26783

XmaI
Query: 24447 cgccggctcccggccaccctggtcccgggccccgtacctctccgccaacgcctcgtcat 24506
              ||||||||||||||||||||||||||||| |||||||||||||||||||||||||||||
Sbjct: 26784 cgccggctcccggccaccctggtcccaggccccgtacctctccgccaacgcctcgtcat 26843

Query: 24507 ggctgccccacttgccagcccagctggagggcacttgggcctgccctgcctgtgccctgc 24566
              |||||||||||||||||||||||||||||||||||||||||||||||||||||||||||
Sbjct: 26844 ggctgccccacttgccagcccagctggagggcacttgggcctgccctgcctgtgccctgc 26903

Query: 24567 ggctgcttgcagccacggaacagctcaccgtgctgctgggcttgaggcccaaccctggac 24626
              |||||||||||||||||||||||||||||||||||||||||||| ||||||||||||| |
Sbjct: 26904 ggctgcttgcagccacggaacagctcaccgtgctgctgggcctgaggcccaaccctggc 26963

Query: 24627 tgcggctgcctgggcgctatgaggtccgggcagaggtgggcaatggcgtgtccaggcaca 24686
              ||||||||||||||||||||||||||||||||||||||||||||||||||||||||||||
Sbjct: 26964 tgcggctgcctgggcgctatgaggtccgggcagaggtgggcaatggcgtgtccaggcaca 27023

Query: 24687 acctctcctgcagctttgacgtggtctcccagtggctgggctgcgggtcatctaccctg 24746
              |||| |||||||||||||||||||||||||||||||||||||||||||||||||||||||
Sbjct: 27024 acctgtcctgcagctttgacgtggtctcccagtggctgggctgcgggtcatctaccctg 27083

Query: 24747 ccccccgcgacggccgcctctacgtgcccaccaacggctcagccttggtgctccaggtgg 24806
              ||||||||||||||||||||||||||||||||||||||||||||||| ||||||||||||
Sbjct: 27084 ccccccgcgacggccgcctctacgtgcccaccaacggctcagcctggtgctccaggtgg 27143

Query: 24807 actctggtgccaacgccacggccacggctcgctggcctgggggcagtgtcagcgcccgct 24866
              |||||||||| |||||||||||||||||||||||||||||||||||||||||||||||||
Sbjct: 27144 actctggtgccagcgccacggccacggctcgctggcctgggggcagtgtcagcgcccgct 27203

Query: 24867 ttgagaatgtctgccctgccctggtggccacttcgtgccccggctgccctgggagacca 24926
              ||||||||| |||||||||||||||||||||||||||||||| |||||||||||||||||
Sbjct: 27204 ttgagaatgctgccctgccctggtggccacttcgtgcccagctgccctggggagacca 27263

Query: 24927 acgatacctgttctcagtggtagcactgccgtggctcagtgaggggagcacgtggtgg 24986
              | ||||||||||||||||||||||||||||||||| |||||| ||||||||||||||| |||
Sbjct: 27264 atgataccctgttctcagtggtagcactgccgtggctcggtgaggggagcacgtgatgg 27323

Query: 24987 acgtggtggtcgaaaacagcgccagccgggccaacctcagcctgcggtgacggcggagg 25046
              |||| |||||||||||||||||||||||||||||||||||||||||||||||||||||||
Sbjct: 27324 acgttgtggtcgaaaacagcgccagccgggccaacctcagcctgcgggtgacggcggagg 27383

Query: 25047 agcccatctgtggcctccgcgccacgccagccccgaggcccgtgtactgcagggagtcc 25106
              |||||||||||||||||||||||||||||||||||||||||||||||||||||||||||
Sbjct: 27384 agcccatctgtggcctccgcgccacgccagccccgaggcccgtgtactgcagggagtcc 27443
```

FIG. 2D

Figure 2 con.

```
Query:  25107  tagtggtgagtatggccgaggctccaccaccagccccaggcaggtgcctgcagacaggg  25166
               |  |||||||||||||||||||||||||||||||||||||||||||||||||||||||
Sbjct:  27444  ca---gtgagtatggccgaggctccaccaccagccccaggcaggtgcctgcagacaggg  27500

Query:  25167  tgctcacacagggcgtgaggcctggcttcccagtgagggcagcagcccagttactgggga  25226
               ||||||||||||| ||||||||||||||||||||||||||||||||||||||||||||
Sbjct:  27501  tgctcacacagggcttgaggcctggcttcccagtgagggcagcagcccagttactgggga  27560
```

Exon 11—Homolog 2

```
Query:  24267  agccctgcgtgtccaccctcatccgtcgtgcggggtccacgggccatgaccgtgaggac  24326
               |||||||||||||||||||||||||||||||| |||||||||||||||||||||||||
Sbjct:  66294  agccctgcgtgtccaccctcatccgtcgtgcaggggtccacgggccatgaccgtgaggac  66353

Query:  24327  gtgatgcagccctgcctccctctccacaggtcacctccacggccaggatgtcctcatgc  24386
               ||||||||||||||||||||||||||||| ||||||||||||||||||||||||||||
Sbjct:  66354  gtgatgcagccctgcctccctctccacaggtcacctccacggccaggatgtcctcatgc  66413

Query:  24387  tccctggtgacctcgttggcttgcagcacgacgctggccctggcgcctccgcactgct  24446
               ||||||||||||||||||||||||||||||||||||||||||||||||||||||| |||||||
Sbjct:  66414  tccctggtgacctcgttggcttgcagcacgacgctggccctggcgcctccgcactgct  66473

Query:  24447  cgccggctcccggccaccctggtccccgggcccgtacctctccgccaacgcctcgtcat  24506
               |||||||||||||||||||||||||| |||||||||||||||||||||||||||||||
Sbjct:  66474  cgccggctcccggccaccctggtcccaggcccgtacctctccgccaacgcctcgtcat  66533

Query:  24507  ggctgccccacttgccagcccagctggagggcacttgggcctgccctgcctgtgccctgc  24566
               |||||||||||||||||||||||||||||||||||||||||||||||||||||||
Sbjct:  66534  ggctgccccacttgccagcccagctggagggcacttgggcctgccctgcctgtgccctgc  66593

Query:  24567  ggctgcttgcagccacggaacagctcaccgtgctgctgggcttgagcccaaccctggac  24626
               |||||||||||||||||||||||||||||||||||||||||||||||||||||||| |
Sbjct:  66594  ggctgcttgcagccacggaacagctcaccgtgctgctgggcctgagcccaaccctgggc  66653

Query:  24627  tgcggctgcctgggcgctatgaggtccgggcagaggtgggcaatggcgtgtccaggcaca  24686
               |||||||||||||||||||||||||||||||||||||||||||||||||||||||||||
Sbjct:  66654  tgcggctgcctgggcgctatgaggtccgggcagaggtgggcaatggcgtgtccaggcaca  66713

Query:  24687  acctctcctgcagctttgacgtggtctcccagtggctgggctgcgggtcatctaccctg  24746
               |||| |||||||||||||||||||||||||||||||||||||||||||||||||||||
Sbjct:  66714  acctgtcctgcagctttgacgtggtctcccagtggctgggctgcgggtcatctaccctg  66773

Query:  24747  ccccccgcgacggccgcctctacgtgcccaccaacggctcagcctggtgctccaggtgg  24806
               ||||||||||||||||||||||||||||||||||||||||||||| ||||||||||||
Sbjct:  66774  ccccccgcgacggccgcctctacgtgcccaccaacggctcagcctggtgctccaggtgg  66833

Query:  24807  actctggtgccaacgccacggccacggctcgctggcctggggcagtgtcagcgcccgct  24866
               ||||||||| ||||||||||||||||||||||||||||||||||||||||||||||
Sbjct:  66834  actctggtgccagcgccacggccacggctcgctggcctggggcagtgtcagcgcccgct  66893

Query:  24867  ttgagaatgtctgccctgccctggtggccaccttcgtgcccggctgccctgggagacca  24926
               |||||||| |||||||||||||||||||||||||||||||||||||||||||||||||
Sbjct:  66894  ttgagaatgcctgccctgccctggtggccaccttcgtgcccggctgccctgggagacca  66953
```

FIG. 2E

Figure 2 con.

```
Query: 24927  acgataccctgttctcagtggtagcactgccgtggctcagtgaggggggagcacgtggtgg 24986
              | ||||||||||||||||||||||||||||||||| |||||||||||||||| |||
Sbjct: 66954  atgataccctgttctcagtggtagcactgccgtggctcggtgaggggggagcacgtgatgg 67013

Query: 24987  acgtggtggtggaaaaacagcgccagccgggccaacctcagcctgcgggtgacggcggagg 25046
              |||| |||||||||||||||||||||||||||||||||||||||||||||||||||||||
Sbjct: 67014  acgttgtggtggaaaaacagcgccagccgggccaacctcagcctgcgggtgacggcggagg 67073

Query: 25047  agcccatctgtggcctccgcgccacgcccagccccgaggcccgtgtactgcagggagtcc 25106
              ||||||||||||||||||||||||||||||||||||||||||||||||||||||||||||
Sbjct: 67074  agcccatctgtggcctccgcgccacgcccagccccgaggcccgtgtactgcagggagtcc 67133

Query: 25107  tagtggtgagtatggccgaggctccaccaccagccccaggcaggtgcctgcagacaggg 25166
              ||||||||||||||||||||||||||||||||||||||||||||||||||||||||||||
Sbjct: 67134  cagtggtgagtatggccgaggctccaccaccagccccaggcaggtgcctgcagacaggg 67193

Query: 25167  tgctcacacagggcgtgaggcctggcttcccagtgagggcagcagcccagttactgggga 25226
              ||||||||||||||||||||||||||||||||||||||||||||||||||||||||||||
Sbjct: 67194  tgctcacacagggcgtgaggcctggcttcccagtgagggcagcagcccagttactgggga 67253
```

FIG. 2F

Figure 2 con.

Exon 15—Homolog 1

```
Query: 27279  tgggacccttaaggctgggccgcaggtgcagccgttcaccccgggctcctcaggcggggg  27338
              ||||||||||||||||||||||||||||||||||||||||||||||||||||||||||||
Sbjct: 29661  tgggacccttaaggctgggccgcaggtgcagccgttcaccccgggctcctcaggcggggg  29720

Query: 27339  gcttctgccgagcgggtggggagcaggtgggggtgccgcggctgccccactcgggcctgt  27398
              ||||||||  |||||||||||||||||||||||| ||||||||||||||||| |||||||
Sbjct: 29721  gcttctgctgagcgggtggggagcaggtggggtgccgcggctgccccacttgggcctgt  29780

Query: 27399  ccccacaggtgagtacctcctgaccgtgctggcatctaatgccttcgagaaccggacgca  27458
              |||||||||||||||  |||||||||||||||||||||||||||||||||||||||||||
Sbjct: 29781  ccccacaggtgagtacgtcctgaccgtgctggcatctaatgccttcgagaaccggacgca  29840

Query: 27459  gcaggtgcctgtgagcgtgcgcgcctccctgccctccgtg  27498
              ||||||||||||||||||| ||||||||||||||||| |||
Sbjct: 29841  gcaggtgcctgtgagcgtgtgcgcctccctgccctctgtg  29880
```

Exon 15—Homolog 2

```
Query: 27279  tgggacccttaaggctgggccgcaggtgcagccgttcaccccgggctcctcaggcggggg  27338
              ||||||||||||||||||||||||||||||||||||||||||||||||||||||||||||
Sbjct: 69326  tgggacccttaaggctgggccgcaggtgcagccgttcaccccgggctcctcaggcggggg  69385

Query: 27339  gcttctgccgagcgggtggggagcaggtgggggtgccgcggctgccccactcgggcctgt  27398
              |||||||||||||||||||||||||||||||| |||||||||||||||||| |||||||
Sbjct: 69386  gcttctgccgagcgggtggggagcaggtgggggtgccgcggctgccccacttgggcctgt  69445

Query: 27399  ccccacaggtgagtacctcctgaccgtgctggcatctaatgccttcgagaaccggacgca  27458
              |||||||||||||| |||||||||||||||||||||||||||||||||||||||||||||
Sbjct: 69446  ccccacaggtgagtacgtcctgaccgtgctggcatctaatgccttcgagaaccggacgca  69505

Query: 27459  gcaggtgcctgtgagcgtgcgcgcctccctgccctccgtggctgtgggtgtgagtgacgg  27518
              ||||||||||||||||||||||||||||||||||||||  ||||||||||||||||||||
Sbjct: 69506  gcaggtgcctgtgagcgtgcgcgcctccctgccctccgaggctgtgggtgtgagtgacgg  69565

Query: 27519  cgtcctggtggccggccggcccgtcaccttctaccgcacccgctgccctcgcctggggg  27578
              |||||||||||||||||||||||||||||||||||| |  |||||||||||||||||||
Sbjct: 69566  cgtcctggtggccggccggcccgtcaccttctaccgcatctgctgccctcgcctgggg  69625

Query: 27579  tgttctttacacgtgggacttcggggacggctccctgtcctgacccagagccagccggc  27638
              |||||||||||||||||||||||||||||||||||||||||||||||||||||||||||
Sbjct: 69626  tgttctttacacgtgggacttcggggacggctccctgtcctgacccagagccagccggc  69685

Query: 27639  tgccaaccacacctatgcctcgagggcacctaccacgtgcgcctggaggtcaacaacac  27698
              ||||||||||||||  |||||||||||||||||||||||||||||||||||||||||||
Sbjct: 69686  tgccaaccacacctatccctcgagggcatctaccacgtgcgcctggaggtcaacaacac  69745

Query: 27699  cgtgagcggtgcgcggcccaggcggatgtgcgcgtctttgaggagctccgcggactcag  27758
              ||||||||||||||||| ||||||||||||||||||||||||||||||||  |||||
Sbjct: 69746  ggtgagcggtgcggcggcccaggcggatgtgcgcgtctttgaggagctccgcgggctcag  69805

Query: 27759  cgtggacatgagcctggccgtggagcagggcgccccgtggtggtcagcgccgcggtgca  27818
```

FIG. 2G

Figure 2 con.

```
                  |||||||||||||||||||||||||||||||||||||||||||| ||||||||||
Sbjct:  69806 cgtggacatgagcctggccgtggagcagggcgccccgtggtggtcagtgccgccgtgca 69865

Query:  27819 gacgggcgacaacatcacgtggaccttcgacatggggacggcaccgtgctgtcgggccc 27878
              |||||||||||||||||||||||||||||||||||||||||||||||||||||||||||
Sbjct:  69866 gacgggcgacaacatcacgtggaccttcgacatggggacggcaccgtgctgtcgggccc 69925

Query:  27879 ggaggcaacagtggagcatgtgtacctgcgggcacagaactgcacagtgaccgtgggtgc 27938
              ||||| ||||||||||||||||||||||||||||||||||||||||||||||||||||
Sbjct:  69926 agaggcaacagtggagcatgtgtacctgcgggcacagaactgcacagtgaccgtgggtgc 69985

Query:  27939 ggccagcccgccggccacctggcccggagcctgcacgtgctggtcttcgtcctggaggt 27998
              |||||||||||||||||||||||||||||||||||||||||||||||||||||||||||
Sbjct:  69986 ggccagcccgccggccacctggcccggagcctgcacgtgctggtcttcgtcctggaggt 70045

Query:  27999 gctgcgcgttgaacccgccgcctgcatcccacgcagcctgacgcgcggctcacggccta 28058
              |||||||| || ||||||||||||||||||||| ||||||||||||||||||||||||
Sbjct:  70046 gctgcgcgtcgagaccgccgcctgcatcccactcagcctgacgcgcggctcacggccta 70105

Query:  28059 cgtcaccgggaacccggcccactacctcttcgactggaccttcggggatggctcctccaa 28118
              ||||||||||||||||||| ||||||||||||||||||||||| |||||||||||||||
Sbjct:  70106 cgtcaccgggaacccggcccgctacctcttcgactggaccttcggggatggctcctccaa 70165

MluI
Query:  28119 cacgaccgtgcggggtgcccgacggtgacacacaacttcacgcggagcggcacgttccc 28178
              |||||| |||||||||||||||||||||||||||||||||||| |||||||||||||
Sbjct:  70166 cacgaccatgcggggtgcccgacggtgacacacaacttcacgcgtagcggcacgttccc 70225

Query:  28179 cctggcgctgtgctgtccagccgcgtgaacagggcgcattacttcaccagcatctgcgt 28238
              ||||| ||||||||||||||||||||||| |||||||||||||||||||||||||||
Sbjct:  70226 cctggcgctggtgctgtccagccgcgtgaacagggcgcgttacttcaccagcatctgcgt 70285

Query:  28239 ggagccagaggtgggcaacgtcaccctgcagccagagaggcagtttgtgcagctcgggga 28298
              |||||||||||||||||||||||||||||||||||||||||||||||||||||||||||
Sbjct:  70286 ggagccagaggtgggcaacgtcaccctgcagccagagaggcagtttgtgcagctcgggga 70345

Query:  28299 cgaggcctggctggtggcatgtgcctggccccgttccctaccgctacacctgggactt 28358
              |||||| |||||||||||||||||||||||||||||||||||||||||||||||||||
Sbjct:  70346 cgaggccggctggtggcatgtgcctggccccgttccctaccgctacacctgggactt 70405

Query:  28359 tggcaccgaggaagccgccccaccgtgccagggcctgaggtgacgttcatctaccg 28418
              |||||||| ||||||| |||| |||||| | |||||||||||||||||||||||||
Sbjct:  70406 tggcaccgaagaagccgtcccgcccgtgtcggggccctgaggtgacgttcatctaccg 70465

Query:  28419 agacccaggctcctatcttgtgacagtcaccgcgtccaacaacatctctgctgccaatga 28478
              ||||||||||||||||||||||||||||||||||||||||||||||| |||||||||
Sbjct:  70466 agacccaggctcctatcttgtgacagtcaccgcgtccaacaacatctccgctgccaatga 70525

Query:  28479 ctcagccctggtggaggtgcaggagcccgtgctggtcaccagcatcaaggtcaatggctc 28538
              |||||||||||||||||||||||||||| |||||||||||||||||||||||||||||
Sbjct:  70526 ctcagccctggtggaggtgcaggagcccatgctggtcaccagcatcaaggtcaatggctc 70585

Query:  28539 ccttggctggagctgcagcagccgtacctgttctctgctgtgggccgtgggcgcccgc 28598
              |||||||||||||||| ||||||||||||||||||||||||||||||||||||||||
Sbjct:  70586 ccttggctggagctgcagtagccgtacctgttctctgctgtgggccgtgggcgcccgc 70645

Query:  28599 cagctacctgtgggatctgggggacggtgggtggctcgaggggtccggaggtcaccacgc 28658
              |||||||||||||||||||||||||||| |||||||||||||||||||||||||||||
```

FIG. 2H

Figure 2 con.

```
Sbjct: 70646  cagctacctgtggvatctgggggacggtgggcggctcgagggtccggaggtcaccacgc  70705

Query: 28659  ttacaacagcacaggtgacttcaccgttagg-tggccggctggaatgaggtgagccgcag  28717
              ||||||||||||||||||||||||||||||| ||||||||| |||||||||||||||||
Sbjct: 70705  ttacaacagcacaggtgacttcaccgttaggvtggccggctgcaatgagctgagccgcag  70765

Query: 28718  cgaggcctggctcaatgtgacggtgaagcggcgcgtgcgggggctcgtcgtcaatgcaag  28777
              ||||||||||||||||||||||||||||||||||||||||||||| |||||||||| ||
Sbjct: 70765  cgaggcctggctcaatgtgacggtgaagcggcgcgtgcgggggctcatcgtcaatgcag   70825

Query: 28778  ccccacggtggtgcccctgaatgggagcgtgagcttcagcacgtcgctggaggccggcag  28837
              | ||||||||||||||||||||||||||||| ||||||||||| |||||||||||||||
Sbjct: 70826  ctgcacggtggtgcccctgaatgggagcatgagcttcagcacctcgctggaggccggcag  70885

Query: 28838  tgatgtgcgctattcctgggtgctctgtgaccgctgcacgcccatcctggggtcctac   28897
              |||||||||||||||||||||||||||||||||||||||||||| ||||||||||||| |
Sbjct: 70886  tgatgtgcgctattcctgggtgctctgtgaccgctgcacgcccatctctgggggtcctgc  70945

Query: 28898  catctctt-acaccttccgctccgtgggcaccttcaatatcatcgtcacggctgagaacg  28956
              |||||||| ||||||||||||||||||||||||||||||||||||||| ||||||||||
Sbjct: 70946  catctctttacaccttccgctccgtgggcaccttcaatatcatcgtcacagctgagaacg  71005

Query: 28957  aggtgggctccgcccaggacagcatcttcgtctatgtcctgcagctcatagagggctgc  29016
              ||||||||||||||||||||||||||||||||||||||||||||||||||||||||||
Sbjct: 71006  aggtgggctccgcccaggacagcatcttcgtctatgtcctgcagctcatagagggctgc  71065

Query: 29017  aggtggtgggcggtggccgctacttcccaccaccacacggtacagctgcaggccgtgg  29076
              |||||||||||||||||||||||||||||||||||||||||||||||||||||||||||
Sbjct: 71066  aggtggtgggcggtggccgctacttcccaccaaccacacggtacagctgcaggccgtgg  71125

Query: 29077  tcagggatggcaccaacgtctcctacagctggactgcctggagggacagggccggcc    29136
              | |||||||||||||||||  |||     |||||||||||||||||||||||||||||
Sbjct: 71126  tcagggatggcaccaacatct---acagctggactgcctggagggacagggccggccc  71182

Query: 29137  tggccggcagcggcaaaggcttctcgctcaccgt-ctcgaggccggcacctaccatgtgc  29195
              |||||||||||||||||||||||||||||||||| |||||||||||||||||||||||||
Sbjct: 71183  tggccggcagcggcaaaggcttctcgctcactgcgctcgaggccggcacctaccatgtgc  71242

Query: 29196  agctgcgggccaccaacatgctgggcagcgcctgggccgactgcaccatggacttcgtgg  29255
              |||||||||||||||||||||||||||||||||||| ||||||||||| |||||||||||
Sbjct: 71243  agctgcgggccaccaacatgctgggcagcgcctgggctgactgcaccgtggacttcgtgg  71302

Query: 29256  agcctgtggggtggctgatggtggccgcctcccgaacccagctgccgtcaacaaagcg   29315
              |||||||||||||||||||||||||||||||||||||||||||||||||||||| || |
Sbjct: 71303  agcctgtggggtggctgatggtggccgcctcccgaacccagctgccgtcaacacaagtg  71362

Query: 29316  tcaccctcagtgccgagctggctggtggcagtggtgtcgtatacacttggtccttggagg  29375
              ||||||||||||||||||||||||||||||||||||||||||||||||||||||||||||
Sbjct: 71363  tcaccctcagtgccgagctggctggtggcagtggtgtcgtatacacttggtccttggagg  71422

Query: 29376  agcggctgagctgggagacctccgagccatttaccacccatagcttccccacacccggcc  29435
              -||||||||||||||||||||| ||||||||||||||||| |||||||||||||||||||
Sbjct: 71423  agcggctgagctgggagacccccgagccatttaccacccacagcttccccacacccggcc  71482

Query: 29436  tgcacttggtcaccatgacggcagggaacccgctgggctcagccaacgccaccgtggaag  29495
              |||||||||||||||||||||||||||||||||||||||||||||||||||||||||||
Sbjct: 71483  tgcacttggtcaccatgacggcagggaacccgctgggctcagccaacgccaccgtggaug  71542
```

FIG. 2I

Figure 2 con.

```
Query: 29496 tggatgtgcaggtgcctgtgagtggcctcagcatcagggccagcgagcccggaggcagct 29555
              ||||||||||||||||||||||||||||||||||||| |||||||||||| |||||||||
Sbjct: 71543 tggatgtgcaggtgcctgtgagtggcctcagcatcagggccagcgagccgggaggcagct 71602

Query: 29556 tcgtggcggccgggtcctctgtgcccttttgggggcagctggccacgggcaccaatgtga 29615
              ||||||||||||||||||||||||||||||||||||||||||||||||||||||||||||
Sbjct: 71603 tcgtggcggccgggtcctctgtgcccttttgggggcagctggccacgggcaccaatgtga 71662

Query: 29616 gctggtgctgggctgtgcccggcggcagcagcaagcgtggccctcatgtcaccatggtct 29675
              ||||||||||||||||||||||||||||||||||||||||||||||||||||||||||||
Sbjct: 71663 gctggtgctgggctgtgcccggcggcagcagcaagcgtggccctcatgtcaccatggtct 71722

Query: 29676 tcccggatgctggcaccttctccatccggctcaatgcctccaacgcagtcagctgggtct 29735
              ||||||||||||||||||||  ||||||||||||||||||||||||||||||||||||||
Sbjct: 71723 tcccggatgctggcaccttcaacatccggctcaatgcctccaacgcagtcagctgggtct 71782

Query: 29736 cagccacgtacaacctcacggcggaggagcccatcgtgggcctggtgctgtgggccagca 29795
              ||||||||||||||||||||| ||||||||||||||||||||||||||||||||||||||
Sbjct: 71783 cagccacgtacaacctcacggtggaggagcccatcgtgggcctggtgctgtgggccagca 71842

Query: 29796 gcaaggtggtggcgcccgggcagctggtccattttcagatcctgctggctgccggctcag 29855
              |||||||||||||||||||||||||| ||||||||||||||||||||||||||||||||
Sbjct: 71843 gcaaggtggtggcgcccgggcagcttgtccattttcagatcctgctggctgccggctcag 71902

PstI                              XmaI
Query: 29856 ctgtcaccttccgcctgcaggtcggcggggccaaccccgaggtgctccccgggcccccgtt 29915
              |||||||||||||  |||||||||||||||||| |||| |||||||| ||||||||||
Sbjct: 71903 ctgtcaccttccgccggcaggtcggcggggccagccccgaagtgctccctgggcccccgtt 71962

Query: 29916 tctcccacagcttcccccgcgtcggagaccacgtggtgagcgtgcgcggcaaaaaccacg 29975
              ||||||||||||||||||||  ||||||||||||||||||||||||| | |||||||||
Sbjct: 71963 tctcccacagcttcccccgcatcggagaccacgtggtgagcgtgcagagcaaaaaccacg 72022

Query: 29976 tgagctgggcccaggcgcaggtgcgcatcgtggtgctggaggccgtgagtgggctgcagg 30035
              |||||||||||||||||||||||||||||||||||||||||||||||  |||||||||||
Sbjct: 72023 tgagctgggcccaggcgcaggtgcgcatcgtggtgctggaggccgtgagcgggctgcagg 72082

Query: 30036 tgcccaactgctgcgagcctggcatcgccacgggcactgagaggaacttcacagcccgcg 30095
              |||||||||||| ||||||| ||||| ||||||||||||||||||||||||||||||||
Sbjct: 72083 tgcccaactgctgtgagcctggcatcgccatgggcactgagaggaacttcacagcccgcg 72142

Query: 30096 tgcagcgcggctctcgggtcgcctacgcctggtacttctcgctgcagaaggtccagggcg 30155
              |||||||||||||||||||||||||||| |||| ||||||||||||||||||| ||| ||
Sbjct: 72143 tgcagcgcggctctcgggtcgcctacgcctggtatttctcgctgcagaaggtccggggcg 72202

Query: 30156 actcgctggtcatcctgtcgggccgcgacgtcacctacacgcccgtggccgcggggctgt 30215
              |||| ||| ||||||||||||||||||||||||| ||||||||||  |||||||||||||
Sbjct: 72203 actctctgttcatcctgtcgggccgcgacgtcacctacacgcc-gtggccgcggggctgt 72261

BssHII
Query: 30216 tggagatccaggtgcgcgccttcaacgccctgggcagtgagaaccgcacgctggtgctgg 30275
              |||||||||||||||| ||||||||||||||||||||||||||||||||||||||||||
Sbjct: 72262 tggagatccaggtgcgtgccttcaacgccctgggcagtgagaaccgcacgctggtgctgg 72321

PstI
Query: 30276 aggttcaggacgccgtccagtatgtggccctgcagagcggcccctgcttcaccaaccgct 30335
              |||||||||||||||||||||||||||||||||| |||||||||||||||||||||||||
Sbjct: 72322 aggttcaggacgccgtccagtatgtggccctgcggagcggcccctgcttcaccaaccgct 72381
```

FIG. 2J

Figure 2 con.

```
Query: 30336 cggcgcagtttgaggccgccaccagccccagccccggcgtgtggcctaccactgggact 30395
              ||||||||||||||||||||||||||||||||||| ||||||||||||||||||||
Sbjct: 72382 tggcgcagtttgaggccgccaccagccccagccccggcgcgtggcctaccactgggact 72441

Query: 30396 ttggggatgggtcgccagggcaggacacagatgagcccagggccgagcactcctacctga 30455
              |||||||||||| ||||||||||||||||||  |||| |||||||| ||||||||||||
Sbjct: 72442 ttggggatgggtccccagggcaggacacagataagcccagggccgagcactcctacctga 72501

Query: 30456 ggcctggggactaccgcgtgcaggtgaacgcctccaacctggtgagcttcttcgtggcgc 30515
              ||||||||||||||||||||||||||||||||||||||||||||||| ||||||||||
Sbjct: 72502 ggcctggggactaccgcgtgcaggtgaacgcctccaacctggtgagctttttcgtggcgc 72561

Query: 30516 aggccacggtgaccgtccaggtgctggcctgccgggagccggaggtggacgtggtcctgc 30575
              |||||||||||||||||||||||||||||||||||||||||||||||||||||||||||
Sbjct: 72562 aggccacggtgaccgtccaggtgctggcctgccgggagccggaggtggacgtggtcctgc 72621

Query: 30576 ccctgcaggtgctgatgcggcgatcacagcgcaactacttggaggcccacgttgacctgc 30635
              ||||||||||||||||||| |||||||||||||||| |||| ||| ||| ||||||||
Sbjct: 72622 ccctgcaggtgctgatgcgacgatcacagcgcaactgcctggatgcctacgttgacctgc 72681

Query: 30636 gcgactgcgtcacctaccagactgagtaccgctggaggtgtatcgcaccgccagctgcc 30695
              ||||||| |||||||||||||||||||||||||||||||||| |||||||||||||||
Sbjct: 72682 gcgactgtgtcacctaccagactgagtaccgctggaggtgtaccgcaccgccagctgcc 72741

Query: 30696 agcggccggggcgcccagcgcgtgtggccctgcccggcgtggacgtgagccggcctcggc 30755
              |||||||| |||| |||||||||||||||||| ||||||||||||||||||||||| ||
Sbjct: 72742 agcggccggggtgcccggcgcgtgtggccctgcccggcgtggacgtgagccggcctcagc 72801

Query: 30756 tggtgctgccgcggctggcgctgcctgtggggcactactgctttgtgtttgtcgtgtcat 30815
              ||||||||||||||||||||||||||||||||||||||||||||||||||||||||||
Sbjct: 72802 tggtgctgccgcggctggcgctgcctgtggggcactactgctttgtgtttgtcgtgtcat 72861

Query: 30816 ttggggacacgccactgacacagagcatccaggccaatgtgacggtggcccccgagcgcc 30875
              |||||||||||||||| ||| |||||||||||||||||||||||||||||||||||||
Sbjct: 72862 ttggggacacgccactggcacggagcatccaggccaatgtgacggtggcccccgagcgcc 72921

Query: 30876 tggtgcccatcattgagggtggctcataccgcgtgtggtcagacacacgggacctggtgc 30935
              |||||||||||| ||||||||||| ||||||||||||||||||||| |||||||||||
Sbjct: 72922 tggtgcccatcactgagggtggctcctaccgcgtgtggtcagacacacaggacctggtgc 72981

Query: 30936 tggatgggagcgagtcctacgaccccaacctggaggacggcgaccagacgccgctcagtt 30995
              |||||||||||| |||||||||||||||||||||||||||||||||||||||||||||
Sbjct: 72982 tggatgggagcgagtcctacgaccccaacctggaggacggcgaccagacgccgctcagtt 73041

Query: 30996 tccactgggcctgtgtggcttcgacacaggtcagtgcgtggcagggccgtcctccatgcc 31055
              |||| |||||||||||||||||||||||||||||||||||||||||||||||| ||||
Sbjct: 73042 tccagtgggcctgtgtggcttcgacacaggtcagtgcgtggcagggccgtcctccctgcc 73101

Query: 31056 cctcacccgtccacacccatgagcccagagaacacccagcttgccaccagggctggcccg 31115
              ||||||||||||||| |||||||||||||||||||||||||||||||||||||||||||
Sbjct: 73102 cctcacccgtccacacccatgagcccagagaacacccagcttgccaccagggctggcccg 73161
```

FIG. 2K

Figure 2 con.

```
                        Exon 16-Homolog 2

Query: 31176 gggccgggctctgctttaaaactggatggggctctcaggccacgtcgcccttgttctcg 31235
              ||||||||||||||||||||||||||||||| |||| |||||||||||||||||||||
Sbjct: 73222 gggccgggctctgctttaaaactggatggggttctcgggccacgtcgcccttgttctcg 73281

Query: 31236 gcctgcagagggaggctggcgggtgtgcgctgaactttgggccccgcgggagcagcacgg 31295
              ||||||||||||||||||||||||||||||||||||||||||||||||||||||||||
Sbjct: 73282 gcctgcagagggaggctggcgggtgtgcgctgaactttgggccccgcgggagcagcacgg 73341

Query: 31296 tcaccattccacgggagcggctggcggctggcgtggagtacaccttcagcctcaccgtgt 31355
              ||||||||||||||| ||||||| ||||||||||||||||||||||||||| |||||||
Sbjct: 73342 tcaccattccacgggaacggctggcagctggcgtggagtacaccttcagcctcaccgtgt 73401
                                         PvuII Query: 31356 ggaaggccggccgcaaggaggaggccaccaaccagacggtgggtgccgccgccctcgg 31415
              ||||||||||||||||||||||||||||||||||||||||||||||||||||||||||
Sbjct: 73402 ggaaggccggccgcaaggaggaggccaccaaccagacggtgggtgccgccgccctcgg 73461
```

Figure 2 con.

Exon 20—Homolog 1

```
Query:  33189 agccaggccgtgggagggcgccccgagactgccacctgctcaccaccc-ctctgctcg 33247
              ||||||||||||||||||||||||||||||||||||||||||||||||| ||||||||
Sbjct:  31282 agccaggccgtgggagggcgccccgagactgccacctgctcaccacccgctctgctcg 31341

Query:  33248 taggtctttggccatcaccctcccagagcccaacggcagcgcaacggggctcacagtctg 33307
              |||||||  |||||||||||||||||||||||||||||||||  ||||||||||||||||
Sbjct:  31342 taggtctctggccatcaccctcccagagcccaacggcagcgtaatggggctcacagtctg 31401

Query:  33308 gctgcacgggctcaccgctagtgtgctcccagggctgctgcggcaggccgatccccagca 33367
              |||||| |||||||||||||||||||||||  |||||||||||||||||||||||||||||
Sbjct:  31402 gctgcacgggctcaccgctagtgtgctcccggggctgctgcggcaggccgatccccagct 31461
                                                                   XmaI Query:  33368 cgtcatcgagtactcgttggccctggtcaccgtgctgaacgaggtgagtgcagcctggga 33427
              |||||||||||||||| ||||||||||||||  |||||||||||||||||||||||||||
Sbjct:  31462 cgtcatcgagtactcgctggccctggtcactgtgctgaacgaggtgagtgcagcctggga 31521

AatII
Query:  33428 gggacgtcacatctgctgcatgcgtgcttgggaccaagacctgtaccctgcctggagc 33487
              ||||| ||||||||||||||||||||||| |||||||||||||| |||||||||||||
Sbjct:  31522 ggggacctcacatctgctgcatgcgtgctgggaccaagacctgttccctgcctggagc 31581
```

Exon 20—Homolog 2

```
Query:  33216 gactgccacctgctcacca-cccctctgctcgtaggtctttggccatcaccctcccaga 33274
              |||||||||||||||||||  |||||||||||||||||| ||||||||||||||||||||
Sbjct:  75262 gactgccacctgctcaccaccccctctgctcgtaggtctctggccatcaccctcccaga 75321

Query:  33275 gcccaacggcagcgcaacggggctcacagtctggctgcacgggctcaccgctagtgtgct 33334
              ||||||||||||||||  |||||||||||||||||||||||||||||||||||||||||
Sbjct:  75322 gcccaacggcagcgcaatggggctcacagtctggctgcacgggctcaccgctagtgtgct 75381

Query:  33335 cccagggctgctgcggcaggccgatccccagcacgtcatcgagtactcgttggccctggt 33394
              ||| ||||||||||||||||||||||||||||||||||||||||||||| |||||||||
Sbjct:  75382 cccgggctgctgcggcaggccgatccccagcacgtcatcgagtactcgctggccctggt 75441

Query:  33395 caccgtgctgaacgaggtgagtgcagcctgggagggacgtcacatctgctgcatgcgtg 33454
              ||| ||||||||||||||||||||||||||||||||||| ||||||||||||||||||
Sbjct:  75442 cactgtgctgaacgaggtgagtgcagcctgggagggacctcacatctgctgcatgcgtg 75501
```

FIG. 2M

Figure 2 con.

Exon 22-Homolog 1

```
Query: 36719 atgtgaagaggtgccttgtgtggtcggtgggctgcatcacgtggtccccaggtggaggcc 36778
              ||||||||||||||||||||||||||||||||||||||||||||||| ||||||||
Sbjct: 32576 atgtgaagaggtgccttgtgtggtcggtgggctgcatcacgtggtcccaagtggaggcc 32635

Query: 36779 ctggtcatgcagagccacagaaaatgcttagtgaggaggctgtgggggtccagtcaagt 36838
              || ||||||||||||||||||||||||||||||||||||| ||||||||||||||||
Sbjct: 32636 ctcggtcatgcagagccacagaaaatgcttagtgaggag actgtgggggtccagtcaagt 32695

Query: 36839 gggctctccagctgcagggctgtgggtcggagccaggtgaggacccgtgtagagaggagg 36898
              |||||||||||||||||||||||| |||||||||||||||||||| ||||||||||||
Sbjct: 32696 gggctctccagctgcagggctggaggtgggagccaggtgaggacccgtgtagagaggagg 32755

Query: 36899 gcgtgtgcaaggagtgtggccaggagcggggctggacactgctggctccacacaggggcc 36958
              ||||||||||||||||||||||||||||||||||||||||||||||||||||||||
Sbjct: 32756 gcgtgtgcaaggagtgggggccaggagcggggctggacactgctggctccacacaggggcc 32815

Query: 36959 cagcagggagctcgtatgctgctcgtgcctgaagcagacgctgcacaagctggaggccat 37018
              ||||||||||||||||||||||||||||||||||||||||||||||||||||||||
Sbjct: 32816 cagcagggagctcgtatgctgctcgtgcctgaagcagacgctgcacaagctggaggccat 32875

Query: 37019 gatgctcatcctgcaggcagagaccaccgcgggcaccgtgacgccaccgccatcggaga 37078
              ||||| |||||||||||||||||||||||||||||||||||||||||||||||||||
Sbjct: 32876 gatgcgcatcctgcaggcagagaccaccgcgggcaccgtgacgccaccgccatcggaga 32935
                     FspI
                                                      NlaIII
Query: 37079 cagcatcctcaacatcacaggtgccgcggcccgtgcccatgccaccgcccgcccc 37135
              |||||||||||||||||||||||||||||||||||||| |||||||||||||
Sbjct: 32936 cagcatcctcaacatcacaggtgccgcggcccgtgcccacgccaccgcccgccc 32992
```

FIG. 2N

Figure 2 con.

```
                        Exon 22-Homolog 2

Query:  36719 atgtgaagaggtgccttgtgtggtcggtgggctgcatcacgtggtccccaggtggaggcc 36778
              ||||||||||||||||||||||||| ||||||||||||||| |||||||||||||||||
Sbjct:  75778 atgtgaagaggtgccttgtgtggtcagtgggctgcatcacgtgttccccaggtggaggcc 75837

Query:  36779 ctgggtcatgcagagccacagaacatgcttagtgaggaggctgtgggggtccagtcaagt 36838
              |||||||||||||||||||||  ||||||||||||||||||||||||||||||||||||
Sbjct:  75838 ctgggtcatgcagagccacaaaaaatgcttagtgaggaggctgtgggggtccagtcaagt 75897

Query:  36839 gggctctccagctgcagggctgggggtgggagccaggtgaggacccgtgtagagaggagg 36898
              ||| |||||||||||||||||||||||||||||||||||||| |||||||||||||||
Sbjct:  75898 gggctctccagctgcagggctgggggtgggagccaggtgaggacccgtgtagagaggagg 75957

Query:  36899 gcgtgtgcaaggagtgggccaggagcggggctggacactgctggctccacacagggggcc 36958
              ||||||||||||||||||||||||||||||||||||||||||||||||||||||||||||
Sbjct:  75958 gcgtgtgcaaggagtgggccaggagcggggctggacactgctggctccacacagggggcc 76017

Query:  36959 cagcagggagctcgtatgccgctcgtgcctgaagcagacgctgcacaagctggaggccat 37018
              |||||||||||||||||||||||||||||||||||||||||||||||||||||||||||
Sbjct:  76018 cagcagggagctcgtatgccgctcgtgcctgaagcagacgctgcacaagctggaggccat 76077

Query:  37019 gatgctcatcctgcaggcagagaccaccgcgggcaccgtgacgcccaccgccatcggaga 37078
              ||||| ||||||||||||||||||||||||||||||||||||||||||||||||||||
Sbjct:  76078 gatgcccatcctgcaggcagagaccaccgcgggcaccgtgacgcccaccgccatcggaga 76137

Query:  37079 cagcatcctcaacatcacaggtgccgcggcccgtgcccatgccaccgccgcccc 37135
              ||||||||||||||||||||||||||||||||||||| |||||||||||||||
Sbjct:  76138 cagcatcctcaacatcacaggtgccgcggcccgtgcccacgccacccgcccgcccc 76194
```

FIG. 20

Figure 2 con.

```
                              Exon 23-Homolog 1

Query: 37663 cctccctgtctctgcactgacctcacgcatgtctgcaggagacctcatccacctggccag 37722
              ||||||||||||||||||||||||||| |||||||||||||||||||||||||||||||
Sbjct: 33404 cctccctgtctctgcactgacctcacgcctgtctgcaggagacctcatccacctggccag 33463

Query: 37723 ctcggacgtgcgggcaccacagcctcagagctgggagccgagtcaccatctcggatggt 37782
              ||| ||||||||||||||||||||||| ||||||||||||||||||||||||||||||| |||||||
Sbjct: 33464 ctcagacgtgcgggcaccacagcgctcagagctgggagccgagtcaccatcgcggatggt 33523

Query: 37783 ggcgtcccaggcctacaacctgacctctgccctcatgcgcatcctcatgcgctcccgcgt 37842
              |||||||||||||||||||||||||||||||||||||||| |  |||  || ||||||||||
Sbjct: 33524 ggcgtcccaggcctacaacctgacctctgccctcacgcccatcgtcacgcgctcccgcgt 33583

Query: 37843 gctcaacgaggagcccctgacgctggcgggcgaggagatcgtggcccagggcaagcgctc 37902
              |||||||||||||||||||||||||||| |||||||||||||||||||||||||||||||
Sbjct: 33584 gctcaacgaggagcccctgacgctggcgggtgaggagatcgtggcccagggcaagcgctc 33643

Query: 37903 ggacccgcggagcctgctgtgctatggcggtgccccagggcctggctgccacttctccat 37962
              ||||||||||||| ||||||||||||||||||||||||||||||||||||| ||||||||
Sbjct: 33644 ggacccgcggagcctgctgtgctatggcggcgccccagggcctggctgccacttctccat 33703
                                     MscI
Query: 37963 ccccgaggctttcagcgggtccctggccaacctcagtgacgtggtgcagctcatctttct 38022
              |||| |||||||||| |||||| ||||||||||||||||||||||||||||||||||||
Sbjct: 33704 ccccaggctttcagcagtgccccggccaacctcagtgacgtggtgcagctcatctttct 33763

Query: 38023 ggtggactccaatcccttccctttggctatatcagcaactacaccgtctccaccaaggt 38082
              |||||||||||||||||||||||||||||||||||||||||||||||||||||||||||
Sbjct: 33764 ggtggactccaatcccttccctttggctatatcagcaactacaccgtctccaccaaggt 33823

Query: 38083 ggcctcgatggcattccagacacaggccggcgcccagatccccatcgagcggctggcctc 38142
              ||||||||||| ||||||||||||||||||| |||||||||||||||| |||||||||||
Sbjct: 33824 ggcctcgatggcgttccagacacaggccggcgcccagatccccatcgagcggctggcctc 33883

Query: 38143 agagcgcgccatcaccgtgaaggtgcccaacaactcggactgggctgcccggggccaccg 38202
              |||| ||||  ||||||||||||||||||||||||||||| |||||||||||||||||||
Sbjct: 33884 agagcgcgcc-tcaccgtgaaggtgcccaacaactcggactgggctgcccggggccaccg 33942

Query: 38203 cagctccgccaactccgccaactccgttgtggtccagcccaggcctccgtcggtgctgt 38262
              |||||||||||||||         |||||||||||||||||||||||||||||||||||
Sbjct: 33943 cagctccgccaact---------ccgttgtggtccagcccaggcctccgtcggtgctgt 33993

Query: 38263 ggtcacccctggacagcagcaaccctgcggccgggctgcatctgcagctcaactatacgct 38322
              |||||||||||||||||||||||||||||||||| |||||||||||||||||||||||||
Sbjct: 33994 ggtcacccctggacagcagcaaccctgcggccgtgctgcatctgcagctcaactatacgct 34053

Query: 38323 gctggacggtgcgtgcagcggtgggcacacgcggcccctggccttgttcttgggggg 38392
              |||||||||| ||||||  ||||||||||||||||||||||||||||| |||||||
Sbjct: 34054 gctggacgctgcatgcagcggttgggcacacgcggcccctggccttgtcttgggggg 34113
                                                   SphI
```

FIG. 2P

Figure 2 con.

```
                           Exon 23-Homolog 2

Query: 37663 cctccctgtctctgcactgacctcacgcatgtctgcaggagacctcatccacctggccag 37722
              ||||||||||||||||||||||||||||| ||||||||||||||||||||||||||||||
Sbjct: 76762 cctccctgtctctgcactgacctcacgcctgtctgcaggagacctcatccacctggccag 76821

Query: 37723 ctcggacgtgcgggcaccacagccctcagagctgggagccgagtcaccatctcggatggt 37782
              ||| |||||||||||||  |||| |||||||||||||||||||||||||||| |||||||
Sbjct: 76822 ctcagacgtgcgggcaccgcagcgctcagagctgggagccgagtcaccattgcggatggt 76881

Query: 37783 ggcgtcccaggcctacaacctgacctctgccctcatgcgcatcctcatgcgctcccgcgt 37843
              |||||||||||||||||||||||||||||||||||||||||||||||| |||||||||||
Sbjct: 76882 ggcgtcccaggcctacaacctgacctctgccctcatgcgcatcctcacgcgctcccgcgt 76941

Query: 37843 gctcaacgaggagcccctgacgctggcgggcgaggagatcctggcccagggcaagcgctc 37902
              |||||||||||||||| |||||||||||||||||||||||| ||||||||||||||||||
Sbjct: 76942 gctcaacgaggagcccgtgacgctggcgggcgaggagatcatggcccagggcaagcgctc 77001

Query: 37903 ggacccgcggagcctgctgtgctatggcggcgcccagggcctggctgccacttctccat 37962
              ||||||| ||||||||||||||||||||||||||||||||||||||||||| |||||||
Sbjct: 77002 ggacccgcggagcctgctgtgctatggcggcgcccagggcctggctgccacctctccat 77061

Query: 37963 ccccgaggctttcagcggggccctggccaacctcagtgacgtggtgcagctcatctttct 38022
              |||| |||||||||| ||||| ||||||||||||||| |||||||||||||| ||||||
Sbjct: 77062 ccccbaggctttcagcagggcccnggccaacctcagtgacgtggtgcagctcgtctttct 77121

Query: 38023 ggtggactccaatcccttlcctttggctatatcagcaactacaccgtctccaccaaggt 38082
              |||||||||||||||||| ||||||||||||||||||||||||||||||||||||||||
Sbjct: 77122 ggtggactccaatccctttctctttggctatatcagcaactacaccgtctccaccaaggt 77181

Query: 38083 ggcctcgatggcattccagacacaggccggcgcccagatccccatcgagcggctggcctc 38142
              |||||||| || ||||||||||||||||||||||||||||||||||||||||||||||||
Sbjct: 77182 ggcctcgatggcgttccagacacaggccggcgcccagatccccatcgagcggctggcctc 77241

Query: 38143 agagcgcgccatcaccgtgaaggtgcccaacaactcggactgggctgcccgtggccaccg 38202
              ||||||||||||||||||||||||||||||||||||||||||||||||||| ||||||||
Sbjct: 77242 agagcgcgccatcaccgtgaaggtgcccaacaactcggactgggctgcccgnggccaccg 77301

Query: 38203 cagctccgccaactccgccaactccgttgtggtccagccccaggcctccgtcggtgctgt 38262
              ||||||         |||||||||||||||||||||||||||||||||||||||||||||
Sbjct: 77302 cagctc---------cgccaactccgttgtggtccagccccaggcctccgtcggtgctgt 77352

Query: 38263 ggtcaccctggacagcagcaaccctgcggccggggctgcatctgcagctcaactatacgct 38322
              ||||||||||||||||||||||||||  |||| ||||||||||||||||||||||||||
Sbjct: 77353 ggtcaccctggacagcagcaaccctgtggccgtgctgcatctgcagctcaactatacgct 77412

Query: 38323 gctggacggtgcgtgcagcggntggggcacacgcggcccctggccttgttcttggggg 38382
              |||||||||| ||||||||||||||||||||||||||||||||||||||||||||||||
Sbjct: 77413 gctggacggtgtgtgcagcgggtgggcacacgcggcccctggccttgttcttngggggg 77472
```

FIG. 2Q

Figure 2 con.

Exon 29 and 30—Homolog 1

```
Query: 41535 ttttgcgcttccggcgcctgctggtggctgagctgcagcgtggcttctttgacaagcaca 41594
              | ||||||||||||||||||||||||| ||||||||||||||||||||||||||||||
Sbjct: 37269 tgttgcgcttccggcgcctgctggtggctg-gctgcagcgtggcttctttgacaagcaca 37327

Query: 41595 tctggctctccatatgggaccggccgcctcgtagccgtttcactcgcatccagaggcca 41654
              |||||||||||| |||||||||||||||||||| ||| ||||||||||||||||||||||
Sbjct: 37328 tctggctctccatatgggaccggccgcctcggagctgtttcactcgcatccagaggcca 37387

Query: 41655 cctgctgcgttctcctcatctgcctcttcctgggcgccaacgccgtgtggtacggggctg 41714
              ||||| |||||||||||||||| ||||||||||||||||||||||||||||||||||||
Sbjct: 37388 cctgctgcgttctcctcatctgtctcttcctgggcgccaacgccgtgtggtacggggctg 37447

Query: 41715 ttgccgactctgcctacaggtgggtgccgtaggggtcggggcagcctcttcctgcccagc 41774
              |||| |||||||||||||||||||||||| ||||||||||||| ||||||||||||||||
Sbjct: 37448 ttggagactctgcctacaggtgggtgccgtaggggtcgggacagcctcttcctgcccagc 37507

Query: 41775 ccttcctgcccctcagcctcacctgtgtggcctcctctcctcacacagcacgggcatg 41834
              |||||||||||||||||||||||||||||||||||||||||||||||||||||| ||||
Sbjct: 37508 ccttcctgcccctcagcctcacctgtgtggcctcctctcctcacacagcacgggcgtg 37567

Query: 41835 tgtccaggctgagcccgctgagcgtcgacacagtcgctgttggcctgctgtccagcgtgg 41894
              |||||||||||  |||||||||||||||||||||||||||||||||| ||||||||||||
Sbjct: 37568 tgtccaggctgaacccgctgagcgtcgacacagtcgctgttggcctggtgtccagcgtgg 37627

Query: 41895 ttgtctatcccgtctacctggccatcctttctcttccggatgtcccggagcaaggtgg 41954
              |||||||||||||||||||||||||| ||||||||||||||||||||||||||||||||
Sbjct: 37628 ttgtctatcccgtctacctggccatcctctcttctcttccggatgtcccggagcaagatgg 37687

AvrII or BlnI
Query: 41955 gctgggctggggacccgggagtactgggaatggagcctggcctcggcaccatgcctac 42014
              |||| ||||||||||||||||||||||||||||||||||||||||||||||||||| ||
Sbjct: 37688 gctgcggctggggacccgggagtactgggaatggagcctggcctcggcaccatgcccag 37747

Query: 42015 ggccgccacttttccagtgctgcagccagagggaaaggcgtccaccaaaggctgctcggga 42074
              ||| |||||||||||||||||||||||||||||||||||||||||||||||||||||||
Sbjct: 37748 ggccgccacttttccagtgctgcagccagagggaaaggcgtccaccaaaggctgctcggga 37807
```

FIG. 2R

Figure 2 con.

```
                     Exon 29 and 30-Homolog 2

Query:  41535  ttttgcgcttccggcgcctgctggtggctgagctgcagcgtggcttctttgacaagcaca  41594
               | |||||||||||||||||||||||||||||||||||||||||||||||||||||||||||
Sbjct:  80620  tgttgcgcttccggcgcctgctggtggctgagctgcagcgtggcttctttgacaagcaca  80679

Query:  41595  tctggctctccatatgggaccggccgcctcgtagccgtttcactcgcatccagagggcca  41654
               ||||||||||||||||||||||||||| ||||||||  |||||||||||||||||||||
Sbjct:  80680  tctggctctccatatgggaccggccacctcgtagctgtttcactcgcatccagagggcca  80739

Query:  41655  cctgctgcgttctcctcatctgcctcttcctgggcgccaacgccgtgtggtacggggctg  41714
               ||||||||||||||||||||||||||||||||||||||||||||||||||||||||||||
Sbjct:  80740  cctgctgcgttctcctcatctgcctcttcctgggcgccaacgccgtgtggtacggggctg  80799

Query:  41715  ttggcgactctgcctacaggtgggtgccgtaggggtcggggcagcctcttcctgcccagc  41774
               ||||  ||||||||||||||||||||||||||||||||||  |||||||||||||||||
Sbjct:  80800  ttggtgactctgcctacaggtgggtgccgtaggggtcgggacagcctcttcctgcccagc  80859

Query:  41775  ccttcctgcccctcagcctcacctgtgtggcctcctctcctccacacagcacgggcatg  41834
               |||||||||||||||||||||||||||||||||||||||||||||||||||||||||||
Sbjct:  80860  ccttcctgcccctcagcctcacctgtgtggcctcctctcctccacacagcacgggcatg  80919

Query:  41835  tgtccaggctgagcccgctgagcgtcgacacagtcgctgttggcctggtgtccagcgtgg  41894
               ||||||||||||||||||||||||||||||||||||||||||||||||||||||||||||
Sbjct:  80920  tgtccaggctgagcccgctgagcgtcgacacagtcgctgttggcctggtgtccagcgtgg  80979

Query:  41895  ttgtctatcccgtctacctggccatcctttttctcttccggatgtcccggagcaaggtgg  41954
               |||||||||||||||||||||||||||||| |||||||||||||||||||||||||||||
Sbjct:  80980  ttgtctatcccgtctacctggccatcctctttctcttccggatgtcccggagcaaggtgg  81039

Query:  41955  gctggggctggggacccgggagtactgggaatggagcctgggcctcggcaccatgcctag  42014
               ||||||||||||||||||||||||||||||||||||||||||||||||||||||||| ||
Sbjct:  81040  gctggggctggggacccgggagtactgggaatggagcctgggcctcggcaccatgcccag  81099

Query:  42015  ggccgccactttccagtgctgcagccagagggaaaggcgtccaccaaaggctgctcggca  42074
               ||||||||||||||||||||||||||||||||||||||||||||||||||||||||||||
Sbjct:  81100  ggccgccactttccagtgctgcagccagagggaaaggcgtccaccaaaggctgctcggga  81159
```

| | Polymorph | Probable | Missense | Frame Shift | Indeterminate | |
|---|---|---|---|---|---|---|
| 1 | 13 | 8 | 1 | 0 | 0 | 22 |
| 2 | 13 | 8 | 1 | 0 | 0 | 22 |
| 3 | 14 | 6 | 0 | 0 | 0 | 20 |
| 4 | 14 | 6 | 0 | 0 | 0 | 20 |
| 5 | 1 | 1 | 1 | 0 | 0 | 3 |
| 6 | 1 | 2 | 0 | 0 | 0 | 3 |
| 7 | 4 | 0 | 0 | 1 | 0 | 5 |
| 8 | 0 | 0 | 2 | 0 | 0 | 2 |
| 9 | 13 | 4 | 0 | 0 | 1 | 18 |
| 10 | 4 | 0 | 1 | 1 | 0 | 6 |
| 11 | 16 | 5 | 0 | 0 | 0 | 21 |
| 12 | 0 | 1 | 0 | 0 | 0 | 1 |
| 13 | 13 | 9 | 2 | 1 | 0 | 25 |
| 14 | 1 | 0 | 1 | 1 | 0 | 3 |
| 15 | 1 | 1 | 1 | 0 | 0 | 3 |
| 16 | 2 | 1 | 0 | 0 | 0 | 3 |
| 17 | 13 | 12 | 2 | 1 | 0 | 28 |
| 18 | 16 | 6 | 0 | 0 | 0 | 22 |
| 19 | 4 | 3 | 0 | 0 | 0 | 7 |
| 20 | 0 | 0 | 0 | 0 | 0 | 0 |

| Gene | Exon | Ampli-con | Temp | PC Ret Time | PC Height | NC Ret Time | NC Height |
|---|---|---|---|---|---|---|---|
| 1 | x | 1 | | | | | |
| 1 | x | 2 | | 66 | 2.25-6.5 | 0.8-3.2 | 2-6.5 | 0.9-3.6 |
| 1 | x | 2 | | 67 | 0.7-5.8 | 0.8-3.2 | 0.7-5.8 | 1-4 |
| 1 | x | 3 | | 56 | 4.2-6.8 | 1-4 | 4-6.75 | 1.1-4.4 |
| 1 | x | 3 | | 57 | 3.5-6.5 | 0.7-2.8 | 4-6.5 | 1-4 |
| 1 | x | 4 | | 66 | 2-6.8 | 1-4 | 2-6.8 | 0.8-3.2 |
| 1 | x | 4 | | 67 | 1.5-6 | 0.5-2.0 | 1.5-6 | 1.1-4.4 |
| 1 | x | 5 | A | 66 | 2.6-4.6 | 1.3-5.4 | 2.7-4.7 | 1.3-5.2 |
| 1 | x | 5 | B | 67 | 2-6.5 | 0.4-7.0 | 3-6.5 | 0.5-4.6 |
| 1 | x | 5 | C | 67 | 3-6.5 | 1-4 | 3-6.5 | 1.2-4.8 |
| 1 | x | 5 | C | 68 | 1.7-5.8 | 0.7-2.8 | 2.5-5.8 | 1-4 |
| 1 | x | 6 | | 66 | 3.5-5.9 | 0.3-1.5 | 3.9-5.9 | 1.0-4.2 |
| 1 | x | 6 | | 67 | 2.5-5.4 | 0.5-2.0 | 3.4-5.4 | 1-4.2 |
| 1 | x | 6 | | 68 | 2.2-4.8 | 0.3-1.4 | 2.8-4.8 | 0.7-3.0 |
| 1 | x | 7 | | 66 | 2.7-6.25 | 0.5-2.0 | 3-6.25 | 0.6-2.4 |
| 1 | x | 7 | | 68 | 1.5-5 | 0.9-3.6 | 1.5-5 | 0.6-2.4 |
| 1 | x | 8 | | 68 | 1.5-5 | 1.3-5.2 | 1.7-5 | 1-4 |
| 1 | x | 9 | | 67 | 3.5-6.5 | 0.5-2.0 | 3.5-6.8 | 0.25-2.0 |
| 1 | x | 10 | | 65 | 2.5-6.5 | 0.9-3.6 | 3-6.5 | 1.9-7.6 |
| 1 | x | 10 | | 67 | 1.5-5 | 1.5-6 | 1.5-5 | 2-8 |
| 1 | x | 11 | A | 67 | 1.5-6.5 | 0.7-2.8 | 2-6.5 | 2-8 |
| 1 | x | 11 | A | 68 | 1.5-5.5 | 0.8-3.2 | 2-5.8 | 1.3-5.2 |
| 1 | x | 11 | B | 66 | 3-6.8 | 1-4 | 3-6.8 | 1-4 |
| 1 | x | 11 | B | 67 | 2-6 | 1.5-6 | 2-6 | 1.2-4.8 |
| 1 | x | 11 | C | 66 | 4.2-6.2 | 1.5-6 | 4.2-6.2 | 2.5-10.2 |
| 1 | x | 11 | C | 67 | 3.6-5.6 | 1.7-7 | 3.6-5.6 | 2.3-9.2 |
| 1 | x | 11 | C | 68 | 2.9-4.9 | 1.1-4.6 | 2.8-4.8 | 1.7-6.8 |
| 1 | x | 12 | | 63 | 4.4-6.6 | 0.6-2.4 | 4.7-6.7 | 1-4 |
| 1 | x | 12 | | 65 | 2.8-4.8 | 0.4-1.6 | 2.6-5.4 | 0.4-1.8 |
| 1 | x | 13 | | | | | | |
| 1 | x | 14 | | 66 | 1.5-5.5 | 0.6-2.4 | 0.7-5.5 | 0.6-2.4 |
| 1 | x | 15 | A | 67 | 2.5-6.5 | 0.8-3.2 | 2.5-6.5 | 1-4 |
| 1 | x | 15 | A | 68 | 1.5-5.75 | 1-4 | 1.5-5.75 | 1.2-4.8 |
| 1 | x | 15 | B | 67 | 2-5.75 | 0.5-2.0 | 2.75-5.75 | 1-4 |
| 1 | x | 15 | B | 68 | 1.5-5.25 | 0.6-2.4 | 2.5-5.5 | 0.9-3.6 |
| 1 | x | 15 | C | 68 | 2-6.5 | 0.4-1.6 | 2-6.5 | 0.8-3.2 |
| 1 | x | 15 | C | 69 | 1.5-6 | 0.5-2.0 | 1.5-6 | 0.75-3.0 |
| 1 | x | 15 | D | 67 | 3.75-7.25 | 1.5-6 | 3.75 | 7.25 |
| 1 | x | 15 | D | 68 | 3-6.5 | 1-4 | 3-6.5 | 1.2-4.8 |
| 1 | x | 15 | E | 65 | 3-6.5 | 1-4 | 3-6.5 | 1.5-6 |
| 1 | x | 15 | E | 66 | 2-6 | 0.8-3.2 | 2-6 | 1.3-5.2 |
| 1 | x | 15 | F | 65 | 4-7 | 1.4-5.6 | 3.75-7 | 1.2-4.8 |
| 1 | x | 15 | F | 66 | 3-6.5 | 1-4 | 3-6.5 | 1-4 |
| 1 | x | 15 | F | 67 | 1.5-5.75 | 1.3-5.2 | 1.5-5.75 | 1-4 |
| 1 | x | 15 | G | 66 | 3-6 | 0.8-3.2 | 3-6 | 1.1-4.4 |
| 1 | x | 15 | G | 68 | 1.5-4.5 | 1-4 | 1.5-4.5 | 1.5-6 |

FIG. 11A

Figure 11 con

| | | | | | | | | |
|---|---|---|---|---|---|---|---|---|
| 1 | x | 15 | H | 65 | 2-6.5 | 1.5-6 | 2-6.5 | 1.5-6 |
| 1 | x | 15 | H | 66 | 1.5-5.5 | 1-4 | 1.5-5.75 | 1-4 |
| 1 | x | 15 | I | 66 | 3-7 | 2-8 | 3-7 | 1.8-7.2 |
| 1 | x | 15 | I | 67 | 2.5-6.5 | 1.5-6 | 2.5-6.5 | 1.5-6 |
| 1 | x | 15 | J | 64 | 4-7.5 | 2.2-8.8 | 4-7.5 | 2-8 |
| 1 | x | 15 | J | 65 | 4-7 | 2-8 | 4-7 | 1.5-6 |
| 1 | x | 15 | J | 66 | 3-6.5 | 1.5-6 | 2-6.5 | 1.1-4.4 |
| 1 | x | 15 | K | 65 | 3.5-6.5 | 1-4 | 3.75-6.5 | 0.8-3.2 |
| 1 | x | 15 | K | 66 | 3-6.5 | 0.7-2.8 | 3.5-6.5 | 0.6-3.2 |
| 1 | x | 15 | K | 67 | 2-6 | 0.6-2.4 | 2-5.5 | 0.5-2.0 |
| 1 | x | 15 | L | | | | | |
| 1 | x | 15 | M | 66 | 4.5-7 | 1-4 | 4.5-7 | 1.5-6 |
| 1 | x | 15 | M | 67 | 4-6.75 | 1-4 | 4-6.75 | 1.3-5.2 |
| 1 | x | 15 | N | | | | | |
| 1 | x | 16 | | 67 | 1.5-5.5 | 2.25-9 | 2.0-5.5 | 3-13 |
| 1 | x | 17 | | 65 | 2.5-6 | 1.5-6 | 2.5-6 | 1.75-7 |
| 1 | x | 17 | | 66 | 1.5-5 | 1.25-5 | 1.5-5 | 1.75-7 |
| 1 | x | 18 | | 66 | 3-6.5 | 2-8 | 3-6.5 | 3.25-13 |
| 1 | x | 18 | | 67 | 4-6.4 | 3.8-16 | 4.25-6.25 | 6.2-24.8 |
| 1 | x | 18 | | 68 | 1.5-5 | 2.5-10 | 1.5-5 | 2.75-11 |
| 1 | x | 19 | | 67 | 3-6.5 | 1.5-6 | 3-6.5 | 3-12 |
| 1 | x | 19 | | 68 | 3.0-6.5 | 1.5-6 | 3-6.5 | 3-12 |
| 1 | x | 20 | | 65 | 3.5-6.5 | 2-8 | 3.5-6.5 | 2.25-9 |
| 1 | x | 20 | | 66 | 2.5-6 | 1.25-5 | 2.5-6 | 1.75-7 |
| 1 | x | 20 | | 67 | 1.5-5.5 | 1.25-5 | 1.5-5.5 | 1.75-7 |
| 1 | x | 21 | | 65 | 3-7 | 1.5-6 | 3-7 | 4-16 |
| 1 | x | 21 | | 67 | 1.5-5.5 | 2.25-9 | 1.5-5.5 | 4.5-18 |
| 1 | x | 22 | | 66 | 4-7.5 | 2-8 | 4-7 | 2-8 |
| 1 | x | 22 | | 67 | 3-7.25 | 1.5-6 | 3.5-6.5 | 1.5-6 |
| 1 | x | 23 | A | 65 | 3.5-6.5 | 0.75-3.0 | 3.5-6.5 | 1.5-6.0 |
| 1 | x | 23 | A | 66 | 2.5-6.0 | 0.5-2.0 | 2.5-6.0 | 1.25-5.0 |
| 1 | x | 23 | A | 68 | 1.5-4.5 | 2.5-10.0 | 1.5-4.5 | 2.5-10.0 |
| 1 | x | 23 | B | 63 | 3.5-7.25 | 1.5-6 | 3.5-7.25 | 1.5-6 |
| 1 | x | 23 | B | 66 | 1.5-6.5 | 0.9-3.5 | 1.5-6.5 | 1-4 |
| 1 | x | 23 | B | 67 | 1.25-5.5 | 1-4 | 1.25-5.5 | 1-4 |
| 1 | x | 23 | C | 61 | 3-6.25 | 1.5-6 | 3-6.25 | 3.25-13 |
| 1 | x | 23 | C | 66 | 1.5-5 | 2.25-9 | 2.5-5 | 4.25-17 |
| 1 | x | 23 | C | 67 | 1.5-5 | 2.75-11 | 2-5 | 5.5-22 |
| 1 | x | 24 | | 65 | 2.5-6.0 | 0.5-2.0 | 2.5-6.0 | 0.6-3.0 |
| 1 | x | 25 | | 65 | 2-6 | 0.7-4 | 2-6 | 0.7-4 |
| 1 | x | 25 | | 67 | 1.5-4.5 | 2-8 | 1.5-4.5 | 2-8 |
| 1 | x | 26 | | 64 | 2.5-6 | 0.9-3.6 | 2.5-6 | 0.9-3.6 |
| 1 | x | 26 | | 66 | 1.5-4.5 | 1.75-7 | 1.5-4.5 | 1.75-7 |
| 1 | x | 27 | | 65 | 3.5-6.7 | 1.5-6 | 3.5-6.7 | 1.5-6 |
| 1 | x | 27 | | 66 | 2.5-6 | 2-8 | 2-5.7 | 1.25-5 |
| 1 | x | 28 | | 66 | 1.5-5.75 | 1-4 | 1.5-5.75 | 1-4 |
| 1 | x | 29 | | 65 | 1.5-6.25 | 1.5-6 | 1.5-6.25 | 3-12 |
| 1 | x | 29 | | 66 | 1.5-5.25 | 1.5-6 | 1.5-5.25 | 2.5-8.5 |
| 1 | x | 30 | | | | | | |

FIG. 11B

Figure 11 con

| | | | | | | | |
|---|---|---|---|---|---|---|---|
| 1 | x | 31 | | 66 | 3-6.5 | 2.5-10 | 3-6.5 | 1-4 |
| 1 | x | 31 | | 68 | 1.5-5.5 | 1.5-6 | 1.5-5.5 | 0.5-2 |
| 1 | x | 32 | | 62 | 2-6.5 | 1.25-5.0 | 2-6.5 | 3.5-14 |
| 1 | x | 33 | | 64 | 4.2-6.2 | 1.4-6 | 4.3-6.3 | 1.5-6 |
| 1 | x | 33 | | 67 | 2.5-4.7 | 0.8-3.5 | 2.7-4.7 | 1.2-4.8 |
| 1 | x | 34 | | | | | | |
| 1 | x | 34 | | | | | | |
| 1 | x | 35 | | 64 | 4.3-6.6 | 1.4-5.5 | 4.5-6.5 | 2.4-9.5 |
| 1 | x | 35 | | 66 | 2.6-5.1 | 1.1-4.4 | 3.1-5.1 | 1.75-7 |
| 1 | x | 36 | | 66 | 3.3-5.7 | 0.5-2.0 | 3.6-5.6 | 1-4 |
| 1 | x | 36 | | 67 | 2.7-5.1 | 0.6-2.5 | 3.1-5.1 | 1.1-4.4 |
| 1 | x | 37 | | 64 | 3-5.75 | 0.65-2.6 | 3.7-5.7 | 1.1-4.5 |
| 1 | x | 37 | | 66 | 2-4.75 | 0.9-3.6 | 2.7-4.7 | 1-4 |
| 1 | x | 38 | | 65 | 3.5-6.5 | 1.1-4.5 | 4.3-6.3 | 1.6-6.5 |
| 1 | x | 38 | | 66 | 3-5.75 | 0.7-3.0 | 3.5-5.5 | 1-4 |
| 1 | x | 39 | | 66 | 1.5-4.5 | 1.1-4.6 | 2-4.6 | 1.25-3.0 |
| 1 | x | 39 | | 67 | 1.5-4 | 1.25-3.0 | 1.5-4 | 0.7-3.0 |
| 1 | x | 40 | | 66 | 1.5-5.5 | 0.6-2.5 | 3.25-5.25 | 0.7-3.0 |
| 1 | x | 41 | | 67 | 2.5-5.75 | 0.9-3.6 | 3.75-5.75 | 1.1-4.4 |
| 1 | x | 42 | | 70 | 2.75-5.75 | 0.5-2.0 | 3-5.8 | 0.3-1.2 |
| 1 | x | 42 | | 71 | 2.5-4.5 | 0.7-3.0 | 2.6-4.6 | 0.6-2.4 |
| 1 | x | 43 | | 67 | 4-6.75 | 0.4-1.6 | 4-6.75 | 0.6-2.4 |
| 1 | x | 43 | | 68 | 3.75-6.5 | 0.4-1.6 | 3.75-6.5 | 0.6-2.4 |
| 1 | x | 43 | | 70 | 2.25-5.25 | 0.25-2 | 2.25-5.25 | 0.6-2.4 |
| 1 | x | 44 | | 66 | 3.25-5.75 | 0.5-2.0 | 3.7-5.7 | 0.8-3.2 |
| 1 | x | 45 | | 65 | 3.5-6.25 | 0.4-1.6 | 4.1-6.1 | 0.9-3.6 |
| 1 | x | 45 | | 66 | 2.5-5.5 | 0.4-1.6 | 3.5-5.5 | 0.8-3.2 |
| 1 | x | 46 | A | 66 | 4.25-6.5 | 0.4-1.6 | 4.4-6.4 | 0.8-3.2 |
| 1 | x | 46 | A | 67 | 3.25-5.25 | 0.3-1.2 | 3.5-5.5 | 0.5-2.0 |
| 1 | x | 46 | B | 65 | 4-6.75 | 1-4 | 4-6.75 | 1.2-4.8 |
| 1 | x | 46 | B | 68 | 1.75-4.75 | 1.3-5.2 | 1.75-4.75 | 1.5-6 |
| 2 | x | 1 | A | 70 | 3-6 | 1.5-6 | 3-6 | 1-4 |
| 2 | x | 1 | A | 71 | 2-5.75 | 0.6-2.4 | 2-5.75 | 0.9-3.6 |
| 2 | x | 1 | A | 72 | 1.5-5.25 | 0.5-3.0 | 1.5-5.25 | 0.5-2 |
| 2 | x | 1 | B | 67 | 2.5-6.5 | 0.6-2.5 | 2.5-6.5 | 0.6-2.5 |
| 2 | x | 1 | B | 70 | 1.5-4.5 | 0.7-3 | 1.5-4.5 | 1-4 |
| 2 | x | 1 | B | 71 | 1-4 | 0.5-2 | 1-4 | 0.7-3 |
| 2 | x | 1 | C | 69 | 2.5-6.5 | 1.25-5 | 2.5-6.5 | 1-4 |
| 2 | x | 1 | C | 70 | 1.5-6.5 | 0.8-2.5 | 1.5-6.5 | 0.8-3.5 |
| 2 | x | 1 | C | 71 | 1.5-5.75 | 0.8-3.5 | 1.5-5.75 | 0.8-3.5 |
| 2 | x | 2 | | 58 | 2.5-4.5 | 1.2-5.0 | 3.2-5.2 | 1.4-5.6 |
| 2 | x | 3 | | 58 | 4.7-6.9 | 2.9-11.6 | 4.9-6.9 | 3.5-14 |
| 2 | x | 3 | | 59 | 4.4-6.9 | 2.1-8.4 | 4.7-6.7 | 2.0-8.0 |
| 2 | x | 3 | | 60 | 3.5-6.1 | 1.3-5.2 | 3.9-5.9 | 1.6-6.4 |
| 2 | x | 4 | | 60 | 3.4-6.1 | 1.7-7.0 | 4.1-6.1 | 0.9-3.8 |
| 2 | x | 5 | | 58 | 4.5-6.5 | 2.3-9.2 | 4.6-6.6 | 2.3-9.4 |
| 2 | x | 5 | | 59 | 3.9-6.2 | 1.6-6.6 | 4.3-6.3 | 1.7-6.8 |
| 2 | x | 6 | | 57 | 1.5-6.25 | 1.5-6 | 1.5-6.25 | 2-8 |
| 2 | x | 7 | | 53 | 3.4-6.6 | 1.2-5.0 | 3.3-6.6 | 1.0-4.0 |

FIG. 11C

Figure 11 con

| 2 | x | 7  |    | 56 | 2.5-4.5   | 2.5-10.2 | 2.6-5.2  | 1.1-4.4  |
|---|---|----|----|----|-----------|----------|----------|----------|
| 2 | x | 8  |    | 54 | 3.7-6.2   | 1.5-6    | 3.7-6.2  | 5.5-22   |
| 2 | x | 8  |    | 58 | 3-6       | 0.8-3.2  | 2.5-6    | 4-16     |
| 2 | x | 9  |    | 54 | 3-6.5     | 0.5-2.0  | 3.5-6.5  | 1-4      |
| 2 | x | 9  |    | 57 | 1.5-4.75  | 0.5-2    | 1.5-4.75 | 0.5-2.0  |
| 2 | x | 10 |    |    |           |          |          |          |
| 2 | x | 10 |    |    |           |          |          |          |
| 2 | x | 11 |    | 58 | 2.5-6.75  | 2.3-9.2  | 2.5-6.75 | 2-8      |
| 2 | x | 11 |    | 59 | 1.75-6.5  | 1.5-6    | 1.5-6.5  | 1-4      |
| 2 | x | 12 |    | 60 | 1.5-5.75  | 0.7-2.8  | 1.5-5.5  | 0.8-3.2  |
| 2 | x | 13 |    | 60 | 3-6.2     | 1.2-4.8  | 4.2-6.2  | 1.2-5    |
| 2 | x | 13 |    | 61 | 2.5-5.5   | 1.2-5    | 2.5-5.5  | 0.9-4.0  |
| 2 | x | 14 |    | 63 | 2.5-4.5   | 1.1-4.4  | 3.2-5.2  | 2.5-10.0 |
| 2 | x | 15 |    | 60 | 2-6.5     | 0.9-3.6  | 2-6.5    | 1-4      |
| 2 | x | 15 |    | 61 | 1.5-6     | 1.3-5.2  | 1.5-6    | 1.5-6    |

Figure 14. Identified ADPKD associated alterations. Novel alterations are indicated by bold text.

PKD Accessions with UPD variants.

A.

```
              nt
           Position    Codon #      Alteration Type

Variant PKD1X1 - 1:     UAA    Transversion C -> A
              318          36      proline ---> histidine Variant PKD1X36 - 1:    KP     Transition C > T
             10976        3589     none Variant PKD1X40 - 1:    UPD    19bp insertion
             11606        3799     frameshift Variant PKD1X43 - 1:    KP     Transition C > T
             12124        3971     none Variant PKD1X44 - 1:    KP     Sequence alteration detected: 1bp deletion
             IVS 44+19delG Variant PKD2X1E - 1:    KP     Transition G > A
              436          140     none
```

B.

```
   Variant PKD1X15A - 1:    UAA    Transition C > T
              3591        1127     proline ---> leucine Variant PKD1X16 - 1:     KP     Transition C > T
              7138        2309     none Variant PKD1X18 - 1:     UPD    1bp insertion of C
              7518        2436     Frame Shift Variant PKD1X23A - 1:    KP     Transition G > A
```

FIG. 14A

```
            8555      2782      valine --> methionine
    Variant  PKD1X5C - 1:       KP    Transition T > C   Homozygous
            1330      373       none
    Variant  PKD2X1A - 1:       KP    Transversion G > C
            149       28        arginine ---> proline C.
    Variant  PKD1X10 - 1:       UP    Transition A > G
            IVS9-4
    Variant  PKD1X11C - 1:      KP    Transition G > A
            2911      900       none
    Variant  PKD1X11C - 2:      KP    Transition C > T
            2941      910       none
    Variant  PKD1X15B - 1:      UAA   Transition C > T
            3713      1168      proline ---> serine
    Variant  PKD1X15G - 1:      KP    Transversion A > C
            4876      1555      none
    Variant  PKD1X15J - 1:      UP    Transition C > T
            5383      1724      none
    Variant  PKD1X15L - 1:      UP    Transition G > A
            5974      1921      none
    Variant  PKD1X15L - 2:      UAA   Transition G > A
            6218      2003      alanine ---> threonine
    Variant  PKD1X17 - 1:       KP    Transition T > C
            7376      2389      none
    Variant  PKD1X18 - 1:       KP    Transition C > T
            7652      2481      none
    Variant  PKD1X25 - 1:       KP    Transition A > G
```

FIG. 14B

```
              IVS24-17
Variant  PKD1X25 - 2:     KP    Transversion G > C
         9406    3065     none
Variant  PKD1X25 - 3:     KP    Transition T > C
         9407    3066     phenylalanine ---> leucine
Variant  PKD1X26 - 1:     KP    Transition T > C
         9541    3110     none
Variant  PKD1X28 - 1:     UP    Transition T > C
              IVS27-13
Variant  PKD1X30 - 1:     UP    Transition A > G
              IVS30+54
Variant  PKD1X35 - 1:     KP    Transition C > T
         10743   3511     alanine ---> valine
Variant  PKD1X44 - 1:     KP    Transition A > G
         12341   4044     isoleucine ---> valine
Variant  PKD1X45 - 1:     KP    Transition C > T
         12384   4058     alanine ---> valine
Variant  PKD1X45 - 2:     KP    Transition A > G
         12484   4091     none
Variant  PKD1X45 - 3:     KP    Transition C > T
         12617   4136     none
Variant  PKD1X46A - 1:    UP    Transition T > C
         12838   4209     none
Variant  PKD1X6 - 1:      UPD   1bp insertion of G
         1502    431      Frame Shift
Variant  PKD1X9 - 1:      UP    7 bp deletion
              IVS9+28del7
              HOMOZYGOUS
```

FIG. 14C

```
      Variant  PKD2X1A - 1:    KP    Transversion G > C
           149       28        arginine ---> proline D.
      Variant  PKD1X15B - 1:   UAA   Transition C > T
           3713      1168      proline ---> serine
      Variant  PKD1X6 - 1:     UPD   1bp insertion of G
           1502      431       Frame Shift
      Variant  PKD2X1A - 1:    KP    Transversion G > C
           149       28        arginine ---> proline E.
      Variant  PKD1X10 - 1:    UP    Transition A > G
           IVS9-4
      Variant  PKD1X11C - 1:   KP    Transition G > A
           2911      900       none
      Variant  PKD1X11C - 2:   KP    Transition C > T
           2941      910       none
      Variant  PKD1X13 - 1:    UP    Transition C > T
           IVS12-15
      Variant  PKD1X15A - 1:   UAA   Transversion C > G
           3527      1106      leucine ---> valine
      Variant  PKD1X15B - 1:   UP    Transversion C > G
           3724      1171      none
      Variant  PKD1X15G - 1:   KP    Transversion A > C
           4876      1555      none
      Variant  PKD1X15J - 1:   UP    Transition C > T
           5383      1724      none
```

FIG. 14D

```
Variant  PKD1X15L - 1:     UP    Transition G > A
      5974      1921       none
Variant  PKD1X17 - 1:      KP    Transition T > C
      7376      2389       none
Variant  PKD1X18 - 1:      KP    Transition C > T
      7652      2481       none
Variant  PKD1X20 - 1:      UAA   Transition C > T
      8024      2605       proline ---> serine
Variant  PKD1X23A - 1:     UP    Transition G > A
      8575      2788       none
Variant  PKD1X25 - 1:      KP    Transition A > G
      IVS24-17
Variant  PKD1X25 - 2:      KP    Transversion G > C
      9406      3065       none
Variant  PKD1X25 - 3:      KP    Transition T > C
      9407      3066       phenylalanine ---> leucine
Variant  PKD1X25 - 4:      UPD   2bp deletion of AG
      9294 & 92953028      Frame Shift
Variant  PKD1X26 - 1:      UP    Transition C > T
      9481      3090       none
Variant  PKD1X26 - 2:      KP    Transition T > C
      9541      3110       none
Variant  PKD1X28 - 1:      UP    Transition T > C
      IVS27-13
Variant  PKD1X30 - 1:      UP    Transition A > G
      IVS30+54
Variant  PKD1X35 - 1:      KP    Transition C > T
      10743     3511       alanine ---> valine
```

FIG. 14E

```
Variant  PKD1X44 - 1:    KP   Transition A > G
     12341     4044      isoleucine ---> valine
Variant  PKD1X45 - 1:    KP   Transition C > T
     12384     4058      alanine ---> valine
Variant  PKD1X45 - 2:    KP   Transition A > G
     12484     4091      none
Variant  PKD1X45 - 3:    KP   Transition C > T
     12617     4136      none
Variant  PKD1X46A - 1:   UP   Transition T > C
     12838     4209      none
Variant  PKD1X9 - 1:     UP   deletion of TGGTGGG
     IVS9+28del7
     Possible homozygous
Variant  PKD2X1A - 1:    KP   Transversion G > C
     149       28        arginine ---> proline
```

F.
```
Variant  PKD1X1 - 1:     UAA  Transversion C > A
     318       36        proline ---> histidine
Variant  PKD1X5C - 1:    KP   Transition C > T
     1234      341       none
Variant  PKD2X5 - 1:     UPD  Transversion T > G
     1224      386       tyrosine ---> stop codon (AMB)
```

G.
```
Variant  PKD1X15G - 1:   KP   Transition G > A
     4885      1558      none
Variant  PKD1X15H - 1:   KP   Transition G > A
```

FIG. 14F

```
        4885        1558        none
Variant  PKD1X19 - 1:    UPD    Transition C > T
        7877        2556        glutamine --> stop codon
Variant  PKD1X5C - 1:    KP     Transition C > T
        1234        341         none
```

H.

```
Variant  PKD1X2 - 1:     UPD    2bp deletion of TC
        482-483     91          Frame Shift
Variant  PKD1X22 - 1:    UP     Transversion G > C
        IVS21-44
Variant  PKD1X41 - 1:    UP     3bp insertion of GGG
        IVS41+5ins3
Variant  PKD1X6 - 1:     UP     Transition C > T
        IVS6+26
Variant  PKD2X1A - 1:    KP     Transversion G > C
        149         28          arginine ---> proline
Variant  PKD2X1B - 1:    KP     Transition G > A
        486         140         none
```

I.

```
Variant  PKD1X15N - 1:   UAA    Transition C > T
        6809        2200        arginine --> cysteine
Variant  PKD1X17 - 1:    KP     Transition T > C
        7376        2389        none
Variant  PKD1X3 - 1:     UPD    5bp deletion of TTTAA
        559-563     116-118     Frame Shift
        STOP CODON CREATED AT CODON 117
```

FIG. 14G

```
Variant  PKD1X5C - 1:      KP    Transition T > C
         1330     373       none
Variant  PKD2X8 - 1:       UAA   Transition G > A
         1815     583       methionine ---> isoleucine
```

J.

```
Variant  PKD1X15F - 1:     UP    Transition C > T
         4706     1499      none
Variant  PKD1X23A - 1:     UPD   Transversion G > T
         8639     2810      glutamic acid --> stop codon
Variant  PKD1X23A - 2:     KP    Transition G > A
         8651     2814      glycine --> arginine
Variant  PKD1X23A - 3:     UAA   Transition T > C
         8658     2816      leucine --> proline
Variant  PKD1X23A - 4:     UP    Transition C > T
         8662     2817      none
Variant  PKD1X23B - 1:     UPD   Transversion G > T
         8639     2810      glutamic acid --> stop codon
Variant  PKD1X23B - 2:     KP    Transition G > A
         8651     2814      glycine --> arginine
Variant  PKD1X23B - 3:     UAA   Transition T > C
         8658     2816      leucine --> proline
Variant  PKD1X23B - 4:     UP    Transition C > T
         8662     2817      none
Variant  PKD1X23C - 1:     UAA   Transition G > A
         8900     2897      valine --> isoleucine
Variant  PKD1X40 - 1:      UP    Transition C > T
         11554    3781      none
```

FIG. 14H

```
Variant PKD1X41 - 1:    UP    3bp insertion of GGG
    IVS41+5ins3
Variant PKD1X45 - 1:    UAA   Transition G > A
    12644    4145        valine ---> isoleucine
```

K.

```
Variant PKD1X10 - 1:    UPD   Transition C > T
    2300     697         glutamine -> stop codon (AMB)
Variant PKD1X15B - 1:   UAA   Transition C > T
    3713     1168        proline --> serine
Variant PKD1X44 - 1:    KP    Transition A > G
    12341    4044        isoleucine ---> valine
Variant PKD1X45 - 1:    KP    Transition C > T
    12384    4058        alanine ---> valine
Variant PKD1X45 - 2:    KP    Transition A > G
    12484    4091        none
Variant PKD1X45 - 3:    KP    Transition C > T
    12617    4136        none
Variant PKD1X46A - 1:   UP    Transition T > C
    12838    4209        none
Variant PKD1X46B - 1:   UAA   Transition C > T
    13034    4275        arginine ---> tryptophan
Variant PKD1X5C - 1:    KP    Transition T > C
    1330     373         none
Variant PKD2X1A - 1:    KP    Transversion G > C
    149      28          arginine ---> proline
```

```
Variant  PKD1X15J - 1:    UPD    1 bp deletion T
         5352     1714     Frame Shift
Variant  PKD1X5C - 1:     KP     Transition T > C
         1330      373    none
Variant  PKD2X1A - 1:     KP     Transversion G > C
         149       28     arginine ---> proline
```

M.

```
Variant  PKD1X13 - 1:     UP     Transition A > G
         3322     1037    none
Variant  PKD1X40 - 1:     UPD    1bp insertion of T
         11556    3783    Frame Shift
Variant  PKD2X1A - 1:     KP     Transversion G > C
         149       28     arginine ---> proline
```

N.

```
Variant  PKD1X29 - 1:     UP     Transition C > T
         10006    3265    none
Variant  PKD1X31 - 1:     UPD    1bp deletion of C
         10287    3359    Frame Shift
Variant  PKD1X43 - 1:     UP     Transversion C > A
         IVS43+42
Variant  PKD1X5C - 1:     KP     Transition T > C
         1330      373    none
Variant  PKD2X1A - 1:     KP     Transversion G > C
         149       28     arginine --> proline
Variant  PKD2X1B - 1:     KP     Transition G > A
         486       140    none
```

Variant PKD1X11B - 1:    UP    Transversion A > C
        2905    898    none

Variant PKD1X11C - 1:    UP    Transversion A > C
        2905    898    none

Variant PKD1X16 - 1:    KP    Transition C > T
        7138    2309    none

Variant PKD1X23A - 1:    KP    Transition C > T
        8650    2813    none

Variant PKD1X23B - 1:    KP    Transition C > T
        8650    2813    none

Variant PKD1X5C - 1:    KP    Transition T > C
        1330    373    none

Variant PKD2X1A - 1:    KP    Transversion G > C    Homozygous
        149    28    arginine --> proline Variant PKD2X5 - 1:    UPD    Transition G > A
        1308    414    tryptophan --> OPA(stop codon)

P.

Variant PKD1X11A - 1:    UAA    Transition A > G
        2427    739    glutamine ---> arginine Variant PKD1X5C - 1:    KP    Transition T > C    Homozygous
        1330    373    none Variant PKD2X1A - 1:    UPD    52 bp insertion
        139-190    25-42    Frame Shift Variant PKD2X1B - 1:    KP    Transition G > A
        486    140    none

```
Variant  PKD1X11A - 1:     UAA    Transition A > G
     2427       739         glutamine ---> arginine
Variant  PKD1X19 - 1:      UPD    Transition C > T
     7877      2556         glutamine ---> stop codon(AMB)
Variant  PKD1X5C - 1:       KP    Transition C > T
     1234       341         none
Variant  PKD1X5C - 2:       KP    Transition T > C
     1330       373         none
```

R.

```
Variant  PKD1X15F - 1:
  Variant  PKD1X23A - 1:    UPD    Transversion G > T
       8639     2810         glutamic acid ---> AMB (stop codon)
  Variant  PKD1X23A - 2:     KP    Transition G > A
       8651     2814         glycine ---> arginine
  Variant  PKD1X23A - 3:    UAA    Transition T > C
       8658     2816         leucine ---> proline
  Variant  PKD1X23A - 4:     UP    Transition C > T
       8662     2817         none
  Variant  PKD1X23B - 1:    UPD    Transversion G > T
       8639     2810         glutamic acid ---> AMB (stop codon)
  Variant  PKD1X23B - 2:     KP    Transition G > A
       8651     2814         glycine ---> arginine
  Variant  PKD1X23B - 3:    UAA    Transition T > C
       8658     2816         leucine ---> proline
  Variant  PKD1X23B - 4:     UP    Transition C > T
```

FIG. 14L

```
                    8662      2817       none
         Variant  PKD1X23C - 1:   UAA    Transition G > A
                    8900      2897       valine ---> isoleucine
         Variant  PKD1X40 - 1:    UP     Transition C > T
                    11554     3781       none
         Variant  PKD1X41 - 1:    UP     3bp insertion (GGG)
                    IVS41+6ins3
         Variant  PKD1X45 - 1:    UAA    Transition G > A
                    12644     4145       valine --> isoleucine s.
         Variant  PKD1X10 - 1:    UP     Transition A > G
                    IVS9-4
         Variant  PKD1X11B - 1:   KP     Transition G > A
                    2911      900        none
         Variant  PKD1X11B - 2:   KP     Transition C > T
                    2941      910        none
         Variant  PKD1X11C - 1:   KP     Transition G > A
                    2911      900        none
         Variant  PKD1X11C - 2:   KP     Transition C > T
                    2941      910        none
         Variant  PKD1X15G - 1:   KP     Transversion A > C
                    4876      1555       none
         Variant  PKD1X15J - 1:   UP     Transition C > T
                    5383      1724       none
         Variant  PKD1X17 - 1:    KP     Transition T > C
                    7376      2389       none
         Variant  PKD1X18 - 1:    KP     Transition C > T
```

FIG. 14M

```
            7652      2481       none
Variant  PKD1X25 - 1:    KP   Transition A > G
        IVS24-17
Variant  PKD1X25 - 2:    KP   Transversion G > C
            9406      3065       none
Variant  PKD1X25 - 3:    KP   Transition T > C
            9407      3066       phenylalanine --> leucine
Variant  PKD1X26 - 1:    KP   Transition T > C
            9541      3110       none
Variant  PKD1X28 - 1:    UP   Transition T > C
        IVS27-13
Variant  PKD1X35 - 1:    KP   Transition C > T
           10743      3511       alanine --> valine
Variant  PKD1X36 - 1:    UPD  13bp insertion
           10884      3558       Frame Shift
Variant  PKD1X42 - 1:    UP   Transversion C > A    Homozygous
        IVS42+33
Variant  PKD1X44 - 1:    KP   Transition A > G
           12341      4044       isoleucine --> valine
Variant  PKD1X45 - 1:    KP   Transition C > T
           12384      4058       alanine --> valine
Variant  PKD1X45 - 2:    KP   Transition A > G
           12484      4091       none
Variant  PKD1X45 - 3:    KP   Transition C > T
           12617      4136       none
Variant  PKD1X46A - 1:   UP   Transition T > C
           12838      4209       none
Variant  PKD1X46B - 1:   UP   Transition G > A
```

FIG. 14N

```
            13135      3'UTR

Variant  PKD1X5A - 1:    UP   Transition C > T
         799       196      none
   Variant  PKD1X9 - 1:     UP   7bp deletion (TGGTGGG)
         IVS9+28del7
   Variant  PKD2X1B - 1:    KP   Transition G > A
         486       140      none

T.

Variant  PKD1X10 - 1:    UPD  Transition A > G
         IVS9-2
   Variant  PKD1X13 - 1:    UP   Transition A > G
         3322      1037     none
   Variant  PKD1X17 - 1:    UAA  Transition C > T
         7358      2383     arginine ---> cysteine
   Variant  PKD1X42 - 1:    UP   Transversion C > A
         IVS42+33
   Variant  PKD2X1B - 1:    KP   Transition G > A
         486       140      none

U.

Variant  PKD1X10 - 1:    UP   Transition A > G
         IVS9-4
   Variant  PKD1X11B - 1:   KP   Transition G > A
         2911      900      none
   Variant  PKD1X11B - 2:   KP   Transition C > T
         2941      910      none
   Variant  PKD1X11C - 1:   KP   Transition G > A
```

FIG. 14O

```
             2911        900         none
   Variant   PKD1X11C - 2:    KP    Transition C > T
             2941        910         none
   Variant   PKD1X13 - 1:     UP    Transition C > T
          IVS12-15
   Variant   PKD1X15G - 1:    KP    Transversion A > C
             4876       1555         none
   Variant   PKD1X15J - 1:    UP    Transition C > T
             5383       1724         none
   Variant   PKD1X15L - 1:    UP    Transition G > A
             5974       1921         none
   Variant   PKD1X17 - 1:     KP    Transition T > C
             7376       2389         none
   Variant   PKD1X18 - 1:     KP    Transition C > T
             7652       2481         none
   Variant   PKD1X26 - 1:     UP    Transition C > T
             9481       3090         none
   Variant   PKD1X46B - 1:    KP    Transition C > T
            12973       4254         none
   Variant   PKD1X9 - 1:      UP    7bp deletion (TGGTGGG)
          IVS9+28del7
Variant   PKD2X1A - 1:      KP    Transversion G > C
             149         28          arginine ---> proline
   Variant   PKD2X4 - 1:      UPD   Transition C > T
             1147        361         arginine ---> OPA (stop codon)

V.
   Variant   PKD1X15M - 1:    UP    Transition C > T
```

FIG. 14P

```
            6415      2068      none
    Variant  PKD2X1C - 1:    UPD   4bp Insertion of CGCC
             596       177      Frame Shift W.
    Variant  PKD1X10 - 1:    UP    Transition A > G
             IVS9-4
    Variant  PKD1X11C - 1:   UP    Transition C > T
             IVS11+23
    Variant  PKD1X13 - 1:    UPD   1 bp deletion of C
             3310      1033     Frame Shift
    Variant  PKD1X13 - 2:    KP    Transition T > C
             3274      1021     none
    Variant  PKD1X14 - 1:    KP    Transition T > C
             3486      1092     methionine --> threonine
    Variant  PKD1X15A - 1:   -UP   Transition C > T
             3583      1124     none
    Variant  PKD1X15A - 2:   UP    Transition C > T
             3586      1125     none
    Variant  PKD1X15E - 1:   KP    Transition T > C
             4406      1399     tryptophan --> arginine
    Variant  PKD1X15G - 1:   KP    Transversion A > C
             4876      1555     none
    Variant  PKD1X15J - 1:   UP    Transition C > T
             5383      1724     none
    Variant  PKD1X17 - 1:    KP    Transition T > C
             7376      2389     none
    Variant  PKD1X18 - 1:    KP    Transition C > T
```

FIG. 14Q

```
              7652        2481        none
Variant  PKD1X20 - 1:       KP    Transition T > C
              7919        2570        none
Variant  PKD1X21 - 1:       KP    Transition A > G
              8124        2638        histidine --> arginine
Variant  PKD1X25 - 1:       KP    Transition A > G
              IVS24-17
Variant  PKD1X25 - 2:       KP    Transversion G > C
              9406        3065        none
Variant  PKD1X25 - 3:       KP    Transition T > C
              9407        3066        phenylalanine --> leucine
Variant  PKD1X26 - 1:       KP    Transition T > C
              9541        3110        none
Variant  PKD1X44 - 1:       KP    Transition A > G
              12341       4044        isoleucine --> valine
Variant  PKD1X45 - 1:       KP    Transition A > G
              12484       4091        none
Variant  PKD1X46A - 1:      UP    Transition T > C
              12838       4209        none
Variant  PKD2X1A - 1:       KP    Transversion G > C
              149         28          arginine --> proline
Variant  PKD2X1B - 1:       KP    Transition G > A
              486         140         none X.
Variant  PKD1X10 - 1:       UP    Transition A > G
              IVS9-4
Variant  PKD1X11C - 1:      UP    Transition C > T
```

FIG. 14R

```
            IVS11+23
Variant  PKD1X13 - 1:    UPD   1 bp deletion of C
        3310     1033    Frame Shift
Variant  PKD1X13 - 2:    KP    Transition T > C
        3274     1021    none
Variant  PKD1X14 - 1:    KP    Transition T > C
        3486     1092    methionine --> threonine
Variant  PKD1X15A - 1:   UP    Transition C > T
        3583     1124    none
Variant  PKD1X15A - 2:   UP    Transition C > T
        3586     1125    none
Variant  PKD1X15E - 1:   KP    Transition T > C
        4406     1399    tryptophan --> arginine
Variant  PKD1X15G - 1:   KP    Transversion A > C
        4876     1555    none
Variant  PKD1X15J - 1:   UP    Transition C > T
        5383     1724    none
Variant  PKD1X17 - 1:    KP    Transition T > C
        7376     2389    none
Variant  PKD1X18 - 1:    KP    Transition C > T
        7652     2481    none
Variant  PKD1X20 - 1:    KP    Transition T > C
        7919     2570    none
Variant  PKD1X21 - 1:    KP    Transition A > G
        8124     2638    histidine --> arginine
Variant  PKD1X25 - 1:    KP    Transition A > G
        IVS24-17
Variant  PKD1X25 - 2:    KP    Transversion G > C
```

FIG. 14S

```
            9406       3065        none
    Variant  PKD1X25 - 3:     KP    Transition T > C
            9407       3065        phenylalanine --> leucine
    Variant  PKD1X26 - 1:     KP    Transition T > C
            9541       3110        none
    Variant  PKD1X44 - 1:     KP    Transition A > G
           12341       4044        isoleucine --> valine
    Variant  PKD1X45 - 1:     KP    Transition A > G
           12484       4091        none
    Variant  PKD1X46A - 1:    UP    Transition T > C
           12838       4209        none
    Variant  PKD2X1A - 1:     KP    Transversion G > C
             149         28        arginine --> proline
    Variant  PKD2X1B - 1:     KP    Transition G > A
             486        140        none Y.
    Variant  PKD1X1 - 1:      UPD   1bp deletion of C
             364         51        Frame Shift
    Variant  PKD1X11A - 1:    UAA   Transition A > G
            2427        739        glutamine --> arginine
    Variant  PKD1X15G - 1:    KP    Transition G > A
            4885       1558        none
    Variant  PKD1X15H - 1:    KP    Transition G > A
            4885       1558        none
    Variant  PKD1X27 - 1:     UAA   Transversion A > T
            9710       3167        isoleucine --> phenylalanine
    Variant  PKD1X42 - 1:
```

FIG. 14T

```
        Variant  PKD1X5C - 1:    KP    Transition T > C
            1330      373        none
        Variant  PKD2X1A - 1:    KP    Transversion G > C
            149       28         arginine --> proline Z.
        Variant  PKD1X13 - 1:    UP    Transition C > T
            IVS12-15

Variant  PKD1X15A - 1:   UPD   Transition G > A
            3694      1161       tryptophan --> OPA (stop codon)

Variant  PKD1X15B - 1:   UPD   Transition G > A
            3694      1161       tryptophan --> OPA (stop codon)

Variant  PKD1X5C - 1:    KP    Transition T > C
            1330      373        none Variant  PKD2X1A - 1:    KP    Transversion G > C
            149       28         arginine --> proline AA.
        Variant  PKD1X10 - 1:    UPD   1 bp insertion of G
            2291      694        Frame Shift Variant  PKD1X26 - 1:    UP    Transition C > T
            9475      3088       none Variant  PKD1X43 - 1:    UP    Transversion C > A
            IVS43+42

Variant  PKD1X5C - 1:    KP    Transition T > C    Homozygous
            1330      373        none Variant  PKD2X1A - 1:    KP    Transversion G > C
            149       28         arginine --> proline
```

Variant PKD1X23A - 1:    UAA    Transition C > T 8516    2769    leucine --> phenylalanine Variant PKD1X32 - 1:    UP    Transition G > A

IVS32+33

Variant PKD1X33 - 1:    UAA    Transversion G > T 10441    3410    tryptophan --> cysteine Variant PKD1X7 - 1:    UP    Transition C > T    Homozygous 1750    513    none

Variant PKD2X1B - 1:    UPD    1 bp deletion of G 405    113    Frameshift --> stop codon (Amber)

CC.

Variant PKD1X13 - 1:    UAA    Transition A > G 3312    1034    asparagine --> serine Variant PKD1X24 - 1:    UPD    Transversion G > C IVS23-1    splice site mutation Variant PKD2X1B - 1:    KP    Transition G > A 486    140    none

DD.

Variant PKD1X10 - 1:    UP    Transition A > G

IVS9-4

Variant PKD1X11A - 1:    UAA    Transition A > G 2427    739    glutamine-->arginine Variant PKD1X11B - 1:    KP    Transition G > A 2911    900    none

FIG. 14V

```
Variant  PKD1X11B - 2:    KP    Transition C > T
         2941     910          None
Variant  PKD1X11C - 1:    KP    Transition G > A
         2911     900          none
Variant  PKD1X11C - 2:    KP    Transition C > T
         2941     910          none
Variant  PKD1X15G - 1:    KP    Transversion A > C
         4876     1555         none
Variant  PKD1X15J - 1:    UP    Transition C > T
         5383     1724         none
Variant  PKD1X17 - 1:     KP    Transition T > C
         7376     2389         None
Variant  PKD1X18 - 1:     KP    Transition C > T
         7652     2481         none
Variant  PKD1X19 - 1:     UP    Transversion C > A
         IVS19+24
Variant  PKD1X24 - 1:     UPD   1bp insertion of T
         9134     2975         Frame Shift
Variant  PKD1X25 - 1:     KP    Transition A > G
         IVS24-17
Variant  PKD1X25 - 2:     KP    Transversion G > C
         9406     3065         none
Variant  PKD1X25 - 3:     KP    Transition T > C
         9407     3066         phenylalanine-->leucine
Variant  PKD1X26 - 1:     KP    Transition T > C
         9541     3110         None
Variant  PKD1X28 - 1:     UP    Transition T > C
         IVS27-13
```

FIG. 14W

```
Variant  PKD1X30 - 1:    UP   Transition C > T
    IVS29-11

Variant  PKD1X35 - 1:    KP   Transition C > T
    10743    3511        alanine --> valine Variant  PKD1X44 - 1:    KP   Transition A > G
    12341    4044        isoleucine --> valine Variant  PKD1X45 - 1:    KP   Transition C > T
    12384    4058        alanine-->valine Variant  PKD1X45 - 2:    KP   Transition A > G
    12484    4091        None Variant  PKD1X45 - 3:    KP   Transition C > T
    12617    4136        None Variant  PKD1X46A - 1:   UP   Transition T > C
    12838    4209        none Variant  PKD1X46B - 1:   UP   Transition G > A
    13135    3'UTR       none Variant  PKD1X5C - 1:    KP   Transition T > C
    1330     373         none Variant  PKD1X9 - 1:     UP   7bp deletion (Homozygous)
    IVS9+28del7

Variant  PKD2X1A - 1:    KP   Transversion G > C
    149      28          arginine --> proline Variant  PKD2X1B - 1:    KP   Transition G > A
    486      140         none
```

EE.

```
Variant  PKD1X10 - 1:    UP   Transition A > G
    IVS9-4
```

FIG. 14X

```
Variant  PKD1X13 - 1:      KP    Transition T > C
       3274      1021      None
Variant  PKD1X14 - 1:      KP    Transition T > C
       3486      1032      methionine --> threonine
Variant  PKD1X15A - 1:     UP    Transition C > T
       3583      1124      None
Variant  PKD1X15A - 2:     UP    Transition C > T
       3586      1125      None
Variant  PKD1X15E - 1:     KP    Transition T > C
       4406      1399      tryptophan --> arginine
Variant  PKD1X15G - 1:     KP    Transversion A > C
       4876      1555      None
Variant  PKD1X15J - 1:     UP    Transition C > T
       5383      1724      None
Variant  PKD1X16 - 1:      UP    Transition G > A
       IVS16+21
Variant  PKD1X17 - 1:      KP    Transition T > C
       7376      2389      None
Variant  PKD1X18 - 1:      KP    Transition C > T
       7652      2481      None
Variant  PKD1X20 - 1:      KP    Transition T > C
       7919      2570      None
Variant  PKD1X21 - 1:      KP    Transition A > G
       8124      2638      histidine --> arginine
Variant  PKD1X35 - 1:      UPD   2bp deletion of GA
       10735-107363508-3509Frame Shift
Variant  PKD1X35 - 2:      KP    Transition C > T
       10743     3511      alanine --> valine
```

FIG. 14Y

```
Variant  PKD1X42 - 1:
Variant  PKD1X44 - 1:    KP    Transition A > G    Homozygous
    12341    4044       isoleucine --> valine
Variant  PKD1X45 - 1:    KP    Transition C > T
    12384    4058       alanine --> valine
Variant  PKD1X45 - 2:    KP    Transition A > G    Homozygous
    12484    4091       None
Variant  PKD1X45 - 3:    KP    Transition C > T
    12617    4136       None
Variant  PKD1X46A - 1:   UP    Transition T > C    Homozygous
    12638    4209       None
Variant  PKD1X8 - 1:     KP    Transition C > T
    1921     570        None
Variant  PKD2X1A - 1:    KP    Transversion G > C
    149      28         arginine --> proline FF.
    Variant  PKD1X42 - 1:    UPD   1 bp deletion (Homozygous)
        11836    3875       Frame Shift
    Variant  PKD1X43 - 1:    UP    Transversion C > G
        12184    3991       None
    Variant  PKD2X1A - 1:    KP    Transversion G > C
        149      28         arginine --> proline
    Variant  PKD2X7 - 1:     UAA   Transversion G > C
        1720     552        alanine --> proline GG.
    Variant  PKD1X42 - 1:    UPD   1 bp deletion (Homozygous)
```

FIG. 14Z

```
            11836      3875      Frame Shift
    Variant  PKD1X43 - 1:    UP    Transversion C > G
            12184      3991      None
    Variant  PKD2X1A - 1:    KP    Transversion G > C
              149        28      arginine --> proline
    Variant  PKD2X7 - 1:     UAA   Transversion G > C
             1720       552      alanine --> proline HH.
    Variant  PKD1X15F - 1:
    Variant  PKD1X23A - 1:   UPD   Transversion G > T
             8639      2810      glutamic acid ---> AMB (stop codon)
    Variant  PKD1X23A - 2:    KP   Transition G > A
             8651      2814      glycine ---> arginine
    Variant  PKD1X23A - 3:   UAA   Transition T > C
             8658      2816      leucine ---> proline
    Variant  PKD1X23A - 4:    UP   Transition C > T
             8662      2817      none
    Variant  PKD1X23B - 1:   UPD   Transversion G > T
             8639      2810      glutamic acid ---> AMB (stop codon)
    Variant  PKD1X23B - 2:    KP   Transition G > A
             8651      2814      glycine ---> arginine
    Variant  PKD1X23B - 3:   UAA   Transition T > C
             8658      2816      leucine ---> proline
    Variant  PKD1X23B - 4:    UP   Transition C > T
             8662      2817      none
    Variant  PKD1X23C - 1:   UAA   Transition G > A
             8900      2897      valine ---> isoleucine
```

FIG. 14AA

```
Variant  PKD1X40 - 1:    UP   Transition C > T
    11554    3781        none
Variant  PKD1X41 - 1:    UP   3bp insertion (GGG)
    IVS41+6ins3
Variant  PKD1X45 - 1:    UAA  Transition G > A
    12644    4145        valine --> isoleucine
```

II.

```
Variant  PKD1X1 - 1:
Variant  PKD1X14 - 1:    UPD  Transition C > T
    3395     1062        Glutamine > AMB (stop codon)
Variant  PKD1X15G - 1:   KP   Transition G > A
    4885     1558        None
Variant  PKD1X15H - 1:   KP   Transition G > A
    4885     1558        None
Variant  PKD1X15K - 1:   UP   Transition C > T
    5893     1894        None
Variant  PKD1X15M - 1:
Variant  PKD1X36 - 1:    KP   Transition C > T
    10976    3589        None
Variant  PKD1X43 - 1:    KP   Transition C > T
    12124    3971        None
Variant  PKD1X44 - 1:    KP   1 bp deletion of G
    IVS44+22delG
Variant  PKD2X1A - 1:    KP   Transversion G > C
    149      28          Arginine > Proline
```

```
Variant  PKD1X15G - 1:    KP   Transition G > A
    4885      1558     None
Variant  PKD1X15H - 1:    KP   Transition G > A
    4985      1559     None
Variant  PKD1X2 - 1:
Variant  PKD1X42 - 1:     UP   Transition C > T
    IVS41-11
Variant  PKD1X46B - 1:    UPD  Transversion G > T
    12926     4239     Glutamic acid --> Stop codon (AMB)
Variant  PKD2X1A - 1:     KP   Transversion G > C   Homozygous
    149       28       Arginine > Proline
```

FIG. 14CC

Figure 15. PKD1 cDNA sequence (GenBank Accesion No. L33243). For a copy of the PKD1 genomic sequence please refer to GenBank (Accesion No. L39891). Exon and PCR product junctions are depicted above the nucleotide sequence. Amino acids are positioned under the center of each codon.

| Codon Number | Position | Sequence / Amino acids |
|---|---|---|
| | | Exon 1 |
| 1 | 212 | atgccgcccgccgcgcccgcccgcctggcgctggccctgggcctg |
| | | M P P A A P A R L A L A L G L |
| 16 | 257 | ggcctgtggctcggggcgctggcggggggcccggggcgcggctgc |
| | | G L W L G A L A G G P G R G C |
| 31 | 302 | gggccctgcgagccccctgcctctgcggcccagcgccggcgcc |
| | | G P C E P P C L C G P A P G A |
| 46 | 347 | gcctgccgcgtcaactgctcggccgcgggctgcggacgctcggt |
| | | A C R V N C S G R G L R T L G |
| | | Exon 2 |
| 61 | 392 | cccgcgctgcgcatccccgcggacgccacagcgct......... |
| | | P A L R I P A D A T A L..... |
| 76 | 437 | ............................................ |
| | | ............................................ |
| | | Exon 3 |
| 91 | 482 | ..............ggatataagcaacaacaagatttctacg |
| | | ......... D I S N N K I S T |
| | | Exon 4 |
| 106 | 527 | ttagaagaaggaatatttgctaatttatttaatttaagtgaaat. |
| | | L E E G I F A N L F N L S E I |
| 121 | 572 | ............................................ |
| | | ............................................ |
| 136 | 617 | ............................................ |
| | | ............................................ |
| 151 | 662 | ............................................ |
| | | ............................................ |
| | | Exon 5-A |
| 166 | 707 | ............................ggtgaggagtat |
| | | ........................... G E E Y |
| 181 | 752 | gtcgcctgcctccctgacaacagctcaggcaccgtggcagcagtg |
| | | V A C L P D N S S G T V A A V |

FIG. 15A

Figure 15 con.

```
 797 tcctttcagctgcccacgaaggcctgcttcagccagaggcctgc
 196    S  F  S  A  H  E  G  L  L  Q  P  E  A  C 842 agcgccttctgcttctccaccggccagggcctcgcagccctctcg
 211    S  A  F  C  F  S  T  G  Q  G  L  A  A  L  S
                                          → 5-B
 887 gagcagggctggtgcctgtgtggggcggcccagccctccagtgcc
 226    E  Q  G  W  C  L  C  G  A  A  Q  P  S  S  A
           ←          5-A
 932 tcctttgcctgcctgtccctctgctccggccccccgccacctcct
 241    S  F  A  C  L  S  L  C  S  G  P  P  P  P  P 977 gcccccacctgtaggggccccaccctcctccagcacgtcttccct
 256    A  P  T  C  R  G  P  T  L  L  Q  H  V  F  P 1022 gcctccccaggggccaccctggtggggccccacggacctctggcc
 271    A  S  P  G  A  T  L  V  G  P  H  G  P  L  A 1067 tctggccagctagcagccttccacatcgctgccccgctccctgtc
 286    S  G  Q  L  A  A  F  H  I  A  A  P  L  P  V
                                          → 5-C
1112 actgccacacgctgggacttcggagacggctccgccgaggtggat
 301    T  A  T  R  W  D  F  G  D  G  S  A  E  V  D
                              ←              5-B
1157 gccgctgggccggctgcctcgcatcgctatgtgctgcctgggcgc
 316    A  A  G  P  A  A  S  H  R  Y  V  L  P  G  R 1202 tatcacgtgacggccgtgctggccctgggggccggctcagccctg
 331    Y  H  V  T  A  V  L  A  L  G  A  G  S  A  L 1247 ctggggacagacgtgcaggtggaagcggcacctgccgccctggag
 346    L  G  T  D  V  Q  V  E  A  A  P  A  A  L  E 1292 ctcgtgtgcccgtcctcggtgcagagtgacgagagccttgacctc
 361    L  V  C  P  S  S  V  Q  S  D  E  S  L  D  L 1337 agcatccagaaccgcggtggttcaggcctggaggccgcctacagc
 376    S  I  Q  N  R  G  G  S  G  L  E  A  A  Y  S
                                          Exon 6
1382 atcgtggccctggcgaggagccggcccgacggtgcaccgtc
 391    I  V  A  L  G  E  E  P  A  R
```

FIG. 15B

Figure 15 con.

```
     1427 ................................................
406       ................................................

1472 ................................................
421       ................................................

1517 ................................................
436       ................................................
                                                  Exon 7
     1562 ......................................gagcctagac
451       .......................................S  L  D 1607 gtgtggatcggcttctcgactgtgcaggggtggaggtgggccca
466       V  W  I  G  F  S  T  V  Q  G  V  E  V  G  P 1652 gcgccgcagggcgaggccttcagcctggagagctgccagaactgg
481       A  P  Q  G  E  A  F  S  L  E  S  C  Q  N  W 1697 ctgcccggggagccacacccagccacagccgagcactgcgtccgg
496       L  P  G  E  P  H  P  A  T  A  E  H  C  V  R 1742 ctcggcccaccgggtggtgtaacaccgacctgtgctcagcgcc
511       L  G  P  T  G  W  C  N  T  D  L  C  S  A  P
                                           Exon 8
     1787 cacagctacgtctgcgagctgcagcccggag.................
526       H  S  Y  V  C  E  L  Q  P  G ...................

1832 ................................................
541       ................................................

1877 ................................................
556       ................................................
                                 Exon 9
     1922 ..............gtcatggtattcccggggcctgcgtctgagccgt
571       ..............V  M  V  F  P  G  L  R  L  S  R 1967 gaagccttcctcaccacggccgaatttgggacccaggagctccgg
586       E  A  F  L  T  T  A  E  F  G  T  Q  E  L  R 2012 cggcccgcccagctgcggctgcaggtgtaccggctcctcagcaca
601       R  P  A  Q  L  R  L  Q  V  Y  R  L  L  S  T
          Exon 10
     2057 gcag............................................
616       A  .............................................
```

FIG. 15C

Figure 15 con.

```
       2102 gccaccaggaccagccgcccggcgtcatgccaggtgccc
631         D  H  Q  D  Q  P  P  G  V  M  P  G  A  R
       2147 ccgtcgcctggcgccaacatccccgccccgaccttcctgc
646         P  S  P  G  A  N  I  P  A  P  D  L  S  R
       2192 cacgccagcgctgcgcaactctggcttcggccgccggctc
661         H  A  S  A  A  Q  L  W  L  R  P  P  A  S
       2237 agccccgccctgcacgcgttgcagggccgcctgctctccg
676         S  P  A  L  H  A  L  Q  G  R  L  L  S  V
                                              Exon 11-A
       2292 gcgccgggcccccgcagccgcagtcaccctccacggccag
691         A  P  G  P  P  Q  P  Q    V  T  L  H  G  Q
       2327 gatgtcctcatgctccctggtgacctcgttggcttgcagcacgac
706         D  V  L  M  L  P  G  D  L  V  G  L  Q  H  D
       2372 gctggccctggcgccctcctgcactgctcgccggctcccggccac
721         A  G  P  G  A  L  L  H  C  S  P  A  P  G  H
       2417 cctggtccccaggccccgtacctctccgccaacgcctcgtcatgg
736         P  G  P  Q  A  P  Y  L  S  A  N  A  S  S  W
                                                    → 11-B
       2462 ctgccccacttgccagcccagctggagggcacttgggcctgccct
751         L  P  H  L  P  A  Q  L  E  G  T  W  A  C  P
       2507 gcctgtgccctgcggctgcttgcagccacggaacagctcaccgtg
766         A  C  A  L  R  L  L  A  A  T  E  Q  L  T  V
            ←          11-A
       2552 ctgctgggcttgaggcccaaccctggactgcggatgcctgggcgc
781         L  L  G  L  R  P  N  P  G  L  R  M  P  G  R
       2597 tatgaggtccgggcagaggtgggcaatggcgtgtccaggcacaac
796         Y  E  V  R  A  E  V  G  N  G  V  S  R  H  N
       2642 ctctcctgcagctttgacgtggtctccccagtggctgggctgcgg
811         L  S  C  S  F  D  V  V  S  P  V  A  G  L  R
       2687 gtcatctaccctgccccccgcgacggccgcctctacgtgcccacc
826         V  I  Y  P  A  P  R  D  G  R  L  Y  V  P  T
       2732 aacggctcagccttggtgctccaggtggactctggtgccaacgcc
841         N  G  S  A  L  V  L  Q  V  D  S  G  A  N  A
```

FIG. 15D

Figure 15 con.

```
2777 acggccacggctcgctggcctggggggcagtgtcagcgcccgctttt
856   T  A  T  A  R  W  P  G  G  S  V  S  A  R  F
                                              → 11-C
2822 gagaatgtctgccctgccctggtggccaccttcgtgcccggctgc
871   E  N  V  C  P  A  L  V  A  T  F  V  P  G  C
2867 ccctgggagaccaacgatacctgttctcagtggtagcactgccg
886   P  W  E  T  N  D  T  L  F  S  V  V  A  L  P
                                        ←  11-B
2912 tggctcagtgagggggagcacgtggtggacgtggtggtggaaaac
901   W  L  S  E  G  E  H  V  V  D  V  V  V  E  N
2957 agcgccagccgggccaacctcagcctgcgggtgacggcggaggag
916   S  A  S  R  A  N  L  S  L  R  V  T  A  E  E
3002 cccatctgtggcctccgcgccacgcccagccccgaggcccgtgta
931   P  I  C  G  L  R  A  T  P  S  P  E  A  R  V
                                 Exon 12
3047 ctgcagggagtcctagtg...
946   L  Q  G  V  L  V  ...
3092 ...
961   ...
3137 ...
976   ...
                     Exon 13
3182 ...ctgacggcctccaaccacgtgagcaacgtc
991   ...  L  T  A  S  N  H  V  S  N  V
3227 accgtgaactacaacgtaaccgtggagcggatgaacaggatgcag
1006  T  V  N  Y  N  V  T  V  E  R  M  N  R  M  Q
3272 ggtctgcaggtctccacagtgccggccgtgctgtcccccaatgcc
1021  G  L  Q  V  S  T  V  P  A  V  L  S  P  N  A
3317 acgctagcactgacggcgggcgtgctggtggactcggccgtggag
1036  T  L  A  L  T  A  G  V  L  V  D  S  A  V  E
                           Exon 14
3362 gtggccttcct...
1051  V  A  F  L  ...
3407 ...
1066  ...
```

FIG. 15E

Figure 15 con.

```
     3452 gctgtgccagcctgctgcaggagaggatgagcacgac
1081      A V P A A C C R R G E D E H D
                            Exon 15-A
     3497 gctgcccaggtgagtacctcctgaccgtgctggcatctaatgcc
1096      A A Q  G  E  Y  L  L  T  V  L  A  S  N  A 3542 ttcgagaacctgacgcagcaggtgcctgtgagcgtgcgcgcctcc
1111      F  E  N  L  T  Q  Q  V  P  V  S  V  R  A  S 3587 ctgccctccgtggctgtgggtgtgagtgacggcgtcctggtggcc
1126      L  P  S  V  A  V  G  V  S  D  G  V  L  V  A
                                              →15-B 3632 ggccggcccgtcaccttctacccgcacccgctgccctcgcctggg
1141      G  R  P  V  T  F  Y  P  H  P  L  P  S  P  G 3677 ggtgttctttacacgtgggacttcggggacggctccctgtcctg
1156      G  V  L  Y  T  W  D  F  G  D  G  S  P  V  L
          ←     15-A 3722 acccagagccagccggctgccaaccacacctatgcctcgagggggc
1171      T  Q  S  Q  P  A  A  N  H  T  Y  A  S  R  G 3767 acctaccacgtgcgcctggaggtcaacaacacggtgagcggtgcg
1186      T  Y  H  V  R  L  E  V  N  N  T  V  S  G  A 3812 gcggcccaggcggatgtgcgcgtctttgaggagctccgcggactc
1201      A  A  Q  A  D  V  R  V  F  E  E  L  R  G  L
                                    →15-C 3857 agcgtggacatgagcctggccgtggagcagggcgcccccgtggtg
1216      S  V  D  M  S  L  A  V  E  Q  G  A  P  V  V
                          ←      15-B 3902 gtcagcgccgcggtgcagacgggcgacaacatcacgtggaccttc
1231      V  S  A  A  V  Q  T  G  D  N  I  T  W  T  F 3947 gacatgggggacggcaccgtgctgtcgggcccggaggcaacagtg
1246      D  M  G  D  G  T  V  L  S  G  P  E  A  T  V 3992 gagcatgtgtacctgcgggcacagaactgcacagtgaccgtgggt
1261      E  H  V  Y  L  R  A  Q  N  C  T  V  T  V  G 4037 gcggccagccccgccggccacctggcccggagcctgcacgtgctg
1276      A  A  S  P  A  G  H  L  A  R  S  L  H  V  L
           →15-D 4082 gtcttcgtcctggaggtgctgcgcgttgaacccgccgcctgcatc
1291      V  F  V  L  E  V  L  R  V  E  P  A  A  C  I
          ←     15-C
```

FIG. 15F

Figure 15 con.

```
     4127 cccacgcagcctgacgcgcggctcacggcctacgtcaccgggaac
1306      P  T  Q  P  D  A  R  L  T  A  Y  V  T  G  N 4172 ccggcccactacctcttcgactggaccttcggggatggctcctcc
1321      P  A  H  Y  L  F  D  W  T  F  G  D  G  S  S 4217 aacacgaccgtgcggggtgcccgacggtgacacacaacttcacg
1336      N  T  T  V  R  G  C  P  T  V  T  H  N  F  T
                                              → 15-E 4262 cggagcggcacgttccccctggcgctggtgctgtccagccgcgtg
1351      R  S  G  T  F  P  L  A  L  V  L  S  S  R  V
                                  ←           15-D 4307 aacagggcgcattacttcaccagcatctgcgtggagccagaggtg
1366      N  R  A  H  Y  F  T  S  I  C  V  E  P  E  V 4352 ggcaacgtcaccctgcagccagagaggcagtttgtgcagctcggg
1381      G  N  V  T  L  Q  P  E  R  Q  F  V  Q  L  G 4397 gacgaggcctggctggtggcatgtgcctggcccccgttccctac
1396      D  E  A  W  L  V  A  C  A  W  P  P  F  P  Y 4442 cgctacacctgggactttggcaccgaggaagccgcccccacccgt
1411      R  Y  T  W  D  F  G  T  E  E  A  A  P  T  R
                                              → 15-F 4487 gccagggggccctgaggtgacgttcatctaccgagacccaggctcc
1426      A  R  G  P  E  V  T  F  I  Y  R  D  P  G  S
                                  ←           15-E 4532 tatcttgtgacagtcaccgcgtccaacaacatctctgctgccaat
1441      Y  L  V  T  V  T  A  S  N  N  I  S  A  A  N 4577 gactcagccctggtggagctgcaggagcccgtgctggtcaccagc
1456      D  S  A  L  V  E  V  Q  E  P  V  L  V  T  S 4622 atcaaggtcaatggctcccttgggctggagctgcagcagccgtac
1471      I  K  V  N  G  S  L  G  L  E  L  Q  Q  P  Y
                                              → 15-G 4667 ctgttctctgctgtgggccgtgggcgccccgccagctacctgtgg
1486      L  F  S  A  V  G  R  G  R  P  A  S  Y  L  W 4712 gatctgggggacggtggtggctcgagggtccggaggtcacccac
1501      D  L  G  D  G  G  W  L  E  P  E  V  T  H
                              ←      15-F 4757 gcttacaacagcacaggtgacttcaccgttagggtggccggctgg
1516      A  Y  N  S  T  G  D  F  T  V  R  V  A  G  W
```

FIG. 15G

Figure 15 con.

```
4802 aatgaggtgagccgcagcgaggcctggctcaatgtgacggtgaag
1531      N  E  V  S  R  S  E  A  W  L  N  V  T  V  K
                      →15-H 4847 cggcgcgtgcggggctcgtcgtcaatgcaagccgcacggtggtg
1546      R  R  V  R  G  L  V  V  N  A  S  R  T  V  V
          ←
                        15-G 4892 ccctgaatgggagcgtgagcttcagcacgtcgctggaggccggc
1561      P  L  N  G  S  V  S  F  S  T  S  L  E  A  G 4937 agtgatgtgcgctattcctgggtgctctgtgaccgctgcacgccc
1576      S  D  V  R  Y  S  W  V  L  C  D  R  C  T  P 4982 atccctggcggtcctaccatctcttacaccttccgctccgtgggc
1591      I  P  G  G  P  T  I  S  Y  T  F  R  S  V  G
                                              →15-I 5027 accttcaatatcatcgtcacggctgagaacgaggtgggctccgcc
1606      T  F  N  I  I  V  T  A  E  N  E  V  G  S  A 5072 caggacagcatcttcgtctatgtcctgcagctcatagagggggctg
1621      Q  D  S  I  F  V  Y  V  L  Q  L  I  E  G  L
     ←         15-H 5117 caggtggtgggcggtggccgctacttcccccaccaaccacacggta
1636      Q  V  V  G  G  G  R  Y  F  P  T  N  H  T  V 5162 cagctgcaggccgtggttagggatggcaccaacgtctcctacagc
1651      Q  L  Q  A  V  V  R  D  G  T  N  V  S  Y  S
                                              →15-J 5207 tggactgcctggagggacagggggcccggccctggccggcagcggc
1666      W  T  A  W  R  D  R  G  P  A  L  A  G  S  G 5252 aaaggcttctcgctcaccgtgctcgaggccggcacctaccatgtc
1681      K  G  F  S  L  T  V  L  E  A  G  T  Y  H  V
                        ←         15-I 5297 cagctgcgggccaccaacatgctgggcagcgcctgggccgactgc
1696      Q  L  R  A  T  N  M  L  G  S  A  W  A  D  C 5342 accatggacttcgtggagcctgtggggtggctgatggtgaccgcc
1711      T  M  D  F  V  E  P  V  G  W  L  M  V  T  A 5387 tccccgaacccagctgccgtcaacacaagcgtcacctcagtgcc
1726      S  P  N  P  A  A  V  N  T  S  V  T  L  S  A 5432 gagctggctggtggcagtggtgtcgtatacacttggtccttggag
1741      E  L  A  G  G  S  G  V  V  Y  T  W  S  L  E
```

FIG. 15H

Figure 15 con.

```
           →15-K
     5477 gagggctgagctgggagacctccgagccatttaccacccatagc
1756       E  G  L  S  W  E  T  S  E  P  F  T  T  H  S 5522 ttccccacacccggcctgcacttggtcaccatgacggcagggaac
1771       F  P  T  P  G  L  H  V  T  M  T  A  G  N 5567 ccgctgggctcagccaacgccaccgtggaagtggatgtgcaggtg
1786       P  L  G  S  A  N  A  T  V  E  V  D  V  Q  V 5612 cctgtgagtggcctcagcatcagggccagcgagcccggaggcagc
1801       P  V  S  G  L  S  I  R  A  S  E  P  G  G  S 5657 ttcgtggcggccggtcctctgtgccctttggggggcagctggcc
1816       F  V  A  A  G  S  S  V  P  F  W  G  Q  L  A
                               ← 15-J
     5702 acgggcaccaatgtgagctggtgctgggctgtgcccggcggcagc
1831       T  G  T  N  V  S  W  C  W  A  V  P  G  G  S 5747 agcaagcgtggccctcatgtcaccatggtcttcccggatgctggc
1846       S  K  R  G  P  H  V  T  M  V  F  P  D  A  G 5792 accttctccatccggctcaatgcctccaacgcagtcagctgggtc
1861       T  F  S  I  R  L  N  A  S  N  A  V  S  W  V 5837 tcagccacgtacaacctcacggcggaggagcccatcgtgggcctg
1876       S  A  T  Y  N  L  T  A  E  E  P  I  V  G  L
                →15-L
     5882 gtgctgtgggccagcagcaaggtggtggcgcccgggcagctggtc
1891       V  L  W  A  S  S  K  V  V  A  P  G  Q  L  V
                     ← 15-K
     5927 cattttcagatcctgctggctgccggctcagctgtcaccttccgc
1906       H  F  Q  I  L  L  A  A  G  S  A  V  T  F  R 5972 ctgcaggtcggcggggccaaccccgaggtgctccccggcccccgt
1921       L  Q  V  G  G  A  N  P  E  V  L  P  G  P  R 6017 ttctcccacagcttccccgcgtcggagaccacgtggtgagcgtg
1936       F  S  H  S  F  P  R  V  G  D  H  V  V  S  V 6062 cggggcaaaaaccacgtgagctgggcccaggcgcaggtgcgcatc
1951       R  G  K  N  H  V  S  W  A  Q  A  Q  V  R  I 6107 gtggtgctggaggccgtgagtgggctgcagatgcccaactgctgc
1966       V  V  L  E  A  V  S  G  L  Q  M  P  N  C  C
```

FIG. 15I

Figure 15 con.

```
6152 gagcctggcatcgccacgggcactgagaggaacttcacagcccgc
1981  E  P  G  I  A  T  G  T  E  R  N  F  T  A  R 6197 gtgcagcgcggctctcgggtcgcctacgcctggtacttctcgctg
1996  V  Q  R  G  S  R  V  A  Y  A  W  Y  F  S  L
              →15-M 6242 cagaaggtccagggcgactcgctggtcatcctgtcgggccgcgac
2011  Q  K  V  Q  G  D  S  L  V  I  L  S  G  R  D 6287 gtcacctacacgcccgtggccgcgggctgttggagatccaggtg
2026  V  T  Y  T  P  V  A  A  G  L  L  E  I  Q  V
                                    ←     15-L 6332 cgcgccttcaacgccctgggcagtgagaaccgcacgctggtgctg
2041  R  A  F  N  A  L  G  S  E  N  R  T  L  V  L 6377 gaggttcaggacgccgtccagtatgtggccctgcagagcggcccc
2056  E  V  Q  D  A  V  Q  Y  V  A  L  Q  S  G  P 6422 tgcttcaccaaccgctcggcgcagtttgaggccgccaccagcccc
2071  C  F  T  N  R  S  A  Q  F  E  A  A  T  S  P 6467 agccccggcgtgtggcctaccactgggactttggggatgggtcg
2086  S  P  R  V  W  P  T  T  G  D  F  G  D  G  S 6512 ccagggcaggacacagatgagcccagggccgagcactcctacctg
2101  P  G  Q  D  T  D  E  P  R  A  E  H  S  Y  L 6557 aggcctggggactaccgcgtgcaggtgaacgcctccaacctggtg
2116  R  P  G  D  Y  R  V  Q  V  N  A  S  N  L  V 6602 agcttcttcgtggcgcaggccacggtgaccgtccaggtgctggcc
2131  S  F  F  V  A  Q  A  T  V  T  V  Q  V  L  A 6647 tgccgggagccggaggtggacgtggtcctgcccctgcaggtgctg
2146  C  R  E  P  E  V  D  V  V  L  P  L  Q  V  L
                              →15-N 6692 atgcggcgatcacagcgcaactacttggaggcccacgttgacctg
2161  M  R  R  S  Q  R  N  Y  L  E  A  H  V  D  L 6737 cgcgactgcgtcacctaccagactgagtaccgctgggaggtgtat
2176  R  D  C  V  T  Y  Q  T  E  Y  R  W  E  V  Y 6782 cgcaccgccagctgccagcggccgggggcgcccagcgcgtgtggcc
2191  R  T  A  S  C  Q  R  P  G  R  P  A  R  V  A
```

FIG. 15J

Figure 15 con.

```
        6827 ctgcccggcgtggacgtgagccggcctcggctggtgctgccgcgg
2206          L  P  G  V  D  V  S  R  P  R  L  V  L  P  R 6872 ctggcgctgcctgtggggcactactgctttgtgtttgtcgtgtca
2221          L  A  L  P  V  G  H  Y  C  F  V  F  V  V  S 6917 tttggggacacgccactgacacagagcatccaggccaatgtgacg
2236          F  G  D  T  P  L  T  Q  S  I  Q  A  N  V  T 6962 gtggcccccgagcgcctggtgcccatcattgagggtggctcatac
2251          V  A  P  E  R  L  V  P  I  I  E  G  G  S  Y 7007 cgcgtgtggtcagacacacgggacctggtgctggatggagcgag
2266          R  V  W  S  D  T  R  D  L  V  L  D  G  S  E 7052 tcctacgaccccaacctggaggacggcgaccagacgccgctcagt
2281          S  Y  D  P  N  L  E  D  G  D  Q  T  P  L  S
                                                    Exon 16
        7097 ttccactgggcctgtgtggcttcgacacag aggagccggcgcc
2296          F  H  W  A  C  V  A  S  T  Q 7142
2311

7187
2326

7232
2341
             Exon 17
        7277 gtgctgatccggagtggccgggtgcccattgtgtccttggagtgt
2356          V  L  I  R  S  G  R  V  P  I  V  S  L  E  C 7322 gtgtcctgcaaggcacaggccgtgtacgaagtgagccgcagctcc
2371          V  S  C  K  A  Q  A  V  Y  E  V  S  R  S  S 7367 tacgtgtacttggagggccgctgcctcaattgcagcagcggctcc
2386          Y  V  Y  L  E  G  R  C  L  N  C  S  S  G  S
                        Exon 18
        7412 aagcgaggg
2401          K  R  G 7457
2416
```

FIG. 15K

Figure 15 con.

FIG. 15L

Figure 15 con.

```
      3177 cacactgtggatgacatccagcagatcgctgctgcgctggcccag
2656       H  T  V  D  D  I  Q  Q  I  A  A  A  L  A  Q
                                Exon 22
      8222 tgcatggggccagcaggagggtcctgtgcgctcgttcctgaag
2671       C  M  G  P  A  Q  G  G  P  C  A  L  V  P  E 8267 cagacgttcaccaagctggaagccttctgctcctcctgcaggca
2686       Q  T  F  T  K  L  E  A  F  C  S  S  C  R  Q 8312 gagacactggcaggcaccgacgaggccaccgccatcgcagacagc
2701       E  T  L  A  G  T  D  E  A  T  A  I  A  D  S
                                   Exon 23-A
      8357 atgctcaacatcacaggagacctcatccacctggccagctcggac
2716       M  L  N  I  T  G  D  L  I  H  L  A  S  S  D 8402 gtgcgggcaccacagccctcagagctgggagccgagtcaccatct
2731       V  R  A  P  Q  P  S  E  L  G  A  E  S  P  S 8447 cggatggtggcgtcccaggcctacaacctgacctctgccctcatg
2746       R  M  V  A  S  Q  A  Y  N  L  T  S  A  L  M 8492 cgcatcctcatgcgctcccgcgtgctcaacgaggagcccctgacg
2761       R  I  L  M  R  S  R  V  L  N  E  E  P  L  T
                                                → 23-B
      8537 ctggcgggcgaggagatcgtggcccagggcaagcgctcggacccg
2776       L  A  G  E  E  I  V  A  Q  G  K  R  S  D  P 8582 cggagcctgctgtgctatggcggcgccccagggcctggctgccac
2791       R  S  L  L  C  Y  G  G  A  P  G  P  G  C  H 8627 ttctccatccccgaggctttcagcggggccctggccaacctcagt
2806       F  S  I  P  E  A  F  S  G  A  L  A  N  L  S
                         → 23-C
      8672 gacgtggtgcagctcatctttctggtggactccaatccctttccc
2821       D  V  V  Q  L  I  F  L  V  D  S  N  P  F  P
           ←        23-A            ←        23-B
      8717 tttggctatatcagcaactacaccgtctccaccaaggtggcctcg
2836       F  G  Y  I  S  N  Y  T  V  S  T  K  V  A  S 8762 atggcattccagacacaggccggcgcccagatccccatcgagcgg
2851       M  A  F  Q  T  Q  A  G  A  Q  I  P  I  E  R 8807 ctggcctcagagcgcgccatcaccgtgaaggtgcccaacaactcg
2866       L  A  S  E  R  A  I  T  V  K  V  P  N  N  S
```

FIG. 15M

Figure 15 con.

```
       8852 gactgggctgccggggccaccgcagctccgccaactccgccaac
2881        D  W  A  A  R  G  H  R  S  S  A  N  S  A  N 8897 tccgttgtggtccagccccaggcctccgtcggtgctgtggtcacc
2896        S  V  V  Q  P  Q  A  S  V  G  A  V  V  T 8942 ctggacagcagcaaccctgcggccgggctgcatctgcagctcaac
2911        L  D  S  S  N  P  A  A  G  L  H  L  Q  L  N
                                    Exon 24
       8987 tatacgctgctggac...
2926        Y  T  L  D ...

9032 ...
2941        ...

9077 ...
2956        ...
                                                Exon 25
       9122 g......gagcaga
2971        ...                              C  S  R 9167 gacccagcggggagttaccatctgaacctctccagccacttccgc
2986        D  P  A  G  S  Y  H  L  N  L  S  H  F  R 9212 tggtcggcgctgcaggtgtccgtgggcctgtacacgtcctgtgc
3001        W  S  A  L  Q  V  S  V  G  L  Y  T  S  L  C 9257 cagtacttcagcgaggaggacatggtgtggcggacagaggggctg
3016        Q  Y  F  S  E  E  D  M  V  W  R  T  E  G  L 9302 ctgcccctggaggagacctcgccccgccaggccgtctgcctcacc
3031        L  P  L  E  E  T  S  P  R  Q  A  V  C  L  T 9347 cgccacctcaccgccttcggcgccagcctcttcgtgccccaagc
3046        R  H  L  T  A  F  G  A  S  L  F  V  P  P  S
                                    Exon 26
       9392 catgtccgctttgtgtttcctgagccgacagcgg...
3061        H  V  R  F  V  F  P ...

Figure 15 con.

```
     9527 ggcggcggccatcgcttctgtggcagcggccgcttcagtgac
3106      G  A        A              R         
                                              Exon 27
     9572 gagacctcgtcaagacaggctggggcggggctcaggtaccacg
3121                          W  G        S  G  T  T 9617 gcccacgtgggcatcatgctgtatggggtggacagccggagcggc
3136      A  H  V  G  I  M  L  Y  G  V  D  S  R  S  G 9662 caccggcacctggacggcgacagagccttccaccgcaacagcctg
3151      H  R  H  L  D  G  D  R  A  F  H  R  N  S  L 9707 gacatcttccggatcgccacccgcacagcctgggtagcgtgtgg
3166      D  I  F  R  I  A  T  P  H  S  L  G  S  V  W
                                         Exon 28
     9752 aagatccgagtgtggcacgacaacaaag
3181      K  I  R  V  W  H  D  N  K 9797 
3196

9842 gccttctcctgtcat
3211      
                                              Exon 29
     9887                                       gcgacgca
3226                                             S  D  A 9932 gccctttttgcgcttccggcgcctgctggtggctgagctgcagcgt
3241      A  L  L  R  F  R  R  L  V  A  E  L  Q  R 9977 ggcttctttgacaagcacatctggctctccatatgggaccggccg
3256      G  F  F  D  K  H  I  W  L  S  I  W  D  R  P 10022 cctcgtagccgtttcactcgcatccagagggccacctgctgcgtt
3271      P  R  S  R  F  T  R  I  Q  R  A  T  C  C  V 10067 ctcctcatctgcctcttcctgggcgccaacgccgtgtggtacggg
3286      L  L  I  C  L  F  L  G  A  N  A  V  W  Y  G
                                         Exon 30
    10112 gctgttggcgactctgcctacag
3301      A  V  G  D  S  A  Y  S 10157 
3316      S        L        V  A     V  G  L        S
```

FIG. 15O

Figure 15 con.

```
       10202 gtgctgctgtctatccgtgcgcgccatcctttcgcctcccg
3331         V V V S I R V R A I L S P P
                                              Exon 31
       10247 actgccccgaagaaggtggctgggagcccgagccccacacctgcc
3346         T A P R R R  V A G S P S P T P A 10292 gggcagcaggtgctggacatcgacagctgcctggactcgtccgtg
3361         G Q Q V L D I D S C L D S S V
                                                                Exon 32
       10337 ctggacagctccttcctcacgttctcaggcctccacgctgaggcc
3376         L D S S F L T F S G L H A E A 10382 acggtggacacctgaactgacttgctgagatgactctagc
3391         T V D T E L T C L R D D S K
             Exon 33
       10427 agtctggtgtgctggccctccggcgagggaacgctcagttggccg
3406         S L V C W P S G E G T L S W P 10472 gacctgctcagtgacccgtccattgtgggtagcaatctgcggcag
3421         D L L S D P S I V G S N L R Q 10517 ctggcacggggccaggcgggccatgggctgggcccagaggaggac
3436         L A R G Q A G H G L G P E E D 10562 ggcttctccctggccagcccctactcgcctgccaaatccttctca
3451         G F S L A S P Y S P A K S F S
             Exon 34
       10607 gcatcag ... 
3466         A S D 10652 ...
3481         
             Exon 35
       10697 ctcagcagcctgtccagcactcctggggagaagacagagacgctg
3496         L S S L S S T P G E K T E T L 10742 gcgctgcagaggctgggggagctggggccacccagcccaggcctg
3511         A L Q R L G E L G P P S P G L
                                                              Exon 36
       10787 aactgggaacagccccaggcagcgaggctgtccaggacagg
3526         N W E Q P Q A A R L S R T G 10832 gtggacgggtctccggaacggctgctgccggcctggtgtgcctcc
3541         V D G S R N R L L P A W C A S
```

FIG. 15P

Figure 15 con.

```
     10877 ctggcccacggccaggcgtcctggtcgctggctgtggct
3556        A  P  R  G  Q  A  S  W  S  L  A  V  A 10922 ggctcaaggtggtacgtgcgagccccgccggccgagtgtc
3571        G  S  R  W  Y  V  R  A  P  A  G  R  V  S 10967 gcgtggctcctgcccagcggcagctttggctccattcctc
3586        A  W  L  L  P  S  A  A  A  L  A  P  S  L
                                              Exon 37
     11012 ggctgggaggccactgaaggtcttgctggaagccctgtacttctca
3601        G  W  E  A  T  E  G  V  L  L  E  A  L  Y  F  S 11057 ctggtggccaagcggctgcacccggatgaagatgacaccctggta
3616        L  V  A  K  R  L  H  P  D  E  D  D  T  L  V 11102 gagagcccggctgtgacgcctgtgagcgcacgtgtgccccgcgta
3631        E  S  P  A  V  T  P  V  S  A  R  V  P  R  V 11147 cggccacccacggctttgcactcttcctggccaaggaagaagcc
3646        R  P  P  H  G  F  A  L  F  L  A  K  E  E  A
                                              Exon 38
     11192 cgcaaggtcaagaggctacatggcatgctgcggcccctctgggtg
3661        R  K  V  K  R  L  H  G  M  L  R  P  L  W  V 11237 tgcatgctttctcgctggtggccgccggtggcagctatgggat
3676        V  H  A  F  S  R  W  W  P  P  V  A  A  M  G  D 11282 ggcctcatgccatggcacggctaccgtatgcaagcgccgtcag
3691        A  S  C  H  G  H  G  Y  R  M  Q  A  P  S  K
                                              Exon 39
     11327 caggagctgcacagccgggcgctctggccatcacccggtctgag
3706        Q  E  L  H  S  R  A  L  W  P  S  P  G  S  E 11372 gagctctggccatggatggcccacgtgctgctgccctacgtccac
3721        E  L  W  P  W  M  A  H  V  L  L  P  Y  V  H 11417 gggaaccagtccagcccagagctggggccccacggctgcggcag
3736        G  N  Q  S  S  P  E  L  G  P  P  R  L  R  Q
                                              Exon 40
     11462 gtgcggctgcaggaagcctgaccagtccctcccgccccagg
3751        V  R  L  Q  E  A  Q  P  V  P  P  R  P  R 11507 gtccacggtgctggcagcaggaggctgcagcaccgattac
3766        V  H  G  A  G  S  R  R  L  Q  H  R  Y
```

FIG. 15Q

Figure 15 con.

```
       11552 gacctggctggaagag.cctcacaatggctgcggggcctggcc
3781         D  V  G  W  S  S  P  .  N  G  C  S  G  L  A  W  .
                                        Exon 41
       11597 catccagcgccgatcctccagcg|ggcatggtcctggggctcctgt
3796         .  S  .  A  .  D  .  .  .  .  A  W  S  W  G  S  C 11642 gccgtgtátgacagcgggggctacgtgcaggagctgggcctgagc
3811         A  V  Y  D  S  G  G  Y  V  Q  E  L  G  L  S 11687 ctggaggagagccgcgaccggctgcgcttcctgcagctgcacaac
3826         L  E  E  S  R  D  R  L  R  F  L  Q  L  H  N
                                Exon 42
       11732 tggctggacaacagg|agccgcgctgtgttcctggagttgacggc
3841         W  L  D  N  R  .  S  .  .  .  A  .  V  .  .  L  .  .  .

11777 acagcccgccgtggggctgcacgtcgccgtcacgtgcccc.
3856         .  S  .  P  .  .  V  .  G  .  L  .  .  A  .  V  .  .  L  .  .

11822 gacttcccggcggccgccgcgccctggcgacctcagcgtccc
3871         .  F  .  .  .  W  .  .  G  .  R  .  A  .  L  .  A  .  .  S  .  V  .  R 11867 ccctgcgctcgccgcctcagcgcgcgcccgctcgctgcctgc
3886         .  .  .  .  A  .  .  .  R  .  .  .  S  .  A  .  R  .  .  .  .  .  .  .  .
                                Exon 43
       11912 ctcactcg|gtgtgcctgctgctgttcgccgtgcacttcgccgtg
3901         .  .  .  .  .  .  V  C  L  L  L  F  A  V  H  F  A  V 11957 gccgaggcccgtacttggcacagggaagggcgctggcgcgtgctg
3916         A  E  A  R  T  W  H  R  E  G  R  W  R  V  L 12002 cggctcggagcctgggcgcggtggctgctggtggcgctgacggcg
3931         R  L  G  A  W  A  R  W  L  L  V  A  L  T  A 12047 gccacggcactggtacgcctcgcccagctgggtgccgctgaccgc
3946         A  T  A  L  V  R  L  A  Q  L  G  A  A  D  R 12092 cagtggacccgtttcgtgcgcggccgccccgcgccgcttcactagc
3961         Q  W  T  R  F  V  R  G  R  P  R  R  F  T  S 12137 ttcgaccaggtggcgcagctgagctccgcagcccgtggcctggcg
3976         F  D  Q  V  A  Q  L  S  S  A  A  R  G  L  A
                                                    Exon 44
       12182 gcctcgctgctcttcctgcttttggtcaag|gcgcaggagctc
3991         A  S  L  L  F  L  L  L  V  K  .  A  .  Q  .  E  .
```

FIG. 15R

Figure 15 con.

```
12227 ggcctcctgcgccactggccctgccgcaagacatctggcga
4006   R  P  P  A  T  G  P  A  R  T  S  G  D 12272 gctctgccagactcctggcgggcacctggagcctggcgctc
4021   A  L  P  D  S  W  R  A  P  G  A  W  A  L Exon 45
12317 gggctagcctacggccaggctgcagcagctcgtgtcttcctgt
4036   G  L  A  Y  G  Q  A  A  A     L  V  S  S  C 12362 gtggactccctctggagcgtggcccaggccctgttggtgctgtgc
4051   V  D  S  L  W  S  V  A  Q  A  L  L  V  L  C 12407 cctgggactgggctctctaccctgtgtcctgccgagtcctggcac
4066   P  G  T  G  L  S  T  L  C  P  A  E  S  W  H 12452 ctgtcacccctgctgtgtgtggggctctgggcactgcggctgtgg
4081   L  S  P  L  L  C  V  G  L  W  A  L  R  L  W 12497 ggcgccctacggctggggctgttattctccgctggcgctaccac
4096   G  A  L  R  L  G  A  V  I  L  R  W  R  Y  H 12542 gccttgcgtggagagctgtaccggccggcctgggagccccaggac
4111   A  L  R  G  E  L  Y  R  P  A  W  E  P  Q  D 12587 tacgagatggtggagttgttcctgcgcaggctgcgcctctggatg
4126   Y  E  M  V  E  L  F  L  R  R  L  R  L  W  M
                                    Exon 46
12632 ggcctcagcaaggtcaaggagtactccagcagtcggcttgac
4141   G  L  S  K  V  K  E  Y  S  S  S  R  L  E 12677 gggctggagcgctgcctccgtctctccaggggctccaggga
4156   G  W  S  A  A  P  L  S  S  R  S  S  R  G  S  R  K 12722 gccccggatgtgccccagccagggctggtccaggacgccac
4171   S  P  D  V  P  Q  P  G  W  S  R  T  P 12767 ccctccagctcctccggcagctgatggcttggtggagcctg
4186   P  S  S  S  G  S  Q  D  G  L  V  E  P 12812 ggcctgctgcggcagccgggcctgaccctccggcccca
4201   G  L  L  R  Q  P  G  L  T  L  R  P  Q 12857 gccctctccaggccgtctcacccagttgaccgcaaccac
4216   A  L  S  R  P  S  H  P  V  D  R  N  H
```

FIG. 15S

Figure 15 con.

Figure 16. PKD2 cDNA sequence Exon and PCR product junctions are depicted above the nucleotide sequence. Amino acids are positioned under the center of each codon.

| Codon Number | | |
|---|---|---|
| | 67 | Exon 1-A atggtgaactccagtcgcgtgcagcctcagcagcccggggacgcc |
| 1 | | M V N S S R V Q P Q Q P G D A |
| | 112 | aagcggccgccgcgccccgcgcgccggacccgggccggctgatg |
| 16 | | K R P P A P R A P D P G R L M |
| | 157 | gctggctgcgcggccgtgggcgccagcctcgccgccccgggcggc |
| 31 | | A G C A A V G A S L A P G G |
| | 202 | ctctgcgagcagcggggcctggagatcgagatgcagcgcatccgg |
| 46 | | L C E Q R G L E I E M Q R I R |
| | | → 1-B |
| | 247 | caggcggccgcgcgggacccccggccggagccgcggcctcccct |
| 61 | | Q A A A R D P P A G A A S P |
| | | ← 1-A |
| | 292 | tctcctccgctctcgtcgtgctccggcaggcgtggagccgcgat |
| 76 | | S P P L S S C S R Q A W S R D |
| | 337 | aaccccggcttcgaggccgaggaggaggaggaggaggtggaaggg |
| 91 | | N P G F E A E E E E E V E G |
| | 382 | gaagaaggcggaatggtggtggagatggacgtagagtggcgcccg |
| 106 | | E E G G M V V E M D V E W R P |
| | 427 | ggcagccggaggtcggccgcctcctcggccgtgagctccgtgggc |
| 121 | | G S R R S A A S S A V S S V G |
| | | → 1-C |
| | 472 | gcgcggagccggggggcttgggggctaccacggcgcgggccacccg |
| 136 | | A R S R G L G G Y H G A G H P |
| | 517 | agcggaggcggcgccggcgagaggaccagggcccgccgtgcccc |
| 151 | | S G R R R R R E D Q G P P C P |
| ← | | 1-B |
| | 562 | agcccagtcggcggcggggacccgctgcatcgccacctcccctg |
| 166 | | S P V G G D P L H R H L P L |
| | 607 | gaagggcagccgccccgagtggcctgggcggagaggctggttcgc |
| 181 | | E G Q P P R V A W A E R L V R |
| | | Exon 2 |
| | 652 | gggctgcgaggtccggggatcagctcatcgagaaagcac |
| 196 | | G L R |
| | 697 | actaacggagagaataccttaagggtcttgggaatggc |
| 211 | | |
| | | Exon 3 |
| | 742 | acataccgcc gtctggtgcatcttgacctacggc |

FIG. 16A

Figure 16 con.

```
226                                            L T Y G
      787 atgatgagctccaatgtgtactactacacccggatgatgtcacag
241        M  M  S  N  V  Y  Y  Y  T  R  M  M  S  Q
      832 ctcttcctagacaccccgtgtccaaaacggagaaaactaacttt
256        L  F  L  D  T  P  V  S  K  T  E  K  T  N  F
                                              Exon 4
      877 aaaactctgtcttccatggaagacttctggaag
271        K  T  L  S  S  M  E  D  F  W  K
      922
286
      967
301
     1012
316
     1057
331
     1102
346
                        Exon 5
     1147            ttggatctacacaagtgaaaagacttgaat
361                  W  I  Y  T  S  E  K  D  L  N
     1192 ggtagtagccactggggaatcattgcaacttatagtggagctggc
376        G  S  S  H  W  G  I  I  A  T  Y  S  G  A  G
     1237 tattatctggatttgtcaagaacaagagaggaaaacagctgcacaa
391        Y  Y  L  D  L  S  R  T  R  E  E  T  A  A  Q
     1282 gttgctagcctcaagaaaaatgtctggctggaccgaggaaccagg
406        V  A  S  L  K  K  N  V  W  L  D  R  G  T  R
     1327 gcaactttattgacttctcagtgtacaacgccaacattaacctg
421        A  T  F  I  D  F  S  V  Y  N  A  N  I  N  L
                   Exon 6
     1372 ttctgtgtggtcag
436        F  C  V  V  R
     1417
451
     1462
466
     1507
481
```

FIG. 16B

Figure 16 con.

```
     1552 ................................................
496       ................................N.C.
                                    Exon 7
     1597 ................ctgtcagtggtagctataggaattaac
511       ............  L  S  V  V  A |I  G  I  N
     1642 atatacagaacatcaaatgtggaggtgctactacagtttctggaa
526        I  Y  R  T  S  N  V  E  V  L  L |Q  F  L  E
     1687 gatcaaaatactttccccaactttgagcatctggcatattggcag
541        D  Q  N  T  F  P  N  F  E  H  L  A  Y  W  Q
     1732 atacagttcaacaatatagctgctgtcacagtatttttgtctgg
556        I  Q  F  N  N  I  A  A  V  T  V |F  F  V  W
                                    Exon 8
     1777 attaac.......................................
571        I  K  ............................
     1822 ................................................
586       ................................................
     1867 ................................................
601       ................................................
     1912 ................................................
616       ................................................
                                    Exon 9
     1957 ..........cttcactcaattccgtatcattttgggcgatatcaac
631       ...... F  T  Q  F  R  I  I  L |G  D  I  N
     2002 tttgcagagattgaggaagctaatcgagttttgggaccaatttat
646        F  A  E  I  E  E  A  N  R  V  L |G  P  I  Y
                                                    Exon 10
     2047 ttcactacatttgtgttctttatgttcttcattctttt......
661        F  T  T  F  V  F  F  M  F  F  I |L  L  ..
     2092 ................................................
676       ................................................
     2137 ................................................
691       ................................................
              Exon 11
     2182 ..ggctaccataaagctttggtcaaactaaaactgaaaaaaaat
706        . G  Y  H  K  A  L  V  K  L  K |L  K  K  N
     2227 accgtggatgacatttcagagagtctgcggcaaggaggaggcaag
721        T  V  D  D  I  S  E  S  L  R  Q |G  G  G  K Exon 12
     2272 ttaaactttg           caagatctcaaagc..........
```

FIG. 16C

Figure 16 con.

```
736                 L  N  F  D  E  L  R  Q  D  L  K  G
        2317   actgatgcagagatggaggcatattcatcaagtgcgaccaagat
751            
        2362   ggagtgcaagaactgaccgtacatgaactcatcagagatgagac
766            
                                    Exon 13
        2407   gactctgagaagagagggaggacctggatttggatcacagttct
781                                   E  D  L  D  L  D  H  S  S
        2452   ttaccacgtcccatgagcagccgaagtttccctcgaagcctggat
796            L  P  R  P  M  S  S  R  S  F  P  R  S  L  D
        2497   gactctgaggaggatgacgatgaagatagcggacatagctccaga
811            D  S  E  E  D  D  D  E  D  S  G  H  S  S  R
        2542   aggaggggaagcatttctagtggcgtttcttacgaagagtttcaa
826            R  R  G  S  I  S  S  G  V  S  Y  E  E  F  Q
                                    Exon 14
        2587   gt
841            V
        2632   
856            
        2677   
871            
                                    Exon 15
        2722            gatgaaaggctgggtcgtgacagtgaaatc
886            D              D  E  R  L  G  R  D  S  E  I
        2767   catagggaacagatggaacggctagtacgtgaagagttggaacgc
901            H  R  E  Q  M  E  R  L  V  R  E  E  L  E  R
        2812   tgggaatccgatgatgcagcttcccagatcagtcatggtttaggc
916            W  E  S  D  D  A  A  S  Q  I  S  H  G  L  G
        2857   acgccagtgggactaaatggtcaacctcgccccagaagctcccgc
931            T  P  V  G  L  N  G  Q  P  R  P  R  S  S  R
        2902   ccatcttcctcccaatctacagaaggcatggaaggtgcaggtgga
946            P  S  S  S  Q  S  T  E  G  M  E  G  A  G  G
        2947   aatgggagttctaatgtccacgtatga  2973  (SEQ ID NO. 170)
961            N  G  S  S  N  V  H  V  *         (SEQ ID NO. 172)
```

FIG. 16D

COMPOSITIONS AND METHODS FOR GENETIC ANALYSIS OF POLYCYSTIC KIDNEY DISEASE

RELATED APPLICATIONS

The present invention is a continuation-in-part application of U.S. patent application with Ser. No. 10/083,246, filed Feb. 26, 2002 (now U.S. Pat. No. 6,916,619), which claims benefit to U.S. Provisional Application with Ser. No. 60/328, 739, filed Oct. 12, 2001, both of which are hereby incorporated by reference in their entirety.

FIELD OF THE INVENTION

The invention relates to a genetic testing method for identifying alterations or the absence of such alterations in a gene associated with Autosomal Dominant Polycystic Kidney Disease.

BACKGROUND OF THE INVENTION

Autosomal dominant polycystic kidney disease (ADPKD) is an exceptionally common hereditary nephropathology with an incidence of about 1 in 800 live births. The disease is progressive, phenotypically characterized by bilaterally enlarged polycystic kidneys, and typically resulting in end-stage renal disease (ESRD) by the age of 65 years. The more common complications include hypertension, macrohaematuria, urinary-tract infection, cardiac-valve abnormalities, and hernia of the anterior abdominal wall. Cyst formation is also commonly observed in the liver, although the occurrence is not associated with functional impairment of the organ. Although not as frequently reported, additional extra-renal manifestations include pancreatic cysts, connective tissue abnormalities, and cerebral-artery aneurysms.

The typical age of onset is in middle life, but the range is from infancy to 80 years. The clinical presentation of ADPKD differs between and within families as partly explained by the genetically heterogeneous nature of the disorder. Mutations in two genes, PKD-1 and PKD-2, account for nearly all cases of ADPKD (e.g., for reviews, see Arnaout, 2001, Annu Rev. Med. 52:93-123; Koptides and Deltas, 2000, Hum. Genet. 107:115-126). PKD-1 and PKD-2 encode integral membrane proteins whose functions have not been fully elucidated. The major gene responsible for ADPKD, PKD-1, has been fully characterized and shown to encode an integral membrane protein, polycystin 1, which is thought to be involved in cell-cell and cell-matrix interaction. PKD-2 gene encodes polycystin-2 which is a predicted integral membrane protein with non-selective cation channel activity. Based on sequence homology with the alpha 1 subunit component of voltage-activated calcium channels, it has been postulated that polycystin-2 may play a role in ion channeling. The C-terminal cytoplasmic tails of polycystin-1 and polycystin-2 have been shown to interact using in vitro binding assays and in a directed two-hybrid interaction. The interaction occurs via a coiled-coil domain in PKD-1 and a region near R872 in PKD-2. Although the biological relevance of the interaction between the polycystins is not yet understood, it does suggest that PKD-1 and PKD-2 are likely to function along a common pathway.

Both ADPKD type 1 and type 2 share the entire range of renal and extrarenal manifestations, but type 2 appears to have a delayed onset relative to type 1. The common phenotypic complications observed for ADPKD including hypertension, hematuria, and urinary tract infection seem to be clinically milder in type 2 patients. The median age at death or onset of ESRD has been reported as 53 years in individuals with PKD-1 and 69 years in those with PKD-2. Women have been reported to have a significantly longer median survival of 71 years than men (67 years). No sex influence is apparent in PKD-1. Mutations in the PKD-1 gene are the cause of ADPKD in approximately 85% of the cases tested, while those in PKD-2 account for 15%. Although a small subset of families with ADPKD fail to demonstrate genetic linkage to either PKD-1 or PKD-2, raising the possibility of a third gene for ADPKD, the existence of a third disease-associated locus has been strongly challenged.

Despite the discovery of strong links between genetic alterations in PKD genes and the onset of ADPKD, the development of a genetic testing method for ADPKD predisposition for routine clinical use has been hindered by several technical obstacles.

One serious obstacle for developing a DNA-based testing method for ADPKD is that sequences related to the PKD transcript, for example, PKD-1, are duplicated at least three times on chromosome 16 proximal to the PKD-1 locus, forming PKD-1 homologues. Another obstacle is that the PKD-1 genomic interval also contains repeat elements that are present in other genomic regions. In addition, the sequences of PKD genes are extremely GC rich and a large number (15,816 bp) of nucleotides need to be analyzed for a thorough evaluation.

There is a need for the identification of segments of these sequences that are unique to the expressed PKD genes and not are present in the duplicated homologous sequences. There is also a need for developing a sensitive and specific genetic testing method for mutational analysis of PKD genes. The development of such genetic testing method would facilitate the diagnosis and management of ADPKD.

SUMMARY OF THE INVENTION

In one aspect, the present invention provides a method of mutation analysis of a target nucleic acid, the method comprising: incubating a sample comprising the target nucleic acid in a reaction mixture, in the presence of at least one first nucleic acid and at least one second nucleic acid, where the first nucleic acid comprises a primer sequence which anneals to a unique site of a sequence of SEQ ID NO. 1 or 2, and the second nucleic acid has an opposite orientation from the first nucleic acid, and where the incubation produces amplified products; generating duplexes in the amplified products; and detecting the presence or absence of a heteroduplex from the duplexes, where the presence of a heteroduplex indicates the presence of a potential mutation in the target nucleic acid, and where the absence of a heteroduplex indicates the absence of a mutation in the target nucleic acid.

In one embodiment, the method further comprises determining the sequence of a heteroduplex region; and comparing the sequence of the heteroduplex region to SEQ ID NO. 1 or 2; where a sequence difference in the heteroduplex region compared to SEQ ID NO. 1 or 2 resulting in a predicted functional change in the protein encoded by the target nucleic acid is indicative of a mutation in the target nucleic acid.

Preferably, the first or second nucleic acid comprises a sequence selected from the group consisting of SEQ ID NOs. 3-49.

In another embodiment, the method further comprising performing a nested amplification reaction using the amplified products generated by the first and second nucleic acids as templates and generating duplexes in amplified products from the nested amplification.

Preferably, the nested amplification reaction is performed using at least one primer selected from the group consisting of SEQ ID NOs. 3-49 and their complementary sequences.

In a preferred embodiment, the presence or absence of a heteroduplex from the duplexes is identified by DHPLC.

In also a preferred embodiment, the sequence of the heteroduplex region is determined by DNA sequencing.

Preferably, the second nucleic acid of the subject method comprises a primer sequence which anneals to a unique site within a sequence of SEQ ID NO. 1 or 2.

Also preferably, the sample comprising the target template is selected from the group consisting of: genomic DNA, cDNA, total RNA, mRNA, and a cell sample.

In one embodiment, the incubating step comprises an amplification reaction selected from the group consisting of: a polymerase chain reaction, a ligase chain reaction (LCR) and a nucleic acid-specific based amplification.

The subject method of the invention may further comprise confirming the amplified product is a PKD-specific product with one or more restriction enzymes.

Preferably, the restriction enzyme cleaves a PKD-specific product to generate a digestion pattern distinguishable from a PKD homologue product.

More preferably, the restriction enzyme is selected from the group consisting of: Pst I, Stu I, Xma I, Mlu I, Pvu II, BssHII, Fsp I, Msc I, and Bln I.

In another aspect, the invention provides a diagnosis method for identifying a patient affected with PKD, the method comprising:

(a) obtaining a sample from an individual;

(b) incubating the sample in a reaction mixture, in the presence of at least one first nucleic acid and at least one second nucleic acid, where the first nucleic acid comprises a primer sequence which anneals to a unique site within a sequence of SEQ ID NO. 1 or 2, and the second nucleic acid has an opposite orientation from the first nucleic acid, and where the incubation produces amplified products;

(c) generating duplexes in the amplified products;

(d) detecting the presence or absence of a heteroduplex from the duplexes, and(e)

determining the sequence of the heteroduplex region where the presence of a mutation in the heteroduplex region as compared to SEQ ID No. 1 or 2 is indicative that the individual is affected with PKD.

Preferably, the detection of a heteroduplex is performed by DHPLC.

Also preferably, the sequence is determined by DNA sequencing.

In one embodiment, the second nucleic acid comprises a primer sequence which anneals to a unique site within a sequence of SEQ ID NO. 1 or 2.

In another embodiment, the first or second nucleic acid comprises a primer sequence selected from the group consisting of SEQ ID NOs. 3-49.

The diagnosis method of the invention may further comprise performing a nested amplification reaction using the amplified products generated by the first and second nucleic acids as templates and generating duplexes from the nested amplification.

In one embodiment, the nested amplification reaction is performed using at least one primer selected from the group consisting of SEQ ID NOs. 3-49 and their complementary sequences.

Preferably, the sample in the diagnosis method is selected from the group consisting of: a genomic DNA, cDNA, total RNA, mRNA, and a cell.

Also preferably, the amplification reaction is selected from the group consisting of: a polymerase chain reaction, a ligase chain reaction (LCR) and a nucleic acid-specific based amplification.

The diagnosis method may further comprise verifying the specifically amplified product with one or more restriction enzymes.

Preferably, the restriction enzyme cleaves a PKD-specific product to generate a digestion pattern distinguishable from a PKD homologue product.

More preferably, the restriction enzyme is selected from the group consisting of: Pst I, Stu I, Xma I, Mlu I, Pvu II, BssHII, Fsp I, Msc I, and Bln I.

In a further aspect, the invention provides one or more nucleic acid primer, where each primer is an isolated nucleic acid selected from the group of SEQ ID NOs 3-49, or the complement thereof.

The invention also provides a pair of nucleic acids, where at least one nucleic acid of the pair is selected from the group of SEQ ID NOs 3-49.

Preferably, the pair of nucleic acids have an opposite orientation and amplify a fragment of a template nucleic acid comprising a sequence of SEQ ID NO. 1 or 2.

In another aspect, the invention provides a composition comprising at least one isolated first nucleic acid and at least one isolated second nucleic acid, where the first nucleic acid is selected from the group of SEQ ID NOs. 3-49 and their complementary sequences, and the second nucleic acid has an opposite orientation from the first nucleic acid, and wherein the first and second nucleic acids amplify a fragment of a template nucleic acid comprising a sequence of SEQ ID NO. 1 or 2.

In one embodiment, the composition of the invention further comprises at least one component selected from the group consisting of: a DNA polymerase, a template nucleic acid, a restriction enzyme, one or more control oligonucleotide primers, ddNTPs, a PCR reaction buffer and their combination thereof.

Preferably, the template nucleic acid in the composition is a genomic DNA or cDNA.

In a further aspect, the invention provides a kit for identifying a PKD patient, the kit comprising at least one isolated first nucleic acid and at least one isolated second nucleic acid, where the first nucleic acid is selected from the group of SEQ ID NOs. 1-49 and their complementary sequences, and the second nucleic acid has an opposite orientation from the first nucleic acid, and where the first and second nucleic acids amplify a fragment of a template nucleic acid comprising a sequence of SEQ ID NO. 1 or 2, and packaging materials therefore.

In one embodiment, the kit of the invention further comprises at least one component selected from the group consisting of: a DNA polymerase, a template nucleic acid, a restriction enzyme, a control oligonucleotide primer, ddNTPs, a PCR reaction buffer and the combination thereof.

Preferably, the template nucleic acid in the kit is a genomic DNA or cDNA molecule.

The invention provides an isolated nucleic acid comprising a sequence selected from the group consisting of SEQ ID NOs. 3-49 and their complementary sequences thereof.

The invention provides a nucleic acid biomarker for ADPKD comprising a PKD-1 or PKD-2 nucleic acid sequence comprising one or more nucleotide alterations as disclosed in FIG. 14.

In one embodiment, the at least one of the one or more nucleotide alterations consists of a novel nucleotide alterations as disclosed in FIG. 14.

The invention also provides a nucleic acid biomarker for ADPKD comprising a PKD-1 or PKD-2 nucleic acid sequence comprising one or more novel nucleotide alterations as disclosed in FIG. 14.

The invention provides a polypeptide biomarker for ADPKD comprising a PKD-1 or PKD-2 polypeptide sequence comprising one or more amino acid alterations as disclosed in FIG. 14.

In one embodiment, at least one the one or more amino acid alterations consists of a novel amino acid alteration as disclosed in FIG. 14.

The invention provides a polypeptide biomarker for ADPKD comprising a PKD-1 or PKD-2 polypeptide sequence comprising one or more novel amino acid alterations as disclosed in FIG. 14.

The present invention further provides a method for diagnosing ADPKD in an individual, comprising identifying nucleotide sequence of PKD-1 or PKD-2 gene of the individual, where the existence of one or more nucleotide sequence alterations in the nucleotide sequence of PKD-1 or PKD-2 gene as disclosed in FIG. 14 is indicative of ADPKD in the individual.

The present invention further provides a method for determining in an individual the presence or absence of a mutant PKD gene, comprising the steps of
a) identifying the nucleotide sequence of a PKD-1 or PKD-2 gene of the individual;
b) comparing the nucleotide sequence of step a) to the nucleotide sequence alteration in the nucleotide sequence of a PKD-1 or PKD-2 gene as disclosed in FIG. 14; and
c) detecting the presence of one or more of the nucleotide sequence alterations disclosed in FIG. 14; wherein the presence of at least one of the nucleotide sequence alterations is indicative of ADPKD in the individual; and wherein the absence of any of said nucleotide sequence alterations indicates the absence of a mutant PKD-1 and/or PKD-2 gene.

In one embodiment, the method for diagnosing ADPKD and/or the method for determining the presence or absence of a mutant PKD gene further comprises obtaining a DNA sample from the individual for the identification of nucleotide sequence of PKD-1 or PKD-2 gene.

Preferably the DNA sample obtained is a genomic DNA sample or a cDNA sample.

In another embodiment, the method for diagnosing ADPKD and/or the method for determining the presence or absence of a mutant PKD gene further comprises amplifying a portion of the PKD-1 or PKD-2 gene from the DNA sample before the identification.

Preferably, the portion of the PKD-1 or PKD-2 gene is amplified by a polymerase chain reaction.

Also preferably, the nucleic acid sequence is identified by DNA sequencing.

More preferably, the DNA sequencing is performed using an isolated nucleic acid comprising a sequence selected from the group consisting of SEQ ID NOs. 3-49 and their complementary sequences thereof.

In one embodiment, the at least one or more of the at least one or more nucleotide alterations consists of a novel nucleotide alterations as disclosed in FIG. 14.

BRIEF DESCRIPTION OF THE DRAWINGS

The objects and features of the invention can be better understood with reference to the following detailed description and accompanying drawings.

FIG. 1 is a figure showing the PKD1 cDNA sequence (GenBank Accesion No. L33243) used in one embodiment of the invention. Exon and PCR product junctions are depicted above the nucleotide sequence. Amino acids are positioned under the center of each codon.

FIG. 2 is a figure showing the comparison of exon sequences of a PKD gene and two homologue sequences according to one embodiment. Restriction enzyme sites which only cleave in either PKD or homologue sequence are indicated.

FIG. 10B is a table showing patient DNA variant genotypes determined in one embodiment of the invention.

FIG. 11 is a table summarizing DHPLC (WAVE) conditions used in some embodiments of the invention.

FIG. 12 is a table summarizing PCR conditions used in some embodiments of the invention.

FIG. 14 is a table showing non-limiting examples of novel and known nucleotide and amino acid alterations identified in PKD-1 and PKD-2 nucleotide and amino acid sequences from ADPKD patients according to one embodiment of the invention. Novel, as used herein, includes the unknown predicted disease causing (UPD) alterations disclosed in bold. X refers to Exon, IVS refers to intervening sequence, KP refers to known polymorphism, UP refers to unknown polymorphism, and UAA refers to unknown amino acid change.

FIG. 16 is a wild-type PKD-2 cDNA sequence according to one embodiment of the invention.

DETAILED DESCRIPTION OF THE INVENTION

Figure 3:
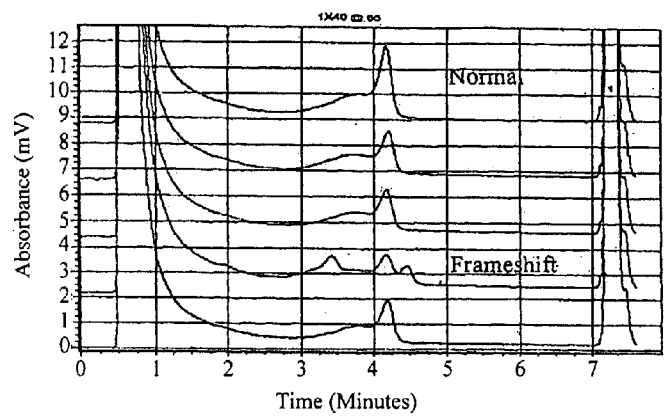
FIG. 3 is a graph showing PKD1 exon 40 DHPLC patterns of 4 normal samples and a 19 bp insertion (duplication) at nucleotide 11606, codon 3799 according to one embodiment.
Figure 4:
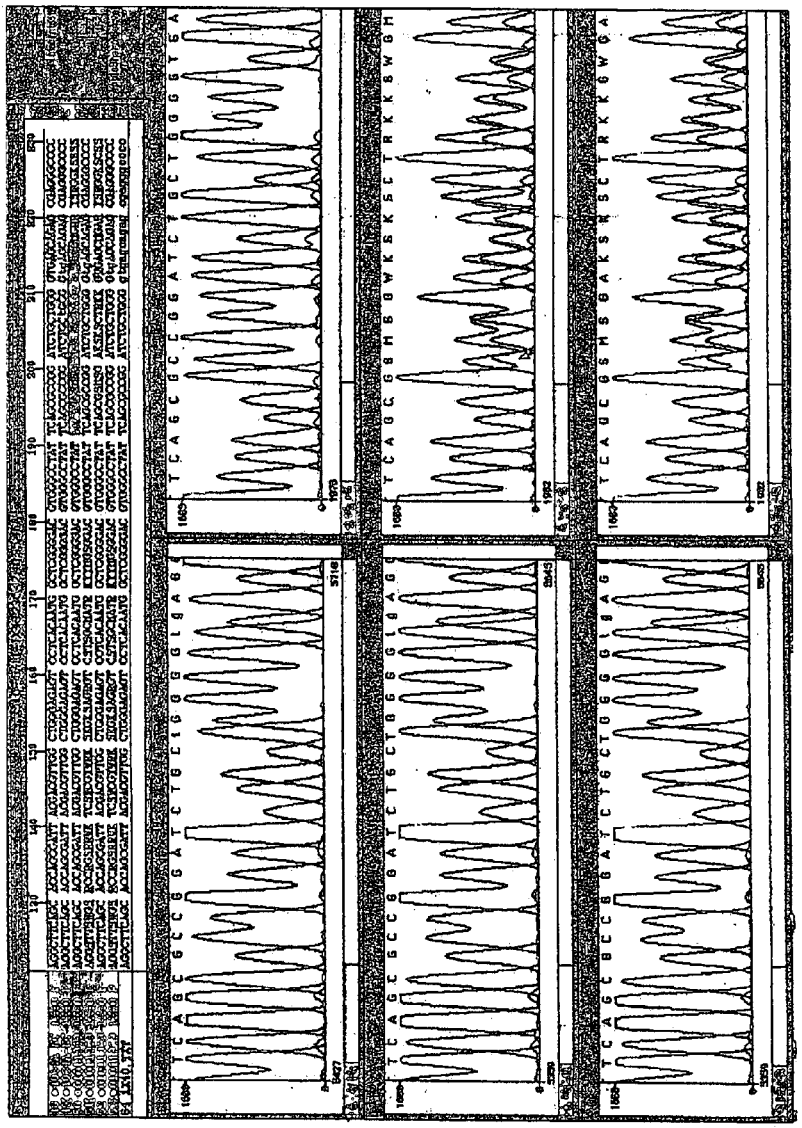
FIG. 4 is a graph showing PKD1 exon 40 sequences of the normal control and a sequence with a 19 bp insertion (duplication) at nucleotide 11606, codon 3799 according to one embodiment.
Figure 5:
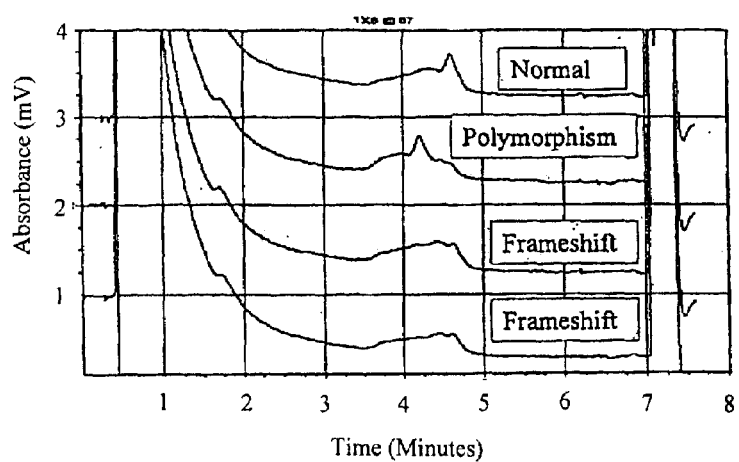
FIG. 5 is a graph showing PKD1 exon 6 DHPLC patterns of an intron 5 probable polymorphism (IVS5-9G->A) and a frameshift at nucleotide 1502 (insert G) in two related patients according to one embodiment.
Figure 6:
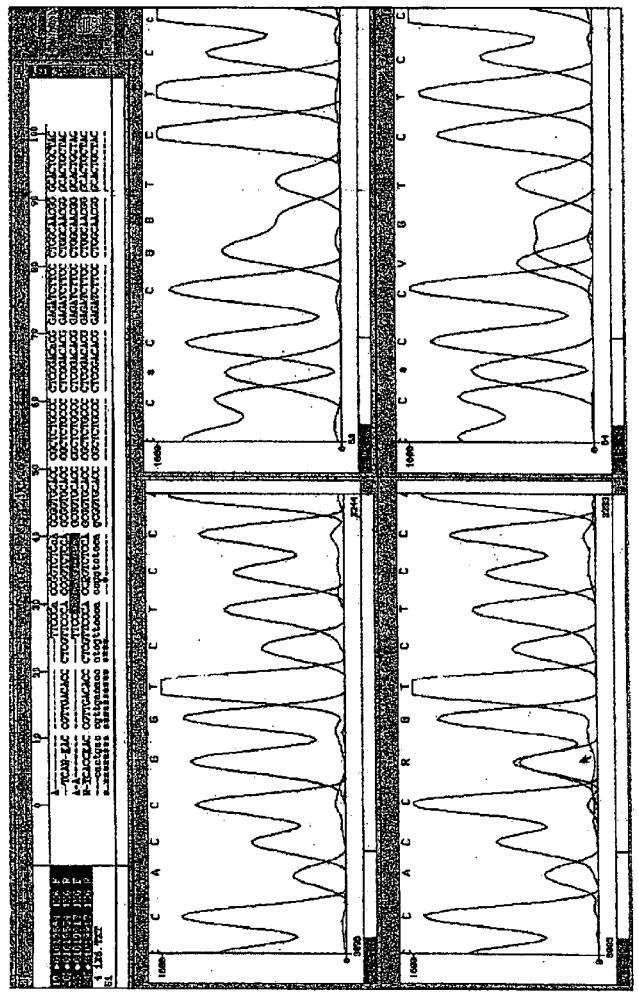
FIG. 6 is a graph showing PKD1 exon 6 sequences of the normal control and a sequence with intron 5 probable polymorphism (IVS5-9G->A) according to one embodiment.
Figure 7:
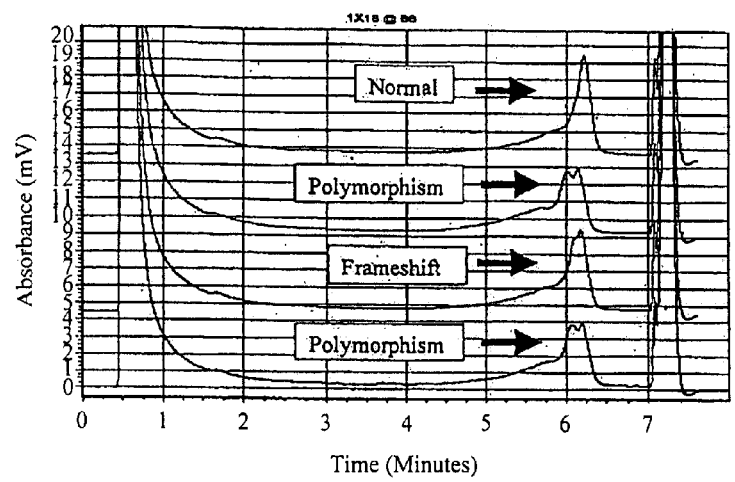
FIG. 7 is a graph showing PKD1 exon 18 DHPLC patterns of a frameshift at nucleotide 7518, codon 2436 (insert C), and a common polymorphism C7652T according to one embodiment.
Figure 8:
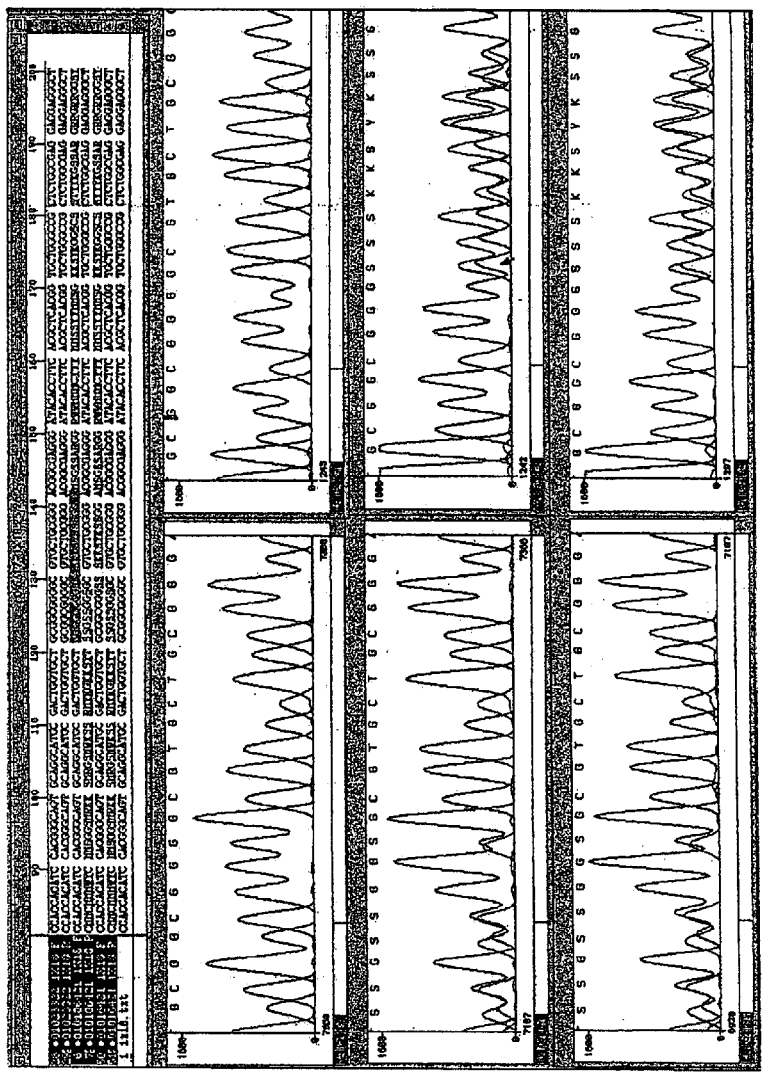
FIG. 8 is a graph showing PKD1 exon 18 sequences of the normal control and a sequence with frameshift at nucleotide 7518, codon 2436 (insert C) according to one embodiment.
Figure 9:
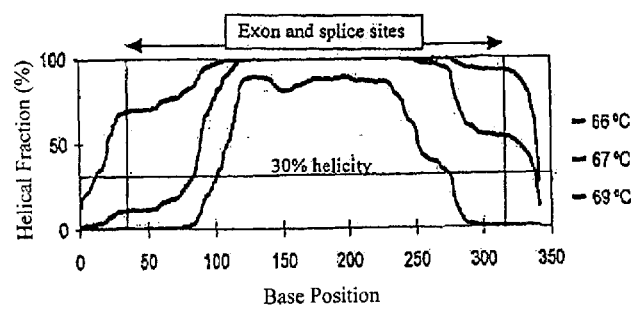
FIG. 9 is a graph showing an example of a software-predicted melt profile and the need for multiple temperatures to establish partial melting near the ends of an exon according to one embodiment.
Figure 10A:
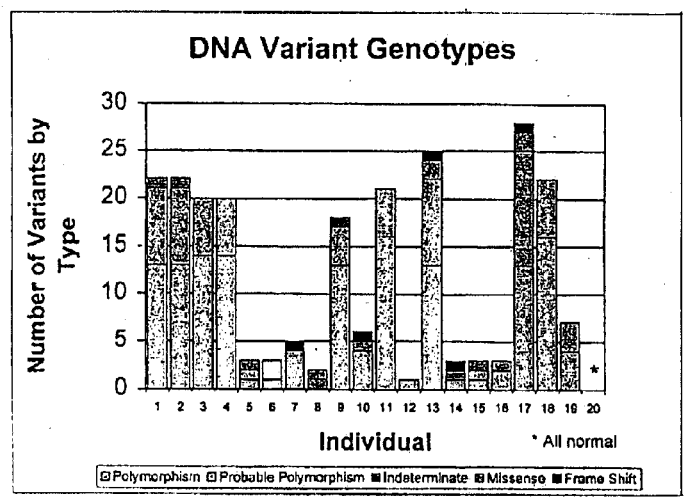
FIG. 10A is a chart showing patient DNA variant genotypes determined in one embodiment of the invention.
Figure 13:
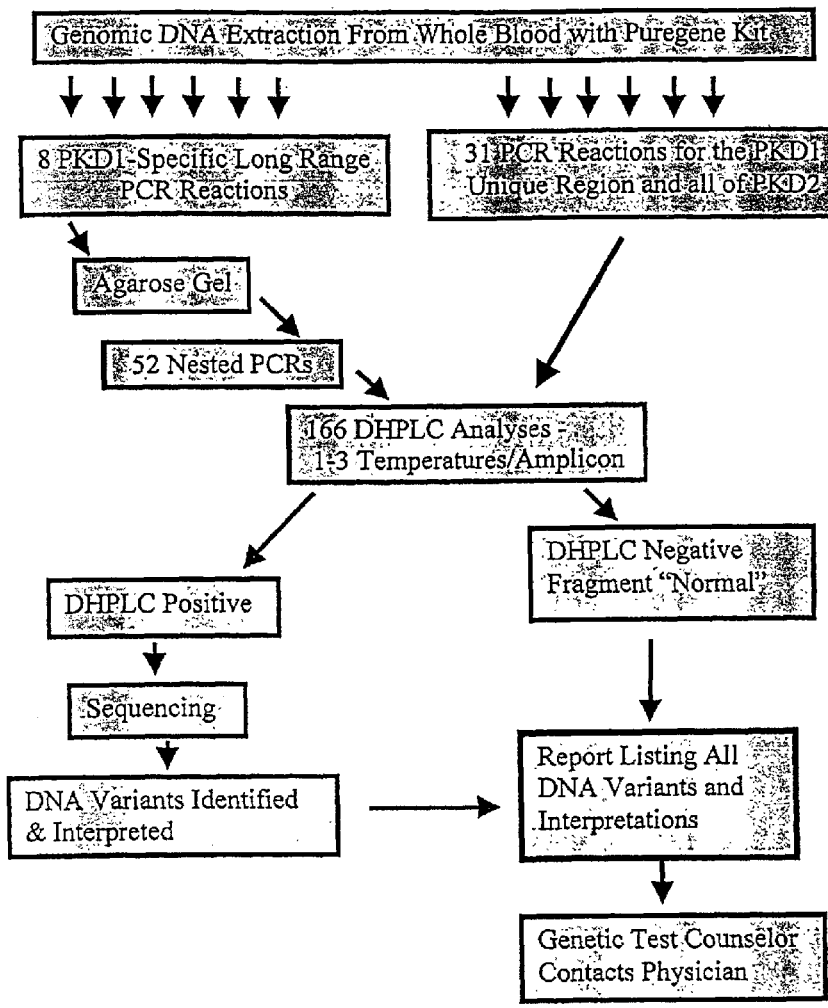
FIG. 13 is a schematic diagram showing patient specimen processing steps in one embodiment of the invention.

The subject invention is based on the identification of unique sites within a PKD gene, the design of PKD-specific primers and the DHPLC analysis of PCR products amplified by using these PKD-specific primers.

I. Definitions

As used herein, "ADPKD" refers to autosomal dominant polycystic kidney disease. ADPKD is an exceptionally common hereditary nephropathology and is characterized by the development of renal cysts and, ultimately, renal failure, and may alternatively or in addition involve cysts in other organs including liver and spleen, as well as gastrointestinal, cardiovascular, and musculoskeletal abnormalities.

The term "PKD gene" refers to a genomic DNA sequence which maps to chromosomal position 16p13.3 (i.e., PKD-1) or chromosomal position 4q21-23 (i.e., PKD-2) and gives rise to a messenger RNA molecule encoding a PKD protein. The PKD-1 and PKD-2 genes comprise the sequences of SEQ ID NO. 1 and SEQ ID NO.2, respectively, which include introns and putative regulatory sequences. Like many other genes, PKD-1 and PKD-2 gene sequences, when compared among individuals, show sequence variations. Those genes having polymorphisms which are silent (i.e., with respect to gene expression or function of a gene product) are "normal" genes as defined herein.

A "normal" PKD gene (e.g., PKD-1 or PKD-2) is defined herein as a PKD gene such as described by SEQ ID NO. 1 or 2, respectively, and includes any gene having silent polymorphisms.

A "mutant" PKD gene is defined herein as a PKD gene (e.g., PKD-1 or PKD-2) whose sequence is modified by mutation comprising one or more substitutions (transitions or transversions), deletions (including loss of locus), insertions (including duplications), translocations, and/or other modifications relative to the normal PKD gene. The mutation causes detectable changes in the expression or function of the PKD gene product, and is causative for ADPKD. The mutations may involve from one to as many as several thousand nucleotides, and result in one or more of a variety of changes in PKD gene expression (e.g. decreased or increased rates of expression) or expression of a defective RNA transcript or protein product. Mutant PKD genes encompass those genes whose presence in one or more copies in the genome of a human individual is associated with ADPKD.

As used herein, "biomarker" refers to a biological molecule, e.g., a nucleic acid or polypeptide or peptide etc . . . whose presence or concentration can be detected and correlated with a known condition, such as a disease state, for example polycystic kidney disease, and in particular, ADPKD.

A "nucleotide sequence alteration" or "nucleotide alteration" refers to a nucleotide sequence modification including one or more substitutions (transitions or transversions), deletions (including loss of locus), insertions (including duplications), translocations, and/or other modifications relative to the normal PKD gene.

An "amino acid alteration" refers to an amino acid modification including a substitution, a frameshift, a deletion, a truncation and an insertion, and/or other modifications relative to the normal PKD amino acid sequence.

The term "basepair mismatch" refers to any nucleic acid sequence which is not complementary to the sequence of SEQ ID. NO. 1 or 2. Therefore, basepair mismatch, according to the present invention may be caused by gene alteration or polymorphism of a normal PKD gene; or by any modifications present in a mutant PKD gene. "Basepair mismatch" may be a single nucleotide basepair mismatch or it may include a nucleic acid sequence of 2 or more nucleotides (i.e., 3, or 4, or 5, or 10, or 20, or 100, or 500 more, or up to 1000 nucleotides). The presence or absence of a mismatch, as defined herein, is indicative of the presence or absence of a potential mutation in the target nucleic acid.

The term "authentic" is used herein to denote the genomic sequence of SEQ ID. NO.1 or 2, as well as sequences derived therefrom, and serves to distinguish these authentic sequences from "PKD homologues" (see below).

A "PKD-1 homologue" is a sequence which is closely related to PKD-1, but which does not encode an expressed PKD-1 gene product. Several examples of such homologues that map to chromosomal location 16p 13.1 or 4q21-23 have been identified and sequenced. A PKD-1 homologue may share more than 95% sequence identity to an authentic PKD gene.

As used herein, a "specifically amplified product" is a product amplified from a fragment within an authentic PKD gene (e.g., SEQ ID NO.1 or 2), but not from a PKD homologue. A "non-specifically amplified product" is a product amplified from a PKD homologue or other sequences due to the annealing of nucleic acid primers to a template sequence which is not completely complementary during the amplification reaction.

As used herein, a "unique site" refers to a stretch of sequence of 10-50 base pairs in length within a PKD gene which comprises at least one nucleotide different form a stretch of sequence in a PKD homologue or other sequences. One exemplary unique site comprises a sequence of 5' AGG TCC AGG GCG ACT CGC TGG 3', or 5' CAG GGC CAC ACG CGC TGG GCG 3', or their complement thereof.

As used herein, a "PKD-specific primer" refers to a nucleic acid sequence which anneals to a sequence within a PKD gene (including introns and exons) under specific stringent conditions. A PKD-specific primer, according to the invention, anneals to a unique site present in the authentic expressed PKD-1 gene or PKD-2 gene, and not to PKD homologues or other sequences under specific stringent conditions. A PKD-specific primer shares more then 95% (e.g., more than 96%, 96%, 97%, 98%, 99%, or up to 100%) sequence identity with a unique site within a PKD gene. A "PKD-specific primer" may be 10 to 60 nucleotides in length, for example, 18-52 nucleotides in length.

As used herein, the term "specific stringent condition" refers to an amplification condition which specifically allows the annealing of a PKD-specific primer to a sequence within a PKD gene. Under a "specific stringent condition", a PKD-specific primer does not anneal to a PKD homologue or other sequences. For example, one specific stringent condition useful to the invention comprises a Taq Precision buffer (TaqPlus Precision buffer, Stratagene, La Jolla, Cat# 600210), a dNTP concentration of more than 50 nM, for example, 100 nM, 200 nM, or 300 nM. The annealing temperature in a specific stringent condition may be higher than or less than or equal to 5° C. below the lowest primer annealing temperature (Tm), for example, 1° C., 2° C., 4° C., 5° C., or 10° C. higher than Tm or 4° C., 3° C., 2° C., or 1° C. below Tm.

"Amplification" of DNA as used herein refers to a reaction that serves to increase the concentration of a particular DNA sequence within a mixture of DNA sequences. Amplification may be carried out using polymerase chain reaction (PCR), ligase chain reaction (LCR), nucleic acid-specific based amplification (NSBA), or any other method known in the art.

"RT-PCR" as used herein refers to coupled reverse transcription and polymerase chain reaction. This method of amplification uses an initial step in which a specific oligonucleotide, oligo dT, or a mixture of random primers is used to prime reverse transcription of RNA into single-stranded cDNA; this cDNA is then amplified using standard amplification techniques e.g. PCR.

A "template nucleic acid" or a "target nucleic acid" (e.g., a genomic DNA or a cDNA), is a normal (e.g., wild type) or a mutant nucleic acid that is or includes a particular sequence (e.g. a PKD-1 or PKD-2 gene sequence). It will be understood that additional nucleotides may be added to the 5' and/or 3' terminus of the disclosed sequence, as part of routine recombinant DNA manipulations. Furthermore, conservative DNA substitutions i.e. changes in the sequence of the protein-coding region that do not change the encoded amino acid sequence, also may be accommodated.

As used herein, "nucleic acid primer" refers to a DNA or RNA molecule capable of annealing to a nucleic acid template and providing a 3' end to produce an extension product which is complementary to the nucleic acid template. The nucleic acid template is catalyzed to produce a primer extension product which is complementary to the target nucleic acid template. The conditions for initiation and extension include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.) and at a suitable temperature. The primer according to the invention may be single or double stranded. The primer is single-stranded for maximum efficiency in amplification, and the primer and its complement form a double-stranded nucleic acid. But it may be double stranded. "Primers" useful in the present invention are less than or equal to 100 nucleotides in length, e.g., less than or equal to 90, or 80, or 70, or 60, or 50, or 40, or 30, or 20, or 15, or equal to 10 nucleotides in length.

As used herein, the term "opposite orientation", when referring to primers, means that one primer comprises a nucleotide sequence complementary to the sense strand of a target nucleic acid template, and another primer comprises a nucleotide sequence complementary to the antisense strand of the same target nucleic acid template. Primers with an opposite orientation may generate a PCR amplified product from matched nucleic acid template to which they complement. Two primers with opposite orientation may be referred to as a reverse primer and a forward primer.

As used herein, the term "same orientation", means that primers comprise nucleotide sequences complementary to the same strand of a target nucleic acid template. Primers with same orientation will not generate a PCR amplified product from matched nucleic acid template to which they complement.

Alternatively, primers of the present invention may be labeled with a detectable label such as a radioactive moiety, or a fluorescent label, or alternatively, the amplification reaction may incorporate labeled nucleotides into the reaction product. Thus, the amplification reaction product may be "detected" by "detecting" the fluorescent or radioactive label.

As used herein, a "nucleic acid" generally refers to any polyribonucleotide or poly-deoxyribonucleotide, which may be unmodified RNA or DNA or modified RNA or DNA. "Nucleic acids" include, without limitation, single- and double-stranded nucleic acids. As used herein, the term "nucleic acid(s)" also includes DNAs or RNAs as described above, that contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells.

As used herein, "isolated" or "purified" when used in reference to a nucleic acid means that a naturally occurring sequence has been removed from its normal cellular (e.g., chromosomal) environment or is synthesized in a non-natural environment (e.g., artificially synthesized). Thus, an "isolated" or "purified" sequence may be in a cell-free solution or placed in a different cellular environment. The term "purified" does not imply that the sequence is the only nucleotide present, but that it is essentially free (about 90-95%, up to 99-100% pure) of non-nucleotide or nucleic acid material naturally associated with it, and thus is distinguished from isolated chromosomes.

As used herein, "genomic DNA" refers to chromosomal DNA, as opposed to complementary DNA copied from an RNA transcript. "Genomic DNA", as used herein, may be all of the DNA present in a single cell, or may be a portion of the DNA in a single cell.

As used herein, "complementary" refers to the ability of a single strand of a nucleic acid (or portion thereof) to hybridize to an anti-parallel nucleic acid strand (or portion thereof) by contiguous base-pairing between the nucleotides (that is not interrupted by any unpaired nucleotides) of the anti-parallel nucleic acid single strands, thereby forming a double-stranded nucleic acid between the complementary strands. A first nucleic acid is said to be "completely complementary" to a second nucleic acid strand if each and every nucleotide of the first nucleic acid forms base-pairing with nucleotides within the complementary region of the second nucleic acid. A first nucleic acid is not completely complementary to the second nucleic acid if one nucleotide in the first nucleic acid does not base pair with the corresponding nucleotide in the second nucleic acid.

As used herein, a "sample" refers to a biological material which is isolated from its natural environment and containing target nucleic acid, and may consist of purified or isolated nucleic acid, or may comprise a biological sample such as a tissue sample, a biological fluid sample, or a cell sample comprising target nucleic acid.

As used herein, a "double stranded DNA" is referred to as a "duplex". When the base sequence of one strand is entirely complementary to base sequence of the other strand, the duplex is called a "homoduplex". When a duplex contains at least one base pair which is not complementary, the duplex is called a "heteroduplex". In the subject invention, the formation of a heteroduplex, when amplified products from a sample taken from an individual are denatured and re-annealed, indicates the presence of a potential mutant PKD gene in that individual.

As used herein, "DHPLC" refers to a separation process called "denaturing high performance liquid chromatography" which has been used to detect sequence variants by separating a heteroduplex (resulting from the presence of a mutation) and a homoduplex having the same bp length. This separation is based on the fact that a heteroduplex has a lower melting temperature (Tm) than a homoduplex. DHPLC can separate heteroduplexes that differ by as little as one base pair under certain conditions. DHPLC can also be used to separate duplexes having different bp in length.

The "heteroduplex site separation temperature" or "midpoint temperature" or "Tm" is defined herein to mean, the temperature at which one or more base pairs denature, i.e., separate, at the site of base pair mismatch in a heteroduplex DNA fragment.

II. General Description of PKD Genes

The PKD-1 gene (e.g., genbank accession number L39891, SEQ ID NO. 1) spans about 54 kb of genomic DNA on chromosome 16 (16p13.3) and contains a 12,906 bp coding sequence divided into 46 exons from which a 14 kb mRNA is transcribed (Mochizuki et al., 1996, Science, 272:1339-1342; Hughes et al., 1995, Nature Genet. 10:151-160). The protein product of PKD-1, Polycystin-1, is a 4303 amino acid protein with a predicted mass of 460 kDa. Until recently, analysis of the PKD-1 gene had not been amenable to genetic analysis largely because of the presence of at least three highly homologous copies of the gene that map proximal to PKD-1 along chromosome 16 (16p13.1). Approximately 75% of the PKD-1 gene is duplicated and shares about 97% identity with its homologous copies. The reiterated region encompasses a 50 kb (5') portion of the gene containing the first 33 exons. Only the most 3', 5.7 kb of the gene, containing exons 34-46, is unique to PKD-1. Another notable feature of the PKD-1 gene is a polypyrimidine tract in intron 21 that is 2.5 kb long, the longest described in the human genome. The PKD-2 gene (e.g., genbank accession number AF004859-004873, SEQ ID NO. 2) spans 68 kb of genomic DNA and is located on chromosome 4 (4q21-23) (Mochizuki et al., 1996, supra). PKD-2 contains 15 exons and encodes a 5.4 kb transcript from which a 968-amino acid protein product of approximately 110 kDa is generated. Mutation analysis of PKD-2 is to a great extent easier than that of PKD-1 because PKD-2 is a single copy gene. See Table 1 for a summary of PKD genes and their protein products.

TABLE 1

PKD gene description

| Gene Description | PKD-1 | PKD-2 |
| --- | --- | --- |
| Chromosome | 16p13.3 | 4q21–23 |
| Genomic length | 54 kb | 68 kb |
| Exons | 46 | 15 |
| Base pairs | 12909 | 2904 |
| Codons | 4303 | 968 |
| Protein | Polycystin-1 | Polycystin-2 |

Based on evidence supporting the occurrence of somatic mutations on the normal allele, a two-hit model similar to the pathogenesis of the many familial cancer predisposition syndromes has been proposed to explain the clinically focal manifestations of the disease (Qian et al., 1996, Cell, 87:979-987; Watnick et al., 1998Mol. Cell. 2:247-251). Briefly, the model suggests that ADPKD is recessive at the cellular level and that a second somatic mutation or "hit" in a heterozygous PKD defective background would result in the homozygous loss of PKD function in the affected renal tubular epithelial cell. The loss of PKD function is postulated to disrupt the signaling mechanisms required for proper cell differentiation and in turn leads to the abnormal proliferation of the afflicted cell into cystic structures.

Direct sequencing of the PKD-1 gene has revealed the presence of polymorphism in normal individuals and a multitude of different sequence alterations in ADPKD affected individuals. Table 2 shows a sypnosis of the PKD-1 sequence alterations described in the literature to date.

TABLE 2

Published PKD-1 sequence alterations including mutations and polymorphisms*

| Codon Number | Nucleotide Number | Fragment number | Nucleotide Change | Amino Acid Change | Consequence |
| --- | --- | --- | --- | --- | --- |
|  |  | Intron 1-Exon 5 | 3 kb del |  |  |
| 5 | 224 | 1 | 13del |  | frameshift |
| 88 | 474 | 2 | GCG-GTG | Ala-Val |  |
| 92 | 487 | 2 | GCG-GCA | Ala-Ala | polymorphism |
| 225 | 885 | 5A + 5B | TCG-TAG | Ser-X | termination |
| 227 | 890 | 5A + 5B | CAG-TAG | Gln-X | termination |
| 230 | 900 | 5A + 5B | TGC-TTC | Cys-Phe |  |
| 324 | 1182 | 5B + 5C | CGC-CTC | Arg-Leu |  |
| 341 | 1234 | 5C | GCC-GCT | Ala-Ala | polymorphism |
| 373 | 1330 | 5C | CTT-CTC | Leu-Leu | polymorphism |
| 403 | 1420 | 6 | CAC-CAT | His-His | polymorphism |
|  |  | 7 | CAG-CAA | splice acceptor | skip exon 7 |
| 570 | 1921 | 8 | CAC-CAT | His-His | polymorphism |
|  |  | 9 | CAG-CAT | splice acceptor | skip exon 9 |
| 695 | 2296 | 10 | C del = ccc-cc^g | Pro-Pro | frameshift |
| 695 | 2296 | 10 | C ins = ccc-cc^c | Pro-Pro | frameshift |
| 705 | 2324 | 11A | CAG-TAG | Gln-X | termination |
| 738 | 2425 | 11A | CCC-CCG | Pro-Pro | polymorphism |
| 749 | 2457 | 11A | TCA-TGA | Ser-X | termination |
| 845 | 2745 | 11B | TTG-TCG | Leu-Ser |  |
| 898 | 2905 | 11B + 11C | GCA-GCC | Ala-Ala | polymorphism |
| 900 | 2911 | 11B + 11C | CCG-CCA | Pro-Pro | polymorphism |
| 910 | 2941 | 11B + 11C | GAC-GAT | Asp-Asp | polymorphism |
| 967 | 3110 | 12 | TGG-CGG | Trp-Arg |  |
| 991 | 3183 | 12 | GTC-GGC | Val-Val | polymorphism |
|  |  | 13 | AGC-TGC | splice acceptor | skip exon 13 |
| 1003 | 3220 | 13 | 4 bp del = agc-ag^g | Ser-Arg | frameshift |

TABLE 2-continued

Published PKD-1 sequence alterations including mutations and polymorphisms*

| Codon Number | Nucleotide Number | Fragment number | Nucleotide Change | Amino Acid Change | Consequence |
|---|---|---|---|---|---|
| 1021 | 3274 | 13 | GGT-GGC | Gly-Gly | polymorphism |
| 1037 | 3322 | 13 | CTA-CTG | Leu-Leu | polymorphism |
| 1041 | 3336 | 13 | del g = ggc-g^cg | Gly-Ala | frameshift |
|  |  | 14 | AGG-AAG | splice acceptor | skip exon 14 |
| 1092 | 3486 | 14 | CAT-CAC | His-His | polymorphism |
| 1124 | 3583 | 15A | GCC-GCT | Ala-Ala | polymorphism |
| 1125 | 3586 | 15A | TCC-TCT | Ser-Ser | polymorphism |
| 1166 | 3707 | 15A + 15B | GGC-AGC | Gly-Ser | probable path. |
| 1198 | 3804 | 15B | 7 bp del = agc-a^gg | Ser-Arg | frameshift |
| 1288 | 4075 | 15C + 15D | CAC-CAT | His-His | polymorphism |
| 1289 | 4077 | 15C + 15D | t del = gtg-g^gc | Val-Gly | frameshift |
| 1309 | 4137 | 15D | ct del = cct-c^ga | Pro-Arg | frameshift |
| 1346 | 4249 | 15D | ac del = aca-ac^a | Thr-Thr | frameshift |
| 1360 | 4291 | 15D + 15E | g del = gtg-gt^c | Val-Val | frameshift |
| 1399 | 4406 | 15E | TGG-CGG | Trp-Arg |  |
| 1525 | 4784 | 15G | g del = gtt-^tta | Val-Leu | frameshift |
| 1537 | 4820 | 15G | GAG-TAG | Glu-X | termination |
| 1545 | 4846 | 15G | AAG-AAA | Lys-Lys | polymorphism |
| 1555 | 4876 | 15G + 15H | GCA-GCC | Ala-Ala | polymorphism |
| 1558 | 4885 | 15G + 15H | ACG-ACA | Thr-Thr | polymorphism |
| 1563 | 4898 | 15G + 15H | t ins = aat-a^ta | Asn-Ile | frameshift |
| 1633 | 5109 | 15I | t ins = gag-gatg | Glu-Asp | frameshift |
| 1653 | 5168 | 15I | CAG-TAG | Gln-X | termination |
| 1672 | 5225 | 15I + 15J | a del = agg-^ggg | Arg-Gly | frameshift |
| 1672 | 5225 | 15I + 15J | ag del = agg-^ggg | Arg-Gly | frameshift |
| 1724 | 5383 | 15J | ACC-ACT | Thr-Thr | polymorphism |
| 1786 | 5566 | 15J + 15K | CCG-CTG | Pro-Leu |  |
| 1787 | 5570 | 15J + 15K | CTG-TTG | Leu-Leu | polymorphism |
| 1826 | 5689 | 15K | TGG-TGA | Trp-X | termination |
| 1829 | 5696 | 15K | CTG-TTG | Leu-Leu | polymorphism |
| 1858 | 5783 | 15K | g del = gat-^atg | Asp-Met | frameshift |
| 1874 | 5833 | 15K | TGG-TGA | Trp-X | termination |
| 1887 | 5870 | 15K | 14del = ccatc-cc^gct | Ile-Val | frameshift |
| 1921 | 5974 | 15L | CTG-CTA | Leu-Leu | polymorphism |
| 1922 | 5975 | 15L | CAG-TAG | Gln-X | termination |
| 1938 | 6024 | 15L | 1 bp ins = cac-ca^** | His-** | frameshift |
| 1949 | 6058 | 15L | AGC-AGT | Ser-Ser | polymorphism |
| 1956 | 6078 | 15L | GTG-GAG | Val-Glu | probable path. |
| 1960 | 6089 | 15L | CAG-TAG | Gln-X | termination |
| 1992 | 6187 | 15L | 4 bp del = ttc-tt^ | ** | frameshift |
| 1995 | 6195 | 15L | CGC-CAC | Arg-His | polymorphism |
| 2039 | 6326 | 15M + 15L | CAG-TAG | Gln-X | termination |
| 2075 | 6434 | 15M | 28 bp del |  | frameshift |
| 2144 | 6642 | 15M | 27 bp del |  | frameshift |
| 2163 | 6698 | 15M | CGA-TGA | Arg-X | termination |
| 2192 | 6785 | 15M + 15N | 7 bp del = acc-^gct | Thr-Ala | frameshift |
| 2220 | 6868 | 15N | 15 bp del = cgg-^gtg | Arg-Val | in frame deletion |
| 2222 | 6876 | 15N | GCG-GTG | Ala-Val |  |
| 2229 | 6898 | 15N | TGC-TGA | Cys-X | termination |
| 2242 | 6937 | 15N | ac del = aca-ac^a | Thr-Thr | frameshift |
| 2243 | 6938 | 15N | CAG-TAG | Gln-X | termination |
| 2250 | 6960 | 15N | ACG-ATG | Thr-Met |  |
|  |  | 15 | GGT-GGG | splice donor |  |
|  |  | 16 | CAG-GAG | splice acceptor | skip exon 16 |
| 2309 | 7138 | 16 | GGC-GGT | Gly-Gly | polymorphism |
| 2113 | 7147 | 16 | GCG-GCA | Ala-Ala | polymorphism |
| 2323 | 7179 | 16 | 14 bp del = gtc-gt^ | Val-X | termination |
| 2329 | 7196 | 16 | CGG-TGG | Arg-Trp |  |
| 2332 | 7205 | 16 | 7del = gct-^tgg | Ala-Trp | frameshift |
| 2334 | 7211 | 16 | 7ins = gtg-^gtg | Val-Val | frameshift |
| 2336 | 7219 | 16 | TAC-TAA | Tyr-X | termination |
|  |  | 17 | CAG-GAG | splice acceptor | skip exon 17 |
| 2370 | 7321 | 17 | TGT-TGA | Cys-X | termination |
| 2371 | 7324 | 17 | gt del = gtg-gt^c | Val-Val | frameshift |
| 2378 | 7345 | 17 | GTG-GTT | Val-Val | polymorphism |
| 2379 | 7347 | 17 | TAC-TGC | Tyr-Cys |  |
| 2389 | 7376 | 17 | TTG-CTG | Leu-Leu | polymorphism |
| 2392 | 7386 | 17 | CGC-CCC | Arg-Pro |  |
| 2396 | 7397 | 17 | 11 bp ins = att-^ttg | Ile-Leu | frameshift |
| 2402 | 7415 | 17 | CGA-TGA | Arg-X | termination |
| 2408 | 7433 | 18 | CGT-TGT | Arg-Cys | probable path. |

TABLE 2-continued

Published PKD-1 sequence alterations including mutations and polymorphisms*

| Codon Number | Nucleotide Number | Fragment number | Nucleotide Change | Amino Acid Change | Consequence |
|---|---|---|---|---|---|
| 2423 | 7479 | 18 | TCC-TTC | Ser-Phe | |
| 2430 | 7499 | 18 | CGA-TGA | Arg-X | termination |
| 2442 | 7535 | 18 | 3 bp ins = gag-g^gcg | Glu-Gly | probable path. |
| 2471 | 7623 | 18 | CCG-CTG | Pro-Leu | |
| 2481 | 7652 | 18 | CTG-TTG | Leu-Leu | polymorphism |
| 2495 | 7696 | 18 | TGC-TGT | Cys-Cys | polymorphism |
| 2519 | 7767 | 19 | CAG-CTG | Gln-Leu | |
| 2548 | 7853 | 19 | GAG-CAG | Glu-Gln | polymorphism |
| 2558 | 7883 | 19 | CAG-TAG | Gln-X | termination |
| 2570 | 7919 | 20 | TTG-CTG | Leu-Leu | polymorphism |
| 2579 | 7945 | 20 | ggc del = ggc-^agc | Gly-Ser | Gly del in frame |
| 2582 | 7956 | 20 | ACG-ATG | Thr-Met | polymorphism |
| 2597 | 8002 | 20 | CCA-CCG | Pro-Pro | polymorphism |
| 2604 | 8021 | 20 | GAT-AAT | Asp-Asn | polymorphism |
| 2607 | 8030 | 20 | 5 bp del = cac-^cat | His-His | frameshift |
| 2612 | 8046 | 20 | gtt del = tcgtt-tc^g | Ser-Ser | Leu del in frame |
| 2638 | 8124 | 21 | CAC-CGC | His-Arg | polymorphism |
| 2639 | 8126 | 21 | CGA-TGA | Arg-X | termination |
| 2639 | 8126 | 21 | 20 ins = cga-c^**** | Arg-** | frameshift |
| 2649 | 8157 | 21 | ACT-ATT | Thr-Ile | |
| 2650 | 8159 | 21 | del ct = ctg-^ggt | Leu-Gly | frameshift |
| 2658 | 8183 | 21 | 8 bp del | Val-X | termination |
| 2674 | 8231 | 22 | CCC-TCC | Pro-Ser | polymorphism |
| 2696 | 8298 | 22 | CTC-CGC | Leu-Arg | |
| 2708 | 8334 | 22 | ACG-ATG | Thr-Met | polymorphism |
| 2734 | 8411 | 23A | CCA-ACA | Pro-Thr | polymorphism |
| 2735 | 8415 | 23A | CAG-CTG | Gln-Leu | polymorphism |
| 2745 | 8446 | 23A | TCT-TCG | Ser-Ser | polymorphism |
| 2760 | 8490 | 23A | ATG-ACG | Met-Thr | |
| 2761 | 8493 | 23A | CGC-CCC | Arg-Pro | |
| 2763 | 8498 | 23A | CTC-GTC | Leu-Val | |
| 2764 | 8502 | 23A | ATG-ACG | Met-Thr | |
| 2765 | 8504 | 23A | CGC-TGC | Arg-Cys | polymorphism |
| 2766 | 8507 | 23A | 12 bp ins/dup | | in frame mutation |
| 2782 | 8556 | 23A | GTG-ATG | Val-Met | polymorphism |
| 2791 | 8583 | 23A + 23B | CGG-CAG | Arg-Gln | |
| 2813 | 8650 | 23A + 23B | AGC-AGT | Ser-Ser | polymorphism |
| 2814 | 8651 | 23A + 23B | GGG-AGG | Gly-Arg | polymorphism |
| 2815 | 8657 | 23A + 23B | c del = gcc-g^cc | Ala-Ala | frameshift |
| 2826 | 8688 | 23B + 23C | ATC-ACC | Ile-Thr | |
| 2888 | 8873 | 23C | CGC-GGC | Arg-Gly | polymorphism |
| 2893 | 8890 | 23C | TCC-TCG | Ser-Ser | polymorphism |
| 2900 | 8909 | 23C | CAG-TAG | Gln-X | termination |
| 2905 | 8924 | 23C | GTC-ATC | Val-Ile | polymorphism |
| 2921 | 8973 | 23C | CAT-CCT | His-Pro | |
| 2966 | 9109 | 24 | GAG-GAC | Glu-Asp | polymorphism |
| 2971 | 9124 | 24 | GCT-GCC | Ala-Ala | polymorphism |
| 2972 | 9125 | 24 | GAC-AAC | Asp-Asn | polymorphism |
| 2978 | 9142 | 24 | ttc del | del of Phe | in frame deletion |
| 2985 | 9164 | 25 | AGA-GGA | Arg-Gly | |
| 2988 | 9175 | 25 | GCG-GCA | Ala-Ala | polymorphism |
| 2993 | 9189 | 25 | CTG-CCG | Leu-Pro | probable path. |
| 3001 | 9213 | 25 | TGG-TAG | Trp-X | termination |
| 3008 | 9233 | 25 | GTG-CTG | Val-Leu | |
| 3012 | 9245 | 25 | 18 bp del | | in frame deletion |
| 3016 | 9258 | 25 | CAG-CGG | Gln-Arg | probable path. |
| 3020 | 9269 | 25 | GAG-TAG | Glu-X | termination |
| 3030 | 9299 | 25 | c del = ctg-^tgc | Leu-Cys | frameshift |
| 2985 | 9326 | 25 | CGC-TCG | Arg-Cys | |
| 3052 | 9367 | 25 | GGC-GGT | Gly-Gly | polymorphism |
| 3064 | 9401 | 25 | TTT-CTT | Phe-Leu | |
| 3065 | 9406 | 25 | GTTT-CCTT | Phe-Leu | polymorphism |
| 3065 | 9406 | 25 | GTG-GTC | Val-Val | polymorphism |
| 3066 | 9407 | 25 | TTT-CTT | Phe-Leu | polymorphism |
| 3090 | 9481 | 26 | GTC-GTT | Val-Val | polymorphism |
| 3110 | 9541 | 26 | CCT-CCC | Pro-Pro | polymorphism |
| 3139 | 9627 | 27 | GGC-TGC | Gly-Cys | |

TABLE 2-continued

Published PKD-1 sequence alterations including mutations and polymorphisms*

| Codon Number | Nucleotide Number | Fragment number | Nucleotide Change | Amino Acid Change | Consequence |
|---|---|---|---|---|---|
| 3180 | 9751 | 27 | TGG-TGA | Trp-X | termination |
| 3193 | 9789 | 28 | CCT-CTT | Pro-Leu | |
| 3206 | 9827 | 28 | CAG-TAG | Gln-X | termination |
| 3219 | 9867 | 28 | t del = ctt-c^tt | Leu-Leu | frameshift |
| 3223 | 9880 | 28 | ACG-ACA | Thr-Thr | polymorphism |
| 3285 | 10064 | 29 | GTT-ATT | Val-Ile | |
| 3311 | 10143 | 30 | CAT-CGT | His-Arg | |
| 3341 | 10234 | 30 | CTT-CTC | Leu-Leu | polymorphism |
| 3348 | 10255 | 30 | CGG-CGT | Arg-Arg | polymorphism |
| 3350 | 10262 | 31–34 | 2 kb del | | frameshift after 3350 |
| 3375 | 10334 | 31 | GTG-ATG | Val-Met | |
|  |  | IVS31 + 25del19 |  |  | frameshift after 3389 |
| 3394 | 10391 | 32 | CAG-TAG | Gln-X | termination |
|  |  | 34-3'UTR | 5.5 kb del |  | |
| 3474 | 10631 | 34 | CAG-TAG | Gln-X | termination |
| 3509 | 10737 | 35 | ACG-ATG | Thr-Met | polymorphism |
| 3510 | 10739 | 35 | CTG-GTG | Leu-Val | probable path. |
| 3511 | 10743 | 35 | GCG-GTG | Ala-Val | |
| 3513 | 10748 | 35 | CAG-TAG | Gln-X | termination |
| 3561 | 10893 | 36 | AGC-AAC | Ser-Asn | probable poly. |
| 3579 | 10947 | 36 | t ins = ttc-tt^t | Phe-Phe | frameshift |
| 3589 | 10976 | 36 | CTG-TTG | Leu-Leu | polymorphism |
|  | IVS37-10C-A | intron 37 |  |  | unknown poly |
| 3631 | 11104 | 37 | GAG-GAC | Glu-Asp | |
| 3677 | 11241 | 38 | ATG-ACG | Met-Thr | |
| 3692 | 11284 | 38 | t ins = ggc-gg^t | Gly-Gly | frameshift |
| 3692 | 11285 | 38 | c ins = tca-^ctc | Ser-Leu | frameshift |
| 3711 | 11342 | 38 | CGG-GGG | Arg-Gly | frameshift |
| 3747 | 11449 | 39 | 15 bp del = cgg-^cgg | Arg-Arg | in frame deletion |
| 3749 | 11457 | 39 | 15 bp del = gcg-^cag | Arg-Gln | in frame deletion |
| 3752 | 11466 | 39 | CGG-CAG | Arg-Gln | |
|  |  | IVS39 + 1G-C | Ggt-Gct | splice donor | |
|  |  | I39E40 − 25 to I39E40 + 47 | 72 bp del |  | |
| 3370 | 11521 | 40 | TCG-TCA | Ser-Ser | polymorphism |
| 3780 | 11549 | 40 | 10 bp ins = tac-t^ac | Tyr-Tyr | frameshift |
| 3781 | 11554 | 40 | GAC-GAT | Asp-Asp | polymorphism |
| 3791 | 11584 | 40 | TCG-TCC | Ser-Ser | polymorphism |
| 3794 | 11592 | 40 | TGG-TAG | Trp-X | termination |
|  | IVS41-11C-T | intron 41 |  |  | unknown poly |
| 3818 | 11665 | 41 | TAC-TAA | Tyr-X | termination |
| 3820 | 11669 | 41 | CAG-TAG | Gln-X | termination |
| 3837 | 11720 | 41 | CAG-TAG | Gln-X | termination |
| 3971 | 12124 | 43 | CGC-CGT | Arg-Arg | polymorphism |
| 3984 | 12163 | 43 | TCC-TCG | Ser-Ser | polymorphism |
| 3985 | 12165 | 43 | GCA-GGA | Ala-Glu | |
| 3985 | 12168 | 43 | GCC-GGG | Ala-Gly | probable poly. |
| 3991 | 12184 | 43 | GCC-GCG | Ala-Ala | polymorphism |
|  | 12187 | 43 | 9 bp ins |  | in frame |
|  |  | IVS43 + 14del20 |  |  | complex splicing |
|  |  | IVS43 + 17del18 |  |  | complex splicing |
|  |  | 44 | CAG-CAC | splice acceptor | skip exon 44 |
| 4010 | 12239 | 44 | CAG-TAG | Gln-X | termination |
| 4011 | 12244 | 44 | TGG-TGA | Trp-X | termination |
| 4014 | 12252 | 44 | tt del = ttt-t^gg | Phe-Trp | frameshift |
| 4017 | 12262 | 44 | at del = aca-ac^t | Thr-Thr | frameshift |
| 4020 | 12269 | 44 | CGA-TGA | Arg-X | termination |
| 4024 | 12281 | 44 | GAG-TAG | Glu-X | termination |
| 4027 | 12290 | 44 | g ins = ggg-gg^g | Gly-Gly | frameshift |
| 4031 | 12303 | 44 | GGC-GAC | Gly-Asp | |
| 4032 | 12307 | 44 | CTG-CTC | Leu-Leu | polymorphism |
| 4039 | 12328 | 44 | TAC-TAA | Tyr-X | termination |
| 4041 | 12332 | 44 | CAG-TAG | Gln-X | termination |
| 4044 | 12341 | 44 | ATC-GTC | Ile-Val | probable poly. |
|  |  | 44 | GGT-GCT | splice donor | del of 4001–4045 |
|  |  | 45 | CAG-CAA | splice acceptor | skip exon 45 |
| 4058 | 12384 | 45 | GCC-GTC | Ala-Val | probable poly. |
| 4059 | 12386 | 45 | CAG-TAG | Gln-X | termination |

TABLE 2-continued

Published PKD-1 sequence alterations including mutations and polymorphisms*

| Codon Number | Nucleotide Number | Fragment number | Nucleotide Change | Amino Acid Change | Consequence |
|---|---|---|---|---|---|
| 4069 | 12416 | 45 | 20 bp ins = ggg-g^**** | Gly-** | frameshift |
| 4075 | 12438 | 45 | 20 bp ins = gcc-gc^g | Ala-Ala | frameshift |
| 4086 | 12469 | 45 | TGT-TGA | Cys-X | termination |
| 4091 | 12483 | 45 | GCA-GCG | Ala-Ala | polymorphism |
| 4101 | 12511 | 45 | g ins = -ggg-gg^g | Gly-Gly | frameshift |
| 4124 | 12581 | 45 | CAG-TAG | Gln-X | termination |
| 4126 | 12589 | 45 | TAC-TAG | Tyr-X | termination |
| 4131 | 12601 | 45 | gtt del = gagtt-ga^gtt | Leu-Phe | frameshift |
| 4135 | 12614 | 45 | AGG-GGG | Arg-Gly | |
| 4136 | 12617 | 45 | CTG-TTG | Leu-Leu | polymorphism |
| 4136 | 12617 | 45 | c del = ctg-^tgc | Leu-Cys | frameshift |
| 4139 | 12628 | 45 | TGG-TGA | Trp-X | termination |
| 4145 | 12644 | 45 | GTC-ATC | Val-Ile | probable poly. |
|  | IVS45 + 17insG | intron 45 |  |  | unknown poly |
| 4153 | 12668 | 46 | CGC-TGC | Arg-Cys |  |
| 4168 | 12714 | 46 | duplication of 23 bp |  | frameshift |
| 4176 | 12739 | 46 | a del = cca-cc^c | Pro-Pro | frameshift |
| 4189 | 12777 | 46 | TCC-TTC | Ser-Phe | polymorphism |
| 4198 | 12801 | 46 | del 28 |  | frameshift |
| 4209 | 12838 | 46 | CCT-CCC | Pro-Pro | polymorphism |
| 4224 | 12882 | 46 | CAG-CCG | Gln-Pro | probable path. |
| 4227 | 12890 | 46 | CGA-TGA | Arg-X | termination |
| 4236 | 12919 | 46 | TAC-TAa/g | Tyr-X | termination |
| 4254 | 12973 | 46 | CCC-CCT | Pro-Pro | polymorphism |
| 4275 | 13034 | 46 | CGG-TGG | Arg-Trp | probable path. |

*Updated March 2001.
**is an unidentified base or amino acid.

III. Identification of Unique Sites Within PKD Genes

Due to the fact that 70% of the PKD-1 gene is replicated as non-functional homologues with more than 95% sequence identity to PKD-1, the identification of PKD-1 unique sites are critical for the development of a genetic testing method. With the successful decoding of human genome sequences, the unique sites within the PKD genes may be identified by comparing genomic DNA sequences comprising a PKD gene with genomic DNA sequences comprising a PKD homologue. Useful databases and computer programs are known in the art (e.g., databases available through NCBI at www.ncbi.nlm.nih.gov; and computer programs available at http://www.ncbi.nlm.nih.gov/BLAST and DNAStar, www.dnastar.com). A unique site refers to a stretch of sequence within a PKD gene which shares less than or equal to 80% (e.g., less than or equal to 70%, or 60%, or 50% or 40% or 30% or 20% or 10%) sequence identity to a PKD homologue or other sequences.

Several unique sites (e.g., single copy site) have been described in Rossetti et al., 2000, Am. J. Hum. Genet. 68:46-63, the entirety of which hereby incorporated by reference. A novel unique site (5' AGG TCC AGG GCG ACT CGC TGG 3', or 5' CAG GGC CAC ACG CGC TGG GCG 3', or their complement thereof) is identified for PKD-1 by Applicants of the present application. Other unique sites may be found in, for example, in U.S. Pat. Nos. 6,228,591 and 6,031,088, each of which is incorporated herein by its entirety.

The identified unique sites can be used for designing PKD-specific primers for the amplification of authentic PKD genes. The length of a unique site may vary from several nucleotides to thousands of nucleotides. Most of unique site identified comprises less than or equal to 100 nucleotides, e.g., less than or equal to 50 nucleotides, or less than or equal to 30 nucleotides. Amplification using PKD-specific primers would increase the specificity of the amplification reaction and reduce the amount by-products amplified from PKD homologues. The specifically amplified product of authentic PKD genes may be subsequently used for sequencing to identify allele variant, e.g., a mutant PKD gene, in an individual or for cloning and/or expression for other analysis.

IV. PKD-Specific Primers Useful for the Invention

Samples to be analyzed for the presence or absence of mutations often contain amounts of material too small to detect. The first step in mutation detection assays is, therefore, sample amplification. A preferred amplification reaction of the invention is PCR. PCR amplification comprises steps such as primer design, choice of DNA polymerase enzyme, the number of amplification cycles and concentration of reagents. Each of these steps, as well as other steps involved in the PCR process affects the purity of the amplified product. Although the PCR process and the factors which affect fidelity of replication and product purity are well known in the PCR art, these factors have not been addressed, heretofore, in relation to mutation detection of PKD genes using the separating method of the invention, e.g., DHPLC.

Any primer which anneals, under specific stringent conditions, to a sequence within an authentic PKD gene, but not to a PKD homologue or other sequences is a useful PKD-specific primer according to the invention. Sequences of the identified unique sites serve as the basis for designing PKD-specific primers useful according to the invention. The primers, according to the subject invention, may be incorporated into a convenient kit for identifying a PKD patient.

A. Criteria for Selecting Primers

A PKD species-specific primers preferably comprise a sequence complementary to a sequence located within a unique site of a PKD gene. The PKD-specific primer may be complementary to a unique site of a normal or a mutant PKD gene, so long as the primer preferably anneals to an authentic PKD gene other than a PKD homologue.

PKD species-specific primers may be selected manually by analyzing sequences of the unique sites identified for a PKD gene. When the sequence of a DNA fragment to be amplified by PCR is known, commercially available software can be used to design primers which will produce either the whole fragment, or any sequence within the fragment. The melting map of a fragment can be constructed using software such as MacMelt™ (BioRad Laboratories, Hercules, Calif.), MELT (Lerman et al. Meth. Enzymol. 155:482 (1987)), or WinMelt™ (BioRad Laboratories).

It is known in the art that primers that are about 18-25 bases long and with 50% G-C content will work well at annealing temperature at about 52-58° C. These properties are preferred when designing primers for the subject invention. Longer primers, or primers with higher G-C contents, have annealing optimums at higher temperatures; similarly, shorter primers, or primers with lower G-C contents, have optimal annealing properties at lower temperatures. A convenient, simplified formula for obtaining a rough estimate of the melting temperature of a primer 17-25 bases long is as follows:

Melting temperature (Tm in ° C.)=4×(# of G+# of C)+2×(# of A+# of T)

The overall design process design consists of both long range (i.e., for the first round PCR) and short range primer (i.e., for the nested PCR) design. In long range primer design, the objective is to design primers that produce good quality PCR products. "Good quality" PCR products are defined herein to mean PCR products produced in high yield and having low amounts of impurities such as primer dimers and PCR induced mutations. Good quality PCR can also be affected by other reaction parameters, such as the enzyme used, the number of PCR cycles, the concentration and type of buffer used, temperature thermal cycling procedures and the quality of the genomic template. Methods for producing good quality PCR products are discussed by Eckert et al. (*PCR: A Practical Approach*, McPherson, Quirke, and Taylor eds., IRL Press, Oxford, Vol. 1, pp. 225-244, 1991). This reference and the references therein are incorporated herein in their entireties.

Short range primer design should fulfill two requirements. First, it should fulfill all the requirements of long range primer design and give good quality PCR products. In addition, it must produce fragments that allow the DHPLC method to detect a mutation or polymorphism regardless of the location of the mutation or polymorphism within the amplified fragment. For example, large DNA fragments, having up to several thousand base pairs, can be amplified by PCR. If the only goal of the amplification is to replicate the desired fragment, then there is a large latitude in the design of primers which can be used for this purpose. However, if the purpose of a PCR amplification is to produce a DNA fragment for mutation detection analysis by DHPLC, then primers must be designed such that the fragment produced in the PCR process is capable of being detected, and will produce a signal, when analyzed by DHPLC. In a preferred embodiment of the invention, the length of an amplified product is 150-600 bps. In a more preferred embodiment, the fragment length for DHPLC mutation detection analysis is 150-400 bp.

There are two goals of designing short range primers. One goal for primer design is if the analysis is used as a "mutation analysis" test. Another goal is in analysis for research or diagnostic purposes, e.g., for identifying a PKD patient. "Mutation analysis" is defined herein as the study or analysis of DNA fragments to determine if the fragments contain variations (i.e., mutations or polymorphisms) in a population and correlate that variation to disease. It is to be understood that, within the context of this invention, the term "mutation" does not include a polymorphism (e.g., normal) which is silent for the disease. When DHPLC is used as a mutation analysis technique, then an important aspect of the present invention is a method for designing primers to produce a fragment in which a putative mutation can be detected, regardless of where the mutation site is located within the fragment. If the mutation is known, on the other hand, then the primer design can be further refined so that the analysis is optimized, i.e., the resolution of the homoduplex and the heteroduplex peaks in DHPLC is maximized. By improving the resolution for the analysis of known mutations, accuracy of analysis can be performed. Improved resolution is required for diagnostic mutation applications. Furthermore, with improved resolution, automatic identification of the positive presence of mutation can be more easily implemented with appropriate software and an algorithm that overlays and comparatively measures the peaks of the normal and mutant DNA samples.

Another method of primer design for mutation analysis applications is to design the primers so that the region of interest is at a lower melting domain within the fragment. In this case the primers are preferred to be designed so that the fragment being measured will overlap the regions of interest as the analysis is performed traveling down the exon. In these cases, the temperature difference between the higher melting domain and the lower melting domain is preferred to be greater than 5° C. and most preferred to be greater than 10° C.

Once the mutation of interest is identified, primers can be redesigned for diagnostic or clinical applications. In these cases, the mutation is preferably located within 25% or 25 bases of the end whichever is closer to the end. The other end of the fragment contains a higher melting domain of preferably 5° C., more preferably 10° C. higher, and most preferably 15° C. higher than the lower domain where the mutation is located. If the primer selection does not result in a high melting domain on the opposite end of the fragment, then a G-C clamp can be applied to increase the melting temperature at the desired end (e.g., an A-T rich end) (Myers et al., 1985, Nucleic Acids Res. 13:3111). G-C clamping is a technique in which additional G or C bases are included on the 5' end of one or both of the primers. The polymerase enzyme will extend over these additional bases incorporating them into the amplified fragment thereby raising the melting temperature of the end(s) of the fragment relative to that in the vicinity of the mutation. For example, in cases where the mutation is in the center of the amplified fragment and the length is less than 100 bp and the melting profile is flat, or in cases where the mutation in a high melting region of the fragment and a higher melting region is in effect a G-C rich region, a G-C clamp may be necessary. In these cases, proper primer selection will result in a fragment in which the mutation can be detected. The size of the G-C clamp can be up to 40 bp and as little as 4 or 5 bp. The most preferred G-C clamp for mutation detection by DHPLC is 10 to 20 bp.

If it is not possible to design primers which will produce, upon PCR amplification, domains having a constant melting range or domains within a fragment which are sufficiently close in Tm, then it may be necessary to lower the Tm of a domain of interest for successful mutation detection by DHPLC. This can be done, for example, by substituting dGTP with the analog 7-deaza-2'-dGTP which is known to effectively lower the melting temperature of G-C base pairs (Dierick et al.,1993, Nucl. Acids Res. 21:4427). If it is necessary to raise the Tm of the domain, then 2, 6-aminopurine can be used in place of dGTP in the PCR amplification.

In a most preferred embodiment, the primers are selected so that the mutation is located in a "lower melting" domain of the fragment. However, a mutation can also be detected by DHPLC in a high melting domain of the fragment either if the high melting domain does not have a melting temperature that is too different from other domains in the fragment or if a higher column temperature is used that is optimized for the higher melting domain of the fragment.

The long range primer design described above can be further refined by local primer design in which several other factors should be considered. For example, primers with non-template tails, such as universal sequencing primers or T7 promoters, may need to be avoided. The preferred primer has a Tm of about 56° C. The difference in Tm between the forward and reverse primers is preferably about 1° C. The difference in Tm between primer and template is preferably 25° C. The 3'-pentomer of each primer is preferably be more stable than $\Delta G°=-6$ kcal/mol (i.e., more negative). Any possible primer dimers are preferably be less stable than the 3'-pentomer by at least 5 kcal/mol (i.e., 5 kcal more positive). Any primer self annealing loops are preferably to have a Tm of less than 12° C. Primers are preferably be of high purity without failure sequences. To avoid degradation, storage in Tris-HCl (pH 8.0) buffer is preferable to pure water.

In some embodiments, it is more convenient to directly separate a long fragment, e.g., an exon, of up to 5 kb (e.g., up to 4 kb, or up to 3 kb, or up to 2 kb, or up to 1 kb) for mutations. Such long fragments generally contain multiple melting temperature domains. Double-stranded DNA fragments melt in a series of discontinuous steps as different regions with differing thermal stabilities which denature in response to increasing temperature. These different regions of thermal stability are referred to as "domains", and each domain is approximately 50-300 bp in length. Each domain has its own respective Tm and will exhibit thermodynamic behavior which is related to its respective Tm. The presence of a base mismatch within a domain will destabilize it, resulting in a decrease in the Tm of that domain in the heteroduplex relative to its fully hydrogen-bonded counterpart found in the homoduplex. Generally the presence of a base mismatch will lower the Tm by approximately 1-2° C.

In accordance with the preferred embodiments, optimal results have been obtained using primers which are 18-51 in length and DNA sequence to the primers with SEQ ID NOs. 3-49 (Table 3 and Table 4). However, one skilled in the art will recognize that the length of the primers used may vary. For example, it is envisioned that shorter primers containing at least 15, and preferably at least 17, consecutive bases of the nucleotide sequences of these primers SEQ ID NOs. 3-49 may be suitable. The exact upper limit of the length of the primers is not critical. However, typically the primers will be less than or equal to approximately 60 bases, preferably less than or equal to 50 bases. Further still, the bases included in the primers may be modified as is conventional in the art, including but not limited to, incorporating detectable labels such as biotin, or fluorescent labels.

TABLE 3

Examples of useful PKD-1 specific primers*

| SEQ ID NO. | Primer Name | Primer Sequence |
|---|---|---|
| | 1X1F | 5' CGT CGC TCA GCA GCA GGT CG 3' |
| | 1X1R | 5' CGT CCT GCT TCC CGT CCC G 3' |
| | 1X2F | 5' GCG GCC CGC CGC CCC CGC CGT TGG GGA TGC TGG CAA TGT GTG 3' |
| | 1X2R | 5' GGG ATT CGG CAA AGC TGA TG 3' |
| | 1X3F | 5' TTC CAT CAG CTT TGC CGA AT 3' |
| | 1X3R | 5' ATC TGG TCT CAA GCC TGG AAG 3' |
| | 1X4F | 5' GCC CCG CGC CCG TCC CGC CGC CCC CGC CGA GAC CCT TCC CAC CAG ACC T 3' |
| | 1X4R | 5' CGC CCC CGC CCG TGA GCC CTG CCC AGT GTC T 3' |
| | 1X5AF | 5' GCG GCC CGC CGC CCC CGC CGG AGC CAG GAG GAG CAG AAC CC 3' |
| | 1X5AR | 5' CAG AGG GAC AGG CAG GCA AAG G 3' |
| | 1X5BF | 5' GCC CCC GCC GCC CAG CCC TCC AGT GCC T 3' |
| | 1X5BR | 5' ATC GCT ATG TGC TGC CTG GG 3' |
| | 1X5CF | 5' CCG AGG TGG ATG CCG CTG 3' |
| | 1X5CR | 5' GAA GGG GAG TGG GCA GCA GAC 3' |
| | 1X6F | 5' CAC TGA CCG TTG ACA CCC TCG 3' |
| | 1X6R | 5' TGC CCC AGT GCT TCA GAG ATC 3' |
| | 1X7F | 5' GGA GTG CCC TGA GCC CCC T 3' |
| | 1X7R | 5' CCC CTA ACC ACA GCC AGC G 3' |
| | 1X8F | 5' TCT GTT CGT CCT GGT GTC CTG 3' |
| | 1X8R | 5' GCA GGA GGG CAG GTT GTA GAA 3' |
| | 1X9F | 5' GCG GCC CGC CGC CCC CGC CGG GTA GGG GGA GTC TGG GCT T 3' |
| | 1X9R | 5' GAG GCC ACC CCG AGT CC 3' |
| | 1X10F | 5' GTT GGG CAT CTC TGA CGG TG 3' |
| | 1X10R | 5' CGC CGC CCC CGC CCG GGA AGG TGG CCT GAG GAG AT 3' |
| | X11AF | 5' GCG GCC CGC CGC CCC CGC CGG GGG TCC ACG GGC CAT G 3' |
| | 1X11AR | 5' AAG CCC AGC AGC ACG GTG AG 3' |

TABLE 3-continued

Examples of useful PKD-1 specific primers*

| SEQ ID NO. | Primer Name | Primer Sequence |
|---|---|---|
| | 1X11BF | 5' CCG CCG CCC CCG CCG CTG CCC TGC CTG TGC CCT G 3' |
| | 1X11BR | 5' GCC CCG CGC CCG TCC CGC CGC CCC CGC CCG TTC CAC CAC CAC GTC CAC CAC 3' |
| | 1X11CF | 5' GTG GTG GAC GTG GTG GTG GAA 3' |
| | 1X11CR | 5' GGC TGC TGC CCT CAC TGG GAA 3' |
| | 1X12F | 5' TAA GGG CAG AGT CCT CCA CAG 3' |
| | 1X12R | 5' CCA CCC CCG CCC ACC TAC TGA G 3' |
| | 1X13F | 5' GCG GCC CGC CGC CCC CGC CGT GGA GGG AGG GAC GCC AAT C 3' |
| | 1X13R | 5' GAG GCT GGG GCT GGG ACA A 3' |
| | 1X14F | 5' CCC GGT TCA CTC ACT GCG 3' |
| | 1X14R | 5' CCC CCG CCC GCC GTG CTC AGA GCC TGA AAG 3' |
| | 1X15AF | 5' GGC GGG GGG CTT CTG CCG AGC GGG TGG GGA GCA GGT GG 3' |
| | 1X15AR | 5' CGC CGC CCC CGC CCG GCT CTG GGT CAG GAC AGG GGA 3' |
| | 1X15BF | 5' CGC CTG GGG GTG TTC TTT 3' |
| | 1X15BR | 5' ACG TGA TGT TGT CGC CCG 3' |
| | 1X15CF | 5' GCC CCC GCC GGG GCG CCC CCG TGG TGG TCA GC 3' |
| | 1X15CR | 5' CAG GCT GCG TGG GGA TGC 3' |
| | 1X15DF | 5' CTG GAG GTG CTG CGC GTT 3' |
| | 1X15DR | 5' CGC CCC CGC CCG CTG GCT CCA CGC AGA TGC 3' |
| | 1X15EF | 5' CGT GAA CAG GGC GCA TTA 3' |
| | 1X15ER | 5' CCC CCG CCC GGC AGC AGA GAT GTT GTT GGA C 3' |
| | 1X15FF | 5' CCG CCG CCC CCG CCG CCA GGC TCC TAT CTT GTG ACA 3' |
| | 1X15FR | 5' TGA AGT CAC CTG TGC TGT TGT 3' |
| | 1X15GF | 5' CTA CCT GTG GGA TCT GGG G 3' |
| | 1X15GR | 5' TGC TGA AGC TCA CGC TCC 3' |
| | 1X15HF | 5' GGG CTC GTC GTC AAT GCA AG 3' |
| | 1X15HR | 5' CGC CGC CCC CGC CCG CCG CCC ACC ACC TGC AGC CCC TCT A 3' |
| | 1X15IF | 5' GCG GCC CGC CGC CCC CGC CGC CGC CCA GGA CAG CAT CTT C 3' |
| | 1X15IR | 5' CGC TGC CCA GCA TGT TGG 3' |
| | 1X15JF | 5' GGC CGG CAG CGG CAA AGG CTT CTC 3' |
| | 1X15JR | 5' GCC CAG CAC CAG CTC ACA T 3' |
| | 1X15KF | 5' CGA GCC ATT TAC CAC CCA TAG 3' |
| | 1X15KR | 5' GGC AGC AGC AGG ATC TG AA 3' |
| | 1X15LF | 5' CTG TGG GCC AGC AGC AAG GTG 3' |
| | 1X15LR | 5' CCT GAA CCT CCA GCA CCA GCG 3' |
| | 1X15MF | 5' AGG TCC AGG GCG ACT CGC TGG 3' |
| | 1X15MR | 5' CAG GGC CAC ACG CGC TGG GCG 3' |
| | 1X15NF | 5' TTG GAG GCC CAC GTT GAC TG 3' |
| | 1X15NR | 5' CCC CCG CCC GCA TGG GTG TGG ACG GGT GAG G 3' |
| | 1X16F | 5' TAA AAC TGG ATG GGG CTC TC 3' |
| | 1X16R | 5' GGC CTC CAC CAG CAC TAA 3' |
| | 1X17F | 5' GGG TCC CCC AGT CCT TCC AG 3' |
| | 1X17R | 5' TCC CCA GCC CGC CCA CA 3' |
| | 1X18F | 5' GCC CCC TCA CCA CCC CTT CT 3' |
| | 1X18R | 5' TCC CGC TGC TCC CCC CAC GCA 3' |
| | 1X19F | 5' GAT GCC GTG GGG ACC GTC 3' |
| | 1X19R | 5' GTG AGC AGG TGG CAG TCT CG 3' |
| | 1X20F | 5' CCA CCC CCT CTG CTC GTA GGT 3' |
| | 1X20R | 5' GGT CCC AAG CAC GCA TGC A 3' |
| | 1X21F | 5' TGC CGG CCT CCT GCG CTG CTG A 3' |
| | 1X21R | 5' GCG GGC AGG GTG AGC AGG TGG GGC CAT CC 3' |
| | 1X22F | 5' GAG GCT GTG GGG GTC CAG TCA AGT GG 3' |
| | 1X22R | 5' AGG GAG GCA GAG GAA AGG GCC GAA C 3' |
| | 1X23AF | 5' CGT CCC GCC TGC ACT GAC CTC ACG CAT GT 3' |
| | 1X23AR | 5' CGG CCC GCC GCC CCC GCC CGG CCA AAG GGA AAG GGA TTG GA 3' |

TABLE 3-continued

Examples of useful PKD-1 specific primers*

| SEQ ID NO. | Primer Name | Primer Sequence |
|---|---|---|
| | 1X23BF | 5' CCG CGG AGC CTG CTG TGC TAT 3' |
| | 1X23BR | 5' CCG CCG CCC CCG CCC GCT TGG TGG AGA CGG TGT AGT TGC 3' |
| | 1X23CF | 5' TCC AAT CCC TTT CCC TTT GGC 3' |
| | 1X23CR | 5' CAG CAG CCC ATG AAA CAG AAA G 3' |
| | 1X24F | 5' TAT GCT TTC AGG CCC GTG GCA 3' |
| | 1X24R | 5' AGA GCC CAT ACC CGG TCC AGT CC 3' |
| | 1X25F | 5' GGA CTG GAC CGG GTA TGG GCT CT 3' |
| | 1X25R | 5' CCC CCG CCC GCA CCC AGG CCC TCC ACT C 3' |
| | 1X26F | 5' CCC CCG CCG CTG GGT GGG CTC GGC TCT ATC 3' |
| | 1X26R | 5' TGG TAG CGA TGC TCA CGT CAC TT 3' |
| | 1X27F | 5' CAG GCC AAA GCT GAG ATG ACT TG 3' |
| | 1X27R | 5' AGA GGC GCA GGA GGG AGG TC 3' |
| | 1X28F | 5' CCC TCT GCC CCC GCA TTG 3' |
| | 1X28R | 5' AAG CGC AAA AGG GCT GCG TCG 3' |
| | 1X29F | 5' GGC CCT CCC TGC CTT CTA GGC G 3' |
| | 1X29R | 5' CCG TGC TGT GTG GAG GAG AG 3' |
| | 1X30F | 5' CCT CTT CCT GCC CAG CCC TTC 3' |
| | 1X30R | 5' CTT CCC GAG CAG CCT TTG GTG 3' |
| | 1X31F | 5' CTG AGC TGC CGC CCG CTG AC 3' |
| | 1X31R | 5' AGG ACC CCA GCC CAG CCC CA 3' |
| | 1X32F | 5' CTT GGC GCA GCT TGG ACT 3' |
| | 1X32R | 5' ACA CCC AGC AAG GAC ACG CA 3' |
| | 1X33F | 5' TGT GAC ACA TCC CCT GGT AC 3' |
| | 1X33R | 5' GCA AGG GTG AGC TTC AGA GC 3' |
| | 1X34F | 5' GCC CCG CGC CCG TCC CGC CGC CCC CGC CCG ACC CTA TGC CTC CTG TAC CTC 3' |
| | 1X34R | 5' CCC CTC CTC TGG CAA TCC 3' |
| 3 | 1X35F | 5' TGG CTG CAA CTG CCT CCT GG 3' |
| 4 | 1X35R | 5' AAG CAG AGA CAG ACC TGT GAG AG 3' |
| 5 | 1X36F | 5' GCC CCC GCC GCT CTC ACA GGT CTG TCT CTG CTT C 3' |
| 6 | 1X36R | 5' GGC CTG TAG CCT ACC CCT GG 3' |
| 7 | 1X37F | 5' GGA CCC CTC TGA AGC CAC C 3' |
| 8 | 1X37R | 5' GGG AGG TGG GAG ACA AGA GAC 3' |
| 9 | 1X38F | 5' AAA GCC CTG CTG TCA CTG TGG 3' |
| 10 | 1X38R | 5' AAC TAA AGC CCA GAA GAC AGA CC 3' |
| 11 | 1X39F | 5' AAC TGT CTG CCC CAG AAC ATC 3' |
| 12 | 1X39R | 5' CTA AAG GCT GCT CTC TCA ACA AG 3' |
| 13 | 1X40F | 5' ACT CCT GTT GGG TTT TGA TGA G 3' |
| 14 | 1X40R | 5' GAG AAC TAC TCC CTT GTC CTT GG 3' |
| 15 | 1X41F | 5' ACG CCA AGG ACA AGG GAG TAG TTC 3' |
| 16 | 1X41R | 5' TGG GCT CCT GGC TGG TGA CTG C 3' |
| 17 | 1X42F | 5' GCG GCC CGC CGC CCC CGC CGC TAC TGA CCC GCA CCC TCT G 3' |
| 18 | 1X42R | 5' GCT GCG AGG GGT GAG ACG 3' |
| 19 | 1X43F | 5' GCG GCC CGC CGC CCC CGC CGC GTC CCT CCC GCC CTC CTG ACC 3' |
| 20 | 1X43R | 5' GCC CCC GCC GCT GCG GAC GAG AAA TCT GTC TGC TTG 3' |
| 21 | 1X44F | 5' CAG GGC TGC AAG CAG ACA GA 3' |
| 22 | 1X44R | 5' CTG AGC TAA GAC GCC CTC CC 3' |
| 23 | 1X45F | 5' CTG TAC GCC CTC ACT GGT GTC 3' |
| 24 | 1X45R | 5' GGC ACA GGG GCT CAG TCA GTC 3' |
| 25 | 1X46AF | 5' GGA CTG ACT GAG CCC CTG TGC 3' |
| 26 | 1X46AR | 5' AGT CGG TCA AAC TGG GTG AG 3' |
| 27 | 1X46BF | 5' CAA GGT GTG AGC CTG AGC CC 3' |
| 28 | 1X46BR | 5' CGG TGT CCA CTC CGA CTC CAC 3' |

*All primer sequences are denoted in the 5'—3' direction. The first number in the name denotes the PKD gene number (<u>1</u>X15AF). The Letter 'X' signifies the word exon (1<u>X</u>15AF). The third number after the 'X' denotes the exon number (1X <u>15</u>AF). The character after the exon number represents the identity of the exon fragment (1X15<u>A</u>F). The last letter indicates the direction of the primer as either forward or reverse (1X15A<u>F</u>).

TABLE 4

Examples of useful PKD-2 specific primers*

| SEQ ID NO. | Primer Name | Primer Sequence |
|---|---|---|
| 29 | 2X1AF | 5' CCG CCC CCG CCG CGC GCC GGA CGC CAG TGA CC 3' |
|  | 2X1AR | 5' CCT GCC GGG AGC ACG ACG AG 3' |
| 30 | 2X1BF | 5' GCC CCC GCC GCC GCG GCC TCC CCT TCT CCT 3' |
|  | 2XIBR | 5' CTG GGC TGG GGC ACG GCG GG 3' |
|  | 2X1CF | 5' GGG GGC TAC CAC GGC GCG GGC 3' |
| 31 | 2X1CR | 5' CGG CCC GCC GCC CCC GCC CGC GGC CGT TCT GGT TCG TGC ATC TG 3' |
| 32 | 2X2F | 5' GCC CCC GCC GAA ATG ATA TCT TTT CTT TTC TTC A 3' |
| 33 | 2X2R | 5' CCC CCG CCC GAA CTT TCC CAT TAG TGC AAG 3' |
|  | 2X3F | 5' TTG GGG CGT TCA TTT GGA TC 3' |
| 34 | 2X3R | 5' CGC CGC CCC CGC CCG TGT GAT AGA GAG GTA CTT TCA 3' |
| 35 | 2X4F | 5' CCG CCG CCC CCG CCG CTT TTT CAA AGA TGT TTC CTT TGC 3' |
| 36 | 2X4R | 5' TAT CAC CGA GTG CCA ATG AG 3' |
| 37 | 2X5F | 5' CCG CCG CCC CCG CCG GCC TCA AGT GTT CCA CTG AT 3' |
|  | 2X5R | 5' ACC ACA CAG AAA TAG GAG GG 3' |
|  | 2X6F | 5' TTG TTA TTG TTT TAA TTG TTC TTA 3' |
| 38 | 2X6R | 5' CCC CCG CCC GTT GTA GAA TAG AAT AGG AAA TTT GG 3' |
| 39 | 2X7F | 5' GCC CCC GCC GTT GGT GAA GAA AAA TAT ACT AGT CA 3' |
| 40 | 2X7R | 5' CGC CGC CCC CGC CCG TGG AAC TCA TTT TTT TTA AAG A 3' |
| 41 | 2X8F | 5' GCG GGG GCG GCG GGC CGT TTT ATT ATA CAC AGT CAC ACC 3' |
|  | 2X8R | 5' CTA CTC TGA CTA AAT TTT TCT TCT T 3' |
|  | 2X9F | 5' TTT GGT TTT GTA TTG TGG TG 3' |
|  | 2X9R | 5' AAG GAT TTA CGA AGT TTA AAT TG 3' |
| 42 | 2X10F | 5' GCC CCC GCC GCT TCC TTT AAT TTT TGC CCT CC 3' |

TABLE 4-continued

Examples of useful PKD-2 specific primers*

| SEQ ID NO. | Primer Name | Primer Sequence |
|---|---|---|
| 43 | 2X10R | 5' CGC CGC CCC CGC CCG GAA ACA ATG CTC ATT TTA TGT CAG 3' |
| 44 | 2X11F | 5' CCG CCG CCC CCG CCG AAA CCA AGT CTT TTA TTT TTT CTC 3' |
|  | 2X11R | 5' AGA ACC TCA GGA AGC ATG ATT 3' |
| 45 | 2X12F | 5' CCG CCG CCC CCG CCG GAT GAA TGT TAT CTG TAT CCT CTC 3' |
|  | 2X12R | 5' TAG GTA CCA AAT CAA ATC CG 3' |
|  | 2X13F | 5' GTC TCA GTG TTC TGC TCC TC 3' |
| 46 | 2X13R | 5' CGC CGC CCC CGC CCG GCA AAT TCT GCC ATT TCC TTT A 3' |
| 47 | 2X14F | 5' GCC CCC GCC GTT TGT CCC TCT GTA CTG TGT TT 3' |
|  | 2X14R | 5' AAA TAC AAC TGT CAG CAA CAT A 3' |
| 48 | 2X15F | 5' CCG CCC CCG CCG TGA CCC CCA ACA CCA GTT TC 3' |
| 49 | 2X15R | 5' CGG CCC GCC GCC CCC GCC CGG GAC AGC CAC TTC CTC ACT T 3' |

*All primer sequences are denoted in the 5'-3' direction. The first number in the name denotes the PKD gene number (<u>2</u>X15R). The Letter 'X' signifies the word exon (2<u>X</u>15R). The third number after the 'X' denotes the exon number (2X<u>15</u>R). The last letter indicates the direction of the primer as either forward or reverse (2X15<u>R</u>).

B. Primer Combinations Useful for PKD-specific Amplification

The specifically amplified product can be generated by using one or more PKD-specific primers. Preferably, both primers used to generate one amplified product are PKD-specific primers. However, one PKD-specific primer can be used in combination with another non PKD-specific primer which is not complementary to a unique site of a PKD gene. The non PKD-specific primer is preferably designed according to the same criteria described above herein for the PKD-specific primers and is preferably to be completely complementary to a sequence other then a unique sequence in a PKD gene. A non PKD-specific primer may also be used as a control primer included in the amplification reaction to generate a control product.

Optimal results may be obtained by using one forward and one reverse primer listed in Table 4 and Table 5, although other combinations may also be used. In a preferred embodiment, a primer pair is selected so that the length of an amplified product is 150-600 bps. In the most preferred embodiment, a primer pair is selected so that the amplified fragment length for DHPLC mutation detection analysis is 150-400 bp.

C. Primer Synthesis

Methods for synthesizing primers are available in the art. The oligonucleotide primers of this invention may be prepared using any conventional DNA synthesis method, such as, phosphotriester methods such as described by Narang et al. (1979, Meth. Enzymol., 68:90) or Itakura (U.S. Pat. No. 4,356,270), or and phosphodiester methods such as described by Brown et al. (1979, Meth. Enzymol., 68:109), or automated embodiments thereof, as described by Mullis et al. (U.S. Pat. No. 4,683,202). Also see particularly Sambrook et al.(1989), Molecular Cloning: A Laboratory Manual (2d ed.; Cold Spring Harbor Laboratory: Plainview, N.Y.), herein incorporated by reference.

V. Preparing Template for Amplification Reaction

Any sample comprising a nucleic acid comprising the entire or a portion of SEQ ID NO. 1 or 2 or their variants (e.g., polymorphism forms or mutant forms) may be used as template for amplification reaction of the present invention. Useful templates, according to the invention, include, but are not limited to, genomic DNA preparation, total RNA preparation, crude cell lysate and tissue sample.

It's preferred to use genomic DNA as template for PKD-specific amplification of the subject invention. While it is envisioned that crude cell lysate or tissue sample may be used, one skilled in the art will recognize that any non-DNA material present in the sample may interfere with the polymerase reaction or subsequent analysis.

Genomic DNA can be isolated from tissue samples or cells. Preferably, the genomic DNA used as template for the invention is isolated under conditions which preclude degradation and contamination. Tissue samples or cells may be digested with a protease so that there is likely to be little or no DNAase activity. The digest is extracted with a DNA solvent. The extracted genomic DNA may be purified by, for example, dialysis or chromatography. Suitable genomic DNA isolation techniques are known in the art, for example, as described in *Current protocols in molecular biology* Ausubel et al., John Weley & Sons, Inc., 1997.

Preferably, genomic DNA or cDNA is extracted from cell lysate of tissue samples taken from an individual and used as template for PKD amplification. Collecting a tissue sample also includes in vitro harvest of cultured human cells derived from an individual's tissue or any means of in vivo sampling directly from a subject, for example, by blood draw, spinal tap, tissue smear or tissue biopsy. Optionally, tissue samples are stored before analysis by well known storage means that will preserve a sample's nucleic acids in an analyzable condition, such as quick freezing, or a controlled freezing regime, in the presence of a cryoprotectant, for example, dimethyl sulfoxide (DMSO), glycerol, or propanediol-sucrose. Tissue samples can also be pooled before or after storage for purposes of amplifying them for analysis. In some embodiments, the sample contains DNA, tissue or cells from two or more different individuals.

Any human tissue containing nucleic acids can be sampled and collected for the purpose of practicing the methods of the present invention. A most preferred and convenient tissue for collecting is blood. No patient preparation is necessary prior to blood draw. No medications are known to interfere with sample collection or testing. Usual aseptic techniques and avoidance of contamination are necessary.

Preferably, DNAs are extracted from blood on the day it was drawn. Blood is preferred to stored at room temperature (72° F. or 25° C.) before use. However, whole blood may be stored for short periods at 4° C. but room temperature is recommended. Whole blood specimens may be stable for 48 hrs. After this time hemolysis may compromise DNA recovery and integrity. The optimal amount of blood for DNA extraction for the PCR assay is preferred to be more than 5 ml, e.g., more than 10.0 ml.

VI. PCR Amplification Using PKD-Specific Primers

The subject invention provides a method of mutation analysis of a target nucleic acid comprising SEQ ID NO. 1 or 2 or their variants by amplifying the DNA from a sample comprising the target nucleic acid in a polymerase chain reaction and detecting in a specifically amplified product the presence or absence of a mutation in the target nucleic acid.

Amplification may be carried out by means well known in the art, for example, polymerase chain reaction (PCR), transcription based amplification (reverse transcription), strand displacement amplification (see *Current Protocol in Molecular Biology*). Preferably, the amplification is carried out by PCR, such as described by Mullis (U.S. Pat. No. 4,683,202), the contents of which are incorporated by reference herein.

PCR makes possible the amplification (replication) of minute samples of DNA or other nucleic acids of any base pair length (size) by taking advantage of highly selective enzymes called DNA polymerases, to extend small DNA strands called "primers" along a "template". The minute DNA sample serves as the template. PCR reproduces the complementary sequence of deoxynucleotide triphosphate (dNTP) bases present in the template or any chosen portion thereof The PCR is commonly used in conjunction with diagnostic techniques where, for example, a DNA sample having a concentration below the limit of detection is amplified by the PCR process, and the larger amount so obtained is subsequently analyzed.

Apparatus for performing PCR amplifications, e.g. Air Thermo Cycler (Idaho Technologies) and reagents are commercially available from numerous sources, e.g. Perkin-Elmer Catalog "PCR Systems, Reagents and Consumables" (Perkin-Elmer Applied Biosystems, Foster City, Calif.).

PCR is typically run in a buffer at pH 5-8. The buffer contains a double stranded DNA sample to be amplified, a forward primer, a reverse primer, magnesium (e.g., as $MgCl_2$), and the four deoxynucleotide triphosphates (dATP, dTTP, dCTP, and dGTP) generally referred to as "dNTPs", the building blocks of DNA. The reaction mixture is heated to a temperature (e.g., >90° C.) sufficient to denature the DNA sample, thereby separating its two complimentary nucleic acid strands. Alternatively, the DNA may be denatured enzymatically at ambient temperature using a helicase enzyme. If denaturing is effected by heat and a thermostable DNA polymerase is used, the DNA polymerase is added before the reaction is started. Other denaturing conditions are well known to those skilled in the art and are described in U.S. Pat. No. 5,698,400. DNA polymerases are commercially available from a variety of sources, e.g. Perkin-Elmer Applied Biosystems, (Foster City, Calif.) and Stratagene (La Jolla, Calif.).

The primer sequence is designed to be complimentary to an identified portion of the denatured DNA strands to be replicated by PCR. Upon cooling the reaction to an appropriate annealing temperature, each of the primers anneals to its complimentary base sequence in each strand of the denatured DNA sample to be replicated. Heated to about 70° C. in the presence of the DNA polymerase, the 4 dNTPs and $Mg^{2+}$, replication extends the primers from their 3'-ends by adding complimentary dNTPs along the length of the strand. dNTPs are commercially available from a variety of sources, e.g. Pharmacia (Piscataway, N.J.). By repeating this process numerous times, a geometric increase in the number of desired DNA strands is achieved in the initial stages of the process or as long as a sufficient excess of reagents are present in the reaction medium. Thus, the amount of the original DNA sample is amplified.

The amount of polymerase must be sufficient to promote DNA synthesis throughout the predetermined number of amplification cycles. Guidelines as to the actual amount of polymerase are generally provided by the supplier of the PCR reagents and are otherwise readily determinable by a person of ordinary skill in the art. Preferably, a DNA polymerase with proof-reading activity is used.

The amount of each primer must be in substantial excess of the amount of target DNA to be amplified. The amount of primer needed for the reaction mixture can be estimated by one skilled in the art in terms of the ultimate number of amplified fragments desired at the conclusion of the reaction.

To prevent false positive results, one skilled in the art will recognize that the assays should include negative controls as is conventional in the art. For instance, suitable negative controls may contain no primer or no DNA (i.e. "water controls"). To prevent false negative results, positive controls are provided by the control primers (see below).

A. Optimization of PCR Conditions

Successful specific amplification, e.g., an amplification which produces maximal amount of specifically amplified products and minimal amount of non-specifically amplified products, according to the invention, depends in great measure on the specific annealing of the PKD-specific primers to the corresponding matched template. If the primer anneals non-specifically to many different sequences in the reaction mixture, the amplification process will not be specific. Although it is unlikely in most of the embodiments to avoid any non-specific annealing or non-specific amplification, it is desirable to optimize the PCR amplification reaction condition so to reduce the non-specific amplification while increase the specific amplification.

In addition, PCR induced mutations, wherein a non-complimentary base is added to a template, are often formed during sample amplification. Such PCR induced mutations make mutation detection results ambiguous, since it may not be clear if a detected mutation was present in the sample or was produced during the PCR process. Applicants have recognized the importance of optimizing PCR sample amplification in order to minimize the formation of PCR induced mutations and ensure an accurate and unambiguous analysis of putative mutation containing samples.

B. Controlling the Specificity of PKD-Specific Annealing of PKD-Specific Primers.

The degree of fidelity of replication of DNA fragments by PCR depends on many factors which have long been recognized in the art. Some of these factors are interrelated in the sense that a change in the PCR product profile caused by an increase or decrease in the quantity or concentration of one factor can be offset, or even reversed by a change in a different factor. For example, an increase in the enzyme concentration may reduce the fidelity of replication, while a decrease in the reaction temperature may increase the replication fidelity. An increase in magnesium ion concentration or dNTP concentration may result in an increased rate of reaction which may have the effect of reducing PCR fidelity. A detailed discussion of the factors contributing to PCR fidelity is presented by Eckert et al., (in *PCR: A Practical Approach*, 1991, McPherson, Quirke, and Taylor eds., IRL Press, Oxford, Vol. 1, pp. 225-244); and Andre, et. al., (1977, *GENOME RESEARCH*, Cold Spring Harbor Laboratory Press, pp. 843-852). These references and the references cited therein are incorporated in their entirety herein. Thus, availability of a product profile of the PCR process, makes possible the optimization of PCR conditions to improve results in a highly efficient manner.

In PCR amplification, the specificity of the annealing is most important in the first few cycles. The remaining cycles only serve to expend the pool of template which is amplified in the first few cycles. The specificity of primer annealing to template is controlled by the ionic strength (primarily the $K^+$ concentration) of the buffer, the $Mg^{2+}$ concentration (which is bound to dNTPs and therefore affected by the amount of dNTPs), and the annealing temperature of each cycle of the amplification. In preferred embodiments, the dNTP concentrations are 50 nM, preferably 100 nM, more preferably 200 nM.

Conditions for specific annealing of primers to particular template targets must be determined empirically, usually by varying the annealing temperature in several degree increments and comparing the specificity and sensitivity of the amplification process by agarose gel electrophoresis (See *Current Protocol in Molecular Biology*, supra).

Because a unique region to which a PKD-specific primer complement to may differ from a homologue sequence only by a few nucleotides, sometimes by only one nucleotide, the specificity of the amplification reaction needs to be tested for each PKD-specific primer used in the reaction.

The formula for calculating primer annealing temperature provided above is only a rough guide, successive trials at different annealing temperatures is the usual way to optimize this important parameter in the PKD-specific amplification reaction. Apparatus are available for simultaneous testing of different annealing temperatures of particular primer-template pairs, which enables the optimal annealing temperature to be determined rapidly and reliably (e.g., Robocycler Gradient Temperature Cycler, Cat # 400864, Stratagene; Eppendorf mastercycler gradient, Cat # 5331 000.045, Brinkmann Instruments, Inc. Westbury, N.Y.).

In some embodiments, the target sequences are amplified at an annealing and extending temperature that is between 1° C. and 10° C. higher than the Tm for the primer pair. Although amplification at this temperature is inefficient, any primer extension that occurs is target specific. Consequently, during the high temperature cycle(s), the sample is enriched for the particular target sequence and any number of cycles, i.e., 1-15 enhances product specificity. The annealing temperature may be then decreased to increase amplification efficiency and provide a detectable amount of PCR product. Or a nested amplification reaction may be performed using the amplified product from the first PCR reaction as template (see below).

Alternatively, one can simultaneously run a set of reactions at a constant temperature but vary the concentration of KCl or $MgCl_2$ or add variable amounts of a denaturant such as formamide (e.g., 0, 2, 4, 6%), DMSO (1-10%) to define the optimum conditions for generating a high yield of specific product with a minimum of nonspecific products.

In one embodiment, a pair of primers comprising at least one selected from the group consisting of SEQ ID NOs. 3-49 is used in the amplification reaction mixture. The orientation of the two primers is opposite to allow the generation of one or more specifically amplified product.

In some embodiments of the invention, when primers used for PKD-specific amplification are selected from SEQ ID NOs. 3-49, AmpliTaq Gold DNA polymerase with GeneAmp PCR buffer II and $MgCl_2$ solution and rTth DNA polymerase XL & XL buffer II pack from Perkin Elmer, and TaqPlus Precision PCR system from Stratagene were used. PFUTurbo™ is another high fidelity DNA polymerase having greater proof reading provided by Stratagene.

In other embodiments, an annealing temperature of above 65° C. (e.g., 68-72° C.) is used for PKD-specific amplification using primers selected from SEQ ID NOs. 3-49.

In general, it is preferred but not essential that the DNA polymerase is added to the amplification reaction mixture after both the primer and template are added. Alternatively, for example, the enzyme and primer are added last or the reaction buffer or template plus buffer are added last. It is generally desirable that at least one component that is essential for polymerization not be present until such time as the primer and template are both present, and the enzyme can bind to and extend the desired primer/template substrate. This method, termed "hot start," minimizes the formation of "primer-dimer" and improves specificity of the amplification.

The degree of specificity of DNA polymerases varies with the reaction conditions employed as well as with the type of enzyme used. No enzyme affords completely error free extension of a primer. Therefore, a non-complimentary base may be introduced from time to time. Such enzyme related errors produce double stranded DNA products which are not exact copies of the original DNA sample, but contain PCR induced mutations. Other PCR process features, such as reaction temperature, primer annealing temperature, enzyme concentration, dNTP concentration, $Mg^{2+}$ concentration, and combinations thereof, all have the potential to contribute to the degradation of the accuracy or fidelity of DNA replication by the PCR process, as described above herein.

C. Sensitivity of PKD-Specific Amplification

The sensitivity of the PKD-specific amplification of the subject invention depends on the template and primers used in an amplification reaction, as well as ionic strength and annealing temperature of each cycle of the amplification.

When genomic DNA is used as template, as few as one or two copies of the template (about 3-5 pg) can be used for successful PCR amplification if the reaction condition has been optimized. However, it's known in the art that a higher template concentration may increase the specificity and efficiency of the amplification.

Shorter fragments are amplified more efficiently than longer fragments. Preferably, primers which generate an amplified product of less than 1 kb, more preferably less than 600 bp, or less than 450 bp in length are used to increase sensitivity of the amplification assay.

Preferably, the sensitivity of the amplification assay is less than 100 ng genomic DNA template. More preferably, the sensitivity of the assay is less than 10 ng genomic DNA template. More preferably, the sensitivity of the assay is less than 1 ng genomic DNA template. More preferably, the sensitivity of the assay is less than 0.1 ng genomic DNA template. Even more preferably, the sensitivity of the assay is less than 0.01 ng genomic DNA template.

D. Nested Amplification

In some embodiments of the invention, a nested amplification is performed using amplified products in a preceding amplification reaction as templates. Preferably, the nested amplification reaction is a nested PCR using PCR amplified products from a preceding PCR reaction as templates. In addition to optimizing the annealing temperature of the primers, "nested" amplification can be used to increase the specificity and sensitivity of the PKD-specific amplification assay.

For example, a method comprising a nested PCR involves two sequential PCR reactions. After multiple cycles of PCR (e.g., 10 to 40, or 10 to 30 or 10 to 20 cycles) with the first pair of primers comprising at least one PKD-specific primer (e.g., a PKD-specific primer and a control primer or two PKD-specific primers), a small amount aliquot of the first reaction (e.g., 1 µl of a 50 µl reaction) serves as the template for a second multiple cycles of PCR reaction (e.g., 10 to 40, or 10 to 30 or 10 to 20 cycles) with a new set of primers comprising at least one PKD-specific primer (e.g., a PKD-specific primer and a control primer or two PKD-specific primers) that anneal to sequences internal to, or nested between, the first pair.

Methods for designing nested primers and for performing nested PCR are known in the art (see *Current Protocol in Molecular Biology*, supra). The general criteria for selecting primers as described above also applies to the design of nested primers. Both nested primers need to anneal to sequences internal to (e.g., within) the first pair of primers and at least one of the nested primers, however, according to the subject invention, needs to be PKD-specific.

Using the nested PCR procedure, the template that is successfully amplified is selected twice for PKD-specificity. The use of nested PCR can also greatly enhance the yield of the species-specific product, therefore the sensitivity of the assay, when a single primer pair fails by itself.

A sample comprising genomic DNA or cDNA may be used to provide DNA template for the amplification reaction. Preferably, genomic DNA is used as template. When a sample comprising genomic DNA is used in the reaction mixture, a pair of primers comprising at least one selected from the group consisting of SEQ ID NOs. 3-49 generate at least two specifically amplified product, one from each PKD allele in the genomic DNA sample.

E. Amplification Controls

Control primers can be used to serve as positive control for the PKD-specific amplification. The control primers may be added to the same reaction mixture for PKD-specific amplification, or it may be added to a control reaction which is run in the same PCR apparatus under the same parameters. A control primer may comprise a sequence complementary to any identical sequence between a PKD gene and a PKD homologue. Preferably, the control primers generate a single amplified product whose size is distinguishable from that amplified by a pair of primers comprising at least one PKD-specific primers. The size of the amplified product by the control primers may be greater or smaller than the size of the amplified products generated by the pair of primers comprising at least one PKD-specific primers. Preferably, the control primers are chosen to generate a control product which has at least 100 bp, more preferably at least 500 bp, more preferably at least 1000 bp difference in size compared to the amplified product generated in the same amplification reaction by the pair of primers comprising at least one PKD-specific primers.

A control amplification is especially important when analyzing a PKD allele with deletions at the location where a PKD-specific primer anneals. The lack of a specific amplification in the presence of an amplified control product may indicate the presence of the deletion at a specific location of a PKD gene. In some embodiments, more than one pair of control primers is used in the reaction mixture.

See Example 2 for various controls that might be used for the genetic testing method of the invention.

Amplified products may be purified to get rid of free primers used in the amplification by methods known in the art (e.g., Current Protocols in Molecular Biology, supra). In a preferred embodiment, the PCR products are purified using the Quickstep™ 96 well PCR Purification Kit from Edge Biosystems.

VII. Detecting the Presence of PCR Amplified Products

The cycle of DNA denaturation, primer annealing and synthesis of the DNA segment defined by the 5' ends of the primers is repeated as many times as is necessary to amplify the template target until a sufficient amount of either a species-specific or a universal product is available for detection. At the conclusion of the amplification reaction, the presence of amplified products may be detected using techniques conventional in the art.

The primers may be labeled for facilitating the detection. The primers can be labeled with a directly detectable tag, for example a radioactive label such as $^{32}P$, $^{35}S$, $^{14}C$ or $^{125}I$, a fluorescent compound such as fluorescein or rhodamine derivatives, an enzyme such as a peroxidase or alkaline phosphatase, or avidin or biotin. The PKD-specific primers used to generate the PKD-specific product and the control primers used only to generate the control product may have the same or different labels.

In a preferred embodiment, the amplification products are conveniently analyzed by gel electrophoresis.

Electrophoresis is conducted under conditions which effect a desired degree of resolution of fragments. A degree of resolution that separates fragments that differ in size by as little as about 500 bp is usually sufficient. Preferably, the resolution is at about 100 bp. More preferably, the resolution is at about 10 bp. Size markers may also be run on the gel to permit estimation of the size of fragments. Preliminary analysis of the size of specifically amplified products may indicate insertions or deletions within a PKD gene, and the information obtained can be interpreted together with results obtained from subsequent DHPLC and sequence analysis.

The amplification product pattern may be visualized. Where an amplification primer has been labeled, this label may be revealed. A substrate carrying the separated labeled DNA fragments is contacted with a reagent which detects the presence of the label. For example, an amplified product generated from a radioactively labeled primer may be detected by radioautography. Where the amplification primers are not labeled, the substrate bearing the PCR product may be contacted with ethidium bromide and the DNA fragments visualized under ultraviolet light.

VIII. Separating PCR Amplified Products

Under the most stringent condition which only allows the annealing of completely complementary sequences but not sequences comprising one or more non-complementary nucleotides, a PKD-specific primer will only anneal to an authentic PKD gene template, but not a PKD homologue. Therefore, under the most stringent condition, a PKD-specific primer, in combination with a primer with opposite orientation, being PKD-specific or not, will only produce amplified product from an authentic PKD template, but not from a PKD homologue. However, during a typical PCR amplification reaction, a PKD-specific may anneal to a template comprising an authentic PKD gene and a PKD homologue, especially due to the temperature cycling required by a PCR reaction. Therefore, both specifically amplified products and non-specifically amplified products may be produced, although the amount of non-specifically amplified products may be reduced by the use of at least one PKD-specific primer.

A. Formation of Homoduplex and Heteroduplex

In one embodiment of the invention, a mixture of homoduplexes and heteroduplexes is formed prior to the DHPLC analysis. A standard nucleic acid homoduplex (e.g., amplified product from a normal PKD allele) may be added to the sample and the mixture is subjected to denaturation, e.g. by heating the mixture to about 90° C. or about 95° C. The denatured single stranded nucleic acids formed during the denaturation process are then annealed by slowly cooling the mixture to ambient temperature. A new mixture of homoduplexes and heteroduplexes is formed if the sample contains a mutation. If the sample does not contain a mutation, only a homoduplex of the standard nucleic acid will be formed. In the preferred embodiment, the standard nucleic acid is the "normal" nucleic acid.

In most cases, a PKD patient individual is heterozygous at the loci comprising a PKD gene. That is, the carrier has only one PKD allele and a mutant form and has the other allele as a normal form (e.g., wild type). Since most of the PKD mutations result in a dominant phenotype, one mutant allele is sufficient to predispose a risk for ADPKD development. Another heterozygous situation is when both alleles are mutated but each carries one or more different mutations. For a heterozygous PKD patient, a PCR amplification using a primer pair comprising at least one PKD-specific primer, including a nested PCR amplification, would result in at least two specifically amplified PKD products, one from each allele. The two specifically amplified PKD products may or may not be of the same length (e.g., different length if the mutation on one allele comprises a deletion or an insertion) and would differ in at least one nucleotide from each other.

The amplified products may be denatured and re-annealed with each other to form duplexes. When a specifically amplified product from a normal allele or a specifically amplified product from a mutant allele anneals to another specifically amplified product from the same allele, they will form homoduplex. However, if a specifically amplified product from a normal allele anneals to a specifically amplified product from a mutant allele, they form a heteroduplex.

In rare cases, a mutation is in homozygous form, that is, both alleles in an individual (e.g., a PKD patient) comprise the same mutations. If a sample is taken from a homozygous PKD patient, the PCR amplification will not generate specifically amplified products which can form heteroduplex upon denaturing and re-annealing. In some embodiments of the invention, a sample comprising a normal (e.g., a wide type) PKD gene is added to the PCR reaction mixture so that amplification using a primer pair comprising at least one PKD-specific primer will produce specifically amplified products from the normal PKD gene, therefore ensuring the formation of a heteroduplex during the denaturation and re-annealing process following PCR amplification.

Homoduplexes formed in the denaturation and re-annealing process may also include those formed by non-specifically amplified products. If in very rare cases, a sequence in a template allele (e.g., a PKD homologue sequence) which give rise to non-specifically amplified products also comprises one or more mutation, a heteroduplex may also form. The heteroduplex formed between non-specifically amplified products will also be subjected to further separating the identification process.

B. Separating and Identifying Heteroduplex

The presence of a heteroduplex formed by PKD-specifically amplified products indicates the presence of a mutation in a PKD gene. By separating for heteroduplexes, one can identify whether a mutant allele present in the sample, e.g., taken from an individual. This separating process gets rid of most of the non-specifically amplified products and specifically amplified products from normal alleles, therefore improves the efficiency and specificity of identifying a mutant allele and a PKD patient.

It is well known in the DNA art that a heteroduplex strand will denature selectively at the site of base pair mismatch, creating a "bubble", at a lower temperature than is necessary to denature the remainder of the heteroduplex strand, i.e., those portions of the heteroduplex strand which contain complimentary base pairs. This phenomenon, generally referred to as partial denaturation, occurs because the hydrogen bonds between mismatched bases are weaker than the hydrogen bonds between complimentary bases. Therefore, less energy is required to denature the heteroduplex at the mutation site, hence the lower temperature required to partially denature the heteroduplex at the site of base pair mismatch than in the remainder of the strand.

Since at least one base pair in a heteroduplex is not complimentary, it takes less energy to separate the bases at that site compared to its fully complimentary base pair analog in a homoduplex. This results in the lower melting temperature of a heteroduplex compared to a homoduplex. The local denaturation creates, what is generally called, a "bubble" at the site of base pair mismatch. The bubble distorts the structure of a DNA fragment compared to a fully complimentary homoduplex of the same base pair length.

This structural distortion under partially denaturing conditions has serves as the basis for DHPLC to separate heteroduplexes and homoduplexes.

A separation process called "Denaturing HPLC" (DHPLC) has been used to detect mutations by separating a heteroduplex (resulting from the presence of a mutation) and a homoduplex having the same bp length. DHPLC has been applied to mutation detection (e.g., see Underhill, et al., 1997, Genome Research 7:996; Liu, et al., 1998, Nucleic Acid Res., 26;1396). This separation is based on the fact that a heteroduplex has a lower melting temperature (Tm) than a homoduplex. When DHPLC is carried out at a partially denaturing temperature, i.e., a temperature sufficient to denature a heteroduplex at the site of base pair mismatch, homoduplexes can be separated from heteroduplexes having the same base pair length (Hayward-Lester, et al., 1995, Genome Research, 5:494; Underhill, et al., 1996, Proc. Natl. Acad. Sci. USA 93:193; Doris, et al., 1997, DHPLC Workshop, Stanford University). These references and the references contained therein are incorporated herein in their entireties. Thus, the use of DHPLC was applied to mutation detection (Underhill, et al., 1997, Genome Research 7:996; Liu, et al., 1998, Nucleic Acid Res., 26:1396). DHPLC can separate heteroduplexes that differ by as little as one base pair under certain conditions. The references cited above and the references contained therein are incorporated in their entireties herein.

The change in the structure of DNA from an orderly helix to a disordered, unstacked structure without base pairs is called the helix-random chain transition, or melting. Statistical-mechanical analysis of equilibria representing this change as a function of temperature for double-stranded molecules of natural sequence has been presented by Wartell and Montroll (1972, Adv. Chem. Phys. 22: 129). The theory assumes that each base pair can exist in only two possible states-either stacked, helical, and hydrogen bonded, or disordered. It permits calculation of the probability that each individual base pair is either helical or melted at any temperature, given only the base sequence and a very small number of empirically calibrated parameters. The statistical-mechanical theories take into account the differing intrinsic stabilities of each base pair or cluster of neighboring base pairs, the influence of adjacent helical structure on the probability that a neighboring base pair is helical or melted (the coopertivity), and the restrictions on the conformational liberty of a disordered region if it is bounded at both ends by helical regions.

Iteration of the probability calculation at a closely spaced series of temperature steps and interpolation permit determination of the midpoint temperature at which each base pair is at 50/50 equilibrium between the helical and melted states. The MELT program provides the midpoint temperature and some other functions. A plot of midpoint temperature as a function of position along the molecule is called a melting map. It clearly shows that the melting of nearby base pairs is closely coupled over substantial lengths of the molecule despite their individual differences in stability. The existence of fairly long regions, 30-300 bp, termed domains, in which all bases melt at very nearly the same temperature, is typical. The melting map directly delineates the lowest melting domains in the molecules.

At a partially denaturing temperature, a heteroduplex having a base pair mismatch within a sample sequence will denature at the site of the mismatch, while the rest of the sample sequence will remain intact. The partially denatured heteroduplex can be separated and detected using DHPLC.

When HPLC is used under partially denaturing conditions (e.g., DHPLC) to separate a mixture of homoduplexes and heteroduplexes, the heteroduplexes usually elute ahead of the homoduplexes.

In particular embodiment of the invention, a heteroduplex is separated and identified from a homoduplex by DHPLC, and the presence of heteroduplex indicates the presence of at least one mutation in the PKD gene, e.g., a substitution of one or more nucleotides (or insertion or deletion of one or more nucleotides) present in the mutant allele.

In another particular embodiment, DHPLC gradient is determined by Wavemaker™ 4.0 software from Transgenomic, Inc. (San Jose, Calif.).

Separating applications require that the mutation can be detected regardless of where the mutation might be located on the fragment. In this situation, the mutation might be located in the middle of the fragment or in a higher melting domain, both cases where it is more difficult to detect. It is preferred than the range of melting variation of the fragment is no greater than 10° C. and most preferred is the range of variation is no greater than 5° C.

In some mutation analyses, only two peaks or a partially resolved peak(s) are observed in DHPLC analysis. The two homoduplex peaks may appear as one peak or a partially resolved peak and the two heteroduplex peaks may appear as one peak or a partially resolved peak. In some cases, only a broadening of the initial peak is observed under partially denaturing conditions.

If a sample contained homozygous DNA fragments of the same length, then hybridization and analysis by DHPLC would only produce a single peak at any temperature since no heteroduplexes could be formed. In the operation of the present method, the determination of a mutation can be made by hybridizing the homozygous sample with the known wild type fragment and performing a DHPLC analysis at a partially denaturing temperature. If the sample contained only normal allele then a single peak would be seen in the DHPLC analysis since no heteroduplexes could be formed. If the sample contained heterozygous mutant alleles, then analysis by DHPLC would show the separation of homoduplexes and heteroduplexes.

The temperature at which 50% of a constant melting domain is denatured may also be determined experimentally by plotting the UV (UV) absorbance of a DNA sample against temperature. The absorbance increases with temperature and the resulting plot is called a melting profile (Breslauer et al., 1986, Proc. Natl. Acad. Sci. USA 83:3746; Breslauer, 1987, *Calculating Thermodynamic Data for Transitions of any Molecularity*, p. 221, Marky et al. eds., J. Wiley and Sons). The midpoint of the absorbance axis on the melting profile represents the melting temperature (Tm), i.e. the temperature at which 50% of the DNA strands in the duplex are denatured. In one embodiment of the present invention, this observed Tm is used as a starting temperature for performing DHPLC for mutation detection. The temperature may be then adjusted according to the patterns observed using different controls (see below). In one embodiment, a consistent Tm is used to analyze the same amplicons (i.e., produced by the same pair of primers) from different samples.

In another embodiment of the present invention, software such as MELT (Lerman, et al., 1987, Meth. Enzymol. 155:482) or WinMelt™, version 2.0, is used to obtain a calculated Tm which is used as a starting temperature for performing DHPLC for mutation detection. These software programs show that despite individual differences in base pair stability, the melting temperature of nearby base pairs is closely coupled, i.e., there is a cooperative effect. Thus, there are long regions of 30 to 300 base pairs, called "domains", in which the melting temperature is fairly constant. In a similar manner, the software MELTSCAN (Brossette, et al., 1994, Nucleic Acid Res. 22:4321) calculates melting domains in a DNA fragment and their corresponding melting temperatures. The concept of a constant temperature melting domain is important since it makes possible the detection of a mutation in any portion of the domain at a single heteromutant site selective temperature.

Another particular method for separating and identifying heteroduplex is Matched Ion Nucleic acid Chromatography (MIPC). MIPC was introduced to effectively separate mixtures of double stranded nucleic acids, in general and DNA, in particular, wherein the separations are based on base pair length (U.S. Pat. Nos. 5,585,236 and 6,287,822; Huber et al., 1993, Chromatographia 37:653; Huber et al., 1993, Anal. Biochem. 212:351). These references and the references contained therein are incorporated herein in their entireties. MIPC separations are complete in less than 10 minutes, and frequently in less than 5 minutes. MIPC systems (WAVE™ DNA Fragment Analysis System, Transgenomic, Inc. San Jose, Calif.) are equipped with computer controlled ovens which enclose the columns and column inlet areas.

Although DHPLC and MICP are the described methods for separating and identifying heteroduplex, it is understood that other methods known in the art may also be used for identifying heteroduplex. For example, heteroduplex analysis on high resolution gel matrices are also able to detect even single nucleotide polymorphisms. (Hauser et al., 1998, Plant. J. 16:117-25). The PCR/OLA procedure can be used for analyzing amplification products to detect SNPs in the 3' end of the human PKD gene (Glick and Pasternak, 1994, *Molecular Biotechnology: Principles and Applications of Recombinant DNA*, ASM Press, Washington, D.C., pp. 197-200). Conformation-sensitive gel electrophoresis of amplification products may also be employed as a means of analysis by the skilled artisan in practicing the methods of the present invention. (Markoff et al., 1998, Eur. J. Genet. 6:145-50). This can also be achieved by techniques such as PCR-restriction fragment-SSCP, which can detect single base substitutions, deletions or insertions (Tawata et al., 1996, Genet. Anal. 12(3-4):125-27; Lee et al., 1992, Anal. Biochem. 205:289-93). Electrophoresis for analyzing amplification products is done rapidly and with high sensitivity by using any of various methods of conventional slab or capillary electrophoresis, with which the practitioner can optionally choose to employ any facilitating means of nucleic acid fragment detection, including, but not limited to, radionuclides, UV-absorbance or laser-induced fluorescence (Keparnik et al., 1998, Electrophoresis 19:249-55; Inoue et al. 1998, J. Chromatogr. A. 802:179-84; Dovichi, 1997, 18:2393-99; Arakawa et al., 1997, J. Pharm. Biomed. Anal. 15:1537-44; Baba, 1996, J. Chromatgr B. Biomed. Appl. 687:271-302; Chan et al., 1997, J. Chromatogr B. Biomed. Sci. Appl. 695:13-15). Any of diverse fluorescent dyes can optionally be used to label primers of the present invention or amplification products for ease of analysis, including but not limited to, SYBR Green I, Y1O-PRO-1, thiazole orange, Hex (i.e., 6-carboxy-2',4',7',4,7-hexachlorofluoroscein), pico green, edans, fluorescein, FAM (i.e., 6-carboxyfluorescein), or TET (i.e., 4,7,2',7'-tetrachloro-6-carboxyfluoroscein) (e.g., Skeidsvoll and Ueland, 1995, Anal. Biochem. 231:359-65; Iwahana et al., 1996, Biotechniques 21:510-14, 516-19).

In using the invention in its preferred embodiment to effect a separation of homoduplexes and heteroduplexes for the purpose of mutation detection, a DNA sample is hybridized with a normal DNA fragment by denaturing and annealing the mixture as described herein above. The DNA sample can be hybridized with normal DNA directly. The DNA sample can also be amplified by PCR and then hybridized with the normal DNA. Alternatively, a normal fragment may be added to the sample prior to PCR amplification. The amplified mixture can then be hybridized following amplification. In each of these three hybridization scenarios, a mixture of homoduplexes and heteroduplexes is produced if a mutation is present in the sample. The sample, so prepared, is analyzed by DHPLC under partially denaturing conditions, preferably at 56 to 58° C., for the presence of a mutation using the method of the invention.

When the method of the invention is used for separating a large number of samples for the presence of a mutation, the throughput of samples may be increased significantly by speeding up the analysis for each sample using a steeper gradient for the fragment bracketing range.

In all embodiments and aspects of the invention, the nucleic acid fragments are detected as they are separated and eluted from the DHPLC column. Any detector capable of detecting nucleic acids can be used in the DHPLC mutation detection method. The preferred detector is an online UV detector. If the DNA fragments are tagged with fluorescent or radioactive tags, then a fluorescence detector or radioactivity detector can be employed, respectively. Following detection, the separated fragments are displayed on a video display separate or printed by a printer. The fragments so displayed appear either as peaks or as bands in a lane.

C. Quality Controls Helpful for Evaluating DHPLC for PKD-2 and PKD-1 Unique Region The chemical principles which permit DHPLC to distinguish between heteroduplex-homoduplex mixtures and homoduplexes alone also make the methodology quite sensitive to (1) buffer composition, (2) oven temperature at the time of analysis, (3) column condition, and (4) system condition at the time a sample is injected. Fluctuation in elution patterns is normal, and varies depending on the size and sequence of the amplicon, and the specific DHPLC conditions under which it is analyzed. On skilled in the art would have the knowledge in interpreting the elution patterns produced, for example, by following the protocol provided by the manufacture of the DHPLC equipment. However, limits on the extent of fluctuation are appropriate to help ensure that conditions are within a range that would be expected to effectively separate for DNA variants. The following quality control requirements are useful examples established for each analytical condition to ensure consistent assay performance.

1. No DNA Control

This control demonstrates that reagents and materials are free of non-specific signal that could interfere with patient analysis. In some embodiment, the control must show minimal signal (<10% of normal control peak height) in a no-DNA sample treated identically to a sample comprising a DNA, e.g., extracted from a tissue. Because all of the analytical system's hardware is re-used for each sample analysis, and because the DHPLC analysis is the separating component, up to 10% peak height of the normal control is permitted. Actual contamination with a different sequence might cause a false positive DHPLC pattern difference which would trigger reflexing to sequencing which would not be expected to detect a 10% contaminant. In the event that a sequence difference is detected, the fragment would be repeated from the point of PCR to confirm the result. Similarly contamination of an actual positive with 10% of a normal sequence would not be expected to significantly alter the pattern since 50% of the DNA present is already normal. Rare cases where a very subtle pattern change might be obscured by 10% extra normal DNA in the injection are accounted for in the sensitivity estimates of 78-96%. However, persistent no DNA signal each time the amplicon is analyzed indicates the need to alter analytical conditions to minimize or eliminate a systematic and persistent no DNA signal.

2. Normal Control

In one embodiment, the normal control pattern must be consistent with historic patterns. Consistency with established patterns indicates acceptable amplification, retention times, peak height, and peak shape. Therefore, PCR and DHPLC conditions (machine and buffers, etc.) are performed as specified in the Examples. Homologues, or other non-specific amplification signals are absent as indicated by comparison with the established normal control pattern.

3. Positive Control

The positive controls are "DHPLC analytical condition controls" used to demonstrate that the established DHPLC analytical conditions (which detect the positive control heteroduplex) are in effect at the time of analysis. A positive control pattern distinct from normal control and consistent with historic patterns indicates acceptable retention time, peak height(s), peak shape and pattern. Heteroduplex detection indicates that the specific DHPLC analysis conditions optimal for the individual fragment were in effect during patient analysis. It is important to note that these controls are not necessarily PKD positive signals. Specific PKD positive samples for each of the 83 PKD fragments are not available. In their absence, another heteroduplex (positive and normal control) is used as the positive indicator demonstrating appropriate analytical conditions at the time of analysis.

4. Additional Positive Controls

Additional positive controls provide pattern(s) consistent with historic patterns for this specific mutation and may be used to separate out very common polymorphisms. Generally, a specific DNA variant will generate a unique signature heteroduplex pattern that is highly reproducible from sample to sample. A pattern consistent with the established pattern indicates acceptable retention time, peak height(s), peak shape and pattern. The specific heteroduplex pattern demonstrates that specific DHPLC analysis conditions optimal for this DNA variant were in effect during patient analysis and, therefore, patient patterns matching this can be considered to possess the common polymorphism. This optional separating method for common polymorphisms is highly specific to the unique amplicon and variant and is dependent upon appropriate validation studies unique to the variant.

D. Analyzing DHPLC Results

Since DHPLC is a separating process, any specimen (e.g., DNA, or cell lysate or tissue sample) with a signal that differs from the normal control should be considered a potential positive and treated by one of several options available depending on the circumstances. For some embodiments, a signal that is too week to interpret (less than 25% of the normal control peak height) could be caused by PCR failure, Wave injection failure, or some other sporadic instrumentation problem unique to the sample. Options include repeat from the point of PCR, repeat the Wave injection (with all controls), or report the wave result as inconclusive and proceed to sequencing. A signal that differs from the normal control in pattern should be considered positive, scored as "P", and sequenced. A signal that differs very slightly from the normal control pattern should be scored as "B" and sequenced. A signal that is much stronger than the normal control signal should be scored as "P" and sequenced. Note that no patient specimens will be resulted based on these results alone. The specific options utilized will vary with the amplicon and its DHPLC performance history, and the specific circumstances for the specimen.

In some embodiments, the only results released from the DHPLC results will be those scored as "normal" by Wave analysis. In order to be scored as normal, the specimen's DHPLC pattern must be consistent with the normal control by the following QC criteria: (a) peak number, (b) peak height, (c) peak pattern, (d) retention time, (e) baseline shape. In other words, the pattern for the individual specimen must look like the normal control, within a reasonable expected range of variation. Consult with the validation data reference patterns if necessary. The sensitivity of DHPLC separating was assessed by counting patterns that differ substantially from the normal control. When a pattern genuinely appears to differ from the normal control, there should be no doubt—it is scored as positive and sent on for sequencing. Only those that meet the requirements for that specific amplicon and have a pattern consistent with the normal control should be scored and released as normal.

Specific numerical criteria used for judging "consistent with" include, but are not limited to, (a) number of peaks where a peak represents a local maximum in the signal intensity, (b) peak heights, or maximum signal intensities, which are usually between 0.5 and 2.0 times the height of the normal control, (c) retention time of peaks, which must be +/−60 seconds compared to the corresponding normal controls. Peak pattern is judged by relative correspondence of each slope change within a peak, and relative intensities and retention times of individual peaks within a complex pattern. Baseline patterns are usually smooth and consistent in all samples. A relatively low baseline change may represent a heteroduplex that elutes and perhaps melts at considerably different retention times from the homoduplex peak(s). The retention time and peak height criteria for each amplicon are specified in the attached tables in the Examples.

In one embodiment, the peak pattern assessment is a combination of (1) the sample signal satisfying the same run control criteria as the normal control, and (2) the sample signal pattern being consistent with the normal control based on the relative comparison for that run. Normal control patterns are expected to vary slightly from run to run, and still be acceptable, so individual samples scored as normal are a combination of satisfying (1) the same run control criteria as the normal control, (2) the relative control criteria inherent in the comparison of the normal control to each patient sample, described above. It seems clear that subtle changes in the pattern of the patient sample might be consistent with the absolute run criteria for the normal control, yet be clearly distinct using relative comparison of normal and patient within a run. The relative comparison within a run always supercedes historic patterns, assuming the normal control has passed control criteria and the run is accepted.

IX. Verification of Heteroduplex

Optionally, the identified heteroduplex may be verified by means of digesting the amplification products with one or more restriction enzymes. The restriction enzymes useful for this purpose are selected by comparing the sequences of authentic PKD genes and PKD homologues, or by comparing PKD polymorphisms. Useful restriction enzymes according to the invention generate distinguishable fragment profiles for an authentic PKD gene and a PKD homologue. Examples of such restriction enzymes include, but are not limited to, Pst I, Stu I, Xma I, Mlu I, Pvu II, BssHII, Fsp I, Msc I, and Bln I. Useful restriction enzymes may also generate distinguishable fragment profile for a normal PKD gene and a mutant PKD gene. It is understood that more restriction enzymes may be identified by simply comparing the sequence of a PKD gene and a PKD homologue gene or a normal PKD allele and a mutant PKD allele. A restriction enzyme with its recognition site or cleavage site in one sequence altered so as to abolish or create a cleavage site but not in the other sequence may be considered a useful restriction enzyme for the subject invention. Restriction of nucleic acids is followed by separation of the resulting fragments and analysis of fragment length or differential fragment migration in denaturing high-performance liquid chromatography (DHPLC) or gel electrophoresis, as above, including restriction-capillary electrophoresis.

X. Sequencing of Heteroduplexes Identified by DHPLC

Heteroduplex indicating the presence of one or more mutation, identified by DHPLC, may be cloned, amplified, and/or sequenced. Any known sequencing method known in the art can be used to sequence the heteroduplex. In some embodiments, the heteroduplex identified was used as template for PCR amplification and amplified products are sequenced by Sequetech Corporation (Mountain View, Calif.). In a preferred embodiment, sequencing is carried out by using one of the primers with SEQ ID NOs. 3-49.

In some embodiments, the identified heteroduplex is amplified and cloned into a plasmid (e.g., Zero Blunt TOPO PCR cloning kit, Invitrogen, Carlsbad, Calif., Cat #4560-01) before sequencing. The plasmid containing the PCR fragment is then propagated by well known methods in the art before subject to sequencing.

Figure 15T:
FIG. 15 is a wild-type PKD-1 cDNA sequence according to one embodiment of the invention.

XI. DNA Alterations Identified According to the Methods of the Present Invention A number of nucleotide and amino acid alterations have been identified in individuals diagnosed with ADPKD. FIG. 14 summarizes a list of non-limiting examples of alterations identified in PKD-1 and PKD-2 nucleotide and amino acid sequences from ADPKD patients according to one embodiment of the invention. The sequence positions indicated in FIG. 14 correspond to the nucleotide or amino acid positions as disclosed in FIGS. 15 and 16, for PKD-1 and PKD-2 (without introns) respectively.

The nucleotide and amino acid alterations listed in FIG. 14 include both known alterations in the art and novel alterations identified the first time by applicants of the present invention. Both known and novel alterations are identified in the present invention as to be associated with an individual diagnosed with ADPKD, therefore, both known and novel alterations disclosed in FIG. 14 may be used as markers for diagnosing PKD-caused ADPKD or for any other clinical use as described below. Primers which can be used to identify each nucleotide sequence alteration are indicated in FIG. 14 as well, e.g., as PKD1X1, PKD1X36, etc. The sequences of the primers are disclosed in Table 3 herein above.

In one embodiment, the invention provides a primer selected from the group consisting of SEQ ID NOs. 3-49.

In one embodiment, the invention provides an isolated PKD-1 or PKD-2 polynucleotide comprising one or more nucleotide sequence alterations as disclosed in FIG. 14.

In another embodiment, the invention provides an isolated PKD-1 or PKD-2 polynucleotide comprising one or more novel nucleotide sequence alterations as disclosed in FIG. 14 (indicated by bold text).

In another embodiment, the invention provides a purified PKD-1 or PKD-2 polypeptide comprising one or more amino acid sequence alterations as disclosed in FIG. 14.

In another embodiment, the invention provides a purified PKD-1 or PKD-2 polypeptide comprising one or more novel amino acid sequence alterations as disclosed in FIG. 14 (indicated by bold text).

Preferably, the PKD-1 or PKD-2 polynucleotide or polypeptide comprising one or more sequence alterations is used as a marker for ADPKD.

XII. Clinical Use of the Subject Method and Identified Alterations

The genetic testing method described in this application is targeted toward identifying DNA alterations in the coding region of the PKD-1 or PKD-2 gene, including the splice junction acceptor/donor sequences, which have been reported to cause ADPKD. The method can be performed to assists physicians to:

A. Diagnose PKD-caused ADPKD in symptomatic individuals.

B. Follow up on ultrasound results indicating the presence of one or two cysts in an individual at or near the age of onset.

C. Diagnose between different variants of ADPKD (type 1 and 2), which may or may not be feasible to determine from family history, ultrasound and other clinical data.

In one embodiment, the invention provides a method for diagnosing ADPKD in an individual, comprising identifying nucleotide sequence of PKD-1 or PKD-2 gene of the individual, where the existence of one or more nucleotide sequence alterations in the nucleotide sequence of PKD-1 or PKD-2 gene as disclosed in FIG. 14 is indicative of ADPKD in the individual.

Determine and provide genetic counseling for other at-risk family members once an ADPKD proband has been identified in a family.

E. Determine the suitability of a living related donor in transplantation cases.

The invention provides methods for detecting the presence of absence of mutant PKD genes, and the presence or absence of ADPKD.

In one embodiment, the present invention provides a method for determining in an individual the presence or absence of a mutant PKD gene, comprising the steps of a) identifying the nucleotide sequence of a PKD-1 or PKD-2 gene of the individual; b) comparing the nucleotide sequence of step a) to the nucleotide sequence alteration in the nucleotide sequence of a PKD-1 or PKD-2 gene as disclosed in FIG. 14; and c) detecting the presence of one or more of the nucleotide sequence alterations disclosed in FIG. 14; wherein the presence of at least one of the nucleotide sequence alterations is indicative of ADPKD in the individual; and wherein the absence of any of said nucleotide sequence alterations indicates the absence of a mutant PKD-1 and/or PKD-2 gene.

XIII. Kits

The invention also provides kits for performing the mutation analysis method and the PKD patient identification method of the invention. The invention provides for kits for detecting the presence of absence of mutant PKD genes, and the presence or absence of ADPKD.

Embodiments of the subject kits, in accordance with the methods of the invention, include at least one isolated first nucleic acid selected from the group of SEQ ID NOs. 3-49 and/or their complementary sequences. The kit may further comprise at least one isolated second nucleic acid which has an opposite orientation from the first nucleic acid, and where the first and second nucleic acids amplify a fragment of a template nucleic acid comprising a sequence of SEQ ID NO. 1 or 2, and packaging materials therefore. The kit of the invention may further comprises at least one component selected from the group consisting of: a DNA polymerase, a template nucleic acid, a restriction enzyme, a control oligonucleotide primer, ddNTPs, a PCR reaction buffer and the combination thereof. Kits of the invention, in addition to the reagents, preferably include written instructions for performing the subject methods. Kits are preferably packaged in a unit container and may contain the reagents in pre-measured amounts designed to operate with each other so as to produce the desired result.

EXAMPLES

The invention is illustrated by the following non-limiting examples wherein the following materials and methods are employed.

Example 1

Reagents, Special Supplies and Equipment
A. Chemicals
The following is a listed of chemicals used for PKD-1 amplification and DHPLC (WAVE) analysis.

1% Agarose, 1×TBE, 54 Well Gel with Ethidium Bromide (Embitec, Catalog Number GE 4580)

2% Agarose, 1×TBE, 54 Well Gel with Ethidium Bromide (Embitec, Catalog Number GE 4582)

96 Well Gel Filtration Block (Edge Biosystems, Catalog Number 91751)

Quickstep™ 96 Well PCR Purification Kit (Edge Biosystems, Catalog Number 99605)

AmpliTaq Gold with GeneAmp PCR Buffer II & $MgCl_2$ Solution (Perkin Elmer, Catalog Number N808-0241)

rTth DNA Polymerase, XL & XL Buffer II Pack (Perkin Elmer, Catalog Number N808-00193)

TapPlus Precision PCR System (Stratagene, Catalog Number 600211)

Dimethyl Sulphoxide (DMSO) (Sigma, Catalog Number D-2650)

Ready-Load 100 bp DNA Ladder or Equivalent (Gibco BRL, Catloag Number 10380-012)

Ready-Load 1 kb DNA Ladder or Equivalent (Gibco BRL, 1800-828-6686, Catlaog Number 10381-010)

Big Dye Terminator Ready Reaction Kit (Perkin Elmer, Catalog Number 4303150)

Gel Filtration Cartridge (Edge Biosystems, Catalog Number 42453)

Long Ranger Singel™ packs (FMC BioProducts, Catalog Number 50691 or 50693).

Oligonucleotides (Operon Technologies, Inc.)

WAVE Mutation Standard (209 bp), Catalog Number 560077 (180 ul)

Acetonitrile-HPLC Grade (VWR, Catalog Number BJ015-1)

HPLC Grade Water (VWR, Catalog Number BJ365-4)

Triethylammonium Acetate (TEAA) (Transgenomic, Catalog Number SP5890)

B. Reagents and Solutions

10 µM oligonucleotide primers: 10 µM working aliquots of PCR primers dissolved in TE buffer should be stored at 4° C. in Pre-PCR refrigerator; sequencing primer working aliquots should be stored at 4° C. in Post-PCR refrigerator.

Solution X-127: Upgrade Blue Dextran in 50 mM EDTA (pH=8.0)

Combine 0.5 ml 50 mM EDTA pH=8.0 (Solution X-35), 500 mg Blue Dextran AND 9.5 ml AUTOCLAVED, STERILE FILTERED $DiH_2O$ in a sterile 15 ml conical centrifuge tube. Thoroughly mix the solution by vortexing.

Solution X-126: Upgrade Gel Loading Buffer: Combine 200 µl deionized Formamide and 40 µl Upgrade Blue Dextran in 50 mM EDTA (Solution X-127) in a 1.5 ml sterile microcentrifuge tube. Vortex thoroughly.

WAVE Solution A: Solution A (0.025% ACN)
Preparation of 2L: 100 ml Ion Pairing Agent (TEAA)
500 µl Acetonitrile (ACN)
Top to 2 L with HPLC grade water WAVE Solution B: Solution B (25% ACN)
Preparation of 2 L: 100 ml Ion Pairing Agent (TEAA)
500 ml Acetonitrile (ACN)
Top to 2 L with HPLC grade water WAVE Syringe Wash Solution: Syringe Wash (8% ACN)
Preparation of 2 L: 160 ml Acetonitrile (ACN)
Top to 2 L with HPLC grade water WAVE Solution D: Solution D (75% ACN)
Preparation of 2 L:500 ml HPLC grade water
Top to 2 L with Acetonitrile (ACN)

C. Equipment and Special Supplies

TABLE 5

| | |
|---|---|
| Perkin Elmer<br>761 Main Avenue<br>Norwalk, CT 06859 | ABI Prism ™ 377 DNA Sequencer |
| VWR Scientific Products<br>P.O. Box 232<br>Boston, MA 02101 | 1. Beckman Allegra ™ 21 Centrifuge<br>2. Eppendorf Microcentrifuge 5415C<br>3. Multichannel pipet<br>4. Sterile reservoirs<br>5. DURX 670 wipers<br>6. VWR Model 1300U Oven |
| Transgenomic, Inc.<br>12325 Emmet Street<br>Omaha, NE 68164 | WAVE Nucleic Acid Fragment Analysis System |

Example 2

Procedure

Stage I: Preparation Of DNA and/or RNA From Patient Specimens

DNA is extracted from whole blood or lymphocytes using the Puregene® DNA extraction kit. DNA extracted using these reagents should be successfully PCR amplified under the conditions specific to the assay. This is tested by performing the assay as specified in the protocol and comparing the results obtained with the positive DNA control that has been previously validated.

Extracted DNA is quantitated and the 260/280 ratio is 1.4 or greater. Samples with lower ratios indicate that the quality of DNA is poor and may not meet PCR standards. If end results of the assay are not interpretable the sample should be re-extracted.

Stage II: Amplification of DNA by PCR

PCR reaction mixtures and cycling parameters (e.g., for exon 1 of PKD-1 gene) were set up as illustrated in Table 5. PCR conditions were set up similarly, but optimized for specific and efficient amplification of other exons.

TABLE 6

PCR Reaction Master Mix Component Concentrations and Thermal Cycling Conditions For First round PCR Products 1–8 (L1–L8)
LOWER MASTER MIX:

| Component: | Reaction Concentration | Volume/reaction |
|---|---|---|
| Water | — | 13.0 ul |
| 10 × Buffer | 1× | 2.0 ul |
| Mg(Oac)$_2$ | 0.9 mM | None |
| dNTP mix | 200 uM | 1.0 ul |
| Primer 1 | 0.25 uM | 1.25 ul |
| Primer 2 | 0.25 uM | 1.25 ul |
| DMSO | 7.5% | 1.5 ul |
| TOTAL VOLUME | | 20 ul |

One wax bead was added to each well and incubated in a thermal cycler@ 80° C. for 5 minutes to melt the wax and incubated at 25° C. for an additional 5 minutes before placed on ice for further handling.

Upper Master Mix:

| Component: | Reaction Concentration | Volume/reaction |
|---|---|---|
| Water | — | 23.15 ul |
| 10 × Buffer | 1× | 3.0 ul |
| TaqPlus Precision Polymerase mixture | 5 U/rxn | 1.0 ul |
| DMSO | 7.5% | 2.25 ul |
| TOTAL VOLUME | | 29.4 ul |
| Genomic DNA @ 500 ng/ul | | 0.6 ul |

Cycling Parameters

| Melting the Wax | | Amplification | |
|---|---|---|---|
| 80° C. 5 min | 1 cycle | 94° C. 3 min | 1 cycle |
| 25° C. forever | | 96° C. 30 sec | |
| *Add Upper Master Mix and DNA before proceeding to next cycling step. | | 68° C. 20 sec | 35 cycles |
| | | 72° C. 3 min + 4 sec/cycle | |
| | | 72° C. 10 min | 1 cycle |

TABLE 7

Example of nested PCR reaction setup

| REAGENT | STOCK CONCENTRATION | VOLUME PER REACTION | REACTION CONCENTRATION |
|---|---|---|---|
| Water | — | 31.0 µl | — |
| Buffer II | 10× | 5.0 µl | 1× |
| MgCl$_2$ | 25 mM | 2.0 µl | 1.0 mM |
| DNTP mix | 10 mM each | 1.0 µl | 200 µM each |
| CAD-18-PF1 (primer) | 10 µM | 3.0 µl | 0.6 µM |
| CAD-18-PR1 (primer) | 10 µM | 3.0 µl | 0.6 µM |
| DMSO | 100% | 2.5 µl | 5% |
| Amplitaq Gold | 5 U/µl | 0.5 µl | 2.5 U |
| TOTAL | | 48.0 µl | |

TABLE 8

Summary of Amplification Conditions For Exons

| CYCLE NUMBER | TEMPERATURE | TIME | DESCRIPTION |
|---|---|---|---|
| 1 cycle | 94° C. | 10 min | AmpliTaq Gold activation |
| 35 cycles | 92° C. | 1 min | Denaturing |
| | 55° C. | 1 min | Annealing |
| | 72° C. | 1 min | Extension |
| 1 cycle | 72° C. | 10 min | Final extension |
| (hold) | 4° C. | forever | |

PCR amplified fragments may be compared in size, signal intensity and migration pattern with positive control DNA control that has been previously validated. The size of the PCR amplified fragments is determined by comparison to the Molecular weight marker (DNA MASS™ Ladder-Gibco BRL) on the gel. The low range DNA Mass Ladder gives 6 bands of double stranded (100-2000 bp) DNA on staining the gel with ethidium bromide.

Stage III: DHPLC Analysis of PCR Products

Heteroduplexes formed by PCR amplified products are analyzed using WAVE nucleic acid fragment analysis system from Transgenomic, Inc. (Omaha, Nebr. 68164).

Stage IV: Cycle Sequencing

Tables 9 and 10 provide examples of sequencing conditions used in one embodiment of the invention.

TABLE 9

Sequencing Reaction Master Mix Component

| REAGENT | STOCK CONCENTRATION | VOLUME PER REACTION | REACTION CONCENTRATION |
|---|---|---|---|
| Water | — | 14.0 µl | — |
| Big Dye Terminator Ready Reaction Mix | 2.5× | 4.0 µl | 0.5× |
| Primer | 10 µM | 1.0 µl | 0.5 µM |
| FINAL VOLUME | | 19.0 µl | |

TABLE 10

Cycle Sequencing Conditions

| CYCLE NUMBER | TEMPERATURE | TIME | DESCRIPTION |
|---|---|---|---|
| 30 cycles | 94° C. | 10 sec | Denaturing |
| | 55° C. | 5 sec | Annealing |
| | 60° C. | 4 min | Extension |
| (hold) | 4° C. | forever | |

Example 3

Summary of Results

In one experiment, detection of mutations in exons 1-34 of the PKD-1 gene was achieved by using eight sets of oligonucleotide primers in eight separate first round PCR reaction to amplify DNA fragments of the following sizes: a) LR1 was 2.2 kb and contains exon 1. b) LR2 was 4.6 kb and contains exons 2-7. c) LR3 was 4.2 kb and contains exons 8-12. d) LR4 was 4.4 kb and contains exons 13-15. e) LR5 was 3.4 kb and contains exons 15 (3'-end) through 21. f) LR6 was 0.3 kb and consists of exon 22. g) LR7 was 4.2 kb and contains exons 23-28. h) LR8 was 5.8 kb and contained exons 29-34 of the duplicated region of the gene. The amplified product from the first round of amplification were then serially diluted to 1:10$^4$ or 1:10$^5$ to remove genomic contamination and subsequently used as template in a second round of nested PCR. The nested PCR products were heteroduplexed and screened for sequence alterations by DHPLC. Each fragment was analyzed against a normal and positive control using a temperature and acetonitrile gradient specific to the amplicon. Any samples testing positive by DHPLC analysis were subsequently purified and sequenced. Cycle sequenced products were then separated on an ABI 377 automated sequencer and the results were analyzed using an assortment of sequencing software. Tables 11-12 and FIGS. 1 to 13 illustrate the results and procedures of some embodiments of the invention.

TABLE 11

Numbers of products analyzed for each PKD gene

| Analysis: | PKD-1 | PKD-2 | Total |
| --- | --- | --- | --- |
| First Round PCRs | 8 | — | 8 |
| Amplicons | 66 | 17 | 83 |
| DHPLC analyses | 133 | 33 | 166 |
| Base Pairs evaluated | 13,830 | 3204 | 17,034 |

TABLE 12

Variant detection rates

| Source of Variant | Naturally occurring - Independent Sequence confirmed | Naturally occurring - SSCP Separated | Mutagenesis Sequence confirmed | Gene Total |
| --- | --- | --- | --- | --- |
| PKD-1 | 14/18 78% | 15/17 88% | 45/47 96% | 74/82 90% |
| PKD-2 | 20/21 95% | 0/0 | 22/23 96% | 42/44 95% |
| Type total | 34/39 87% | 15/17 88% | 67/70 96% | 116/126 92% |

OTHER EMBODIMENTS

The foregoing examples demonstrate experiments performed and contemplated by the present inventors in making and carrying out the invention. It is believed that these examples include a disclosure of techniques which serve to both apprise the art of the practice of the invention and to demonstrate its usefulness. It will be appreciated by those of skill in the art that the techniques and embodiments disclosed herein are preferred embodiments only and that in general numerous equivalent methods and techniques may be employed to achieve the same result. All applications, patents and literature referred to in the specification are hereby incorporated by reference, in their entirety, including figures and tables.

SEQUENCE LISTING

<160> NUMBER OF SEQ ID NOS: 172

<210> SEQ ID NO 1
<211> LENGTH: 14136
<212> TYPE: DNA
<213> ORGANISM: Homo sapiens

<400> SEQUENCE: 1

| | | | | | |
|---|---|---|---|---|---|
| gcactgcagc | gccagcgtcc | gagcgggcgg | ccgagctccc | ggagcggcct | ggccccgagc | 60 |
| cccgagcggg | cgtcgctcag | cagcaggtcg | cggccgcgca | gccccatcca | gccccgcgcc | 120 |
| cgccatgccg | tccgcgggcc | ccgcctgagc | tgcggtctcc | gcgcgcgggc | gggcctgggg | 180 |
| acggcggggc | catgcgcgcg | ctgccctaac | gatgccgccc | gccgcgcccg | cccgcctggc | 240 |
| gctggccctg | ggcctgggcc | tgtggctcgg | ggcgctggcg | gggggccccg | ggcgcggctg | 300 |
| cgggccctgc | gagcccccct | gcctctgcgg | cccagcgccc | ggcgccgcct | gccgcgtcaa | 360 |
| ctgctcgggc | cgcgggctgc | ggacgctcgg | tcccgcgctg | cgcatccccg | cggacgccac | 420 |
| agcgctagac | gtctcccaca | acctgctccg | ggcgctggac | gttgggctcc | tggcgaacct | 480 |
| ctcggcgctg | gcagagctgg | atataagcaa | caacaagatt | tctacgttag | aagaaggaat | 540 |
| atttgctaat | ttatttaatt | taagtgaaat | aaacctgagt | gggaacccgt | ttgagtgtga | 600 |
| ctgtggcctg | gcgtggctgc | cgcgatgggc | ggaggagcag | caggtgcggg | tggtgcagcc | 660 |
| cgaggcagcc | acgtgtgctg | ggcctggctc | cctggctggc | cagcctctgc | ttggcatccc | 720 |
| cttgctggac | agtggctgtg | gtgaggagta | tgtcgcctgc | ctccctgaca | acagctcagg | 780 |

```
caccgtggca gcagtgtcct tttcagctgc ccacgaaggc ctgcttcagc cagaggcctg      840
cagcgccttc tgcttctcca ccggccaggg cctcgcagcc ctctcggagc agggctggtg      900
cctgtgtggg gcggcccagc cctccagtgc ctcctttgcc tgcctgtccc tctgctccgg      960 cccccgcca cctcctgccc ccacctgtag ggccccacc ctcctccagc acgtcttccc       1020
tgcctcccca ggggccaccc tggtggggcc ccacggacct ctggcctctg gccagctagc     1080
agccttccac atcgctgccc cgctccctgt cactgccaca cgctgggact tcggagacgg     1140
ctccgccgag gtggatgccg ctgggccggc tgcctcgcat cgctatgtgc tgcctgggcg     1200
ctatcacgtg acgccgtgc tggccctggg ggccggctca gccctgctgg ggacagacgt      1260
gcaggtggaa gcggcacctg ccgccctgga gctcgtgtgc ccgtcctcgg tgcagagtga     1320
cgagagcctt gacctcagca tccagaaccg cggtggttca ggcctggagg ccgcctacag     1380
catcgtggcc ctgggcgagg agccggcccg agcggtgcac ccgctctgcc cctcggacac     1440
ggagatcttc cctggcaacg gcactgcta ccgcctggtg gtggagaagg cggcctggct      1500
gcaggcgcag gagcagtgtc aggcctgggc cggggccgcc ctggcaatgg tggacagtcc     1560
cgccgtgcag cgcttcctgg tctcccgggt caccaggagc ctagacgtgt ggatcggctt     1620
ctcgactgtg caggggtgg aggtgggccc agcgccgcag ggcgaggcct tcagcctgga      1680
gagctgccaa aactggctgc ccggggagcc acacccagcc acagccgagc actgcgtccg     1740
gctcgggccc accgggtggt gtaacaccga cctgtgctca cgccgcaca gctacgtctg      1800 cgagctgcag cccggaggcc cagtgcagga tgccagaaac ctcctcgtgg agcgcccag      1860 tggggacctg cagggacccc tgacgcctct ggcacagcag gacggcctct cagccccgca     1920
cgagcccgtg gaggtcatgg tattcccggg cctgcgtctg agccgtgaag ccttcctcac     1980
cacggccgaa tttgggaccc aggagctccg gcggcccgcc cagctgcggc tgcaggtgta     2040
ccggctcctc agcacagcag ggaccccgga gaacggcagc gagcctgaga gcaggtcccc     2100
ggacaacagg acccagctgg cccccgcgtg catgccaggg ggacgctggt gccctggagc     2160
caacatctgc ttgccgctgg acgcctcttg ccaccccag gcctgcgcca atggctgcac      2220
gtcagggcca gggctacccg ggcccccta tgcgctatgg agagagttcc tcttctccgt      2280
tgccgcgggg ccccccgcgc agtactcggt caccctccac ggccaggatg tcctcatgct     2340
ccctggtgac ctcgttggct tgcagcacga cgctggccct ggcgcccctcc tgcactgctc    2400 gccggctccc ggccaccctg gtccccaggc cccgtacctc tccgccaacg cctcgtcatg     2460 gctgcccac ttgccagccc agctggaggg cacttgggcc tgccctgcct gtgccctgcg      2520
gctgcttgca gccacggaac agctcaccgt gctgctgggc ttgaggccca accctggact    2580
gcggatgcct gggcgctatg aggtccgggc agaggtgggc aatggcgtgt ccaggcacaa     2640
cctctcctgc agctttgacg tggtctcccc agtggctggg ctgcgggtca tctaccctgc    2700 ccccccgcgac ggccgcctct acgtgcccac caacggctca gccttggtgc tccaggtgga   2760
ctctggtgcc aacgccacgg ccacggctcg ctggcctggg gcagtgtca gcgcccgctt      2820 tgagaatgtc tgccctgccc tggtggccac cttcgtgccc ggctgcccct gggagaccaa    2880
cgataccctg ttctcagtgg tagcactgcc gtggctcagt gaggggagc acgtggtgga    2940 cgtggtggts gaaaacagcg ccagccgggc caacctcagc ctgcgggtga cggcggagga    3000
gcccatctgt ggcctccgcg ccacgcccag ccccgaggcc cgtgtactgc agggagtcct    3060
agtgaggtac agccccgtgg tggaggccgg ctcggacatg gtcttccggt ggaccatcaa    3120
cgacaagcag tccctgacct tccagaacgt ggtcttcaat gtcatttatc agagcgcggc    3180
```

```
ggtcttcaag ctctcactga cggcctccaa ccacgtgagc aacgtcaccg tgaactacaa    3240
cgtaaccgtg gagcggatga acaggatgca gggtctgcag gtctccacag tgccggccgt    3300
gctgtccccc aatgccacgc tagcactgac ggcgggcgtg ctggtggact cggccgtgga    3360
ggtggccttc ctgtggaact ttggggatgg ggagcaggcc ctccaccagt tccagcctcc    3420
gtacaacgag tccttcccgg ttccagaccc ctcggtggcc caggtgctgg tggagcacaa    3480
tgtcatgcac acctacgctg ccccaggtga gtacctcctg accgtgctgg catctaatgc    3540
cttcgagaac ctgacgcagc aggtgcctgt gagcgtgcgc gcctccctgc cctccgtggc    3600
tgtgggtgtg agtgacggcg tcctggtggc cggccggccc gtcaccttct acccgcaccc    3660
gctgccctcg cctgggggtg ttctttacac gtgggacttc ggggacggct ccctgtcct    3720 gacccagagc cagccggctg ccaaccacac ctatgcctcg aggggcacct accacgtgcg    3780
cctggaggtc aacaacacgg tgagcggtgc ggcggcccag gcggatgtgc gcgtctttga    3840
ggagctccgc ggactcagcg tggacatgag cctggccgtg gagcagggcg cccccgtggt    3900
ggtcagcgcc gcggtgcaga cgggcgacaa catcacgtgg accttcgaca tgggggacgg    3960
caccgtgctg tcgggcccgg aggcaacagt ggagcatgtg tacctgcggg cacagaactg    4020
cacagtgacc gtgggtgcgg ccagccccgc cggccacctg gcccggagcc tgcacgtgct    4080
ggtcttcgtc ctggaggtgc tgcgcgttga acccgccgcc tgcatcccca cgcagcctga    4140
cgcgcggctc acggcctacg tcaccgggaa cccggcccac tacctcttcg actggacctt    4200
cggggatggc tcctccaaca cgaccgtgcg ggggtgcccg acggtgacac acaacttcac    4260
gcggagcggc acgttccccc tggcgctggt gctgtccagc cgcgtgaaca gggcgcatta    4320
cttcaccagc atctgcgtgg agccagaggt gggcaacgtc accctgcagc cagagaggca    4380
gtttgtgcag ctcggggacg aggcctggct ggtggcatgt gcctggcccc cgttcccta    4440 ccgctacacc tgggacttg gcaccgagga agccgccccc accgtgcca ggggccctga    4500 ggtgacgttc atctaccgag acccaggctc ctatcttgtg acagtcaccg cgtccaacaa    4560
catctctgct gccaatgact cagccctggt ggaggtgcag gagcccgtgc tggtcaccag    4620
catcaaggtc aatggctccc ttgggctgga gctgcagcag ccgtacctgt tctctgctgt    4680
gggccgtggg cgccccgcca gctacctgtg ggatctgggg gacggtgggt ggctcgaggg    4740
tccggaggtc acccacgctt acaacagcac aggtgacttc accgttaggg tggccggctg    4800
gaatgaggtg agccgcagcg aggcctggct caatgtgacg gtgaagcggc gcgtgcgggg    4860
gctcgtcgtc aatgcaagcc gcacggtggt gcccctgaat gggagcgtga gcttcagcac    4920
gtcgctggag gccggcagtg atgtgcgcta ttcctgggtg ctctgtgacc gctgcacgcc    4980
catccctggg ggtcctacca tctcttacac cttccgctcc gtgggcacct tcaatatcat    5040
cgtcacggct gagaacgagg tgggctccgc ccaggacagc atcttcgtct atgtcctgca    5100
gctcatagag gggctgcagg tggtgggcgg tggccgctac ttccccacca accacacggt    5160
acagctgcag gccgtggtta gggatggcac caacgtctcc tacagctgga ctgcctggag    5220
ggacaggggc ccggccctgg ccggcagcgg caaaggcttc tcgctcaccg tgctcgaggc    5280
cggcacctac catgtgcagc tgcgggccac caacatgctg gcagcgcct gggccgactg    5340 caccatggac ttcgtggagc ctgtggggtg gctgatggtg accgcctccc cgaacccagc    5400
tgccgtcaac acaagcgtca ccctcagtgc cgagctggct ggtggcagtg gtgtcgtata    5460
cacttggtcc ttggaggagg ggctgagctg ggagacctcc gagccattta ccacccatag    5520
```

```
cttccccaca cccggcctgc acttggtcac catgacggca gggaacccgc tgggctcagc   5580
caacgccacc gtggaagtgg atgtgcaggt gcctgtgagt ggcctcagca tcagggccag   5640
cgagcccgga ggcagcttcg tggcggccgg gtcctctgtg ccctttttgggg ggcagctggc  5700
cacgggcacc aatgtgagct ggtgctgggc tgtgcccggc ggcagcagca agcgtggccc   5760
tcatgtcacc atggtcttcc cggatgctgg caccttctcc atccggctca atgcctccaa   5820
cgcagtcagc tgggtctcag ccacgtacaa cctcacggcg gaggagccca tcgtgggcct   5880
ggtgctgtgg gccagcagca aggtggtggc gcccgggcag ctggtccatt ttcagatcct   5940
gctggctgcc ggctcagctg tcaccttccg cctgcaggtc ggcggggcca cccccgaggt   6000
gctccccggg ccccgtttct cccacagctt ccccgcgtc ggagaccacg tggtgagcgt    6060
gcggggcaaa accacgtga gctgggccca ggcgcaggtg cgcatcgtgg tgctggaggc    6120
cgtgagtggg ctgcagatgc ccaactgctg cgagcctggc atcgccacgg cactgagag    6180
gaacttcaca gcccgcgtgc agcgcggctc tcgggtcgcc tacgcctggt acttctcgct   6240
gcagaaggtc cagggcgact cgctggtcat cctgtcgggc cgcgacgtca cctacacgcc   6300
cgtgccgcg gggctgttgg agatccaggt gcgcgccttc aacgccctgg gcagtgagaa    6360
ccgcacgctg gtgctggagg ttcaggacgc cgtccagtat gtggccctgc agagcggccc   6420
ctgcttcacc aaccgctcgg cgcagtttga ggccgccacc agcccagcc cccggcgtgt    6480
ggcctaccac tgggactttg gggatgggtc gccagggcag gacacagatg agcccagggc   6540
cgagcactcc tacctgaggc ctggggacta ccgcgtgcag gtgaacgcct ccaacctggt   6600
gagcttcttc gtggcgcagg ccacggtgac cgtccaggtg ctggcctgcc gggagccgga   6660
ggtggacgtg gtcctgcccc tgcaggtgct gatgcggcga tcacagcgca actacttgga   6720
ggcccacgtt gacctgcgcg actgcgtcac ctaccagact gagtaccgct gggaggtgta   6780
tcgcaccgcc agctgccagc ggccggggcg cccagcgcgt gtggccctgc ccggcgtgga   6840
cgtgagccgg cctcggctgg tgctgccgcg gctggcgctg cctgtggggc actactgctt   6900
tgtgtttgtc gtgtcatttg gggacacgcc actgacacag agcatccagg ccaatgtgac   6960
ggtggccccc gagcgcctgg tgcccatcat tgagggtggc tcataccgcg tgtggtcaga   7020
cacacgggac ctggtgctgg atgggagcga gtcctacgac cccaacctgg aggacgcgca   7080
ccagacgccg ctcagttcc actgggcctg tgtggcttcg acacagaggg aggctggcgg   7140
gtgtgcgctg aactttgggc cccgcgggag cagcacggtc accattccac gggagcggct   7200
ggcggctggc gtggagtaca ccttcagcct gaccgtgtgg aaggccggcc gcaaggagga   7260
ggccaccaac cagacggtgc tgatccggag tggccgggtg cccattgtgt ccttggagtg   7320
tgtgtcctgc aaggcacagg ccgtgtacga agtgagccgc agctcctacg tgtacttgga   7380
gggccgctgc ctcaattgca gcagcggctc caagcgaggg cggtgggctg cacgtacgtt   7440
cagcaacaag acgctggtgc tggatgagac caccacatcc acgggcagtg caggcatgcg   7500
actggtgctg cggcggggcg tgctgcggga cggcgaggga tacaccttca cgctcacggt   7560
gctgggccgc tctggcgagg aggagggctg cgcctccatc cgcctgtccc caaccgccc   7620
gccgctgggg ggctcttgcc gcctcttccc actgggcgct gtgcacgccc tcaccaccaa   7680
ggtgcacttc gaatgcacgg gctggcatga gcgcgaggat gctggcgccc gctggtgta   7740
cgccctgctg ctgcggcgct gtcgccaggg ccactgcgag gagttctgtg tctacaaggg   7800
cagcctctcc agctacggag ccgtgctgcc cccgggtttc aggccacact cgaggtggg   7860
cctggccgtg gtggtgcagg accagctggg agccgctgtg gtcgccctca acaggtcttt   7920
```

-continued

```
ggccatcacc ctcccagagc ccaacggcag cgcaacgggg ctcacagtct ggctgcacgg    7980
gctcaccgct agtgtgctcc cagggctgct gcggcaggcc gatccccagc acgtcatcga    8040
gtactcgttg gccctggtca ccgtgctgaa cgagtacgag cgggccctgg acgtggcggc    8100
agagcccaag cacgagcggc agcaccgagc ccagatacgc aagaacatca cggagactct    8160
ggtgtccctg agggtccaca ctgtggatga catccagcag atcgctgctg cgctggccca    8220
gtgcatgggg cccagcaggg agctcgtatg ccgctcgtgc ctgaagcaga cgctgcacaa    8280
gctggaggcc atgatgctca tcctgcaggc agagaccacc gcgggcaccg tgacgcccac    8340
cgccatcgga gacagcatcc tcaacatcac aggagacctc atccacctgg ccagctcgga    8400
cgtgcgggca ccacagccct cagagctggg agccgagtca ccatctcgga tggtggcgtc    8460
ccaggcctac aacctgacct ctgccctcat gcgcatcctc atgcgctccc gcgtgctcaa    8520
cgaggagccc ctgacgctgg cgggcgagga gatcgtggcc cagggcaagc gctcggaccc    8580
gcggagcctg ctgtgctatg cggcgccccc agggcctggc tgccacttct ccatcccga    8640 ggctttcagc ggggcccgg ccaacctcag tgacgtggtg cagctcatct ttctggtgga    8700
ctccaatccc tttccctttg gctatatcag caactacacc gtctccacca aggtggcctc    8760
gatggcattc cagacacagg ccggcgccca gatccccatc gagcggctgg cctcagagcg    8820
cgccatcacc gtgaaggtgc ccaacaactc ggactgggct gccgggggcc accgcagctc    8880
cgccaactcc gccaactccg ttgtggtcca gccccaggcc tccgtcggtg ctgtggtcac    8940 cctgacagc agcaacccctg cggccgggct gcatctgcag ctcaactata cgctgctgga    9000
cggccactac ctgtctgagg aacctgagcc ctacctggca gtctacctac actcggagcc    9060
ccggcccaat gagcacaaact gctcggctag caggaggatc cgcccagagt cactccaggg    9120
tgctgaccac cggccctaca ccttcttcat tccccgggg agcagagacc cagcggggag    9180
ttaccatctg aacctctcca gccacttccg ctggtcggcg ctgcaggtgt ccgtgggcct    9240
gtacacgtcc ctgtgccagt acttcagcga ggaggacatg gtgtggcgga cagggggct    9300 gctgccctg gaggagacct cgcccgcca ggccgtctgc ctcacccgcc acctcaccgc    9360
cttcggcgcc agcctcttcg tgccccaag ccatgtccgc tttgtgtttc ctgagccgac    9420
agcggatgta aactacatcg tcatgctgac atgtgctgtg tgcctggtga cctacatggt    9480
catggccgcc atcctgcaca agctggacca gttggatgcc agccggggcc gcgccatccc    9540
tttctgtggg cagcgggggcc gcttcaagta cgagatcctc gtcaagacag gctggggccg    9600
gggctcaggt accacggccc acgtgggcat catgctgtat ggggtggaca gccggagcgg    9660
ccaccggcac ctggacggcg acagagcctt ccaccgcaac agcctggaca tcttccggat    9720
cgccaccccg cacagcctgg gtagcgtgtg gaagatccga gtgtggcacg acaacaaagg    9780
gctcagccct gcctggttcc tgcagcacgt catcgtcagg gacctgcaga cggcacgcag    9840
cgccttcttc ctggtcaatg actggctttc ggtggagacg gaggccaacg ggggcctggt    9900
ggagaaggag gtgctggccg cgagcgacgc agccctttg cgcttccggc gcctgctggt    9960
ggctgagctg cagcgtggct ctttgacaa gcacatctgg ctctccatat gggaccggcc    10020
gcctcgtagc cgtttcactc gcatccgag ggccacctgc tgcgttctcc tcatctgcct    10080
cttcctgggc gccaacgccg tgtggtacgg ggctgttggc gactctgcct acagcacggg    10140
gcatgtgtcc aggctgagcc cgctgagcgt cgacacagtc gctgttggcc tggtgtccag    10200
cgtggttgtc tatcccgtct acctggccat ccttttttctc ttccggatgt cccggagcaa    10260
```

```
ggtggctggg agcccgagcc ccacacctgc cgggcagcag gtgctggaca tcgacagctg    10320
cctggactcg tccgtgctgg acagctcctt cctcacgttc tcaggcctcc acgctgaggc    10380
ctttgttgga cagatgaaga gtgacttgtt tctggatgat tctaagagtc tggtgtgctg    10440
gccctccggc gagggaacgc tcagttggcc ggacctgctc agtgacccgt ccattgtggg    10500
tagcaatctg cggcagctgg cacggggcca ggcgggccat gggctgggcc cagaggagga    10560
cggcttctcc ctggccagcc cctactcgcc tgccaaatcc ttctcagcat cagatgaaga    10620
cctgatccag caggtccttg ccgagggggt cagcagccca gcccctaccc aagacaccca    10680
catgaaaacg gacctgctca gcagcctgtc cagcactcct ggggagaaga cagagacgct    10740
ggcgctgcag aggctggggg agctgggggcc acccagccca ggcctgaact gggaacagcc    10800
ccaggcagcg aggctgtcca ggacaggact ggtggaggt ctgcggaagc gcctgctgcc    10860
ggcctggtgt gcctccctgg cccacgggct cagcctgctc ctggtggctg tggctgtggc    10920
tgtctcaggg tgggtgggtg cgagcttccc cccgggcgtg agtgttgcgt ggctcctgtc    10980
cagcagcgcc agcttcctgg cctcattcct cggctgggag ccactgaagg tcttgctgga    11040
agccctgtac ttctcactgg tggccaagcg gctgcacccg gatgaagatg acaccctggt    11100
agagagcccg gctgtgacgc ctgtgagcgc acgtgtgccc cgcgtacggc caccccacgg    11160
ctttgcactc ttcctggcca aggaagaagc ccgcaaggtc aagaggctac atggcatgct    11220
gcggagcctc ctggtgtaca tgcttttttct gctggtgacc ctgctggcca gctatgggga    11280
tgcctcatgc catgggcacg cctaccgtct gcaaagcgcc atcaagcagg agctgcacag    11340
ccgggccttc ctggccatca cgcggtctga ggagctctgg ccatggatgg cccacgtgct    11400
gctgccctac gtccacggga accagtccag cccagagctg ggcccccac ggctgcggca    11460
ggtgcggctg caggaagcac tctacccaga ccctcccggc cccagggtcc acacgtgctc    11520
ggccgcagga ggcttcagca ccagcgatta cgacgttggc tgggagagtc ctcacaatgg    11580
ctcgggacg tgggcctatt cagcgccgga tctgctgggg gcatggtcct ggggctcctg    11640
tgccgtgtat gacagcgggg gctacgtgca ggagctgggc ctgagcctgg aggagagccg    11700
cgaccggctg cgcttcctgc agctgcacaa ctggctggac aacaggagcc gcgctgtgtt    11760
cctggagctc acgcgctaca gcccggccgt ggggctgcac gccgccgtca cgctgcgcct    11820
cgagttcccg gcggccggcc gcgccctggc cgccctcagc gtccgcccct ttgcgctgcg    11880
ccgcctcagc gcgggcctct cgctgcctct gctcacctcg gtgtgcctgc tgctgttcgc    11940
cgtgcacttc gccgtggccg aggcccgtac ttggcacagg gaagggcgct ggcgcgtgct    12000
gcggctcgga gcctgggcgc ggtggctgct ggtggcgctg acggcggcca cggcactggt    12060
acgcctcgcc cagctgggtg ccgctgaccg ccagtggacc cgtttcgtgc gcggccgccc    12120
gcgccgcttc actagcttcg accaggtggc gcagctgagc tccgcagccc gtggcctggc    12180
ggcctcgctg ctcttcctgc ttttggtcaa ggctgcccag cagctacgct tcgtgcgcca    12240
gtggtccgtc tttggcaaga cattatgccg agctctgcca gagctcctgg ggtcaccctt    12300
gggcctggtg gtgctcgggg tagcctacgc ccagctggcc atcctgctcg tgtcttcctg    12360
tgtggactcc ctctggagcg tgcccaggc cctgttggtg ctgtgccctg ggactgggct    12420
ctctaccctg tgtcctgccg agtcctgca cctgtcaccc ctgctgtgtg tggggctctg    12480
ggcactgcgg ctgtggggcg ccctacggct gggggctgtt attctccgct ggcgctacca    12540
cgccttgcgt ggagagctgt accggccggc ctggagcccc caggactacg agatggtgga    12600
gttgttcctg cgcaggctgc gcctctggat gggcctcagc aaggtcaagg agttccgcca    12660
```

-continued

```
caaagtccgc tttgaaggga tggagccgct gccctctcgc tcctccaggg gctccaaggt    12720
atccccggat gtgccccccac ccagcgctgg ctccgatgcc tcgcacccct ccacctcctc    12780
cagccagctg gatgggctga gcgtgagcct gggccggctg gggacaaggt gtgagcctga    12840
gccctcccgc ctccaagccg tgttcgaggc cctgctcacc cagtttgacc gactcaacca    12900
ggccacagag gacgtctacc agctggagca gcagctgcac agcctgcaag ccgcaggag    12960 cagccgggcg cccgccggat cttcccgtgg cccatccccg ggcctgcggc cagcactgcc    13020
cagccgcctt gcccgggcca gtcggggtgt ggacctggcc actggcccca gcaggacacc    13080
ccttcgggcc aagaacaagg tccaccccag cagcacttag tcctccttcc tggcggggt    13140 gggccgtgga gtcggagtgg acaccgctca gtattacttt ctgccgctgt caaggccgag    13200
ggccaggcag aatggctgca cgtaggttcc ccagagagca ggcagggca tctgtctgtc    13260 tgtgggcttc agcactttaa agaggctgtg tggccaacca ggacccaggg tcccctcccc    13320
agctcccttg ggaaggacac agcagtattg gacggtttct agcctctgag atgctaattt    13380
atttccccga gtcctcaggt acagcgggct gtgcccggcc ccaccccctg gcagatgtc    13440 ccccactgct aaggctgctg gcttcaggga gggttagcct gcaccgccgc caccctgccc    13500
ctaagttatt acctctccag ttcctaccgt actccctgca ccgtctcact gtgtgtctcg    13560
tgtcagtaat ttatatggtg ttaaaatgtg tatatttttg tatgtcacta ttttcactag    13620
ggctgagggg cctgcgccca gagctggcct ccccccaacac ctgctgcgct tggtaggtgt    13680
ggtggcgtta tggcagcccg gctgctgctt ggatgcgagc ttggccttgg gccggtgctg    13740
ggggcacagc tgtctgccag gcactctcat caccccagag gccttgtcat cctcccttgc    13800
cccaggccag gtagcaagag agcagcgccc aggcctgctg gcatcaggtc tgggcaagta    13860
gcaggactag gcatgtcaga ggaccccagg gtggttagag gaaaagactc ctcctggggg    13920
ctggctccca gggtggagga aggtgactgt gtgtgtgtgt gtgtgcgcgc gcgacgcgcg    13980
agtgtgctgt atggcccagg cagcctcaag gccctcggag ctggctgtgc ctgcttctgt    14040
gtaccacttc tgtgggcatg gccgcttcta gagcctcgac accccccccaa ccccccgcacc    14100 aagcagacaa agtcaataaa agagctgtct gactgc                               14136
```

<210> SEQ ID NO 2
<211> LENGTH: 6749
<212> TYPE: DNA
<213> ORGANISM: Homo sapiens
<220> FEATURE:
<221> NAME/KEY: misc_feature
<222> LOCATION: (1)..(6749)
<223> OTHER INFORMATION: "n" at position 719, 1277, 1278, 1279, 1280,
     1288, 1289, 1638, 1967, 2248, 2251, 2254, 2283, 2585, 2586, 2625,
     2932, 2949, 2972, 2978, 3406, is any of A, T, G, and C.
<223> OTHER INFORMATION: "n" at position 3419, 3604, 3675, 3849, 4132,
     4337, 4367, 4368, 4369, 4396, 4404, 5700, 5701, 5702, 6611, 6628,
     6637, 6700, 6733 is any of A, T, G, and C.

<400> SEQUENCE: 2

```
ggctcctgag gcgcacagcg ccgagcgcgg cgccgcgcac ccgcgcgccg gacgccagtg       60
accgcgatgg tgaactccag tcgcgtgcag cctcagcagc ccggggacgc caagcggccg      120
cccgcgcccc gcgcgccgga cccggggccgg ctgatggctg gctgcgcggc cgtgggcgcc      180
agcctcgccg ccccggggccg cctctgcgag cagcggggcc tggagatcga gatgcagcgc      240
atccggcagg cggccgcgcg ggaccccccg gccggagccg cggcctcccc ttctcctccg      300
ctctcgtcgt gctcccggca ggcgtggagc cgcgataacc ccggcttcga ggccgaggag      360
```

```
gaggaggagg aggtggaagg ggaagaaggc ggaatggtgg tggagatgga cgtagagtgg       420
cgcccgggca gccggaggtc ggccgcctcc tcggccgtga gctccgtggg cgcgcggagc       480
cgggggcttg ggggctacca cggcgcgggc cacccgagcg ggaggcggcg ccggcgagag       540
gaccagggcc cgccgtgccc cagcccagtc ggcggcgggg acccgctgca tcgccacctc       600
cccctggaag ggcagccgcc ccgagtggcc tgggcggaga ggctggttcg cgggctgcga       660
ggtgtaagag cgcgcgaccc gcagcggcag atgcacgaac cagaacggcc ggcgccggng       720
gcttcttaaa taaaatgata tcttttcttt tcttcattat tattttaaag gtctctgggg       780
aacaagactc atggaggaaa gcagcactaa ccgagagaaa taccttaaaa gtgttttacg       840
ggaactggtc atacctcc tttttctcat agtcttgtgc atctgtaagt agaatatttc         900
cttgcactaa tgggaaagtt ttgaaacgat gtgaatttgt ccaaaatgtt tatccacagg       960
aacaatccct ttgtgaaggc tgctggtatg tggatgtgtg ccggttccct tggggcgttc      1020
atttggatct ttctgtgttc cagtgaccta cggcatgatg agctccaatg tgtactacta      1080
cacccggatg atgtcacagc tcttcctaga cacccccgtg tccaaaacgg agaaaactaa      1140
ctttaaaact ctgtcttcca tggaagactt ctggaaggta tttggaaata actttgaaag      1200
tacctctcta tcacaagcca atgcttggtt atgcaacgat gcaggcaggg caaagcagcg      1260
gcatgagctt gaacttnnnn agatgttnnc tttcttttag ttcacagaag gctccttatt      1320
ggatgggctg tactgaaga tgcagcccag caaccagact gaagctgaca accgaagttt       1380
catcttctat gagaacctgc tgttaggggt tccacgaata cggcaactcc gagtcagaaa      1440
tggatcctgc tctatccccc aggacttgag agatgaaatt aaagagtgct atgatgtcta      1500
ctctgtcagt agtgaagata gggctcccct tgggccccga aatggaaccg cgtaagtgtc      1560
tgtgactcat tggcactcgg tgatattcat ccttgtaatt gcctcaagtg ttccactgat      1620
tgtaactgtt tgttttngg ttttgttttt aatcagttgg atctacacaa gtgaaaaga        1680
cttgaatggt agtagccact ggggaatcat tgcaacttat agtggagctg ctattatct       1740
ggatttgtca agaacaagag aggaaacagc tgcacaagtt gctagcctca agaaaaatgt      1800
ctggctggac cgaggaacca gggcaacttt tattgacttc tcagtgtaca acgccaacat      1860
taacctgttc tgtgtggtca ggtgtgtgac tgaggacatg catccctcct atttctgtgt      1920
ggttgtacat acatcctatt ctagggttac ccagaaaaac ctttttntgc aggttgttat      1980
tgttttaatt gttcttattt acatgcaggt tattggttga attcccagca acaggtggtg      2040
tgattccatc ttggcaattt cagcctttaa agctgatccg atatgtcaca acttttgatt      2100
tcttcctggc agcctgtgag attatctttt gtttctttat cttttactat gtggtggaag      2160
agatattgga aattcgcatt cacaaactac actatttcag gagtttctgg aattgtctgg      2220
atgttgtgat cgttgtggta ggtccgganca ncancaccaa atttcctatt ctattctaca     2280
agnatgttaa caattaatac attggtgaag aaaaatatac tagtcatatt aaggtaagtt      2340
tcatatttct aaaacactgt aataaaatat aaatattttg cttttcagct gtcagtggta     2400
gctataggaa ttaacatata cagaacatca aatgtggagg tgctactaca gtttctggaa      2460
gatcaaaata ctttccccaa ctttgagcat ctggcatatt ggcagataca gttcaacaat      2520
atagctgctg tcacagtatt ttttgtctgg attaaggtaa tttataaatt tcatgttcta      2580
cattnnaaat aatattttct ttaaaaaaaa tgagttccac aaaancatgc gaaacaatgt      2640
tttattatac acagtcacac catttggttt atccattcat ctattgatgt cttctctctc      2700
```

```
ttacagctct tcaaattcat caattttaac aggaccatga gccagctctc gacaaccatg    2760
tctcgatgtg ccaaagacct gtttggcttt gctattatgt tcttcattat tttcctagcg    2820
tatgctcagt tggcatacct tgtctttggc actcaggtcg atgacttcag tactttccaa    2880
gagtgtatgt aagtatatat gaaattaaga agaaaaattt agtcagagta gncactgttg    2940
cgtggacant ctttggtttt gtattgtggt gntttgtntt attttttatag cttcactcaa    3000 ttccgtatca ttttgggcga tatcaacttt gcagagatta aggaagctaa tcgagttttg    3060
ggaccaattt atttcactac atttgtgttc tttatgttct tcattctttt ggtatgtaca    3120
tttatattta tagtggaggt tcaatttaaa cttcgtaaat ccttgtcttc tcttttttga    3180
ttgataattc caaattatgt ttcttccttt aattttttgcc ctcctttcat ttacaaacag    3240
aatatgtttt tggctatcat caatgatact tactctgaag tgaaatctga cttggcacag    3300
cagaaagctg aaatggaact ctcagatctt atcagaaagg taggaaaaac cttaattctc    3360
aaaaattctt ctgtttctga cataaaatga gcattgtttc acccanattt tagaatacnc    3420
taaaccaagt cttttatttt ttctctctct gatagggcta ccataaagct tggtcaaac    3480 taaaactgaa aaaaaatacc gtggatgaca tttcagagag tctgcggcaa ggaggaggca    3540
agttaaactt tgacgaactt cgacaagatc tcaaagggtg agaatcatgc ttcctgaggt    3600
tctnaaaaat tcctgcttct aaagataaat tcctggtgat aagagtattt ctagcccaag    3660
ggctcatggg aacanaggat gaatgttatc tgtatcctct ctctaatttc aggaagggcc    3720
atactgatgc agagattgag gcaatattca caaagtacga ccaagatgga gaccaagaac    3780
tgaccgaaca tgaacatcag cagatgagag acgacttgga gaaagagagg gtgggtctgg    3840
tttaggagna accggatttg atttggtacc tacaacacca cacttctgtg gggtctcagt    3900
gttctgctcc tcactcagtg accccttgtt cttcaggagg acctggatttt ggatcacagt    3960 tctttaccac gtcccatgag cagccgaagt ttccctcgaa gcctggatga ctctgaggag    4020
gatgacgatg aagatagcgg acatagctcc agaaggaggg gaagcatttc tagtggcgtt    4080
tcttacgaag agtttcaagt gtaagtataa aggaattggc agaatttgcg tngacaattt    4140
gtccctctgt actgtgtttt ccttgcagcc tggtgagacg agtggaccgg atggagcatt    4200
ccatcggcag catagtgtcc aagattgacg ccgtgatcgt gaagctagag attatggagc    4260
gagccaaact gaagaggagg gaggtgctgg gaaggctgtt ggatggggtg gccgaggtca    4320
gtagtcatga gctgaanaca ccgctgctga gcatggtgtt attaatnnna atatatgttg    4380
ctgacagttg tatttnaagt attnactgac ccccaacacc agtttcttttt tccctttta    4440 ggatgaaagg ctgggtcgtg acagtgaaat ccatagggaa cagatggaac ggctagtacg    4500
tgaagagttg gaacgctggg aatccgatga tgcagcttcc cagatcagtc atggtttagg    4560
cacgccagtg ggactaaatg gtcaacctcg ccccagaagc tcccgcccat cttcctccca    4620
atctacagaa ggcatggaag gtgcaggtgg aaatgggagt tctaatgtcc acgtatgata    4680
tgtgtgtttc agtatgtgtg tttctaataa gtgaggaagt ggctgtcctg aattgctgta    4740
acaagcacac tatttatatg ccctgaccac cataggatgc tagtctttgt gaccgattgc    4800
taatcttctg cactttaatt tattttatat aaactttacc catggttcaa agattttttt    4860 ttcttttttct catataagaa atctaggtgt aaatattgag tacagaaaaa aaatcttcat    4920
gatgtgtatt gagcggtacg cccagttgcc accatgactg agtcttctca gttgacaatg    4980
aagtagcctt ttaaagctag aaaactgtca aagggcttct gagtttcatt tccagtcaca    5040
aaaatcagta ttgttatttt tttccaagag tgtgaaggaa aatgggcaa ttcctttcca    5100
```

```
ctctggcata gttcatgagc ttaatacata gctttctttt aagaaaggag cctttttttt      5160
caactagctt cctggggtaa acttttctaa aagataaaat gggaaggaac tccaaactat      5220
gatagaatct gtgtgaatgg ttaagatgaa tgttaaatac tatgctttt tgtaagttga       5280 tcgtatctga tgtctgtggg actaactgta tcacttaatt tttaccttat tttggctcta      5340
atttgaataa gctgagtaaa accaccaaag atcagttata ggataaaatg gcatctctaa      5400
ccataacaca ggagaattgg aaggagccct aagttgtcac tcagtttaat ttcttttaat      5460
ggttagttta gcctaaagat ttatctgcat attcttttc ccatgtggct ctactcattt       5520
gcaactgaat ttaatgttat aactcatcta gtgagaccaa cttactaaat ttttagtatg      5580
cactgaaagt ttttatccaa caattatgtt cattttaagc aaaattttaa gaaagttttg      5640
aaattcataa agcatttggt tttaaactat tttaagaata tagtactcgg tcaggtatgn      5700
nncacgcctg taatcccagc actttgggag gccgaaacag gcgaatcact tgagcccagg      5760
agttcaagac caacatgggc aatgtggcga aactccatct ctacaaaaaa tgcaaaaata      5820
aaaaatatag tactcaagta ttcttgatcc tgtgtttcaa aactagaatt tgtaatgcaa      5880
atggagctca gtctaataaa aaagaggttt tggtattaaa agttcataca ttagacagta      5940
tcagccaaaa tttgagttag caacactgtt ttctttacga gagggtctca cccaaattta      6000
tggggagaaa tctatttctc aaaaaaaaaa aatcttcttt tacagaaatg ttgagtaagg      6060
tgacattttg agcgctaata agcaaaagag catgcagtgc tgttgaataa ccctcacttg      6120
gagaaccaag agaatcctgt cgtttaatgc tatattttaa tttcacaagt tgttcattta      6180
actggtagaa tgtcagtcca atctccaatg agaacatgag caaatagacc tttccaggtt      6240
gaaagtgaaa catactgggt ttctgtaagt ttttcctcat ggcttcatct ctatctttac      6300
tttctcttga atatgctaca caaagttctt tattactaca tactaaagtt tgcattccag      6360
ggatattgac tgtacatatt tatgtatatg taccatgttg ttacatgtaa acaaacttca      6420
atttgaagtg cagctattat gtggtatcca tgtgtatcga ccatgtgcca tatatcaatt      6480
atggtcacta gaaagtctct ttatgatact ttttattgta ctgttttca tttcacttgc       6540 aaaattttgc agaattcctc ctttctaccc ataaattaca tataattttt cttctttagt      6600
catggagaac nccccccat catctcancc ctattanctt tcccatgtgt actggtatta       6660
ttaaaaagac atttacatac gcaagttttt cactgacaan caagaatgtt attaatgtgt      6720
aatactgagc acntttactt cttaataaa                                        6749
```

<210> SEQ ID NO 3
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 3

```
tggctgcaac tgcctcctgg                                                    20
```

<210> SEQ ID NO 4
<211> LENGTH: 23
<212> TYPE: DNA
<213> ORGANISM: Artificial Sequence
<220> FEATURE:
<221> NAME/KEY: misc_feature
<222> LOCATION: (1)..(23)

<223> OTHER INFORMATION: Synthetic primer

<400> SEQUENCE: 4
aagcagagac agacctgtga gag                                    23

<210> SEQ ID NO 5
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: Synthetic primer

<400> SEQUENCE: 5
gcccccgccg ctctcacagg tctgtctctg cttc                        34

<210> SEQ ID NO 6
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 6
ggcctgtagc ctaccccctgg                                       20

<210> SEQ ID NO 7
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 7
ggacccctct gaagccacc                                         19

<210> SEQ ID NO 8
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 8
gggaggtggg agacaagaga c                                      21

<210> SEQ ID NO 9
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 9
aaagccctgc tgtcactgtg g                                      21

<210> SEQ ID NO 10
<211> LENGTH: 23

```
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 10
aactaaagcc cagaagacag acc                                            23

<210> SEQ ID NO 11
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 11
aactgtctgc cccagaacat c                                              21

<210> SEQ ID NO 12
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 12
ctaaaggctg ctctctcaac aag                                            23

<210> SEQ ID NO 13
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 13
actcctgttg ggttttgatg ag                                             22

<210> SEQ ID NO 14
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 14
gagaactact cccttgtcct tgg                                            23

<210> SEQ ID NO 15
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic primer

<400> SEQUENCE: 15
```
acgccaagga caagggagta gttc                                              24

<210> SEQ ID NO 16
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 16
tgggctcctg gctggtgact gc                                                22

<210> SEQ ID NO 17
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 17
gcggcccgcc gccccgccg ctactgaccc gcaccctctg                              40

<210> SEQ ID NO 18
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 18
gctgcgaggg gtgagacg                                                     18

<210> SEQ ID NO 19
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic primer

<400> SEQUENCE: 19
gcggcccgcc gccccgccg cgtccctccc gccctcctga cc                           42

<210> SEQ ID NO 20
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic primer

<400> SEQUENCE: 20 gccccgccg ctgcggacga gaaatctgtc tgcttg                                  36

<210> SEQ ID NO 21
<211> LENGTH: 20
<212> TYPE: DNA
<213> ORGANISM: Artificial Sequence
<220> FEATURE:
<221> NAME/KEY: misc_feature

```
<222> LOCATION: (1)..(20)
<223> OTHER INFORMATION: Synthetic primer

<400> SEQUENCE: 21
cagggctgca agcagacaga                                                    20

<210> SEQ ID NO 22
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 22
ctgagctaag acgccctccc                                                    20

<210> SEQ ID NO 23
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 23
ctgtacgccc tcactggtgt c                                                  21

<210> SEQ ID NO 24
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 24
ggcacagggg ctcagtcagt c                                                  21

<210> SEQ ID NO 25
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 25
ggactgactg agcccctgtg c                                                  21

<210> SEQ ID NO 26
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 26
agtcggtcaa actgggtgag                                                    20

<210> SEQ ID NO 27
```

<210> SEQ ID NO 27
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 27
caaggtgtga gcctgagccc                                               20

<210> SEQ ID NO 28
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 28
cggtgtccac tccgactcca c                                             21

<210> SEQ ID NO 29
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 29 ccgccccgc cgcgcgccgg acgccagtga cc                                  32

<210> SEQ ID NO 30
<211> LENGTH: 30
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 30
gcccccgccg ccgcggcctc cccttctcct                                    30

<210> SEQ ID NO 31
<211> LENGTH: 44
<212> TYPE: DNA
<213> ORGANISM: Artificial Sequence
<220> FEATURE:
<221> NAME/KEY: misc_feature
<222> LOCATION: (1)..(44)
<223> OTHER INFORMATION: Synthetic primer

<400> SEQUENCE: 31
cggcccgccg ccccgcccg cggccgttct ggttcgtgca tctg                     44

<210> SEQ ID NO 32
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: Synthetic primer

<400> SEQUENCE: 32
gcccccgccg aaatgatatc ttttcttttc ttca                                    34

<210> SEQ ID NO 33
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic primer

<400> SEQUENCE: 33
cccccgcccg aactttccca ttagtgcaag                                         30

<210> SEQ ID NO 34
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic primer

<400> SEQUENCE: 34
cgccgccccc gcccgtgtga tagagaggta ctttca                                  36

<210> SEQ ID NO 35
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 35
ccgccgcccc cgccgctttt tcaaagatgt ttcctttgc                               39

<210> SEQ ID NO 36
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 36
tatcaccgag tgccaatgag                                                    20

<210> SEQ ID NO 37
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Synthetic primer

<400> SEQUENCE: 37
ccgccgcccc cgccggcctc aagtgttcca ctgat                                   35

<210> SEQ ID NO 38
<211> LENGTH: 35
<212> TYPE: DNA
<213> ORGANISM: Artificial Sequence
<220> FEATURE:

```
<221> NAME/KEY: misc_feature
<222> LOCATION: (1)..(35)
<223> OTHER INFORMATION: Synthetic primer

<400> SEQUENCE: 38
cccccgcccg ttgtagaata gaataggaaa tttgg                                35

<210> SEQ ID NO 39
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Synthetic primer

<400> SEQUENCE: 39
gcccccgccg ttggtgaaga aaatatact agtca                                 35

<210> SEQ ID NO 40
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: Synthetic primer

<400> SEQUENCE: 40
cgccgccccc gcccgtggaa ctcatttttt ttaaaga                              37

<210> SEQ ID NO 41
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 41 gcggggggcgg cgggccgttt tattatacac agtcacacc                          39

<210> SEQ ID NO 42
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 42
gcccccgccg cttcctttaa tttttgccct cc                                  32

<210> SEQ ID NO 43
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 43
cgccgccccc gcccggaaac aatgctcatt ttatgtcag                           39
```

<210> SEQ ID NO 44
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 44
ccgccgcccc cgccgaaacc aagtcttta tttttctc                39

<210> SEQ ID NO 45
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 45
ccgccgcccc cgccggatga atgttatctg tatcctctc                39

<210> SEQ ID NO 46
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: Synthetic primer

<400> SEQUENCE: 46
cgccgccccc gcccggcaaa ttctgccaat tccttta                37

<210> SEQ ID NO 47
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 47
gcccccgccg tttgtccctc tgtactgtgt tt                32

<210> SEQ ID NO 48
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 48 ccgccccgc cgtgaccccc aacaccagtt tc                32

<210> SEQ ID NO 49
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

```
<400> SEQUENCE: 49
cggcccgccg cccccgcccg ggacagccac ttcctcactt                    40

<210> SEQ ID NO 50
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 50
cgtcgctcag cagcaggtcg                                          20

<210> SEQ ID NO 51
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 51
cgtcctgctt cccgtcccg                                           19

<210> SEQ ID NO 52
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: Synthetic primer

<400> SEQUENCE: 52
gcggcccgcc gccccgccg ttggggatgc tggcaatgtg tg                  42

<210> SEQ ID NO 53
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 53
gggattcggc aaagctgatg                                          20

<210> SEQ ID NO 54
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 54
ttccatcagc tttgccgaat                                          20

<210> SEQ ID NO 55
<211> LENGTH: 21
<212> TYPE: DNA
<213> ORGANISM: Artificial Sequence
```

```
<220> FEATURE:
<221> NAME/KEY: misc_feature
<222> LOCATION: (1)..(21)
<223> OTHER INFORMATION: Synthetic primer

<400> SEQUENCE: 55
atctggtctc aagcctggaa g                                              21

<210> SEQ ID NO 56
<211> LENGTH: 49
<212> TYPE: DNA
<213> ORGANISM: Artificial Sequence
<220> FEATURE:
<221> NAME/KEY: misc_feature
<222> LOCATION: (1)..(49)
<223> OTHER INFORMATION: Synthetic primer

<400> SEQUENCE: 56
gccccgcgcc cgtcccgccg ccccgccga gacccttccc accagacct               49

<210> SEQ ID NO 57
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic primer

<400> SEQUENCE: 57
cgcccccgcc cgtgagccct gcccagtgtc t                                   31

<210> SEQ ID NO 58
<211> LENGTH: 41
<212> TYPE: DNA
<213> ORGANISM: Artificial Sequence
<220> FEATURE:
<221> NAME/KEY: misc_feature
<222> LOCATION: (1)..(41)
<223> OTHER INFORMATION: Synthetic primer

<400> SEQUENCE: 58
gcggcccgcc gccccgccg gagccaggag gagcagaacc c                         41

<210> SEQ ID NO 59
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 59
cagagggaca ggcaggcaaa gg                                             22

<210> SEQ ID NO 60
<211> LENGTH: 28
<212> TYPE: DNA
<213> ORGANISM: Artificial Sequence
<220> FEATURE:
<221> NAME/KEY: misc_feature
<222> LOCATION: (1)..(28)
<223> OTHER INFORMATION: Synthetic primer

<400> SEQUENCE: 60 gccccgccg cccagccctc cagtgcct                                        28
```

<210> SEQ ID NO 61
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 61
atcgctatgt gctgcctggg                                                     20

<210> SEQ ID NO 62
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 62
ccgaggtgga tgccgctg                                                       18

<210> SEQ ID NO 63
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 63 gaagggagt gggcagcaga c                                                    21

<210> SEQ ID NO 64
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 64
cactgaccgt tgacaccctc g                                                   21

<210> SEQ ID NO 65
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 65
tgccccagtg cttcagagat c                                                   21

<210> SEQ ID NO 66
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

```
<400> SEQUENCE: 66
ggagtgccct gagccccct                                              19

<210> SEQ ID NO 67
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 67
cccctaacca cagccagcg                                              19

<210> SEQ ID NO 68
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 68
tctgttcgtc ctggtgtcct g                                           21

<210> SEQ ID NO 69
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 69
gcaggagggc aggttgtaga a                                           21

<210> SEQ ID NO 70
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 70
gcggcccgcc gccccgccg ggtaggggga gtctgggctt                        40

<210> SEQ ID NO 71
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Synthetic primer

<400> SEQUENCE: 71
gaggccaccc cgagtcc                                                17

<210> SEQ ID NO 72
<211> LENGTH: 20
<212> TYPE: DNA
```

```
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 72
gttgggcatc tctgacggtg                                              20

<210> SEQ ID NO 73
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: Synthetic primer

<400> SEQUENCE: 73
cgccgccccc gcccgggaag gtggcctgag gagat                             35

<210> SEQ ID NO 74
<211> LENGTH: 37
<212> TYPE: DNA
<213> ORGANISM: Artificial Sequence
<220> FEATURE:
<221> NAME/KEY: misc_feature
<222> LOCATION: (1)..(37)
<223> OTHER INFORMATION: Synthetic primer

<400> SEQUENCE: 74
gcggcccgcc gccccgccg ggggtccacg ggccatg                            37

<210> SEQ ID NO 75
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 75
aagcccagca gcacggtgag                                              20

<210> SEQ ID NO 76
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: Synthetic primer

<400> SEQUENCE: 76
ccgccgcccc cgccgctgcc ctgcctgtgc cctg                              34

<210> SEQ ID NO 77
<211> LENGTH: 51
<212> TYPE: DNA
<213> ORGANISM: Artificial Sequence
<220> FEATURE:
<221> NAME/KEY: misc_feature
<222> LOCATION: (1)..(51)
<223> OTHER INFORMATION: Synthetic primer

<400> SEQUENCE: 77
gccccgcgcc cgtcccgccg ccccgcccg ttccaccacc acgtccacca c             51
```

<210> SEQ ID NO 78
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 78
gtggtggacg tggtggtgga a                                           21

<210> SEQ ID NO 79
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 79
ggctgctgcc ctcactggga a                                           21

<210> SEQ ID NO 80
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 80
taagggcaga gtcctccaca g                                           21

<210> SEQ ID NO 81
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 81 ccaccccgc ccacctactg ag                                           22

<210> SEQ ID NO 82
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 82
gcggcccgcc gccccgccg tgagggagg gacgccaatc                         40

<210> SEQ ID NO 83
<211> LENGTH: 19
<212> TYPE: DNA
<213> ORGANISM: Artificial Sequence
<220> FEATURE:
<221> NAME/KEY: misc_feature
<222> LOCATION: (1)..(19)

<223> OTHER INFORMATION: Synthetic primer

<400> SEQUENCE: 83 gaggctggggg ctgggacaa                                                    19

<210> SEQ ID NO 84
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 84
cccggttcac tcactgcg                                                      18

<210> SEQ ID NO 85
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic primer

<400> SEQUENCE: 85
cccccgcccg ccgtgctcag agcctgaaag                                         30

<210> SEQ ID NO 86
<211> LENGTH: 38
<212> TYPE: DNA
<213> ORGANISM: Artificial Sequence
<220> FEATURE:
<221> NAME/KEY: misc_feature
<222> LOCATION: (1)..(38)
<223> OTHER INFORMATION: Synthetic primer

<400> SEQUENCE: 86 ggcgggggc ttctgccgag cgggtgggga gcaggtgg                                 38

<210> SEQ ID NO 87
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic primer

<400> SEQUENCE: 87
cgccgccccc gcccggctct ggtcaggac agggga                                   36

<210> SEQ ID NO 88
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 88
cgcctggggg tgttctttt                                                     18

<210> SEQ ID NO 89
<211> LENGTH: 18

```
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 89
acgtgatgtt gtcgcccg                                                        18

<210> SEQ ID NO 90
<211> LENGTH: 32
<212> TYPE: DNA
<213> ORGANISM: Artificial Sequence
<220> FEATURE:
<221> NAME/KEY: misc_feature
<222> LOCATION: (1)..(32)
<223> OTHER INFORMATION: Synthetic primer

<400> SEQUENCE: 90
gcccccgccg gggcgccccc gtggtggtca gc                                        32

<210> SEQ ID NO 91
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 91
caggctgcgt ggggatgc                                                        18

<210> SEQ ID NO 92
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 92
ctggaggtgc tgcgcgtt                                                        18

<210> SEQ ID NO 93
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic primer

<400> SEQUENCE: 93
cgcccccgcc cgctggctcc acgcagatgc                                           30

<210> SEQ ID NO 94
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 94
```

-continued cgtgaacagg gcgcatta                                                                18

<210> SEQ ID NO 95
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic primer

<400> SEQUENCE: 95
cccccgcccg gcagcagaga tgttgttgga c                                                 31

<210> SEQ ID NO 96
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Synthetic primer

<400> SEQUENCE: 96
ccgccgcccc cgccgccagg ctcctatctt gtgaca                                            36

<210> SEQ ID NO 97
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 97
tgaagtcacc tgtgctgttg t                                                            21

<210> SEQ ID NO 98
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 98
ctacctgtgg gatctggggg                                                              19

<210> SEQ ID NO 99
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 99
tgctgaagct cacgctcc                                                                18

<210> SEQ ID NO 100
<211> LENGTH: 20
<212> TYPE: DNA
<213> ORGANISM: Artificial Sequence
<220> FEATURE:
<221> NAME/KEY: misc_feature

```
<222> LOCATION: (1)..(20)
<223> OTHER INFORMATION: Synthetic primer

<400> SEQUENCE: 100
gggctcgtcg tcaatgcaag                                                    20

<210> SEQ ID NO 101
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 101
cgccgccccc gcccgccgcc caccacctgc agcccctcta                              40

<210> SEQ ID NO 102
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: Synthetic primer

<400> SEQUENCE: 102
gcggcccgcc gcccccgccg ccgcccagga cagcatcttc                              40

<210> SEQ ID NO 103
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 103
cgctgcccag catgttgg                                                      18

<210> SEQ ID NO 104
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic primer

<400> SEQUENCE: 104
ggccggcagc ggcaaaggct tctc                                               24

<210> SEQ ID NO 105
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 105
gcccagcacc agctcacat                                                     19

<210> SEQ ID NO 106
```

```
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 106
cgagccattt accacccata g                                              21

<210> SEQ ID NO 107
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 107
ggcagccagc aggatctgaa                                                20

<210> SEQ ID NO 108
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 108
ctgtgggcca gcagcaaggt g                                              21

<210> SEQ ID NO 109
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 109
cctgaacctc cagcaccagc g                                              21

<210> SEQ ID NO 110
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 110
aggtccaggg cgactcgctg g                                              21

<210> SEQ ID NO 111
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 111
```

```
cagggccaca cgcgctgggc g                                         21

<210> SEQ ID NO 112
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 112
ttggaggccc acgttgacct g                                         21

<210> SEQ ID NO 113
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic primer

<400> SEQUENCE: 113
cccccgcccg catgggtgtg gacgggtgag g                              31

<210> SEQ ID NO 114
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 114
taaaactgga tggggctctc                                           20

<210> SEQ ID NO 115
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 115
ggcctccacc agcactaa                                             18

<210> SEQ ID NO 116
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 116
gggtccccca gtccttccag                                           20

<210> SEQ ID NO 117
<211> LENGTH: 17
<212> TYPE: DNA
<213> ORGANISM: Artificial Sequence
<220> FEATURE:
```

-continued

```
<221> NAME/KEY: misc_feature
<222> LOCATION: (1)..(17)
<223> OTHER INFORMATION: Synthetic primer

<400> SEQUENCE: 117
tccccagccc gcccaca                                                    17

<210> SEQ ID NO 118
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 118 gcccccctcac caccccttct                                                20

<210> SEQ ID NO 119
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 119
tcccgctgct cccccacgc a                                                21

<210> SEQ ID NO 120
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 120
gatgccgtgg ggaccgtc                                                   18

<210> SEQ ID NO 121
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 121
gtgagcaggt ggcagtctcg                                                 20

<210> SEQ ID NO 122
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 122
ccaccccctc tgctcgtagg t                                               21
```

<210> SEQ ID NO 123
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Synthetic primer

<400> SEQUENCE: 123
ggtcccaagc acgcatgca                                              19

<210> SEQ ID NO 124
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 124
tgccggcctc ctgcgctgct ga                                          22

<210> SEQ ID NO 125
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: Synthetic primer

<400> SEQUENCE: 125
gcgggcaggg tgagcaggtg gggccatcc                                   29

<210> SEQ ID NO 126
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Synthetic primer

<400> SEQUENCE: 126
gaggctgtgg gggtccagtc aagtgg                                      26

<210> SEQ ID NO 127
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: Synthetic primer

<400> SEQUENCE: 127
agggaggcag aggaaagggc cgaac                                       25

<210> SEQ ID NO 128
<211> LENGTH: 29
<212> TYPE: DNA
<213> ORGANISM: Artificial Sequence
<220> FEATURE:
<221> NAME/KEY: misc_feature
<222> LOCATION: (1)..(29)
<223> OTHER INFORMATION: Synthetic primer

```
<400> SEQUENCE: 128
cgtcccgcct gcactgacct cacgcatgt                                    29

<210> SEQ ID NO 129
<211> LENGTH: 41
<212> TYPE: DNA
<213> ORGANISM: Artificial Sequence
<220> FEATURE:
<221> NAME/KEY: misc_feature
<222> LOCATION: (1)..(41)
<223> OTHER INFORMATION: Synthetic primer

<400> SEQUENCE: 129
cggcccgccg cccccgcccg gccaaaggga aagggattgg a                      41

<210> SEQ ID NO 130
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 130
ccgcggagcc tgctgtgcta t                                            21

<210> SEQ ID NO 131
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: Synthetic primer

<400> SEQUENCE: 131
ccgccgcccc cgcccgcttg gtggagacgg tgtagttgc                         39

<210> SEQ ID NO 132
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 132
tccaatccct ttccctttgg c                                            21

<210> SEQ ID NO 133
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 133
cagcagccca tgaaacagaa ag                                           22

<210> SEQ ID NO 134
<211> LENGTH: 21
<212> TYPE: DNA
<213> ORGANISM: Artificial Sequence
```

```
<220> FEATURE:
<221> NAME/KEY: misc_feature
<222> LOCATION: (1)..(21)
<223> OTHER INFORMATION: Synthetic primer

<400> SEQUENCE: 134
tatgctttca ggcccgtggc a                                           21

<210> SEQ ID NO 135
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 135
agagcccata cccggtccag tcc                                         23

<210> SEQ ID NO 136
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 136
ggactggacc gggtatgggc tct                                         23

<210> SEQ ID NO 137
<211> LENGTH: 31
<212> TYPE: DNA
<213> ORGANISM: Artificial Sequence
<220> FEATURE:
<221> NAME/KEY: misc_feature
<222> LOCATION: (1)..(31)
<223> OTHER INFORMATION: Synthetic primer

<400> SEQUENCE: 137
cccccgcccg cacccaggcc ctcctcgact c                                31

<210> SEQ ID NO 138
<211> LENGTH: 30
<212> TYPE: DNA
<213> ORGANISM: Artificial Sequence
<220> FEATURE:
<221> NAME/KEY: misc_feature
<222> LOCATION: (1)..(30)
<223> OTHER INFORMATION: Synthetic primer

<400> SEQUENCE: 138
cccccgccgc tgggtgggct cggctctatc                                  30

<210> SEQ ID NO 139
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 139
tggtagcgat gctcacgtca ctt                                         23
```

```
<210> SEQ ID NO 140
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 140
caggccaaag ctgagatgac ttg                                             23

<210> SEQ ID NO 141
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 141
agaggcgcag gagggaggtc                                                 20

<210> SEQ ID NO 142
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 142
ccctctgccc ccgcattg                                                   18

<210> SEQ ID NO 143
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 143
aagcgcaaaa gggctgcgtc g                                               21

<210> SEQ ID NO 144
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Synthetic primer

<400> SEQUENCE: 144
ggccctccct gccttctagg cg                                              22

<210> SEQ ID NO 145
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer
```

```
<400> SEQUENCE: 145
ccgtgctgtg tggaggagag                                              20

<210> SEQ ID NO 146
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 146
cctcttcctg cccagcccct c                                            21

<210> SEQ ID NO 147
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 147
cttcccgagc agcctttggt g                                            21

<210> SEQ ID NO 148
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 148
ctgagctgcc gcccgctgac                                              20

<210> SEQ ID NO 149
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 149 aggacccccca gcccagccca                                             20

<210> SEQ ID NO 150
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 150
cttggcgcag cttggact                                                18

<210> SEQ ID NO 151
<211> LENGTH: 20
<212> TYPE: DNA
```

<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 151
acacccagca aggacacgca                                               20

<210> SEQ ID NO 152
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 152
tgtgacacat ccctggtac                                                20

<210> SEQ ID NO 153
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 153
gcaagggtga gcttcagagc                                               20

<210> SEQ ID NO 154
<211> LENGTH: 51
<212> TYPE: DNA
<213> ORGANISM: Artificial Sequence
<220> FEATURE:
<221> NAME/KEY: misc_feature
<222> LOCATION: (1)..(51)
<223> OTHER INFORMATION: Synthetic primer

<400> SEQUENCE: 154
gccccgcgcc cgtcccgccg ccccgcccg accctatgcc tcctgtacct c             51

<210> SEQ ID NO 155
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Synthetic primer

<400> SEQUENCE: 155
cccctcctct ggcaatcc                                                 18

<210> SEQ ID NO 156
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 156
cctgccggga gcacgacgag                                               20

```
<210> SEQ ID NO 157
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 157
ctgggctggg gcacggcggg                                                   20

<210> SEQ ID NO 158
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 158
gggggctacc acggcgcggg c                                                 21

<210> SEQ ID NO 159
<211> LENGTH: 20
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 159
ttggggcgtt catttggatc                                                   20

<210> SEQ ID NO 160
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 160
accacacaga aataggaggg                                                   20

<210> SEQ ID NO 161
<211> LENGTH: 24
<212> TYPE: DNA
<213> ORGANISM: Artificial Sequence
<220> FEATURE:
<221> NAME/KEY: misc_feature
<222> LOCATION: (1)..(24)
<223> OTHER INFORMATION: Synthetic primer

<400> SEQUENCE: 161
ttgttattgt tttaattgtt ctta                                              24

<210> SEQ ID NO 162
<211> LENGTH: 25
<212> TYPE: DNA
<213> ORGANISM: Artificial Sequence
<220> FEATURE:
<221> NAME/KEY: misc_feature
<222> LOCATION: (1)..(25)
```

<223> OTHER INFORMATION: Synthetic primer

<400> SEQUENCE: 162
ctactctgac taaattttc ttctt                        25

<210> SEQ ID NO 163
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 163
tttggttttg tattgtggtg                             20

<210> SEQ ID NO 164
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: Synthetic primer

<400> SEQUENCE: 164
aaggatttac gaagtttaaa ttg                         23

<210> SEQ ID NO 165
<211> LENGTH: 21
<212> TYPE: DNA
<213> ORGANISM: Artificial Sequence
<220> FEATURE:
<221> NAME/KEY: misc_feature
<222> LOCATION: (1)..(21)
<223> OTHER INFORMATION: Synthetic primer

<400> SEQUENCE: 165
agaacctcag gaagcatgat t                           21

<210> SEQ ID NO 166
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 166
taggtaccaa atcaaatccg                             20

<210> SEQ ID NO 167
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: Synthetic primer

<400> SEQUENCE: 167
gtctcagtgt tctgctcctc                             20

<210> SEQ ID NO 168
<211> LENGTH: 22

```
<212> TYPE: DNA
<213> ORGANISM: Artificial Sequence Sequence
<220> FEATURE:
<221> NAME/KEY: misc_feature
<222> LOCATION: (1)..(22)
<223> OTHER INFORMATION: Synthetic primer

<400> SEQUENCE: 168
aaatacaact gtcagcaaca ta                                              22

<210> SEQ ID NO 169
<211> LENGTH: 12909
<212> TYPE: DNA
<213> ORGANISM: Homo sapiens

<400> SEQUENCE: 169
atgccgcccg ccgcgcccgc ccgcctggcg ctggccctgg gcctgggcct gtggctcggg      60
gcgctggcgg ggggcccggg gcgcggctgc gggccctgcg agccccctg cctctgcggc      120 ccagcgcccg gcgccgcctg ccgcgtcaac tgctcgggcc gcgggctgcg gacgctcggt      180
cccgcgctgc gcatccccgc ggacgccaca gcgctagacg tctcccacaa cctgctccgg      240
gcgctggacg ttgggctcct ggcgaacctc tcggcgctgg cagagctgga tataagcaac      300
aacaagattt ctacgttaga agaaggaata tttgctaatt tatttaattt aagtgaaata      360
aacctgagtg ggaacccgtt tgagtgtgac tgtggcctgg cgtggctgcc gcgatgggcg      420
gaggagcagc aggtgcgggt ggtgcagccc gaggcagcca cgtgtgctgg gcctggctcc      480
ctggctggcc agcctctgct tggcatcccc ttgctggaca gtggctgtgg tgaggagtat      540
gtcgcctgcc tccctgacaa cagctcaggc accgtggcag cagtgtcctt ttcagctgcc      600
cacgaaggcc tgcttcagcc agaggcctgc agcgccttct gcttctccac cggccagggc      660
ctcgcagccc tctcggagca gggctggtgc ctgtgtgggg cggcccagcc ctccagtgcc      720
tcctttgcct gcctgtccct ctgctccggc cccccgccac ctcctgcccc cacctgtagg      780
ggccccaccc tcctccagca cgtcttccct gcctcccag gggccaccct ggtggggccc      840
cacggacctc tggcctctgg ccagctagca gccttccaca tcgctgcccc gctccctgtc      900
actgccacac gctgggactt cggagacggc tccgccgagg tggatgccgc tgggccggct      960
gcctcgcatc gctatgtgct gcctgggcgc tatcacgtga cggccgtgct ggccctgggg      1020
gccggctcag ccctgctggg gacagacgtg caggtggaag cggcacctgc cgccctggag      1080
ctcgtgtgcc cgtcctcggt gcagagtgac gagagccttg acctcagcat ccagaaccgc      1140
ggtggttcag gcctggaggc cgcctacagc atcgtggccc tgggcgagga gccggcccga      1200
gcggtgcacc cgctctgccc ctcggacacg gagatcttcc ctgcaacgg gcactgctac      1260 cgcctggtgg tggagaaggc ggcctggctg caggcgcagg agcagtgtca ggcctgggcc      1320
ggggccgccc tggcaatggt ggacagtccc gccgtgcagc gcttcctggt ctcccgggtc      1380
accaggagcc tagacgtgtg gatcggcttc tcgactgtgc aggggtgga ggtgggccca      1440 gcgccgcagg gcgaggcctt cagcctggag agctgccaga actggctgcc cgggagcca      1500 cacccagcca cagccgagca ctgcgtccgg ctcgggccca ccgggtggtg taacaccgac      1560
ctgtgctcag cgccgcacag ctacgtctgc gagctgcagc ccgaggccc agtgcaggat      1620 gccgagaacc tcctcgtggg agcgcccagt ggggacctgc agggacccct gacgcctctg      1680
gcacagcagg acggcctctc agccccgcac gagcccgtgg aggtcatggt attcccgggc      1740
ctgcgtctga gccgtgaagc cttcctcacc acggccgaat ttgggaccca ggagctccgg      1800
```

```
cggcccgccc agctgcggct gcaggtgtac cggctcctca gcacagcagg gaccccggag   1860
aacggcagcg agcctgagag caggtccccg gacaacagga cccagctggc ccccgcgtgc   1920
atgccagggg gacgctggtg ccctggagcc aacatctgct tgccgctgga cgcctcttgc   1980 caccccagg cctgcgccaa tggctgcacg tcagggccag ggctaccgg ggcccctat    2040 gcgctatgga gagagttcct cttctccgtt gccgcgggc ccccgcgca gtactcggtc   2100 accctccacg gccaggatgt cctcatgctc cctggtgacc tcgttggctt gcagcacgac   2160
gctggccctg gcgccctcct gcactgctcg ccggctcccg gccaccctgg tccccaggcc   2220
ccgtacctct ccgccaacgc ctcgtcatgg ctgccccact tgccagccca gctggagggc   2280
acttgggcct gccctgcctg tgccctgcgg ctgcttgcag ccacggaaca gctcaccgtg   2340
ctgctgggct tgaggcccaa ccctggactg cggatgcctg ggcgctatga ggtccgggca   2400
gaggtgggca atggcgtgtc caggcacaac ctctcctgca gctttgacgt ggtctcccca   2460
gtggctgggc tgcgggtcat ctaccctgcc ccccgcgacg gccgcctcta cgtgcccacc   2520
aacggctcag ccttggtgct ccaggtggac tctggtgcca acgccacggc cacggctcgc   2580
tggcctgggg gcagtgtcag cgcccgcttt gagaatgtct gccctgccct ggtgccacc    2640 ttcgtgcccg gctgcccctg ggagaccaac gatacctgt tctcagtggt agcactgccg   2700
tggctcagtg aggggagca cgtggtggac gtggtggtgg aaaacagcgc cagccgggcc   2760
aacctcagcc tgcgggtgac ggcggaggag cccatctgtg gcctccgcgc cacgcccagc   2820
cccgaggccc gtgtactgca gggagtccta gtgaggtaca gccccgtggt ggaggccggc   2880
tcggacatgg tcttccggtg gaccatcaac gacaagcagt ccctgacctt ccagaacgtg   2940
gtcttcaatg tcatttatca gagcgcggcg gtcttcaagc tctcactgac ggcctccaac   3000
cacgtgagca acgtcaccgt gaactacaac gtaaccgtgg agcggatgaa caggatgcag   3060
ggtctgcagg tctccacagt gccggccgtg ctgtccccca tgccacgct agcactgacg   3120 gcgggcgtgc tggtggactc ggccgtggag gtggccttcc tgtgaacttt ggggatggg    3180 gagcaggccc tccaccagtt ccagcctccg tacaacgagt ccttcccggt tccagacccc   3240
tcggtggccc aggtgctggt ggagcacaat gtcatgcaca cctacgctgc cccaggtgag   3300
tacctcctga ccgtgctggc atctaatgcc ttcgagaacc tgacgcagca ggtgcctgtg   3360
agcgtgcgcg cctccctgcc ctccgtggct gtgggtgtga gtgacggcgt cctggtggcc   3420
ggccggcccg tcaccttcta cccgcacccg ctgccctcgc ctgggggtgt tctttacacg   3480
tgggacttcg gggacggctc ccctgtcctg acccagagcc agccggctgc caaccacacc   3540
tatgcctcga ggggcaccta ccacgtgcgc ctggaggtca acaacacggt gagcggtgcg   3600
gcggcccagg cggatgtgcg cgtctttgag gagctccgcg gactcagcgt ggacatgagc   3660
ctggccgtgg agcagggcgc ccccgtggtg gtcagcgccg cggtgcagac gggcgacaac   3720
atcacgtgga ccttcgacat ggggacggc accgtgctgt cgggcccgga ggcaacagtg   3780
gagcatgtgt acctgcgggc acagaactgc acagtgaccg tgggtgcggc cagccccgcc   3840
ggccacctgg cccggagcct gcacgtgctg gtcttcgtcc tggaggtgct gcgcgttgaa   3900
cccgccgcct gcatccccac gcagcctgac gcgcggctca cggcctacgt caccgggaac   3960
ccggcccact acctcttcga ctggaccttc ggggatggct cctccaacac gaccgtgcgg   4020
gggtgcccga cggtgacaca caacttcacg cggagcggca cgttccccct ggcgctggtg   4080
ctgtccagcc gcgtgaacag ggcgcattac ttcaccagca tctgcgtgga ccagaggtg   4140 ggcaacgtca ccctgcagcc agagaggcag tttgtgcagc tcggggacga ggcctggctg   4200
```

```
gtggcatgtg cctggccccc gttcccctac cgctacacct gggactttgg caccgaggaa    4260
gccgccccca cccgtgccag gggccctgag gtgacgttca tctaccgaga cccaggctcc    4320
tatcttgtga cagtcaccgc gtccaacaac atctctgctg ccaatgactc agccctggtg    4380
gaggtgcagg agcccgtgct ggtcaccagc atcaaggtca atggctccct tgggctggag    4440
ctgcagcagc cgtacctgtt ctctgctgtg ggccgtgggc ccccgccag ctacctgtgg    4500 gatctggggg acggtgggtg gctcgagggt ccggaggtca cccacgctta caacagcaca    4560
ggtgacttca ccgttagggt ggccggctgg aatgaggtga gccgcagcga ggcctggctc    4620
aatgtgacgg tgaagcggcg cgtgcggggg ctcgtcgtca atgcaagccg cacggtggtg    4680
cccctgaatg ggagcgtgag cttcagcacg tcgctggagg ccggcagtga tgtgcgctat    4740
tcctgggtgc tctgtgaccg ctgcacgccc atccctgggg gtcctaccat ctcttacacc    4800
ttccgctccg tgggcacctt caatatcatc gtcacggctg agaacgaggt gggctccgcc    4860
caggacagca tcttcgtcta tgtcctgcag ctcatagagg ggctgcaggt ggtgggcggt    4920
ggccgctact tccccaccaa ccacacggta cagctgcagg ccgtggttag ggatggcacc    4980
aacgtctcct acagctggac tgcctggagg gacagggggcc cggccctggc cggcagcggc    5040
aaaggcttct cgctcaccgt gctcgaggcc ggcacctacc atgtgcagct gcgggccacc    5100
aacatgctgg gcagcgcctg gccgactgc accatggact tcgtgagcc tgtggggtgg    5160 ctgatggtga ccgcctcccc gaacccagct gccgtcaaca caagcgtcac cctcagtgcc    5220
gagctggctg tgtgcagtgg tgtcgtatac acttggtcct tggaggaggg gctgagctgg    5280
gagacctccg agccattta caccccatagc ttccccacac ccggcctgca cttggtcacc    5340 atgacgcag ggaacccgct gggctcagcc aacgccaccg tggaagtgga tgtgcaggtg    5400
cctgtgagtg gcctcagcat cagggccagc gagcccggag gcagcttcgt ggcggccggg    5460
tcctctgtgc cctttgggg gcagctggcc acgggcacca atgtgagctg gtgctgggct    5520
gtgcccggcg gcagcagcaa gcgtggccct catgtcacca tggtcttccc ggatgctggc    5580
accttctcca tccggctcaa tgcctccaac gcagtcagct gggtctcagc cacgtacaac    5640
ctcacggcgg aggagcccat cgtgggcctg gtgctgtggg ccagcagcaa ggtggtggcg    5700
cccgggcagc tggtccattt tcagatcctg ctggctgccg gctcagctgt caccttccgc    5760
ctgcaggtcg gcggggccaa ccccgaggtg ctccccgggc ccgtttctc ccacagcttc    5820 ccccgcgtcg gagaccacgt ggtgagcgtg cggggcaaaa accacgtgag ctgggcccag    5880
gcgcaggtgc gcatcgtggt gctggaggcc gtgagtgggc tgcagatgcc caactgctgc    5940
gagcctggca tcgccacggg cactgagagg aacttcacag cccgcgtgca gcgcggctct    6000
cgggtcgcct acgcctggta cttctcgctg cagaaggtcc agggcgactc gctggtcatc    6060
ctgtcgggcc gcgacgtcac ctacacgccc gtggccgcgg ggctgttgga gatccaggtg    6120
cgcgccttca acgccctggg cagtgagaac cgcacgctgg tgctggaggt tcaggacgcc    6180
gtccagtatg tggccctgca gagcggcccc tgcttcacca accgctcggc gcagtttgag    6240
gccgccacca gccccagccc ccggcgtgtg gcctaccact gggactttgg ggatgggtcg    6300
ccagggcagg acacagatga gcccaggggc gagcactcct acctgaggcc tgggactac    6360 cgcgtgcagg tgaacgcctc caacctggtg agcttcttcg tggcgcaggc cacggtgacc    6420
gtccaggtgc tggcctgccg ggagccggag gtgacgtgg tcctgcccct gcaggtgctg    6480
atgcggcgat cacagcgcaa ctacttggag gcccacgttg acctgcgcga ctgcgtcacc    6540
```

-continued

```
taccagactg agtaccgctg ggaggtgtat cgcaccgcca gctgccagcg gccggggcgc    6600
ccagcgcgtg tggccctgcc cggcgtggac gtgagccggc ctcggctggt gctgccgcgg    6660
ctggcgctgc ctgtggggca ctactgcttt gtgtttgtcg tgtcatttgg ggacacgcca    6720
ctgacacaga gcatccaggc caatgtgacg gtggcccccg agcgcctggt gcccatcatt    6780
gagggtggct cataccgcgt gtggtcagac acacgggacc tggtgctgga tgggagcgag    6840
tcctacgacc ccaacctgga ggacggcgac cagacgccgc tcagtttcca ctgggcctgt    6900
gtggcttcga cacagaggga ggctggcggg tgtgcgctga actttgggcc ccgcgggagc    6960
agcacggtca ccattccacg ggagcggctg gcggctggcg tggagtacac cttcagcctg    7020
accgtgtgga aggccggccg caaggaggag gccaccaacc agacggtgct gatccggagt    7080
ggccgggtgc ccattgtgtc cttggagtgt gtgtcctgca aggcacaggc cgtgtacgaa    7140
gtgagccgca gctcctacgt gtacttggag ggccgctgcc tcaattgcag cagcggctcc    7200
aagcgagggc ggtgggctgc acgtacgttc agcaacaaga cgctggtgct ggatgagacc    7260
accacatcca cgggcagtgc aggcatgcga ctggtgctgc ggcggggcgt gctgcgggac    7320
ggcgagggat acaccttcac gctcacggtg ctgggccgct ctggcgagga ggagggctgc    7380
gcctccatcc gcctgtcccc caaccgcccg ccgctggggg gctcttgccg cctcttccca    7440
ctgggcgctg tgcacgccct caccaccaag gtgcacttcg aatgcacggg ctggcatgac    7500
gcggaggatg ctggcgcccc gctggtgtac gccctgctgc tgcggcgctg tcgccagggc    7560
cactgcgagg agttctgtgt ctacaagggc agcctctcca gctacggagc cgtgctgccc    7620
ccgggtttca ggccacactt cgaggtgggc ctggccgtgg tggtgcagga ccagctggga    7680
gccgctgtgg tcgccctcaa caggtctttg gccatcaccc tcccagagcc caacggcagc    7740
gcaacggggc tcacagtctg gctgcacggg ctcaccgcta gtgtgctccc agggctgctg    7800
cggcaggccg atccccagca cgtcatcgag tactcgttgg ccctggtcac cgtgctgaac    7860
gagtacgagc gggccctgga cgtggcggca gagcccaagc acgagcggca gcaccgagcc    7920
cagatacgca agaacatcac ggagactctg gtgtccctga gggtccacac tgtggatgac    7980
atccagcaga tcgctgctgc gctggcccag tgcatggggc ccagcaggga gctcgtatgc    8040
cgctcgtgcc tgaagcagac gctgcacaag ctggaggcca tgatgctcat cctgcaggca    8100
gagaccaccg cgggcaccgt gacgcccacc gccatcggag acagcatcct caacatcaca    8160
ggagacctca tccacctggc cagctcggac gtgcgggcac cacagccctc agagctggga    8220
gccgagtcac catctcggat ggtggcgtcc caggcctaca acctgacctc tgccctcatg    8280
cgcatcctca tgcgctcccg cgtgctcaac gaggagcccc tgacgctggc gggcgaggag    8340
atcgtggccc agggcaagcg ctcggacccg cggagcctgc tgtgctatgg cggcgcccca    8400
gggcctggct gccacttctc catccccgag gctttcagcg gggccctggc caacctcagt    8460
gacgtggtgc agctcatctt tctggtggac tccaatccct ttccctttgg ctatatcagc    8520
aactacaccg tctccaccaa ggtggcctcg atggcattcc agacacaggc cggcgcccag    8580
atccccatcg agcggctggc ctcagagcgc gccatcaccg tgaaggtgcc caacaactcg    8640
gactgggctg cccggggcca ccgcagctcc gccaactccg ccaactccgt tgtggtccag    8700
ccccaggcct ccgtcggtgc tgtggtcacc ctggacagca gcaaccctgc ggccgggctg    8760
catctgcagc tcaactatac gctgctggac ggccactacc tgtctgagga acctgagccc    8820
tacctgcag tctacctaca ctcggagccc cggcccaatg agcacaactg ctcggctagc    8880
aggaggatcc gcccagagtc actccagggt gctgaccacc ggccctacac cttcttcatt    8940
```

-continued

| | |
|---|---|
| tccccgggga gcagagaccc agcggggagt taccatctga acctctccag ccacttccgc | 9000 |
| tggtcggcgc tgcaggtgtc cgtgggcctg tacacgtccc tgtgccagta cttcagcgag | 9060 |
| gaggacatgg tgtggcggac agaggggctg ctgcccctgg aggagacctc gccccgccag | 9120 |
| gccgtctgcc tcacccgcca cctcaccgcc ttcggcgcca gcctcttcgt gcccccaagc | 9180 |
| catgtccgct ttgtgtttcc tgagccgaca gcggatgtaa actacatcgt catgctgaca | 9240 |
| tgtgctgtgt gcctggtgac ctacatggtc atggccgcca tcctgcacaa gctggaccag | 9300 |
| ttggatgcca gccggggccg cgccatccct tctgtgggc agcggggccg cttcaagtac | 9360 |
| gagatcctcg tcaagacagg ctggggccgg ggctcaggta ccacggccca cgtgggcatc | 9420 |
| atgctgtatg gggtggacag ccggagcggc accggcacc tggacggcga cagagccttc | 9480 |
| caccgcaaca gcctggacat cttccggatc gccacccgc acagcctggg tagcgtgtgg | 9540 |
| aagatccgag tgtggcacga caacaaaggg ctcagccctg cctggttcct gcagcacgtc | 9600 |
| atcgtcaggg acctgcagac ggcacgcagc gccttcttcc tggtcaatga ctggctttcg | 9660 |
| gtggagacgg aggccaacgg gggcctggtg gagaaggagg tgctggccgc gagcgacgca | 9720 |
| gccccttttgc gcttccggcg cctgctggtg gctgagctgc agcgtggctt ctttgacaag | 9780 |
| cacatctggc tctccatatg ggaccggccg cctcgtagcc gtttcactcg catccagagg | 9840 |
| gccacctgct gcgttctcct catctgcctc ttcctgggcg ccaacgccgt gtggtacggg | 9900 |
| gctgttggcg actctgccta cagcacgggg catgtgtcca ggctgagccc gctgagcgtc | 9960 |
| gacacagtcg ctgttggcct ggtgtccagc gtggttgtct atcccgtcta cctggccatc | 10020 |
| cttttttctct tccggatgtc ccggagcaag gtggctggga gcccgagccc cacacctgcc | 10080 |
| gggcagcagg tgctggacat cgacagctgc ctggactcgt ccgtgctgga cagctccttc | 10140 |
| ctcacgttct caggcctcca cgctgaggcc tttgttggac agatgaagag tgacttgttt | 10200 |
| ctggatgatt ctaagagtct ggtgtgctgg ccctccggcg agggaacgct cagttggccg | 10260 |
| gacctgctca gtgacccgtc cattgtgggt agcaatctgc ggcagctggc acggggccag | 10320 |
| gcgggccatg ggctgggccc agaggaggac ggcttctccc tggccagccc ctactcgcct | 10380 |
| gccaaatcct tctcagcatc agatgaagac ctgatccagc aggtccttgc cgagggggtc | 10440 |
| agcagcccag cccctaccca agacacccac atggaaacgg acctgctcag cagcctgtcc | 10500 |
| agcactcctg gggagaagac agagacgctg cgcctgcaga ggctggggga gctggggcca | 10560 |
| cccagcccag gcctgaactg gaacagccc caggcagcga ggctgtccag gacaggactg | 10620 |
| gtggagggtc tgcggaagcg cctgctgccg gcctggtgtg cctccctggc ccacgggctc | 10680 |
| agcctgctcc tggtggctgt ggctgtggct gtctcagggt gggtgggtgc gagcttcccc | 10740 |
| ccgggcgtga gtgttgcgtg gctcctgtcc agcagcgcca gcttcctggc ctcattcctc | 10800 |
| ggctgggagc cactgaaggt cttgctggaa gccctgtact tctcactggt ggccaagcgg | 10860 |
| ctgcacccgg atgaagatga caccctggta gagagcccgg ctgtgacgcc tgtgagcgca | 10920 |
| cgtgtgcccc gcgtacggcc acccccacgg tttgcactct tcctggccaa ggaagaagcc | 10980 |
| cgcaaggtca agaggctaca tggcatgctg cggagcctcc tggtgtacat gcttttttctg | 11040 |
| ctggtgaccc tgctggccag ctatgggggat gcctcatgcc atgggcacgc ctaccgtctg | 11100 |
| caaagcgcca tcaagcagga gctgcacagc cgggccttcc tggccatcac gcggtctgag | 11160 |
| gagctctgc catggatggc ccacgtgctg ctgcccacg tccacgggaa ccagtccagc | 11220 |
| ccagagctgg ggccccacg gctgcggcag gtgcggctgc aggaagcact ctacccagac | 11280 |

-continued

| | | | | |
|---|---|---|---|---|
| cctcccggcc | ccagggtcca | cacgtgctcg | gccgcaggag | gcttcagcac cagcgattac | 11340 |
| gacgttggct | gggagagtcc | tcacaatggc | tcggggacgt | gggcctattc agcgccggat | 11400 |
| ctgctggggg | catggtcctg | gggctcctgt | gccgtgtatg | acagcggggg ctacgtgcag | 11460 |
| gagctgggcc | tgagcctgga | ggagagccgc | gaccggctgc | gcttcctgca gctgcacaac | 11520 |
| tggctggaca | acaggagccg | cgctgtgttc | ctggagctca | cgcgctacag cccgccgtg | 11580 |
| gggctgcacg | ccgccgtcac | gctgcgcctc | gagttcccgg | cggccggccg cgccctggcc | 11640 |
| gccctcagcg | tccgcccctt | tgcgctgcgc | cgcctcagcg | cgggcctctc gctgcctctg | 11700 |
| ctcacctcgg | tgtgcctgct | gctgttcgcc | gtgcacttcg | ccgtggccga ggcccgtact | 11760 |
| tggcacaggg | aagggcgctg | gcgcgtgctg | cggctcggag | cctgggcgcg gtggctgctg | 11820 |
| gtggcgctga | cggcggccac | ggcactggta | cgcctcgccc | agctgggtgc cgctgaccgc | 11880 |
| cagtggaccc | gtttcgtgcg | cggccgcccg | cgccgcttca | ctagcttcga ccaggtggcg | 11940 |
| cagctgagct | ccgcagcccg | tggcctggcg | gcctcgctgc | tcttcctgct tttggtcaag | 12000 |
| gctgcccagc | agctacgctt | cgtgcgccag | tggtccgtct | ttggcaagac attatgccga | 12060 |
| gctctgccag | agctcctggg | ggtcaccttg | ggctggtgg | tgctcggggt agcctacgcc | 12120 |
| cagctggcca | tcctgctcgt | gtcttcctgt | gtggactccc | tctggagcgt ggcccaggcc | 12180 |
| ctgttggtgc | tgtgccctgg | gactgggctc | tctaccctgt | gtcctgccga gtcctggcac | 12240 |
| ctgtcaccc | tgctgtgtgt | ggggctctgg | gcactgcggc | tgtggggcgc cctacggctg | 12300 |
| ggggctgtta | ttctccgctg | gcgctaccac | gccttgcgtg | gagagctgta ccggccggcc | 12360 |
| tgggagcccc | aggactacga | gatggtggag | ttgttcctgc | gcaggctgcg cctctggatg | 12420 |
| ggcctcagca | aggtcaagga | gttccgccac | aaagtccgct | ttgaagggat ggagccgctg | 12480 |
| ccctctcgct | cctccagggg | ctccaaggta | tccccggatg | tgcccccacc cagcgctggc | 12540 |
| tccgatgcct | cgcaccccctc | cacctcctcc | agccagctgg | atgggctgag cgtgagcctg | 12600 |
| ggccggctgg | ggacaaggtg | tgagcctgag | ccctcccgcc | tccaagccgt gttcgaggcc | 12660 |
| ctgctcaccc | agtttgaccg | actcaaccag | gccacagagg | acgtctacca gctgagcag | 12720 |
| cagctgcaca | gcctgcaagg | ccgcaggagc | agccgggcgc | ccgccggatc ttcccgtggc | 12780 |
| ccatccccgg | gcctgcggcc | agcactgccc | agccgccttg | cccgggccag tcggggtgtg | 12840 |
| gacctggcca | ctggccccag | caggacaccc | cttcgggcca | agaacaaggt tccaccccagc | 12900 |
| agcacttag | | | | | 12909 |

<210> SEQ ID NO 170
<211> LENGTH: 2907
<212> TYPE: DNA
<213> ORGANISM: Homo sapiens

<400> SEQUENCE: 170

| | | | | | |
|---|---|---|---|---|---|
| atggtgaact | ccagtcgcgt | gcagcctcag | cagcccgggg | acgccaagcg gccgcccgcg | 60 |
| ccccgcgcgc | cggacccggg | ccggctgatg | gctggctgcg | cggccgtggg cgccagcctc | 120 |
| gccgccccgg | gcgcctctg | cgagcagcgg | ggcctggaga | tcgagatgca gcgcatccgg | 180 |
| caggcggccg | cgcgggaccc | cccggccgga | gccgcggcct | ccccttctcc tccgctctcg | 240 |
| tcgtgctccc | ggcaggcgtg | gagccgcgat | aaccccggct | tcgaggccga ggaggaggag | 300 |
| gaggaggtgg | aagggaaga | aggcggaatg | gtggtggaga | tggacgtaga gtggcgcccg | 360 |
| ggcagccgga | ggtcgccgc | ctcctcggcc | gtgagctccg | tgggcgcgcg gagccgggg | 420 |
| cttgggggct | accacggcgc | gggccaccccg | agcgggaggc | ggcgccggcg agaggaccag | 480 |

-continued

```
ggcccgccgt gccccagccc agtcggcggc ggggacccgc tgcatcgcca cctcccctg      540
gaagggcagc cgccccgagt ggcctgggcg gagaggctgg ttcgcgggct gcgaggtctc      600
tggggaacaa gactcatgga ggaaagcagc actaaccgag agaaatacct taaaagtgtt      660
ttacgggaac tggtcacata cctccttttt ctcatagtct tgtgcatctt gacctacggc      720
atgatgagct ccaatgtgta ctactacacc cggatgatgt cacagctctt cctagacacc      780
cccgtgtcca aaacggagaa aactaacttt aaaactctgt cttccatgga agacttctgg      840
aagttcacag aaggctcctt attggatggg ctgtactgga agatgcagcc cagcaaccag      900
actgaagctg acaaccgaag tttcatcttc tatgagaacc tgctgttagg ggttccacga      960
atacggcaac tccgagtcag aaatggatcc tgctctatcc cccaggactt gagagatgaa     1020
attaaagagt gctatgatgt ctactctgtc agtagtgaag atagggctcc ctttgggccc     1080
cgaaatggaa ccgcttggat ctacacaagt gaaaaagact tgaatggtag tagccactgg     1140
ggaatcattg caacttatag tggagctggc tattatctgg atttgtcaag aacaagagag     1200
gaaacagctg cacaagttgc tagcctcaag aaaaatgtct ggctggaccg aggaaccagg     1260
gcaacttttc ttgacttctc agtgtacaac gccaacatta acctgttctg tgtggtcagg     1320
ttattggttg aattcccagc aacaggtggt gtgattccat cttggcaatt tcagcccttta    1380
aagctgatcc gatatgtcac aacttttgat ttcttcctgg cagcctgtga gattatcttt     1440
tgtttcttta tcttttacta tgtggtggaa gagatattgg aaattcgcat tcacaaacta     1500
cactatttca ggagtttctg gaattgtctg atgttgtga tcgttgtgct gtcagtggta      1560
gctataggaa ttaacatata cagaacatca aatgtggagg tgctactaca gtttctggaa     1620
gatcaaaata ctttccccaa ctttgagcat ctggcatatt ggcagataca gttcaacaat     1680
atagctgctg tcacagtatt ttttgtctgg attaagctct tcaaattcat caattttaac     1740
aggaccatga gccagctctc gacaaccatg tctcgatgtg ccaaagacct gtttggcttt     1800
gctattatgt tcttcattat tttcctagcg tatgctcagt ggcatacct tgtctttggc     1860
actcaggtcg atgacttcag tacttttccaa gagtgtatct tcactcaatt ccgtatcatt     1920
ttgggcgata tcaactttgc agagattgag gaagctaatc gagtttttggg accaatttat     1980
ttcactacat ttgtgttctt tatgttcttc attcttttga atatgttttt ggctatcatc     2040
aatgatactt actctgaagt gaaatctgac ttggcacagc agaaagctga atggaactc      2100
tcagatctta tcagaaaggg ctaccataaa gctttggtca aactaaaact gaaaaaaat     2160
accgtggatg acatttcaga gagtctgcgg caaggaggag gcaagttaaa ctttgacgaa     2220
cttcgacaag atctcaaagg gaagggccat actgatgcag agattgaggc aatattcaca     2280
aagtacgacc aagatggaga ccaagaactg accgaacatg aacatcagca gatgagagac     2340
gacttggaga agagaggga ggacctggat ttggatcaca gttcttttacc acgtcccatg     2400
agcagccgaa gtttccctcg aagcctggat gactctgagg aggatgacga tgaagatagc     2460
ggacatagct ccagaaggag gggaagcatt tctagtggcg tttcttacga agagtttcaa     2520
gtcctggtga gacgagtgga ccggatggag cattccatcg gcagcatagt gtccaagatt     2580
gacgccgtga tcgtgaagct agagattatg agcgagcca actgaagag gagggaggtg      2640
ctgggaaggc tgttggatgg ggtggccgag gatgaaaggc tgggtcgtga cagtgaaatc     2700
catagggaac agatgaacg gctagtacgt gaagagttgg aacgctggga atccgatgat     2760
gcagcttccc agatcagtca tggtttaggc acgccagtgg gactaaatgg tcaacctcgc     2820
```

```
cccagaagct cccgcccatc ttcctcccaa tctacagaag gcatggaagg tgcaggtgga    2880
aatgggagtt ctaatgtcca cgtatga                                        2907
```

<210> SEQ ID NO 171
<211> LENGTH: 4302
<212> TYPE: PRT
<213> ORGANISM: Homo sapiens

<400> SEQUENCE: 171

```
Met Pro Pro Ala Ala Pro Ala Arg Leu Ala Leu Ala Leu Gly Leu Gly
1               5                   10                  15

Leu Trp Leu Gly Ala Leu Ala Gly Gly Pro Gly Arg Gly Cys Gly Pro
                20                  25                  30

Cys Glu Pro Pro Cys Leu Cys Gly Pro Ala Pro Gly Ala Ala Cys Arg
            35                  40                  45

Val Asn Cys Ser Gly Arg Gly Leu Arg Thr Leu Gly Pro Ala Leu Arg
    50                  55                  60

Ile Pro Ala Asp Ala Thr Ala Leu Asp Val Ser His Asn Leu Leu Arg
65                  70                  75                  80

Ala Leu Asp Val Gly Leu Leu Ala Asn Leu Ser Ala Leu Ala Glu Leu
                85                  90                  95

Asp Ile Ser Asn Asn Lys Ile Ser Thr Leu Glu Glu Gly Ile Phe Ala
            100                 105                 110

Asn Leu Phe Asn Leu Ser Glu Ile Asn Leu Ser Gly Asn Pro Phe Glu
        115                 120                 125

Cys Asp Cys Gly Leu Ala Trp Leu Pro Arg Trp Ala Glu Glu Gln Gln
    130                 135                 140

Val Arg Val Val Gln Pro Glu Ala Ala Thr Cys Ala Gly Pro Gly Ser
145                 150                 155                 160

Leu Ala Gly Gln Pro Leu Leu Gly Ile Pro Leu Leu Asp Ser Gly Cys
                165                 170                 175

Gly Glu Glu Tyr Val Ala Cys Leu Pro Asp Asn Ser Ser Gly Thr Val
            180                 185                 190

Ala Ala Val Ser Phe Ser Ala His Glu Gly Leu Leu Gln Pro Glu
        195                 200                 205

Ala Cys Ser Ala Phe Cys Phe Ser Thr Gly Gln Gly Leu Ala Ala Leu
    210                 215                 220

Ser Glu Gln Gly Trp Cys Leu Cys Gly Ala Ala Gln Pro Ser Ser Ala
225                 230                 235                 240

Ser Phe Ala Cys Leu Ser Leu Cys Ser Gly Pro Pro Pro Pro Pro Ala
                245                 250                 255

Pro Thr Cys Arg Gly Pro Thr Leu Leu Gln His Val Phe Pro Ala Ser
            260                 265                 270

Pro Gly Ala Thr Leu Val Gly Pro His Gly Pro Leu Ala Ser Gly Gln
        275                 280                 285

Leu Ala Ala Phe His Ile Ala Ala Pro Leu Pro Val Thr Ala Thr Arg
    290                 295                 300

Trp Asp Phe Gly Asp Gly Ser Ala Glu Val Ala Ala Gly Pro Ala
305                 310                 315                 320

Ala Ser His Arg Tyr Val Leu Pro Gly Arg Tyr His Val Thr Ala Val
                325                 330                 335

Leu Ala Leu Gly Ala Gly Ser Ala Leu Leu Gly Thr Asp Val Gln Val
            340                 345                 350

Glu Ala Ala Pro Ala Ala Leu Glu Leu Val Cys Pro Ser Ser Val Gln
```

-continued

```
            355                 360                 365
Ser Asp Glu Ser Leu Asp Leu Ser Ile Gln Asn Arg Gly Gly Ser Gly
    370                 375                 380

Leu Glu Ala Ala Tyr Ser Ile Val Ala Leu Gly Glu Glu Pro Ala Arg
385                 390                 395                 400

Ala Val His Pro Leu Cys Pro Ser Asp Thr Glu Ile Phe Pro Gly Asn
                405                 410                 415

Gly His Cys Tyr Arg Leu Val Val Glu Lys Ala Ala Trp Leu Gln Ala
                420                 425                 430

Gln Glu Gln Cys Gln Ala Trp Ala Gly Ala Ala Leu Ala Met Val Asp
                435                 440                 445

Ser Pro Ala Val Gln Arg Phe Leu Val Ser Arg Val Thr Arg Ser Leu
    450                 455                 460

Asp Val Trp Ile Gly Phe Ser Thr Val Gln Gly Val Glu Val Gly Pro
465                 470                 475                 480

Ala Pro Gln Gly Glu Ala Phe Ser Leu Glu Ser Cys Gln Asn Trp Leu
                485                 490                 495

Pro Gly Glu Pro His Pro Ala Thr Ala Glu His Cys Val Arg Leu Gly
                500                 505                 510

Pro Thr Gly Trp Cys Asn Thr Asp Leu Cys Ser Ala Pro His Ser Tyr
                515                 520                 525

Val Cys Glu Leu Gln Pro Gly Gly Pro Val Gln Asp Ala Glu Asn Leu
    530                 535                 540

Leu Val Gly Ala Pro Ser Gly Asp Leu Gln Gly Pro Leu Thr Pro Leu
545                 550                 555                 560

Ala Gln Gln Asp Gly Leu Ser Ala Pro His Glu Pro Val Glu Val Met
                565                 570                 575

Val Phe Pro Gly Leu Arg Leu Ser Arg Glu Ala Phe Leu Thr Thr Ala
                580                 585                 590

Glu Phe Gly Thr Gln Glu Leu Arg Arg Pro Ala Gln Leu Arg Leu Gln
                595                 600                 605

Val Tyr Arg Leu Leu Ser Thr Ala Gly Thr Pro Glu Asn Gly Ser Glu
    610                 615                 620

Pro Glu Ser Arg Ser Pro Asp Asn Arg Thr Gln Leu Ala Pro Ala Cys
625                 630                 635                 640

Met Pro Gly Gly Arg Trp Cys Pro Gly Ala Asn Ile Cys Leu Pro Leu
                645                 650                 655

Asp Ala Ser Cys His Pro Gln Ala Cys Ala Asn Gly Cys Thr Ser Gly
                660                 665                 670

Pro Gly Leu Pro Gly Ala Pro Tyr Ala Leu Trp Arg Glu Phe Leu Phe
                675                 680                 685

Ser Val Ala Ala Gly Pro Pro Ala Gln Tyr Ser Val Thr Leu His Gly
    690                 695                 700

Gln Asp Val Leu Met Leu Pro Gly Asp Leu Val Gly Leu Gln His Asp
705                 710                 715                 720

Ala Gly Pro Gly Ala Leu Leu His Cys Ser Pro Ala Pro Gly His Pro
                725                 730                 735

Gly Pro Gln Ala Pro Tyr Leu Ser Ala Asn Ala Ser Ser Trp Leu Pro
                740                 745                 750

His Leu Pro Ala Gln Leu Glu Gly Thr Trp Ala Cys Pro Ala Cys Ala
                755                 760                 765

Leu Arg Leu Leu Ala Ala Thr Glu Gln Leu Thr Val Leu Leu Gly Leu
770                 775                 780
```

-continued

```
Arg Pro Asn Pro Gly Leu Arg Met Pro Gly Arg Tyr Glu Val Arg Ala
785                 790                 795                 800

Glu Val Gly Asn Gly Val Ser Arg His Asn Leu Ser Cys Ser Phe Asp
                805                 810                 815

Val Val Ser Pro Val Ala Gly Leu Arg Val Ile Tyr Pro Ala Pro Arg
            820                 825                 830

Asp Gly Arg Leu Tyr Val Pro Thr Asn Gly Ser Ala Leu Val Leu Gln
                835                 840                 845

Val Asp Ser Gly Ala Asn Ala Thr Ala Ala Arg Trp Pro Gly Gly
850                 855                 860

Ser Val Ser Ala Arg Phe Glu Asn Val Cys Pro Ala Leu Val Ala Thr
865                 870                 875                 880

Phe Val Pro Gly Cys Pro Trp Glu Thr Asn Asp Thr Leu Phe Ser Val
                885                 890                 895

Val Ala Leu Pro Trp Leu Ser Glu Gly Glu His Val Val Asp Val Val
                900                 905                 910

Val Glu Asn Ser Ala Ser Arg Ala Asn Leu Ser Leu Arg Val Thr Ala
                915                 920                 925

Glu Glu Pro Ile Cys Gly Leu Arg Ala Thr Pro Ser Pro Glu Ala Arg
930                 935                 940

Val Leu Gln Gly Val Leu Val Arg Tyr Ser Pro Val Val Glu Ala Gly
945                 950                 955                 960

Ser Asp Met Val Phe Arg Trp Thr Ile Asn Asp Lys Gln Ser Leu Thr
                965                 970                 975

Phe Gln Asn Val Val Phe Asn Val Ile Tyr Gln Ser Ala Ala Val Phe
                980                 985                 990

Lys Leu Ser Leu Thr Ala Ser Asn  His Val Ser Asn Val  Thr Val Asn
                995                 1000                1005

Tyr Asn  Val Thr Val Glu Arg  Met Asn Arg Met Gln  Gly Leu Gln
    1010                1015                1020

Val Ser  Thr Val Pro Ala Val  Leu Ser Pro Asn Ala  Thr Leu Ala
    1025                1030                1035

Leu Thr  Ala Gly Val Leu Val  Asp Ser Ala Val Glu  Val Ala Phe
    1040                1045                1050

Leu Trp  Asn Phe Gly Asp Gly  Glu Gln Ala Leu His  Gln Phe Gln
    1055                1060                1065

Pro Pro  Tyr Asn Glu Ser Phe  Pro Val Pro Asp Pro  Ser Val Ala
    1070                1075                1080

Gln Val  Leu Val Glu His Asn  Val Met His Thr Tyr  Ala Ala Pro
    1085                1090                1095

Gly Glu  Tyr Leu Leu Thr Val  Leu Ala Ser Asn Ala  Phe Glu Asn
    1100                1105                1110

Leu Thr  Gln Gln Val Pro Val  Ser Val Arg Ala Ser  Leu Pro Ser
    1115                1120                1125

Val Ala  Val Gly Val Ser Asp  Gly Val Leu Val Ala  Gly Arg Pro
    1130                1135                1140

Val Thr  Phe Tyr Pro His Pro  Leu Pro Ser Pro Gly  Gly Val Leu
    1145                1150                1155

Tyr Thr  Trp Asp Phe Gly Asp  Gly Ser Pro Val Leu  Thr Gln Ser
    1160                1165                1170

Gln Pro  Ala Ala Asn His Thr  Tyr Ala Ser Arg Gly  Thr Tyr His
    1175                1180                1185
```

-continued

```
Val Arg Leu Glu Val Asn Asn Thr Val Ser Gly Ala Ala Ala Gln
    1190            1195                1200

Ala Asp Val Arg Val Phe Glu Glu Leu Arg Gly Leu Ser Val Asp
    1205            1210                1215

Met Ser Leu Ala Val Glu Gln Gly Ala Pro Val Val Val Ser Ala
    1220            1225                1230

Ala Val Gln Thr Gly Asp Asn Ile Thr Trp Thr Phe Asp Met Gly
    1235            1240                1245

Asp Gly Thr Val Leu Ser Gly Pro Glu Ala Thr Val Glu His Val
    1250            1255                1260

Tyr Leu Arg Ala Gln Asn Cys Thr Val Thr Val Gly Ala Ala Ser
    1265            1270                1275

Pro Ala Gly His Leu Ala Arg Ser Leu His Val Leu Val Phe Val
    1280            1285                1290

Leu Glu Val Leu Arg Val Glu Pro Ala Ala Cys Ile Pro Thr Gln
    1295            1300                1305

Pro Asp Ala Arg Leu Thr Ala Tyr Val Thr Gly Asn Pro Ala His
    1310            1315                1320

Tyr Leu Phe Asp Trp Thr Phe Gly Asp Gly Ser Ser Asn Thr Thr
    1325            1330                1335

Val Arg Gly Cys Pro Thr Val Thr His Asn Phe Thr Arg Ser Gly
    1340            1345                1350

Thr Phe Pro Leu Ala Leu Val Leu Ser Ser Arg Val Asn Arg Ala
    1355            1360                1365

His Tyr Phe Thr Ser Ile Cys Val Glu Pro Glu Val Gly Asn Val
    1370            1375                1380

Thr Leu Gln Pro Glu Arg Gln Phe Val Gln Leu Gly Asp Glu Ala
    1385            1390                1395

Trp Leu Val Ala Cys Ala Trp Pro Pro Phe Pro Tyr Arg Tyr Thr
    1400            1405                1410

Trp Asp Phe Gly Thr Glu Glu Ala Ala Pro Thr Arg Ala Arg Gly
    1415            1420                1425

Pro Glu Val Thr Phe Ile Tyr Arg Asp Pro Gly Ser Tyr Leu Val
    1430            1435                1440

Thr Val Thr Ala Ser Asn Asn Ile Ser Ala Ala Asn Asp Ser Ala
    1445            1450                1455

Leu Val Glu Val Gln Glu Pro Val Leu Val Thr Ser Ile Lys Val
    1460            1465                1470

Asn Gly Ser Leu Gly Leu Glu Leu Gln Gln Pro Tyr Leu Phe Ser
    1475            1480                1485

Ala Val Gly Arg Gly Arg Pro Ala Ser Tyr Leu Trp Asp Leu Gly
    1490            1495                1500

Asp Gly Gly Trp Leu Glu Gly Pro Glu Val Thr His Ala Tyr Asn
    1505            1510                1515

Ser Thr Gly Asp Phe Thr Val Arg Val Ala Gly Trp Asn Glu Val
    1520            1525                1530

Ser Arg Ser Glu Ala Trp Leu Asn Val Thr Val Lys Arg Arg Val
    1535            1540                1545

Arg Gly Leu Val Val Asn Ala Ser Arg Thr Val Val Pro Leu Asn
    1550            1555                1560

Gly Ser Val Ser Phe Ser Thr Ser Leu Glu Ala Gly Ser Asp Val
    1565            1570                1575

Arg Tyr Ser Trp Val Leu Cys Asp Arg Cys Thr Pro Ile Pro Gly
```

-continued

```
            1580                1585                1590
Gly Pro Thr Ile Ser Tyr Thr Phe Arg Ser Val Gly Thr Phe Asn
    1595                1600                1605
Ile Ile Val Thr Ala Glu Asn Glu Val Gly Ser Ala Gln Asp Ser
    1610                1615                1620
Ile Phe Val Tyr Val Leu Gln Leu Ile Glu Gly Leu Gln Val Val
    1625                1630                1635
Gly Gly Gly Arg Tyr Phe Pro Thr Asn His Thr Val Gln Leu Gln
    1640                1645                1650
Ala Val Val Arg Asp Gly Thr Asn Val Ser Tyr Ser Trp Thr Ala
    1655                1660                1665
Trp Arg Asp Arg Gly Pro Ala Leu Ala Gly Ser Gly Lys Gly Phe
    1670                1675                1680
Ser Leu Thr Val Leu Glu Ala Gly Thr Tyr His Val Gln Leu Arg
    1685                1690                1695
Ala Thr Asn Met Leu Gly Ser Ala Trp Ala Asp Cys Thr Met Asp
    1700                1705                1710
Phe Val Glu Pro Val Gly Trp Leu Met Val Thr Ala Ser Pro Asn
    1715                1720                1725
Pro Ala Ala Val Asn Thr Ser Val Thr Leu Ser Ala Glu Leu Ala
    1730                1735                1740
Gly Gly Ser Gly Val Val Tyr Thr Trp Ser Leu Glu Glu Gly Leu
    1745                1750                1755
Ser Trp Glu Thr Ser Glu Pro Phe Thr Thr His Ser Phe Pro Thr
    1760                1765                1770
Pro Gly Leu His Leu Val Thr Met Thr Ala Gly Asn Pro Leu Gly
    1775                1780                1785
Ser Ala Asn Ala Thr Val Glu Val Asp Val Gln Val Pro Val Ser
    1790                1795                1800
Gly Leu Ser Ile Arg Ala Ser Glu Pro Gly Gly Ser Phe Val Ala
    1805                1810                1815
Ala Gly Ser Ser Val Pro Phe Trp Gly Gln Leu Ala Thr Gly Thr
    1820                1825                1830
Asn Val Ser Trp Cys Trp Ala Val Pro Gly Gly Ser Ser Lys Arg
    1835                1840                1845
Gly Pro His Val Thr Met Val Phe Pro Asp Ala Gly Thr Phe Ser
    1850                1855                1860
Ile Arg Leu Asn Ala Ser Asn Ala Val Ser Trp Val Ser Ala Thr
    1865                1870                1875
Tyr Asn Leu Thr Ala Glu Glu Pro Ile Val Gly Leu Val Leu Trp
    1880                1885                1890
Ala Ser Ser Lys Val Val Ala Pro Gly Gln Leu Val His Phe Gln
    1895                1900                1905
Ile Leu Leu Ala Ala Gly Ser Ala Val Thr Phe Arg Leu Gln Val
    1910                1915                1920
Gly Gly Ala Asn Pro Glu Val Leu Pro Gly Pro Arg Phe Ser His
    1925                1930                1935
Ser Phe Pro Arg Val Gly Asp His Val Val Ser Val Arg Gly Lys
    1940                1945                1950
Asn His Val Ser Trp Ala Gln Ala Gln Val Arg Ile Val Val Leu
    1955                1960                1965
Glu Ala Val Ser Gly Leu Gln Met Pro Asn Cys Cys Glu Pro Gly
    1970                1975                1980
```

-continued

```
Ile Ala Thr Gly Thr Glu Arg Asn Phe Thr Ala Arg  Val Gln Arg
1985                1990                1995

Gly Ser Arg Val Ala Tyr Ala Trp Tyr Phe Ser Leu  Gln Lys Val
2000                2005                2010

Gln Gly Asp Ser Leu Val Ile Leu Ser Gly Arg Asp  Val Thr Tyr
2015                2020                2025

Thr Pro Val Ala Ala Gly Leu Leu Glu Ile Gln Val  Arg Ala Phe
2030                2035                2040

Asn Ala Leu Gly Ser Glu Asn Arg Thr Leu Val Leu  Glu Val Gln
2045                2050                2055

Asp Ala Val Gln Tyr Val Ala Leu Gln Ser Gly Pro  Cys Phe Thr
2060                2065                2070

Asn Arg Ser Ala Gln Phe Glu Ala Ala Thr Ser Pro  Ser Pro Arg
2075                2080                2085

Arg Val Ala Tyr His Trp Asp Phe Gly Asp Gly Ser  Pro Gly Gln
2090                2095                2100

Asp Thr Asp Glu Pro Arg Ala Glu His Ser Tyr Leu  Arg Pro Gly
2105                2110                2115

Asp Tyr Arg Val Gln Val Asn Ala Ser Asn Leu Val  Ser Phe Phe
2120                2125                2130

Val Ala Gln Ala Thr Val Thr Val Gln Val Leu Ala  Cys Arg Glu
2135                2140                2145

Pro Glu Val Asp Val Val Leu Pro Leu Gln Val Leu  Met Arg Arg
2150                2155                2160

Ser Gln Arg Asn Tyr Leu Glu Ala His Val Asp Leu  Arg Asp Cys
2165                2170                2175

Val Thr Tyr Gln Thr Glu Tyr Arg Trp Glu Val Tyr  Arg Thr Ala
2180                2185                2190

Ser Cys Gln Arg Pro Gly Arg Pro Ala Arg Val Ala  Leu Pro Gly
2195                2200                2205

Val Asp Val Ser Arg Pro Arg Leu Val Leu Pro Arg  Leu Ala Leu
2210                2215                2220

Pro Val Gly His Tyr Cys Phe Val Phe Val Val Ser  Phe Gly Asp
2225                2230                2235

Thr Pro Leu Thr Gln Ser Ile Gln Ala Asn Val Thr  Val Ala Pro
2240                2245                2250

Glu Arg Leu Val Pro Ile Ile Glu Gly Gly Ser Tyr  Arg Val Trp
2255                2260                2265

Ser Asp Thr Arg Asp Leu Val Leu Asp Gly Ser Glu  Ser Tyr Asp
2270                2275                2280

Pro Asn Leu Glu Asp Gly Asp Gln Thr Pro Leu Ser  Phe His Trp
2285                2290                2295

Ala Cys Val Ala Ser Thr Gln Arg Glu Ala Gly Gly  Cys Ala Leu
2300                2305                2310

Asn Phe Gly Pro Arg Gly Ser Ser Thr Val Thr Ile  Pro Arg Glu
2315                2320                2325

Arg Leu Ala Ala Gly Val Glu Tyr Thr Phe Ser Leu  Thr Val Trp
2330                2335                2340

Lys Ala Gly Arg Lys Glu Glu Ala Thr Asn Gln Thr  Val Leu Ile
2345                2350                2355

Arg Ser Gly Arg Val Pro Ile Val Ser Leu Glu Cys  Val Ser Cys
2360                2365                2370
```

-continued

| | | | | | | | | | |
|---|---|---|---|---|---|---|---|---|---|
| Lys | Ala | Gln | Ala | Val | Tyr | Glu | Val | Ser | Arg | Ser | Tyr | Val | Tyr |
| | 2375 | | | | 2380 | | | | 2385 | | | | |
| Leu | Glu | Gly | Arg | Cys | Leu | Asn | Cys | Ser | Ser | Gly | Ser | Lys | Arg | Gly |
| | 2390 | | | | 2395 | | | | 2400 | | | | |
| Arg | Trp | Ala | Ala | Arg | Thr | Phe | Ser | Asn | Lys | Thr | Leu | Val | Leu | Asp |
| | 2405 | | | | 2410 | | | | 2415 | | | | |
| Glu | Thr | Thr | Thr | Ser | Thr | Gly | Ser | Ala | Gly | Met | Arg | Leu | Val | Leu |
| | 2420 | | | | 2425 | | | | 2430 | | | | |
| Arg | Arg | Gly | Val | Leu | Arg | Asp | Gly | Glu | Gly | Tyr | Thr | Phe | Thr | Leu |
| | 2435 | | | | 2440 | | | | 2445 | | | | |
| Thr | Val | Leu | Gly | Arg | Ser | Gly | Glu | Glu | Glu | Gly | Cys | Ala | Ser | Ile |
| | 2450 | | | | 2455 | | | | 2460 | | | | |
| Arg | Leu | Ser | Pro | Asn | Arg | Pro | Pro | Leu | Gly | Gly | Ser | Cys | Arg | Leu |
| | 2465 | | | | 2470 | | | | 2475 | | | | |
| Phe | Pro | Leu | Gly | Ala | Val | His | Ala | Leu | Thr | Thr | Lys | Val | His | Phe |
| | 2480 | | | | 2485 | | | | 2490 | | | | |
| Glu | Cys | Thr | Gly | Trp | His | Asp | Ala | Glu | Asp | Ala | Gly | Ala | Pro | Leu |
| | 2495 | | | | 2500 | | | | 2505 | | | | |
| Val | Tyr | Ala | Leu | Leu | Leu | Arg | Arg | Cys | Arg | Gln | Gly | His | Cys | Glu |
| | 2510 | | | | 2515 | | | | 2520 | | | | |
| Glu | Phe | Cys | Val | Tyr | Lys | Gly | Ser | Leu | Ser | Ser | Tyr | Gly | Ala | Val |
| | 2525 | | | | 2530 | | | | 2535 | | | | |
| Leu | Pro | Pro | Gly | Phe | Arg | Pro | His | Phe | Glu | Val | Gly | Leu | Ala | Val |
| | 2540 | | | | 2545 | | | | 2550 | | | | |
| Val | Val | Gln | Asp | Gln | Leu | Gly | Ala | Ala | Val | Val | Ala | Leu | Asn | Arg |
| | 2555 | | | | 2560 | | | | 2565 | | | | |
| Ser | Leu | Ala | Ile | Thr | Leu | Pro | Glu | Pro | Asn | Gly | Ser | Ala | Thr | Gly |
| | 2570 | | | | 2575 | | | | 2580 | | | | |
| Leu | Thr | Val | Trp | Leu | His | Gly | Leu | Thr | Ala | Ser | Val | Leu | Pro | Gly |
| | 2585 | | | | 2590 | | | | 2595 | | | | |
| Leu | Leu | Arg | Gln | Ala | Asp | Pro | Gln | His | Val | Ile | Glu | Tyr | Ser | Leu |
| | 2600 | | | | 2605 | | | | 2610 | | | | |
| Ala | Leu | Val | Thr | Val | Leu | Asn | Glu | Tyr | Glu | Arg | Ala | Leu | Asp | Val |
| | 2615 | | | | 2620 | | | | 2625 | | | | |
| Ala | Ala | Glu | Pro | Lys | His | Glu | Arg | Gln | His | Arg | Ala | Gln | Ile | Arg |
| | 2630 | | | | 2635 | | | | 2640 | | | | |
| Lys | Asn | Ile | Thr | Glu | Thr | Leu | Val | Ser | Leu | Arg | Val | His | Thr | Val |
| | 2645 | | | | 2650 | | | | 2655 | | | | |
| Asp | Asp | Ile | Gln | Gln | Ile | Ala | Ala | Ala | Leu | Ala | Gln | Cys | Met | Gly |
| | 2660 | | | | 2665 | | | | 2670 | | | | |
| Pro | Ser | Arg | Glu | Leu | Val | Cys | Arg | Ser | Cys | Leu | Lys | Gln | Thr | Leu |
| | 2675 | | | | 2680 | | | | 2685 | | | | |
| His | Lys | Leu | Glu | Ala | Met | Met | Leu | Ile | Leu | Gln | Ala | Glu | Thr | Thr |
| | 2690 | | | | 2695 | | | | 2700 | | | | |
| Ala | Gly | Thr | Val | Thr | Pro | Thr | Ala | Ile | Gly | Asp | Ser | Ile | Leu | Asn |
| | 2705 | | | | 2710 | | | | 2715 | | | | |
| Ile | Thr | Gly | Asp | Leu | Ile | His | Leu | Ala | Ser | Ser | Asp | Val | Arg | Ala |
| | 2720 | | | | 2725 | | | | 2730 | | | | |
| Pro | Gln | Pro | Ser | Glu | Leu | Gly | Ala | Glu | Ser | Pro | Ser | Arg | Met | Val |
| | 2735 | | | | 2740 | | | | 2745 | | | | |
| Ala | Ser | Gln | Ala | Tyr | Asn | Leu | Thr | Ser | Ala | Leu | Met | Arg | Ile | Leu |
| | 2750 | | | | 2755 | | | | 2760 | | | | |
| Met | Arg | Ser | Arg | Val | Leu | Asn | Glu | Glu | Pro | Leu | Thr | Leu | Ala | Gly |

-continued

| | | | | | | | | | | |
|---|---|---|---|---|---|---|---|---|---|---|
| | | 2765 | | | 2770 | | | 2775 | | |
| Glu | Glu | Ile | Val | Ala | Gln | Gly | Lys | Arg | Ser | Asp | Pro | Arg | Ser | Leu |
| | 2780 | | | | | 2785 | | | | | 2790 | | | |
| Leu | Cys | Tyr | Gly | Gly | Ala | Pro | Gly | Pro | Gly | Cys | His | Phe | Ser | Ile |
| | 2795 | | | | | 2800 | | | | | 2805 | | | |
| Pro | Glu | Ala | Phe | Ser | Gly | Ala | Leu | Ala | Asn | Leu | Ser | Asp | Val | Val |
| | 2810 | | | | | 2815 | | | | | 2820 | | | |
| Gln | Leu | Ile | Phe | Leu | Val | Asp | Ser | Asn | Pro | Phe | Pro | Phe | Gly | Tyr |
| | 2825 | | | | | 2830 | | | | | 2835 | | | |
| Ile | Ser | Asn | Tyr | Thr | Val | Ser | Thr | Lys | Val | Ala | Ser | Met | Ala | Phe |
| | 2840 | | | | | 2845 | | | | | 2850 | | | |
| Gln | Thr | Gln | Ala | Gly | Ala | Gln | Ile | Pro | Ile | Glu | Arg | Leu | Ala | Ser |
| | 2855 | | | | | 2860 | | | | | 2865 | | | |
| Glu | Arg | Ala | Ile | Thr | Val | Lys | Val | Pro | Asn | Asn | Ser | Asp | Trp | Ala |
| | 2870 | | | | | 2875 | | | | | 2880 | | | |
| Ala | Arg | Gly | His | Arg | Ser | Ser | Ala | Asn | Ser | Ala | Asn | Ser | Val | Val |
| | 2885 | | | | | 2890 | | | | | 2895 | | | |
| Val | Gln | Pro | Gln | Ala | Ser | Val | Gly | Ala | Val | Val | Thr | Leu | Asp | Ser |
| | 2900 | | | | | 2905 | | | | | 2910 | | | |
| Ser | Asn | Pro | Ala | Ala | Gly | Leu | His | Leu | Gln | Leu | Asn | Tyr | Thr | Leu |
| | 2915 | | | | | 2920 | | | | | 2925 | | | |
| Leu | Asp | Gly | His | Tyr | Leu | Ser | Glu | Glu | Pro | Glu | Pro | Tyr | Leu | Ala |
| | 2930 | | | | | 2935 | | | | | 2940 | | | |
| Val | Tyr | Leu | His | Ser | Glu | Pro | Arg | Pro | Asn | Glu | His | Asn | Cys | Ser |
| | 2945 | | | | | 2950 | | | | | 2955 | | | |
| Ala | Ser | Arg | Arg | Ile | Arg | Pro | Glu | Ser | Leu | Gln | Gly | Ala | Asp | His |
| | 2960 | | | | | 2965 | | | | | 2970 | | | |
| Arg | Pro | Tyr | Thr | Phe | Phe | Ile | Ser | Pro | Gly | Ser | Arg | Asp | Pro | Ala |
| | 2975 | | | | | 2980 | | | | | 2985 | | | |
| Gly | Ser | Tyr | His | Leu | Asn | Leu | Ser | Ser | His | Phe | Arg | Trp | Ser | Ala |
| | 2990 | | | | | 2995 | | | | | 3000 | | | |
| Leu | Gln | Val | Ser | Val | Gly | Leu | Tyr | Thr | Ser | Leu | Cys | Gln | Tyr | Phe |
| | 3005 | | | | | 3010 | | | | | 3015 | | | |
| Ser | Glu | Glu | Asp | Met | Val | Trp | Arg | Thr | Glu | Gly | Leu | Leu | Pro | Leu |
| | 3020 | | | | | 3025 | | | | | 3030 | | | |
| Glu | Glu | Thr | Ser | Pro | Arg | Gln | Ala | Val | Cys | Leu | Thr | Arg | His | Leu |
| | 3035 | | | | | 3040 | | | | | 3045 | | | |
| Thr | Ala | Phe | Gly | Ala | Ser | Leu | Phe | Val | Pro | Pro | Ser | His | Val | Arg |
| | 3050 | | | | | 3055 | | | | | 3060 | | | |
| Phe | Val | Phe | Pro | Glu | Pro | Thr | Ala | Asp | Val | Asn | Tyr | Ile | Val | Met |
| | 3065 | | | | | 3070 | | | | | 3075 | | | |
| Leu | Thr | Cys | Ala | Val | Cys | Leu | Val | Thr | Tyr | Met | Val | Met | Ala | Ala |
| | 3080 | | | | | 3085 | | | | | 3090 | | | |
| Ile | Leu | His | Lys | Leu | Asp | Gln | Leu | Asp | Ala | Ser | Arg | Gly | Arg | Ala |
| | 3095 | | | | | 3100 | | | | | 3105 | | | |
| Ile | Pro | Phe | Cys | Gly | Gln | Arg | Gly | Arg | Phe | Lys | Tyr | Glu | Ile | Leu |
| | 3110 | | | | | 3115 | | | | | 3120 | | | |
| Val | Lys | Thr | Gly | Trp | Gly | Arg | Gly | Ser | Gly | Thr | Thr | Ala | His | Val |
| | 3125 | | | | | 3130 | | | | | 3135 | | | |
| Gly | Ile | Met | Leu | Tyr | Gly | Val | Asp | Ser | Arg | Ser | Gly | His | Arg | His |
| | 3140 | | | | | 3145 | | | | | 3150 | | | |
| Leu | Asp | Gly | Asp | Arg | Ala | Phe | His | Arg | Asn | Ser | Leu | Asp | Ile | Phe |
| | 3155 | | | | | 3160 | | | | | 3165 | | | |

-continued

```
Arg Ile Ala Thr Pro His Ser Leu Gly Ser Val Trp Lys Ile Arg
    3170            3175                3180

Val Trp His Asp Asn Lys Gly Leu Ser Pro Ala Trp Phe Leu Gln
    3185            3190                3195

His Val Ile Val Arg Asp Leu Gln Thr Ala Arg Ser Ala Phe Phe
    3200            3205                3210

Leu Val Asn Asp Trp Leu Ser Val Glu Thr Glu Ala Asn Gly Gly
    3215            3220                3225

Leu Val Glu Lys Glu Val Leu Ala Ala Ser Asp Ala Ala Leu Leu
    3230            3235                3240

Arg Phe Arg Arg Leu Leu Val Ala Glu Leu Gln Arg Gly Phe Phe
    3245            3250                3255

Asp Lys His Ile Trp Leu Ser Ile Trp Asp Arg Pro Pro Arg Ser
    3260            3265                3270

Arg Phe Thr Arg Ile Gln Arg Ala Thr Cys Cys Val Leu Leu Ile
    3275            3280                3285

Cys Leu Phe Leu Gly Ala Asn Ala Val Trp Tyr Gly Ala Val Gly
    3290            3295                3300

Asp Ser Ala Tyr Ser Thr Gly His Val Ser Arg Leu Ser Pro Leu
    3305            3310                3315

Ser Val Asp Thr Val Ala Val Gly Leu Val Ser Ser Val Val Val
    3320            3325                3330

Tyr Pro Val Tyr Leu Ala Ile Leu Phe Leu Phe Arg Met Ser Arg
    3335            3340                3345

Ser Lys Val Ala Gly Ser Pro Ser Pro Thr Pro Ala Gly Gln Gln
    3350            3355                3360

Val Leu Asp Ile Asp Ser Cys Leu Asp Ser Ser Val Leu Asp Ser
    3365            3370                3375

Ser Phe Leu Thr Phe Ser Gly Leu His Ala Glu Ala Phe Val Gly
    3380            3385                3390

Gln Met Lys Ser Asp Leu Phe Leu Asp Asp Ser Lys Ser Leu Val
    3395            3400                3405

Cys Trp Pro Ser Gly Glu Gly Thr Leu Ser Trp Pro Asp Leu Leu
    3410            3415                3420

Ser Asp Pro Ser Ile Val Gly Ser Asn Leu Arg Gln Leu Ala Arg
    3425            3430                3435

Gly Gln Ala Gly His Gly Leu Gly Pro Glu Glu Asp Gly Phe Ser
    3440            3445                3450

Leu Ala Ser Pro Tyr Ser Pro Ala Lys Ser Phe Ser Ala Ser Asp
    3455            3460                3465

Glu Asp Leu Ile Gln Gln Val Leu Ala Glu Gly Val Ser Ser Pro
    3470            3475                3480

Ala Pro Thr Gln Asp Thr His Met Glu Thr Asp Leu Leu Ser Ser
    3485            3490                3495

Leu Ser Ser Thr Pro Gly Glu Lys Thr Glu Thr Leu Ala Leu Gln
    3500            3505                3510

Arg Leu Gly Glu Leu Gly Pro Pro Ser Pro Gly Leu Asn Trp Glu
    3515            3520                3525

Gln Pro Gln Ala Ala Arg Leu Ser Arg Thr Gly Leu Val Glu Gly
    3530            3535                3540

Leu Arg Lys Arg Leu Leu Pro Ala Trp Cys Ala Ser Leu Ala His
    3545            3550                3555
```

-continued

| | | | | | | | | | | | |
|---|---|---|---|---|---|---|---|---|---|---|---|
|Gly|Leu|Ser|Leu|Leu|Leu|Val|Ala|Val|Ala|Val|Ser|Gly
3560| | | | |3565| | | |3570| | |

Trp Val Gly Ala Ser Phe Pro Pro Gly Val Ser Val Ala Trp Leu
    3575            3580            3585

Leu Ser Ser Ser Ala Ser Phe Leu Ala Ser Phe Leu Gly Trp Glu
    3590            3595            3600

Pro Leu Lys Val Leu Leu Glu Ala Leu Tyr Phe Ser Leu Val Ala
    3605            3610            3615

Lys Arg Leu His Pro Asp Glu Asp Asp Thr Leu Val Glu Ser Pro
    3620            3625            3630

Ala Val Thr Pro Val Ser Ala Arg Val Pro Arg Val Arg Pro Pro
    3635            3640            3645

His Gly Phe Ala Leu Phe Leu Ala Lys Glu Glu Ala Arg Lys Val
    3650            3655            3660

Lys Arg Leu His Gly Met Leu Arg Ser Leu Leu Val Tyr Met Leu
    3665            3670            3675

Phe Leu Leu Val Thr Leu Leu Ala Ser Tyr Gly Asp Ala Ser Cys
    3680            3685            3690

His Gly His Ala Tyr Arg Leu Gln Ser Ala Ile Lys Gln Glu Leu
    3695            3700            3705

His Ser Arg Ala Phe Leu Ala Ile Thr Arg Ser Glu Glu Leu Trp
    3710            3715            3720

Pro Trp Met Ala His Val Leu Leu Pro Tyr Val His Gly Asn Gln
    3725            3730            3735

Ser Ser Pro Glu Leu Gly Pro Pro Arg Leu Arg Gln Val Arg Leu
    3740            3745            3750

Gln Glu Ala Leu Tyr Pro Asp Pro Pro Gly Pro Arg Val His Thr
    3755            3760            3765

Cys Ser Ala Ala Gly Gly Phe Ser Thr Ser Asp Tyr Asp Val Gly
    3770            3775            3780

Trp Glu Ser Pro His Asn Gly Ser Gly Thr Trp Ala Tyr Ser Ala
    3785            3790            3795

Pro Asp Leu Leu Gly Ala Trp Ser Trp Gly Ser Cys Ala Val Tyr
    3800            3805            3810

Asp Ser Gly Gly Tyr Val Gln Glu Leu Gly Leu Ser Leu Glu Glu
    3815            3820            3825

Ser Arg Asp Arg Leu Arg Phe Leu Gln Leu His Asn Trp Leu Asp
    3830            3835            3840

Asn Arg Ser Arg Ala Val Phe Leu Glu Leu Thr Arg Tyr Ser Pro
    3845            3850            3855

Ala Val Gly Leu His Ala Ala Val Thr Leu Arg Leu Glu Phe Pro
    3860            3865            3870

Ala Ala Gly Arg Ala Leu Ala Ala Leu Ser Val Arg Pro Phe Ala
    3875            3880            3885

Leu Arg Arg Leu Ser Ala Gly Leu Ser Leu Pro Leu Leu Thr Ser
    3890            3895            3900

Val Cys Leu Leu Leu Phe Ala Val His Phe Ala Val Ala Glu Ala
    3905            3910            3915

Arg Thr Trp His Arg Glu Gly Arg Trp Arg Val Leu Arg Leu Gly
    3920            3925            3930

Ala Trp Ala Arg Trp Leu Leu Val Ala Leu Thr Ala Ala Thr Ala
    3935            3940            3945

Leu Val Arg Leu Ala Gln Leu Gly Ala Ala Asp Arg Gln Trp Thr

-continued

|  | 3950 |  |  | 3955 |  |  | 3960 |  |  |
|---|---|---|---|---|---|---|---|---|---|
| Arg | Phe | Val | Arg | Gly | Arg | Pro | Arg | Arg | Phe | Thr | Ser | Phe | Asp | Gln |
|  | 3965 |  |  |  | 3970 |  |  | 3975 |  |
| Val | Ala | Gln | Leu | Ser | Ser | Ala | Ala | Arg | Gly | Leu | Ala | Ala | Ser | Leu |
|  | 3980 |  |  |  | 3985 |  |  | 3990 |  |
| Leu | Phe | Leu | Leu | Leu | Val | Lys | Ala | Ala | Gln | Gln | Leu | Arg | Phe | Val |
|  | 3995 |  |  |  | 4000 |  |  | 4005 |  |
| Arg | Gln | Trp | Ser | Val | Phe | Gly | Lys | Thr | Leu | Cys | Arg | Ala | Leu | Pro |
|  | 4010 |  |  |  | 4015 |  |  | 4020 |  |
| Glu | Leu | Leu | Gly | Val | Thr | Leu | Gly | Leu | Val | Val | Leu | Gly | Val | Ala |
|  | 4025 |  |  |  | 4030 |  |  | 4035 |  |
| Tyr | Ala | Gln | Leu | Ala | Ile | Leu | Leu | Val | Ser | Ser | Cys | Val | Asp | Ser |
|  | 4040 |  |  |  | 4045 |  |  | 4050 |  |
| Leu | Trp | Ser | Val | Ala | Gln | Ala | Leu | Leu | Val | Leu | Cys | Pro | Gly | Thr |
|  | 4055 |  |  |  | 4060 |  |  | 4065 |  |
| Gly | Leu | Ser | Thr | Leu | Cys | Pro | Ala | Glu | Ser | Trp | His | Leu | Ser | Pro |
|  | 4070 |  |  |  | 4075 |  |  | 4080 |  |
| Leu | Leu | Cys | Val | Gly | Leu | Trp | Ala | Leu | Arg | Leu | Trp | Gly | Ala | Leu |
|  | 4085 |  |  |  | 4090 |  |  | 4095 |  |
| Arg | Leu | Gly | Ala | Val | Ile | Leu | Arg | Trp | Arg | Tyr | His | Ala | Leu | Arg |
|  | 4100 |  |  |  | 4105 |  |  | 4110 |  |
| Gly | Glu | Leu | Tyr | Arg | Pro | Ala | Trp | Glu | Pro | Gln | Asp | Tyr | Glu | Met |
|  | 4115 |  |  |  | 4120 |  |  | 4125 |  |
| Val | Glu | Leu | Phe | Leu | Arg | Arg | Leu | Arg | Leu | Trp | Met | Gly | Leu | Ser |
|  | 4130 |  |  |  | 4135 |  |  | 4140 |  |
| Lys | Val | Lys | Glu | Phe | Arg | His | Lys | Val | Arg | Phe | Glu | Gly | Met | Glu |
|  | 4145 |  |  |  | 4150 |  |  | 4155 |  |
| Pro | Leu | Pro | Ser | Arg | Ser | Ser | Arg | Gly | Ser | Lys | Val | Ser | Pro | Asp |
|  | 4160 |  |  |  | 4165 |  |  | 4170 |  |
| Val | Pro | Pro | Pro | Ser | Ala | Gly | Ser | Asp | Ala | Ser | His | Pro | Ser | Thr |
|  | 4175 |  |  |  | 4180 |  |  | 4185 |  |
| Ser | Ser | Ser | Gln | Leu | Asp | Gly | Leu | Ser | Val | Ser | Leu | Gly | Arg | Leu |
|  | 4190 |  |  |  | 4195 |  |  | 4200 |  |
| Gly | Thr | Arg | Cys | Glu | Pro | Glu | Pro | Ser | Arg | Leu | Gln | Ala | Val | Phe |
|  | 4205 |  |  |  | 4210 |  |  | 4215 |  |
| Glu | Ala | Leu | Leu | Thr | Gln | Phe | Asp | Arg | Leu | Asn | Gln | Ala | Thr | Glu |
|  | 4220 |  |  |  | 4225 |  |  | 4230 |  |
| Asp | Val | Tyr | Gln | Leu | Glu | Gln | Gln | Leu | His | Ser | Leu | Gln | Gly | Arg |
|  | 4235 |  |  |  | 4240 |  |  | 4245 |  |
| Arg | Ser | Ser | Arg | Ala | Pro | Ala | Gly | Ser | Ser | Arg | Gly | Pro | Ser | Pro |
|  | 4250 |  |  |  | 4255 |  |  | 4260 |  |
| Gly | Leu | Arg | Pro | Ala | Leu | Pro | Ser | Arg | Leu | Ala | Arg | Ala | Ser | Arg |
|  | 4265 |  |  |  | 4270 |  |  | 4275 |  |
| Gly | Val | Asp | Leu | Ala | Thr | Gly | Pro | Ser | Arg | Thr | Pro | Leu | Arg | Ala |
|  | 4280 |  |  |  | 4285 |  |  | 4290 |  |
| Lys | Asn | Lys | Val | His | Pro | Ser | Ser | Thr |  |  |  |  |  |  |
|  | 4295 |  |  |  | 4300 |  |  |  |  |

<210> SEQ ID NO 172
<211> LENGTH: 968
<212> TYPE: PRT
<213> ORGANISM: Homo sapiens

<400> SEQUENCE: 172

-continued

```
Met Val Asn Ser Ser Arg Val Gln Pro Gln Pro Gly Asp Ala Lys
1               5                   10                  15

Arg Pro Pro Ala Pro Arg Ala Pro Asp Pro Gly Arg Leu Met Ala Gly
                20                  25                  30

Cys Ala Ala Val Gly Ala Ser Leu Ala Ala Pro Gly Gly Leu Cys Glu
            35                  40                  45

Gln Arg Gly Leu Glu Ile Glu Met Gln Arg Ile Arg Gln Ala Ala Ala
50                  55                  60

Arg Asp Pro Pro Ala Gly Ala Ala Ser Pro Ser Pro Pro Leu Ser
65                  70                  75                  80

Ser Cys Ser Arg Gln Ala Trp Ser Arg Asp Asn Pro Gly Phe Glu Ala
                85                  90                  95

Glu Glu Glu Glu Glu Glu Val Glu Gly Glu Glu Gly Gly Met Val Val
                100                 105                 110

Glu Met Asp Val Glu Trp Arg Pro Gly Ser Arg Arg Ser Ala Ala Ser
            115                 120                 125

Ser Ala Val Ser Ser Val Gly Ala Arg Ser Arg Gly Leu Gly Gly Tyr
130                 135                 140

His Gly Ala Gly His Pro Ser Gly Arg Arg Arg Arg Glu Asp Gln
145                 150                 155                 160

Gly Pro Pro Cys Pro Ser Pro Val Gly Gly Asp Pro Leu His Arg
                165                 170                 175

His Leu Pro Leu Glu Gly Gln Pro Pro Arg Val Ala Trp Ala Glu Arg
            180                 185                 190

Leu Val Arg Gly Leu Arg Gly Leu Trp Gly Thr Arg Leu Met Glu Glu
        195                 200                 205

Ser Ser Thr Asn Arg Glu Lys Tyr Leu Lys Ser Val Leu Arg Glu Leu
210                 215                 220

Val Thr Tyr Leu Leu Phe Leu Ile Val Leu Cys Ile Leu Thr Tyr Gly
225                 230                 235                 240

Met Met Ser Ser Asn Val Tyr Tyr Thr Arg Met Met Ser Gln Leu
            245                 250                 255

Phe Leu Asp Thr Pro Val Ser Lys Thr Glu Lys Thr Asn Phe Lys Thr
            260                 265                 270

Leu Ser Ser Met Glu Asp Phe Trp Lys Phe Thr Glu Gly Ser Leu Leu
        275                 280                 285

Asp Gly Leu Tyr Trp Lys Met Gln Pro Ser Asn Gln Thr Glu Ala Asp
290                 295                 300

Asn Arg Ser Phe Ile Phe Tyr Glu Asn Leu Leu Leu Gly Val Pro Arg
305                 310                 315                 320

Ile Arg Gln Leu Arg Val Arg Asn Gly Ser Cys Ser Ile Pro Gln Asp
            325                 330                 335

Leu Arg Asp Glu Ile Lys Glu Cys Tyr Asp Val Tyr Ser Val Ser Ser
            340                 345                 350

Glu Asp Arg Ala Pro Phe Gly Pro Arg Asn Gly Thr Ala Trp Ile Tyr
        355                 360                 365

Thr Ser Glu Lys Asp Leu Asn Gly Ser Ser His Trp Gly Ile Ile Ala
370                 375                 380

Thr Tyr Ser Gly Ala Gly Tyr Tyr Leu Asp Leu Ser Arg Thr Arg Glu
385                 390                 395                 400

Glu Thr Ala Ala Gln Val Ala Ser Leu Lys Lys Asn Val Trp Leu Asp
            405                 410                 415

Arg Gly Thr Arg Ala Thr Phe Ile Asp Phe Ser Val Tyr Asn Ala Asn
```

-continued

```
                420             425             430
Ile Asn Leu Phe Cys Val Val Arg Leu Val Glu Phe Pro Ala Thr
            435             440             445
Gly Gly Val Ile Pro Ser Trp Gln Phe Gln Pro Leu Lys Leu Ile Arg
450             455             460
Tyr Val Thr Thr Phe Asp Phe Phe Leu Ala Ala Cys Glu Ile Ile Phe
465             470             475             480
Cys Phe Phe Ile Phe Tyr Tyr Val Val Glu Glu Ile Leu Glu Ile Arg
                485             490             495
Ile His Lys Leu His Tyr Phe Arg Ser Phe Trp Asn Cys Leu Asp Val
            500             505             510
Val Ile Val Val Leu Ser Val Val Ala Ile Gly Ile Asn Ile Tyr Arg
            515             520             525
Thr Ser Asn Val Glu Val Leu Leu Gln Phe Leu Glu Asp Gln Asn Thr
            530             535             540
Phe Pro Asn Phe Glu His Leu Ala Tyr Trp Gln Ile Gln Phe Asn Asn
545             550             555             560
Ile Ala Ala Val Thr Val Phe Phe Val Trp Ile Lys Leu Phe Lys Phe
                565             570             575
Ile Asn Phe Asn Arg Thr Met Ser Gln Leu Ser Thr Thr Met Ser Arg
                580             585             590
Cys Ala Lys Asp Leu Phe Gly Phe Ala Ile Met Phe Phe Ile Ile Phe
            595             600             605
Leu Ala Tyr Ala Gln Leu Ala Tyr Leu Val Phe Gly Thr Gln Val Asp
            610             615             620
Asp Phe Ser Thr Phe Gln Glu Cys Ile Phe Thr Gln Phe Arg Ile Ile
625             630             635             640
Leu Gly Asp Ile Asn Phe Ala Glu Ile Glu Glu Ala Asn Arg Val Leu
                645             650             655
Gly Pro Ile Tyr Phe Thr Thr Phe Val Phe Phe Met Phe Phe Ile Leu
                660             665             670
Leu Asn Met Phe Leu Ala Ile Ile Asn Asp Thr Tyr Ser Glu Val Lys
            675             680             685
Ser Asp Leu Ala Gln Gln Lys Ala Glu Met Glu Leu Ser Asp Leu Ile
690             695             700
Arg Lys Gly Tyr His Lys Ala Leu Val Lys Leu Lys Leu Lys Lys Asn
705             710             715             720
Thr Val Asp Asp Ile Ser Glu Ser Leu Arg Gln Gly Gly Gly Lys Leu
                725             730             735
Asn Phe Asp Glu Leu Arg Gln Asp Leu Lys Gly Lys Gly His Thr Asp
            740             745             750
Ala Glu Ile Glu Ala Ile Phe Thr Lys Tyr Asp Gln Asp Gly Asp Gln
            755             760             765
Glu Leu Thr Glu His Glu His Gln Gln Met Arg Asp Asp Leu Glu Lys
            770             775             780
Glu Arg Glu Asp Leu Asp Leu Asp His Ser Ser Leu Pro Arg Pro Met
785             790             795             800
Ser Ser Arg Ser Phe Pro Arg Ser Leu Asp Asp Ser Glu Glu Asp Asp
                805             810             815
Asp Glu Asp Ser Gly His Ser Ser Arg Arg Arg Gly Ser Ile Ser Ser
                820             825             830
Gly Val Ser Tyr Glu Glu Phe Gln Val Leu Val Arg Arg Val Asp Arg
            835             840             845
```

-continued

```
Met Glu His Ser Ile Gly Ser Ile Val Ser Lys Ile Asp Ala Val Ile
            850             855             860

Val Lys Leu Glu Ile Met Glu Arg Ala Lys Leu Lys Arg Arg Glu Val
865             870             875             880

Leu Gly Arg Leu Leu Asp Gly Val Ala Glu Asp Arg Leu Gly Arg
                885             890             895

Asp Ser Glu Ile His Arg Glu Gln Met Glu Arg Leu Val Arg Glu Glu
            900             905             910

Leu Glu Arg Trp Glu Ser Asp Asp Ala Ala Ser Gln Ile Ser His Gly
        915             920             925

Leu Gly Thr Pro Val Gly Leu Asn Gly Gln Pro Arg Pro Arg Ser Ser
    930             935             940

Arg Pro Ser Ser Ser Gln Ser Thr Glu Gly Met Glu Gly Ala Gly Gly
945             950             955             960

Asn Gly Ser Ser Asn Val His Val
                965
```

The invention claimed is:

1. A method for diagnosing ADPKD in an individual, comprising identifying one or more nucleotide sequence alterations selected from the group consisting of PKD1X40-1, PKD1X18, PKD1X6, PKD1X25, PKD2X5, PKD1X19, PKD1X2, and PKD1X3 in the nucleotide sequence of a PKD-1 or PKD-2 gene of an individual, wherein the presence of one or more of said sequence alterations is indicative of ADPKD in said individual.

2. The method of claim 1, further comprising obtaining a DNA sample from said individual for the identification of nucleotide sequence of PKD-1 or PKD-2 gene.

3. The method of claim 2, wherein said DNA sample obtained is a genomic DNA sample or a cDNA sample.

4. The method of claim 2, further comprising amplifying a portion of the PKD-1 or PKD-2 gene from said DNA sample before said identification.

5. The method of claim 4, wherein said portion of the PKD-1 or PKD-2 gene is amplified by a polymerase chain reaction.

6. The method of claim 2, wherein said identification is by DNA sequencing.

7. The method of claim 6, wherein said DNA sequencing is performed using an isolated nucleic acid comprising a sequence selected from the group consisting of SEQ ID NOs. 3-49 and their complementary sequences thereof.

8. The method of claim 1, wherein the nucleotide sequence of said PKD-1 or PKD-2 gene comprises at least two of said nucleotide sequence alterations.

9. A method for determining in an individual the presence or absence of a mutant PKD gene, comprising the steps of:
 a) identifying the nucleotide sequence of a PKD-1 or PKD-2 gene of said individual;
 b) comparing said nucleotide sequence of step a) to the nucleotide sequence alterations selected from the group consisting of PKD1X40-1, PKD1X18, PKD1X6, PKD1X25, PKD2X5, PKD1X19, PKD1X2, and PKD1X3; and
 c) detecting the presence of one or more of said nucleotide sequence alterations in said nucleotide sequence of step a);
 wherein the presence of at least one of said nucleotide sequence alterations is indicative of ADPKD in said individual.

10. The method of claim 9, further comprising obtaining a DNA sample from said individual for the identification of nucleotide sequence of PKD-1 or PKD-2 gene.

11. The method of claim 10, wherein said DNA sample obtained is a genomic DNA sample or a cDNA sample.

12. The method of claim 10, further comprising amplifying a portion of the PKD-1 or PKD-2 gene from said DNA sample before said identification.

13. The method of claim 12, wherein said portion of the PKD-1 or PKD-2 gene is amplified by a polymerase chain reaction.

14. The method of claim 10, wherein said identification is by DNA sequencing.

15. The method of claim 14, wherein said DNA sequencing is performed using an isolated nucleic acid comprising a sequence selected from the group consisting of SEQ ID NOs. 3-49 and their complementary sequences thereof.

16. The method of claim 9, wherein the nucleotide sequence of said PKD-1 or PKD-2 gene comprises at least two of said nucleotide sequence alterations.

17. The method of claim 1 further comprising identifying the nucleotide sequence alteration PKD1X23A.

18. The method of claim 9 further comprising identifying the nucleotide sequence alteration PKD1X23A.

* * * * *